US008815598B2

(12) United States Patent
Okabe et al.

(10) Patent No.: US 8,815,598 B2
(45) Date of Patent: Aug. 26, 2014

(54) TROPHECTODERMAL CELL-SPECIFIC GENE TRANSFER METHODS

(75) Inventors: Masaru Okabe, Minoo (JP); Masahito Ikawa, Osaka (JP)

(73) Assignees: Masaru Okabe, Osaka (JP); Masahito Ikawa, Osaka (JP); Fuso Pharmaceutical Industries, Ltd., Osaka (JP)

( * ) Notice: Subject to any disclaimer, the term of this patent is extended or adjusted under 35 U.S.C. 154(b) by 393 days.

(21) Appl. No.: 12/063,576

(22) PCT Filed: Jul. 31, 2006

(86) PCT No.: PCT/JP2006/315102

§ 371 (c)(1), (2), (4) Date: Jun. 25, 2008

(87) PCT Pub. No.: WO2007/020786

PCT Pub. Date: Feb. 22, 2007

(65) Prior Publication Data

US 2009/0013418 A1 Jan. 8, 2009

(30) Foreign Application Priority Data

Aug. 12, 2005 (JP) ................................ 2005-234258

(51) Int. Cl.

| | |
|---|---|
| ***C12N 15/00*** | (2006.01) |
| ***C12N 15/86*** | (2006.01) |
| ***C12N 5/00*** | (2006.01) |
| ***C12N 5/02*** | (2006.01) |
| ***C12N 5/073*** | (2010.01) |

(52) U.S. Cl.

CPC .......... *C12N 5/0605* (2013.01); *A01K 2217/05* (2013.01); *A01K 2227/10* (2013.01); *A01K 2267/03* (2013.01); *A01K 2267/0393* (2013.01)

USPC .......... 435/456; 435/325; 435/455; 435/354; 435/363; 435/366

(58) Field of Classification Search

None

See application file for complete search history.

(56) References Cited

U.S. PATENT DOCUMENTS

2005/0241012 A1* 10/2005 Nigam et al. .................. 800/18

FOREIGN PATENT DOCUMENTS

| | | |
|---|---|---|
| EP | 0782862 | 7/1997 |
| JP | 11-29498 | 2/1999 |
| WO | 96/11713 | 4/1996 |
| WO | 2011/108711 | 9/2011 |

OTHER PUBLICATIONS

Kothary et al, 1989, Development, 105:707-714.*

Malashicheva, A et al, 2007, Genesis, 45:456-459.*

Cherry et al., "Retroviral Expression in Embryonic Stem Cells and Hematopoietic Stem Cells" Mol Cell Biol., Oct. 2000; 20(20):7419-26.

Hamaguchi et al., "Lentivirus Vector Gene Expression during ES Cell-Derived Hematopoietic Development In Vitro" J Virol., Nov. 2000; 74(22):10778-84.

Jahner et al., "Insertion of the bacterial gpt gene into the germ line of mice by retroviral infection" Proc Natl Acad Sci USA, Oct. 1985; 82(20):6927-31.

Pfeifer et al., "Transgenesis by lentiviral vectors: Lack of gene silencing in mammalian embryonic stem cells and preimplantation embryos" Proc Natl Acad Sci USA, Feb. 19, 2002; 99(4):2140-5.

Tsukamoto et al., "Gene transfer and expression in progeny after intravenous DNA injection into pregnant mice" Nat Genet., Mar. 1995; 9(3):243-8.

Ueshin, Osaka University and Graduate School of Pharmaceutical Sciences Master Thesis Presentation. "Development of Novel Gene Therapy Method Using Lentivirus Vectors." Feb. 14, 2005.

Van Der Putten et al., "Efficient insertion of genes into the mouse germ line via retroviral vectors" Proc Natl Acad Sci USA, Sep. 1985; 82(18):6148-52.

Cross, "How to Make a Placenta: Mechanisms of Trophoblast Cell Differentiation in Mice - A Review" Placenta (Apr. 2005); 26 Suppl. A:S3-9.

Ikawa et al., "Generation of Transgenic Mice Using Lentiviral Vectors: A Novel Preclinical Assessment of Lentiviral Vectors for Gene Therapy" Mol. Ther. (Oct. 2003); 8(4):666-73.

Okada et al., "Complementation of placental defects and embryonic lethality by trophoblast-specific lentiviral gene transfer" Nature Biotechnology (Feb. 2007); 25(2):233-7 (Epub Jan. 14, 2007).

Wolfgang et al., "Rhesus monkey placental transgene expression after lentiviral gene transfer into preimplantation embryos" Proc Natl Acad Sci U S A (Sep. 11, 2001); 98(19):10728-32.

(Continued)

*Primary Examiner* — Valarie Bertoglio

(74) *Attorney, Agent, or Firm* — Karl Bozicevic; Bozicevic, Field & Francis LLP

(57) ABSTRACT

The present inventors discovered that genes could be introduced specifically into trophectodermal cells with high efficiency, by infecting blastocysts with viral vectors carrying an arbitrary polynucleotide, or by using a nucleic acid transfection reagent in blastocysts, from which zona pellucida (extracellular matrix covering preimplantation early embryos to protect them from infection of viruses and the like) is removed. This method has no risk of infecting cells of the inner cell mass, which develops into a fetus in the future, with the introduced polynucleotide because the trophectoderm serves as a barrier. The present invention provides methods for introducing foreign genes into only placenta but not fetus, which enables rescue of genetically mutant animals from embryonic lethality due to placental abnormality and allows their birth. Furthermore, it is possible to analyze expression and effect of genes that regulate placental formation or placental function by using these methods.

4 Claims, 5 Drawing Sheets

(56) References Cited

OTHER PUBLICATIONS

Xing et al., "Comparative in Vivo Approaches for Selective Adenovirus-Mediated Gene Delivery to the Placenta" Human Gene Therapy (Jan. 1, 2000); 11(1):167-77.
Carballada et al., "Transfection of Mouse Eggs and Embryos Using DNA Combined to Cationic Liposomes" Molecular Reproduction and Development, 56:360-365 (2000).
Tsukui et al., "Transgenesis by adenovirus-mediated gene transfer into mouse zona-free eggs" Nature Biotechnology, 14:982-985 (1996).
Unpublished U.S. Appl. No. 13/581,510, internationally filed Mar. 4, 2011 entitled "Model Animal for Pregnancy-induced Hypertension Syndrome, and Treatment Method Therefor" and assigned to Fuso Pharmaceutical Industries, Ltd. which is a 371 National Phase of WO 2011/108711.
Website of "American Pregnancy Associate" (http://www.americanpregnancy.org/infertility/embryotransfer.html) (accessed Dec. 1, 2011).
Hasler, John F., "Current Status and Potential of Embryo Transfer and Reproductive Technology in Dairy Cattle" J. Dairy Sci., 75:2857-2879 (1992).
Kunkel, J.R., "Embryo Transfer", West Virginia University Extension Service (http://www.wvu.edu/~agexten/forglvst/Dairy/dirm26.pdf) (accessed Nov. 16, 2011).
Selk, Glenn, "ANSI-3158 Embryo Transfer in Cattle Version 3", Oklahoma Cooperative Extension Service (http://pods.dasnr.okstate.edu/docushare/dsweb/Services/Document-1993) (2007).
Japanese Version of: Alberts et al., "Molecular Biology of the Cell". 4th Edition (2004), pp. 1223-1224 (translation supervised by K Nakamura et al. and published by Newton Press Inc.) together with the original English version of Alberts et al., "Molecular Biology of the Cell" fourth edition, Garland Science, (2004) pp. 1223-1224.

* cited by examiner a:VISIBLE LIGHT 80ms b:FLUORESCENCE 5s a: HE STAINING 200ms    b: FLUORESCENCE 5s c

| $ERK2^{+/-}$ × $ERK2^{+/-}$ | +/+ | +/− | −/− | TOTAL NUMBER |
|---|---|---|---|---|
| NATURAL MATING* | 18 | 30 | 0 | 48 |
| PLACENTA-SPECIFIC GENE TRANSFER | 27 | 46 | 16 | 89 |

c

| p38α+/− × p38α+/− | +/+ | +/− | −/− | TOTAL NUMBER |
|---|---|---|---|---|
| NATURAL MATING* | 117 | 204 | 0 | 321 |
| PLACENTA-SPECIFIC GENE TRANSFER | 50 | 86 | 34 | 170 |

TROPHECTODERMAL CELL-SPECIFIC GENE TRANSFER METHODS

TECHNICAL FIELD

The present invention relates to methods for introducing arbitrary polynucleotides specifically into whole placenta. The present invention also relates to methods for producing non-human animals rescued from embryonic lethality. Furthermore, the present invention also relates to methods of screening for polynucleotides that rescue embryonic lethality.

BACKGROUND ART

Methods for producing transgenic mice using retroviral vectors (Non-Patent Document 1) are known as methods for introducing genes at the individual level using viral vectors. Transgenic mice can be efficiently produced by using retroviral vectors; however, a disadvantage is that silencing of gene expression occurs as a result of methylation of introduced genes, or the like (Non-Patent Document 2).

Long term expression of introduced genes can be expected with the lentivirus vector which is a retroviral vector, because it enables integration of foreign genes into chromosome. Furthermore, unlike typical retroviral vectors, lentivirus vectors have a nuclear translocation signal, and thus can introduce genes into non-dividing cells. When transgenic mice are produced using lentivirus vectors, the efficiency of production increases and gene silencing does not occur in long-term gene expression (Non-Patent Documents 3 to 5).

In these methods of transgenic mouse production, genes are introduced into most viral vector-infected fertilized eggs. Furthermore, these methods introduce genes into both placenta and embryo, and thus are regarded as very excellent techniques in developmental studies.

[Non-Patent Document 1] Proc. Natl. Acad. Sci. USA., 1985, September; 82(18): 6148-6152
[Non-Patent Document 2] Proc. Natl. Acad. Sci. USA., 1985, October; 82(20): 6927-6931
[Non-Patent Document 3] Mol. Cell. Biol., 2000, October; 20(20): 7419-7426
[Non-Patent Document 4] J. Virol., 2000, November; 74(22): 10778-10784
[Non-Patent Document 5] Proc. Natl. Acad. Sci. USA., 2002, Feb. 19; 99(4): 2140-2145

DISCLOSURE OF THE INVENTION

Problems to be Solved by the Invention

To analyze gene expression in placenta and its effects during embryogenesis, foreign genes must be introduced into only the placenta but not embryo. A conventional method for introducing genes into the placenta comprises direct injection of a viral vector or such into the placenta using an injection needle or the like after laparotomy during pregnancy. However, the disadvantages of the method are the great burden imposed by surgery and that the method cannot be expected to introduce genes into the entire area of placenta.

Furthermore, as LV-based methods for introducing genes into the placenta, a transgenic method using infection of fertilized eggs (two-cell stage embryos) and a method for microinjection into blastocyst cavity are known. The former method has an advantage that the operation is convenient and a disadvantage that genes are introduced into both placenta and embryo.

Meanwhile, although the latter method for microinjection into blastocyst cavity enables genes to be specifically introduced into the placenta, it is not generally used because the method requires an expensive system and skillful techniques. Furthermore, the method is problematic in that embryos are greatly damaged because a glass capillary is directly penetrated into blastocysts. In addition, it is difficult to treat embryos on a large scale by this method.

There is also a known method for preparing animals rescued from embryonic lethality due to placental abnormality, and it is based on a tetraploid rescue method. In this method, in addition to a mutant animal, two-cell stage embryos of a wild type animal are prepared and then fused together to prepare tetraploid embryos by electric treatment or such. Then, chimeric embryos are prepared by aggregating eight-cell stage embryos of the mutant animal with the tetraploid four-cell stage embryos of the wild type animal, from both of which the zona pellucida has been removed. Chimeric animals are created by transplanting the chimeric embryos into pseudopregnant animals.

However, experiments using this method are also time-consuming, because the method requires embryos of a wild type animal in addition to those of a mutant animal. In addition, the wild type embryos must be tetraploidized by electric fusion or such. Furthermore, the method is used for the purpose of complementing placental function in mutant animals and is thus not suitable for analyzing gene function in placenta.

The present invention was achieved in view of the above circumstances. An objective of the present invention is to provide methods for introducing genes specifically into whole placenta.

Means for Solving the Problems

The present inventors conducted various examinations to achieve the objective described above. As a result, the inventors found that genes could be introduced specifically into trophectodermal cells with high efficiency by infecting blastocysts, from which zona pellucida (extracellular matrix covering preimplantation early embryos to protect them from viral infection and the like) has been removed, with viral vectors.

More specifically, the present inventors successfully introduced genes into the trophectoderm, which is the outer layer of blastocyst, by removing the zona pellucida with acid treatment, enzyme treatment, or physical treatment and co-culturing blastocysts with viral vectors. Thus, the inventors completed the present invention. Furthermore, the inventors found that this method has no risk of infecting cells of the inner cell mass, which develop into a fetus in the future, with the viral vector because the trophectoderm serves as a barrier. Specifically, the present invention provides the following [1] to [21]:

[1] a method for introducing an arbitrary polynucleotide specifically into a trophectodermal cell, which comprises the steps of:
(a) removing zona pellucida from a blastocyst; and
(b) introducing an arbitrary polynucleotide into the blastocyst obtained in step (a);

[2] the method of [1], wherein the arbitrary polynucleotide is a polynucleotide encoding a protein essential for fetal development or a polynucleotide that regulates expression of the protein;

[3] the method of [2], wherein the polynucleotide encoding a protein essential for fetal development is at least a polynucleotide selected from the group consisting of: Dlx3, Fgfr2, Fra1, Fzd5, Gab1, Gcm1, Grb2 hypomorph, Gja7, Hgf, Hsp84-1, Itgav, Junb, Lifr, ERK1, ER 2, ERK5, MEK1, MEKk3, p38α, p38β, Met, Pdgfra, Pdgfb, Pparg, Rxra, Rxrb, Sos1, Vhlh, Wnt2, Ets2, Mash2, Egfr, Hsf1, Bmp5, Bmp7, Dnmt1, Itga4, Lhx1, Mrj, Tcf, Lef, Cdx2, Eomes, Fgf4, Esrrb, Hand1, Mdfi, Esx1, Amt, Tcfeb, and Gjb2;

[4] the method of any one of [1] to [3], wherein the blastocyst is derived from an animal having abnormality in a protein essential for fetal development or in the regulation of expression of the protein;

[5] a method for producing a blastocyst comprising a trophectodermal cell specifically introduced with an arbitrary polynucleotide, which comprises the steps of:
(a) removing zona pellucida from a blastocyst; and
(b) introducing an arbitrary polynucleotide into the blastocyst obtained in step (a);

[6] the method of [5], wherein the arbitrary polynucleotide is a polynucleotide encoding a protein essential for fetal development or a polynucleotide that regulates expression of the protein;

[7] the method of [6], wherein the polynucleotide encoding a protein essential for fetal development is at least a polynucleotide selected from the group consisting of: Dlx3, Fgfr2, Fra1, Fzd5, Gab1, Gcm1, Grb2 hypomorph, Gja7, Hgf, Hsp84-1, Itgav, Junb, Lifr, ERK1, ERK2, ERK5, MEK1, MEKk3, p38α, p38β, Met, Pdgfra, Pdgfb, Pparg, Rxra, Rxrb, Sos1, Vhlh, Wnt2, Ets2, Mash2, Egfr, Hsf1, Bmp5, Bmp7, Dnmt1, Itga4, Lhx1, Mrj, Tcf, Lef, Cdx2, Eomes, Fgf4, Esrrb, Hand1, Mdfi, Esx1, Amt, Tcfeb, and Gjb2;

[8] the method of any one of [5] to [7], wherein the blastocyst is derived from an animal having abnormality in a protein essential for fetal development or in the regulation of expression of the protein;

[9] a method for producing a non-human animal, which comprises the steps of:
(a) removing zona pellucida from a blastocyst of a non-human animal;
(b) introducing an arbitrary polynucleotide into the blastocyst obtained in step (a); and
(c) transplanting the blastocyst obtained in step (b) into a recipient;

[10] the method of [9], wherein the arbitrary polynucleotide is a polynucleotide encoding a protein essential for fetal development or a polynucleotide that regulates expression of the protein;

[11] a method for producing a non-human animal, which comprises the steps of:
(a) removing zona pellucida from a blastocyst of a non-human animal having abnormality in a protein essential for fetal development or in the regulation of expression of the protein;
(b) introducing a polynucleotide encoding the protein essential for fetal development or a polynucleotide that normalizes the regulation of expression of the protein into the blastocyst obtained in step (a); and
(c) transplanting the blastocyst obtained in step (b) into a recipient;

[12] the method of [10] or [11], wherein the polynucleotide encoding a protein essential for fetal development is at least a polynucleotide selected from the group consisting of: Dlx3, Fgfr2, Fra1, Fzd5, Gab1, Gcm1, Grb2 hypomorph, Gja7, Hgf, Hsp84-1, Itgav, Junb, Lifr, ERK1, ERK2, ERK5, MEK1, MEKk3, p38α, p38β, Met, Pdgfra, Pdgfb, Pparg, Rxra, Rxrb, Sos1, Vhlh, Wnt2, Ets2, Mash2, Egfr, Hsf1, Bmp5, Bmp7, Dnmt1, Itga4, Lhx1, Mrj, Tcf, Lef, Cdx2, Eomes, Fgf4, Esrrb, Hand1, Mdfi, Esx1, Amt, Tcfeb, and Gjb2;

[13] a method for rescuing a non-human animal from embryonic lethality, which comprises the steps of:
(a) removing zona pellucida from a blastocyst of a non-human animal having abnormality in a protein essential for fetal development or in the regulation of expression of the protein;
(b) introducing a polynucleotide encoding the protein essential for fetal development or a polynucleotide that normalizes the regulation of expression of the protein into the blastocyst obtained in step (a); and
(c) transplanting the blastocyst obtained in step (b) into a recipient to give birth to a newborn animal;

[14] the method of [13], wherein the polynucleotide encoding a protein essential for fetal development is at least a polynucleotide selected from the group consisting of: Dlx3, Fgfr2, Fra1, Fzd5, Gab1, Gcm1, Grb2 hypomorph, Gja7, Hgf, Hsp84-1, Itgav, Junb, Lifr, ERK1, ERK2, ERK5, MEK1, MEKk3, p38α, p38β, Met, Pdgfra, Pdgfb, Pparg, Rxra, Rxrb, Sos1, Vhlh, Wnt2, Ets2, Mash2, Egfr, Hsf1, Bmp5, Bmp7, Dnmt1, Itga4, Lhx1, Mrj, Tcf, Lef, Cdx2, Eomes, Fgf4, Esrrb, Hand1, Mdfi, Esx1, Arnt, Tcfeb, and Gjb2;

[15] a method of screening for a polynucleotide that rescues embryonic lethality, which comprises the steps of:
(a) removing zona pellucida from a blastocyst of a non-human animal having abnormality in a protein essential for fetal development or in the regulation of expression of the protein;
(b) introducing an arbitrary polynucleotide into the blastocyst obtained in step (a);
(c) transplanting the blastocyst obtained in step (b) into a recipient to give birth to a newborn animal; and
(d) selecting a polynucleotide that rescues embryonic lethality as compared to when the arbitrary polynucleotide is not introduced;

[16] the method of any one of [9] to [15], wherein the non-human animal is selected from the group consisting of: mouse, rat, rabbit, dog, cat, bovine, horse, pig, goat, sheep, and monkey;

[17] the method of any one of [I] to [16], wherein the zona pellucida is removed by acid treatment, enzyme treatment, or physical treatment;

[18] the method of [17], wherein the acid treatment is a treatment with acidic Tyrode's solution;

[19] the method of [17], wherein the enzyme treatment is a pronase treatment;

[20] the method of any one of [1] to [19], wherein the polynucleotide is introduced by infecting a blastocyst with a viral vector carrying a desired polynucleotide; and

[21] the method of any one of [1] to [19], wherein the polynucleotide is introduced by using a nucleic acid transfection reagent.

BEST MODE FOR CARRYING OUT THE INVENTION

Figure 1:
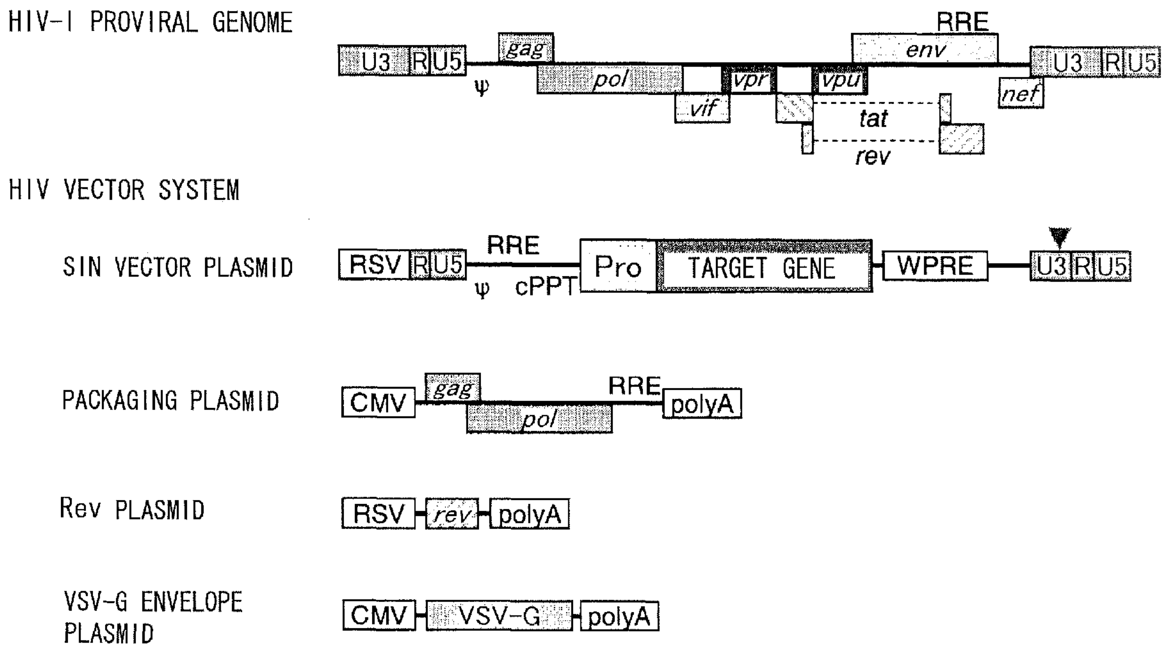
FIG. 1 is a diagram showing structure of the LV vector (LV-CAG-EGFP) used in the present invention.

The present invention is based on the present inventors' finding that arbitrary genes can be introduced specifically into trophectodermal cells with high efficiency, by infecting viral vectors carrying an arbitrary polynucleotide into blastocysts, from which zona pellucida (extracellular matrix covering preimplantation early embryos to protect them from viral infection and the like) has been removed, with viral vectors. More specifically, the present invention relates to methods for introducing arbitrary polynucleotides specifically into trophectodermal cells.

In the methods of the present invention, first, blastocysts are obtained. Blastocyst refers to an embryo that has finished the segmentation stage during early mammalian fetal development. Mammalian eggs are alecithal; they divide holoblastically and form aggregates of blastomeres. At the 32-cell stage, eggs are divided into trophectoderm which enfolds the outside of the aggregate and inner cell mass inside of the aggregate. The inner cell mass develops into the body of a fetus in the future, while the trophectoderm differentiates into the placenta. In the methods of the present invention, arbitrary polynucleotides are introduced specifically into trophectodermal cells that constitute the outmost layer of a blastocyst.

Blastocysts can be prepared by the methods described below. Specifically, eggs and sperms are collected from arbitrary animals, and then fertilization is carried out by methods known to those skilled in the art. Blastocysts can be prepared from the resulting fertilized eggs by methods known to those skilled in the art, for example, by culturing the eggs in kSOM medium for 96 hours. Alternatively, blastocysts can be obtained directly from animals according to methods that are conventionally used by those skilled in the art (for example, methods described in: Manipulating the mouse embryo, a laboratory manual, 3rd edition, p 201-203, Cold Spring Harbor Laboratory Press).

In the methods of the present invention, the zona pellucida is then removed from the blastocysts obtained above. Embryos (preimplantation early embryos) are covered with zona pellucida, which is extracellular matrix, to protect them from infection of viruses or the like. In the methods of the present invention, the zona pellucida is removed.

The zona pellucida can be removed by known methods, for example, acid treatment, enzyme treatment, or physical treatment. One example of such acid treatment is a treatment that uses acidic Tyrode's solution (Manipulating the mouse embryo, a laboratory manual, 3rd edition, p 485-486, Cold Spring Harbor Laboratory Press). The zona pellucida can be partially dissolved, for example, by sucking acidic Tyrode's solution (pH 2.3 to 2.5) with a micropipette and then gently spraying immobilized embryos with the solution. Alternatively, the zona pellucida can be dissolved by immersing embryos in acidic Tyrode's solution.

Enzyme treatment for removal of zona pellucida includes pronase treatment (Calbiochem 537088, Sigma P5147) and the like. For example, embryos are placed in a solution of 0.5% pronase until the zona pellucida dissolves. After the zona pellucida dissolves, the embryos are washed well with a medium, and then zona pellucida-removed blastocysts can be obtained (Manipulating the mouse embryo, a laboratory manual, 3rd edition, p 731, Cold Spring Harbor Laboratory Press).

Furthermore, in the present invention, zona pellucida can also be removed by physical methods. Such physical methods of removal include a zona pellucida dissection method in which embryos are immobilized and part of the zona pellucida is dissected with a micropipette (Hum. Reprod., 5:7-13, 1990), methods for dissecting, drilling, or thinning zona pellucida with a laser (Hum. Reprod., 15:1061-1064, 2000) or piezomicromanipulator (Developmental Biology, 250:348-357, 2002) and the like.

Zona pellucida can be removed by the methods described above. In the present invention, however, methods for removing zona pellucida are not limited to the examples described above, and the methods include all methods that can remove zona pellucida.

In the methods of the present invention, finally, arbitrary polynucleotides are introduced into zona pellucida-removed blastocysts. In a preferred embodiment, methods for introducing arbitrary polynucleotides into zona pellucida-removed blastocysts include methods for introducing a vector carrying an arbitrary polynucleotide into blastocysts, but are not particularly limited thereto.

Vectors carrying an arbitrary polynucleotide to be introduced into blastocysts include viral vectors. Such viral vectors include arbitrary viral vectors conventionally used by those skilled in the art, for example, lentivirus vectors (Molecular Therapy 2003, 8; 666-673), retroviral vectors (Molecular Therapy 2003, 8; 666-673), adenovirus vectors, HVJ liposomes, Lipofectamine, and the like. HVJ (hemagglutinating virus of Japan: Sendai virus) liposome is a vector which can efficiently introduce liposome-encapsulated genes and oligonucleotides to various organs in the body using activity of the fusion protein of HVJ, a virus causing cell fusion, and HMG-1, a DNA-binding protein.

Of such vectors, lentivirus vectors are preferred. Lentivirus belongs to the retrovirus family, and is an immunodeficiency virus in human, monkey, cat, and bovine. With respect to gene structure, the virus is constituted by several regulatory genes in addition to structural genes fundamental to the retrovirus (gag, pol, and env). Lentivirus vectors constructed by altering the lentivirus can integrate foreign genes into chromosome, and thus long term expression of the genes introduced therein can be expected. Furthermore, unlike other retroviral vectors, lentivirus vectors have a nuclear translocation signal, and thus can introduce genes into non-dividing cells.

Lentivirus vectors used in the present invention include lentivirus vectors having at least LTR, RRE, and GAG Lentivirus vectors used in the methods of the present invention should have at least these requirements, but may additionally have other genes, for example, deltaU3, PPT, and WPRE. Such lentivirus vectors are also preferably used as the viral vector in the methods of the present invention.

In a particularly preferred embodiment, lentivirus vectors used in the present invention have LTR (deltaU3), GAG, RRE, PPT, and WPRE. A representative example of lentivirus vectors having such structures is a vector constructed by substituting a cDNA of interest for the GFP moiety of the GFP viral vector disclosed in Example 1 and the following document: Molecular Therapy 2003, 8; 666-673. The vector structure and construction method are disclosed in the document indicated above.

Blastocysts can be infected with a lentivirus vector carrying an arbitrary polynucleotide, for example, by mixing zona pellucida-removed blastocysts with a solution containing the lentivirus vector carrying the arbitrary polynucleotide, and then leaving the mixture to stand for 4 to 5 hours. By this method, a lentivirus vector having an arbitrary polynucleotide can be specifically introduced into the trophectoderm.

Alternatively, arbitrary polynucleotides may also be introduced into zona pellucida-removed blastocysts by using a nucleic acid transfection reagent. Herein, the nucleic acid transfection reagent refers to any reagent that can introduce an arbitrary polynucleotide into blastocysts. Such nucleic acid transfection reagents include, but are not limited to, for example, Lipofectoamine 2000 (Invitrogen), Effectene (Qiagen), and FuGene (Roche).

A polynucleotide to be introduced may be in a form such as DNA, RNA, cDNA, mRNA, or artificial nucleic acid. Such DNAs, RNAs, cDNAs, and mRNAs also include derivatives thereof. Such artificial nucleic acids include, but are not limited to, for example, DNAs, RNAs, cDNAs, mRNAs, in which their sugar chain structures are modified, or derivatives thereof. Furthermore, polynucleotides to be introduced may be naked polynucleotides or polynucleotides introduced into a vector. Those skilled in the art can design and use appropriate vectors depending on the purpose. Vectors used in the present invention may comprise, in addition to an arbitrary polynucleotide to be introduced, polynucleotide regions that function in expression hosts, such as transcriptional initiation site and transcription termination site, for more efficient expression of the arbitrary polynucleotide.

In a preferred embodiment of the present invention, polynucleotides to be introduced include, but are not particularly limited to, polynucleotides encoding a protein essential for fetal development or polynucleotides that regulate the expression of a protein essential for fetal development.

Such polynucleotides encoding a protein essential for fetal development include any polynucleotides that encode a protein directly or indirectly involved in the fetal development. Such polynucleotides include, but are not limited to, for example, Dlx3 (SEQ ID NO: 1), Fgfr2 (SEQ ID NO: 2), Fra1 (SEQ ID NO: 3), Fzd5 (SEQ ID NO: 4), Gab1 (SEQ ID NO: 5), Gcm1 (SEQ ID NO: 6), Grb2 hypomorph (SEQ ID NO: 7), Gja7 (SEQ ID NO: 8), Hgf (SEQ ID NO: 9), Hsp84-1 (SEQ ID NO: 10), Itgav (SEQ ID NO: 11), Junb (SEQ ID NO: 12), Lifr (SEQ ID NO: 13), ERK1 (SEQ ID NO: 14), ERK2 (SEQ ID NO: 15), ERK5 (SEQ ID NO: 16), MEK1 (polynucleotide encoding the amino acid sequence of SEQ ID NO: 17), MEKk3 (polynucleotide encoding the amino acid sequence of SEQ ID NO: 18), p38α (SEQ ID NO: 19), p38β (SEQ ID NO: 20), Met (SEQ ID NO: 21), Pdgfra (SEQ ID NO: 22), Pdgfb (SEQ ID NO: 23), Pparg (SEQ ID NO: 24), Rxra (SEQ ID NO: 25), Rxrb (SEQ ID NO: 26), Sos1 (SEQ ID NO: 27), Vhlh (SEQ ID NO: 28), Wnt2 (SEQ ID NO: 29), Ets2 (SEQ ID NO: 30), Mash2 (SEQ ID NO: 31), Egfr (SEQ ID NO: 32), Hsf1 (SEQ ID NO: 33), Bmp5 (SEQ ID NO: 34), Bmp7 (SEQ ID NO: 35), Dnmt1 (SEQ ID NO: 36), Itga4 (SEQ ID NO: 37), Lhx1 (SEQ ID NO: 38), Mrj (SEQ ID NO: 39), Tcf1 (SEQ ID NO: 40), Lef1 (SEQ ID NO: 41), Cdx2 (SEQ ID NO: 42), Eomes (SEQ ID NO: 43), Fgf4 (SEQ ID NO: 44), Esrrb (SEQ ID NO: 45), Hand1 (SEQ ID NO: 46), Mdfi (SEQ ID NO: 47), Esx1 (SEQ ID NO: 48), Arnt (SEQ ID NO: 49), Tcfeb (SEQ ID NO: 51), and Gjb (SEQ ID NO: 52).

Those skilled in the art can readily obtain the above-described polynucleotides encoding a protein essential for fetal development. For example, such polynucleotides can be isolated from natural sources, using various biological samples such as placental tissues, trophoblast stem cells, and differentiated cells thereof as a source, based on their physicochemical properties and the like. Alternatively, the polynucleotides may be chemically synthesized based on known sequence information. Alternatively, the polynucleotides can be obtained by using gene recombination techniques to transform host cells with a vector carrying polynucleotides encoding a protein essential for fetal development, then culturing the resulting transformed cells that produce the gene recombinant protein, and collecting the protein from the cells or culture supernatant thereof.

The above-mentioned polynucleotides encoding a protein essential for fetal development include homologous genes from various animals. Herein, "homologous gene" refers to the above-listed polynucleotides of SEQ ID NOs: 1 to 16 and 19 to 51, polynucleotides encoding a protein comprising the amino acid sequence of SEQ ID NO: 17 or 18, or polynucleotides encoding a protein having a biological function equivalent to that of the transcription/translation products of such polynucleotides, in various animals.

Methods that are well known to those skilled in the art for isolating homologous genes include hybridization techniques (Southern, E. M., Journal of Molecular Biology, Vol. 98, 503, 1975) and polymerase chain reaction (PCR) techniques (Saiki, R. K., et al. Science, vol. 230, 1350-1354, 1985, Saiki, R. K. et al. Science, vol. 239, 487-491, 1988). More specifically, those skilled in the art can routinely isolate polynucleotides encoding a protein essential for fetal development from various animal cells and tissues (for example, placental tissues, trophoblast stem cells, and differentiated cells thereof), using as a probe, polynucleotides encoding a protein essential for fetal development (for example, the polynucleotide sequences of SEQ ID NOs: 1 to 16 and 19 to 51, and the polynucleotide sequences encoding a protein comprising the amino acid sequence of SEQ ID NO: 17 or 18) or a portion thereof, or using as a primer, oligonucleotides that specifically hybridize to the polynucleotides encoding a protein essential for fetal development. Alternatively, sequences of homologous genes may be obtained from known databases.

The polynucleotides of present invention encoding a protein essential for fetal development are preferably derived from, but are not particularly limited to, humans, mice, rats, rabbits, dogs, cats, bovines, horses, pigs, goats, sheep, and monkeys, more preferably from humans.

Furthermore, in a preferred embodiment, arbitrary polynucleotides used in the present invention include polynucleotides that regulate the expression of a protein essential for fetal development. Such polynucleotides include, for example:

(a) DNAs that expresses RNAs complementary to the transcription product of a DNA encoding a protein essential for fetal development;

(b) DNAs that expresses RNAs having a ribozyme activity of cleaving specifically the transcription product of a DNA encoding a protein essential for fetal development;

(c) DNAs that expresses RNAs having an RNAi activity of cleaving specifically the transcription product of a DNA encoding a protein essential for fetal development; and (d) DNAs that bind specifically to a transcriptional regulatory factor of a DNA encoding a protein essential for fetal development and regulates expression thereof.

Herein, "regulation of expression of a protein essential for fetal development" includes enhancement or suppression of the transcription of a gene encoding a protein essential for fetal development, or enhancement or suppression of its translation into protein.

In an embodiment, "polynucleotide that regulates the expression of a protein essential for fetal development" is a DNA encoding an antisense RNA complementary to the transcription product of a DNA encoding a protein essential for fetal development. The antisense effect was for the first time proven using the transient gene expression method, based on the finding that antisense RNAs exert an antisense effect when introduced into plants by electroporation (Ecker and Davis, Proc. Natl. Acad. USA, 83: 5372, 1986). After this finding, other cases were reported, where the expression levels of target genes were reduced by antisense RNA expression in tobacco or petunia (Krol et al., Nature 333: 866, 1988). To date, the antisense effect has been established as a method for suppressing gene expression in eukaryotes, including both animals and plants.

The action of antisense nucleic acids in suppressing target gene expression includes: inhibition of transcription initiation by triplex formation; transcription suppression by hybrid formation with a site having a local open loop structure generated by RNA polymerase; transcription inhibition by hybrid formation with RNA as its synthesis advances; splicing suppression by hybrid formation at an intron-exon junction; splicing suppression by hybrid formation with the site of spliceosome formation; suppression of transport from the nucleus to the cytoplasm by hybrid formation with mRNA; splicing suppression by hybrid formation with the capping site or poly(A) addition site; suppression of translation initiation by hybrid formation with the translation initiation factor binding site; suppression of translation by hybrid formation with the ribosome binding site adjacent to the start codon; prevention of peptide chain elongation by hybrid formation with the translational region or the polysome binding site of mRNA; and suppression of gene expression by hybrid formation with the nucleic acid-protein interaction site. These inhibit the process of transcription, splicing, or translation and suppress target gene expression (Hirashima and Inoue, Shin Seikagaku Jikkenkoza 2 (New Lecture for Experimental Biochemistry 2), Kakusan IV (Nucleic Acid IV), Replication and Expression of Genes; Ed., Japanese Biochemical Society, Tokyo Kagaku Dojin Co., Ltd., pp. 319-347, 1993).

The expression of an endogenous protein essential for fetal development can also be suppressed by using ribozyme-encoding DNAs. The ribozyme refers to a RNA molecule with catalytic activity. There are various ribozymes with different activities, and particularly studies of ribozymes that serve as RNA-cleaving enzymes have enabled the design of ribozymes for site-specific RNA cleavage. Ribozymes include those comprising 400 nucleotides or more, such as group-I intron-type and M1 RNA included in RNAseP, as well as ribozymes with an active domain of about 40 nucleotides, called hammerhead- or hairpin-type ribozymes (Makoto Koizumi and Eiko Otsuka, Tanpakushitu, Kakusan, Koso (Protein, Nucleic acid and Enzyme), 35:2191, 1990).

For example, the autocleavage domain of hammerhead-type ribozymes cleaves G13U14C15 at the 3' end of C15. The base pairing of U14 with A at position 9 is important for this activity, and cleavage has been shown to occur even when the nucleotide at position 15 is A or U, instead of C (Koizumi et al., FEBS Lett. 228:225, 1988). When the substrate-binding site of a ribozyme is designed to be complementary to an RNA sequence adjacent to the target site, it is possible to create a restriction enzyme-like RNA-cleaving ribozyme that recognizes the sequence UC, UU, or UA in the target RNA (Koizumi et al., FEBS Lett. 239:285, 1988; Makoto Koizumi and Eiko Otsuka, Tanpakushitu, Kakusan, Koso (Protein, Nucleic acid and Enzyme), 35:2191, 1990; Koizumi et al., Nucleic Acids Res. 17:7059, 1989).

Hairpin-type ribozymes are also useful for the purpose of the present invention. For example, hairpin-type ribozymes are found in the minus strand of satellite RNA in tobacco ringspot viruses (Buzayan, Nature 323:349, 1986). It has been demonstrated that this ribozyme can also be designed to cleave RNA in a target-specific manner (Kikuchi and Sasaki, Nucleic Acids Res. 19:6751, 1992; Yo Kikuchi, Kagaku To Seibutsu (Chemistry and Biology) 30:112, 1992).

In an alternative embodiment, "polynucleotide that regulates the expression of a protein essential for fetal development" is a DNA encoding double-stranded RNA (dsRNA) complementary to the transcription product of an endogenous DNA encoding a protein essential for fetal development. The introduction of a dsRNA comprising a sequence identical or similar to a target gene sequence into cells can cause the phenomenon called RNA interference (RNAi), where the expressions of both introduced foreign gene and target endogenous gene are suppressed. When about 40 to a few hundred base pairs of dsRNAs are introduced into cells, an RNase III-like nuclease called Dicer, which has a helicase domain, processes the dsRNAs from their 3' end into about 21 to 23 base pairs of short interference RNAs (siRNAs) in the presence of ATP. Specific proteins bind to the siRNAs to form nuclease complexes (RNA-induced silencing complexes (RISC)). The complexes recognize and bind to the same sequence as siRNA, and then cleave the transcription product (mRNA) of a target gene at the position corresponding to the center of the siRNA by the RNaseIII-like enzymatic activity.

In another pathway, the antisense strand of siRNA binds to mRNA and serves as a primer for RNA-dependent RNA polymerase (RsRP) to synthesize dsRNA. Another pathway is also considered where this dsRNA also serves as a substrate for Dicer, producing new siRNAs to amplify the effect.

The RNAi was originally found in *Caenorhabditis elegans* (Fire, A. et al. Potent and specific genetic interference by double-stranded RNA in *Caenorhabditis elegans*. Nature 391, 806-811, 1998), and so far has been observed not only in *Caenorhabditis elegans* but also in various organisms such as plants, Nematoda, *Drosophila*, and Protozoa (Fire, A. RNA-triggered gene silencing. Trends Genet. 15, 358-363 (1999); Sharp, P. A. RNA interference 2001. Genes Dev. 15, 485-490 (2001); Hammond, S. M., Caudy, A. A. & Hannon, G. J. Post-transcriptional gene silencing by double-stranded RNA. Nature Rev. Genet. 2, 110-119 (2001); Zamore, P. D. RNA interference: listening to the sound of silence. Nat Struct Biol. 8, 746-750 (2001)). Target gene expression has been confirmed to be suppressed when exogenous dsRNAs are introduced into these organisms. RNAi is also being used as a method for creating knockout animals.

At the time when RNAi was disclosed, only a particular length (40 nucleotides) or longer of dsRNAs was believed to be effective. However, Tuschl et al. at the Rockefeller University in the U.S. reported that introducing about 21 base pairs of short-strand dsRNA (siRNA) into cells produces an RNAi effect without inducing PKR-mediated anti-viral response, not even in mammalian cells (Tuschl, Nature, 411, 494-498 (2001)). Since then, RNAi has drawn much more attention as a technology applicable to differentiated mammalian cells such as human cells.

A DNA of the present invention comprises an antisense-coding DNA which encodes an antisense RNA for any region within the transcription product (mRNA) of a target gene and a sense-coding DNA which encodes a sense RNA for any region within the same mRNA, and allows expression of the antisense RNA and the sense RNA from the antisense-coding DNA and the sense-coding DNA, respectively. Furthermore, a dsRNA can also be prepared from the antisense and sense RNAs. In the present invention, the target sequence is not particularly limited, as long as a dsRNA comprising a sequence identical or similar to the target sequence suppresses the expression of a DNA encoding a protein essential for fetal development when introduced into cells.

When an expression system for the dsRNA of the present invention is maintained in a vector or such, the construction may that that both antisense and sense RNAs are expressed from a single vector or independently from different vectors. For example, when both antisense and sense RNAs are expressed from a single vector, a construct can be prepared by separately constructing an expression cassette for the antisense RNA and an expression cassette for the sense RNA, where a promoter such as polIII series, which enables the expression of a short RNA, is linked upstream of the antisense-coding DNA and sense-coding DNA, respectively, and then inserting these cassettes into a vector in the same or reverse orientation.

Alternatively, the expression system may be constructed, such that the antisense-coding DNA and sense-coding DNA are arranged on separate strands and in the opposite direction. This construct comprises a double-stranded DNA (siRNA-coding DNA) in which the antisense RNA-coding strand and sense RNA-coding strand are paired with each other and promoters are arranged at both ends thereof in the opposite direction, such that the antisense RNA or sense RNA can be expressed from each strand. In this case, it is preferred that a terminator is arranged at the 3' end of each strand (antisense RNA-coding strand or sense RNA-coding strand) to avoid addition of extra sequences downstream of the sense RNA and antisense RNA. A sequence of four or more consecutive adenine (A) nucleotides or the like may be used as the terminator. Furthermore, the two promoters are preferably different in this palindromic expression system.

Meanwhile, when the antisense RNA and sense RNA are expressed from separate vectors, constructs can be prepared, for example, by separately constructing an expression cassette for the antisense RNA and an expression cassette for the sense RNA, where a promoter such as polIII series, which enables the expression of a short RNA, is linked upstream of the antisense-coding DNA and sense-coding DNA, respectively, and then inserting these cassettes into separate vectors.

An siRNA may be used as the dsRNA for RNAi. "siRNA" refers to a double-stranded RNA consisted of short strands within a non-cytotoxic range, and is not limited to siRNAs with a full length of 21 to 23 base pairs as reported by Tuschl et al. (supra). The siRNA is not particularly limited, as long as its length is within a non-toxic range; for example, the length may be in the range of 15 to 49 base pairs, preferably 15 to 35 base pairs, and more preferably 21 to 30 base pairs. Alternatively, the final length of the formed double-stranded RNA portion of the expressed siRNA as a result of transcription may be, for example, in the range of 15 to 49 base pairs, preferably 15 to 35 base pairs, and more preferably 21 to 30 base pairs.

As the DNAs of present invention, constructs that form a double-stranded RNA with a hairpin structure (self-complementary "hairpin" RNA (hpRNA)) prepared by inserting an appropriate sequence (preferably intron sequence) between the inverted repeats of a target sequence (Smith, N. A., et al. Nature, 407: 319, 2000; Wesley, S. V et al. Plant J. 27: 581, 2001; Piccin, A. et al. Nucleic Acids Res. 29:E55, 2001) can be used.

It is not necessary that DNAs used for RNAi be perfectly identical to the target gene; however, they have at least 70% or higher, preferably 80% or higher, and more preferably 90% or higher (for example, 95%, 96%, 97%, 98%, 99% or higher) sequence identity. The sequence identity can be determined by the methods described above.

Those skilled in the art can prepare the above DNAs of the present invention using common genetic engineering techniques. The DNAs of the present invention can be prepared, for example, by synthesizing arbitrary sequences using well known oligonucleotide synthesis methods.

The DNAs of the present invention can be introduced into cellular chromosomes and expressed within the cells as the way they are; however, the above DNAs are preferably carried by vectors for efficient gene transfer into cells, and the like. Vectors comprising the DNAs of the present invention are also included in the present invention.

Furthermore, in another embodiment, "polynucleotide that regulates the expression of a polynucleotide encoding a protein essential for fetal development" includes DNAs that regulate expression by binding specifically to a transcriptional regulatory factor for the DNA encoding a protein essential for fetal development. As an example of such DNAs, decoy DNAs are known. Decoy DNAs include, for example, about 20 nucleotides of DNAs comprising a sequence complementary to a transcriptional regulatory factor such as NF-kB. Decoy DNAs inhibit the function of a transcriptional regulatory factor by binding to the factor. As a result, the expression of a protein which is regulated by the transcriptional regulatory factor is also suppressed.

Thus, polynucleotides that are introduced specifically into the trophectoderm by the methods of the present invention include not only polynucleotides encoding a protein essential for fetal development but also polynucleotides that regulate the expression of a protein essential for fetal development. For example, a gene function in embryogenesis can be analyzed by introducing into blastocysts a polynucleotide that regulates the expression of a protein essential for fetal development.

It is possible to determine whether an arbitrary polynucleotide has been introduced specifically into the trophectoderm of a blastocyst by the methods of the present invention, by using methods known to those skilled in the art, for example, by amplifying introduced genes with PCR, or by detecting the expression of a reporter gene such as EGFP or lacZ with a fluorescence or luminescence method, or such.

Blastocysts to be introduced with the above polynucleotides encoding a protein essential for fetal development or polynucleotides that regulate the expression of a protein essential for fetal development are not particularly limited. Blastocysts to be introduced with such polynucleotides include, for example, blastocysts derived from animals that have abnormality in a protein essential for fetal development or in the protein expression regulation thereof. Herein, "protein essential for fetal development" refers to a protein directly or indirectly involved in fetal development, as described above. Specifically, the proteins include those comprising the amino acid sequences encoded by the nucleotide sequences of SEQ ID NOs: 1 to 16 and 19 to 51, and proteins comprising the amino acid sequence of SEQ ID NO: 17 or 18. Furthermore, "having abnormality in a protein essential for fetal development" refers a condition that the protein essential for fetal development is structurally or functionally abnormal. Alternatively, "having abnormality in the regulation of expression of a protein essential for fetal development" refers to having abnormality in either or both of the following processes: transcription of a DNA encoding a protein essential for fetal development into RNA and translation of said RNA into protein. Furthermore, in the present invention, "having abnormality in the regulation of expression of a protein" includes not only the case that production of the protein is completely inhibited due to the abnormality in either or both of the transcription and translation processes, but also the case where the level or timing of the protein expression is not normal or that the protein is produced with abnormality in part of the normal protein function or structure.

For example, animals that could not be naturally born due to embryonic lethality can be born by introducing a polynucleotide encoding a protein essential for fetal development into blastocysts of the animals having abnormality in the protein that is essential for fetal development or in the protein expression regulation thereof.

Animals from which blastocysts are derived include, but are not particularly limited to, humans, mice, rats, rabbits, dogs, cats, bovines, horses, pigs, goats, sheep, monkeys, and the like.

As described above, in the methods of the present invention, "polynucleotides that regulate the expression of a protein essential for fetal development" can also be introduced into blastocysts. Specific embodiments of such polynucleotides are described above. Furthermore, blastocysts into which such polynucleotides are to be introduced include blastocysts of animals that have abnormality in a protein essential for fetal development or in the protein expression regulation thereof, and blastocysts that do not have abnormality in essential proteins for fetal development or in the protein expression regulation thereof. When a polynucleotide that regulates the expression of a protein essential for fetal development is a polynucleotide that enhances the expression of a protein essential for fetal development, for example, animals that could not be naturally born due to embryonic lethality can be born by introducing the polynucleotide into blastocysts of animals having abnormality in a protein essential for fetal development or in the protein expression regulation thereof. Alternatively, when a polynucleotide that regulates the expression of a protein essential for fetal development is a polynucleotide that suppresses the expression of a protein essential for fetal development, for example, genes essential for fetal development can be identified, or gene function in fetal development can be analyzed by introducing the polynucleotide into blastocysts that do not have abnormality in essential proteins for fetal development or in the protein expression regulation thereof.

Thus, those skilled in the art can use the methods of the present invention for various purposes and applications by selecting appropriate polynucleotides to be introduced and appropriate blastocysts into which the polynucleotides are introduced. In the methods of the present invention, polynucleotides to be introduced and blastocysts into which the polynucleotides are introduced are not particularly limited. Furthermore, combinations of polynucleotide to be introduced and blastocyst into which the polynucleotide is introduced are not limited.

The present invention also relates to methods for producing blastocysts where an arbitrary polynucleotide is introduced specifically into the trophectodermal cells.

In the methods of the present invention for producing blastocysts, first, the zona pellucida is removed from blastocysts. Any blastocysts may be used. The blastocysts can also be obtained, for example, by the methods described above. Furthermore, the zona pellucida can be removed, for example, by the methods described above, but the methods are not limited thereto.

In the methods of the present invention for producing blastocysts, arbitrary polynucleotides are then introduced into the above blastocysts. The polynucleotides can be introduced by the methods described above, but the methods are not limited thereto.

In the methods of the present invention for producing blastocysts, there is no limitation on the type of polynucleotide to be introduced, and any polynucleotides can be introduced. In a preferred embodiment, such polynucleotides include polynucleotides encoding a protein essential for fetal development or polynucleotides that regulate the expression of a protein essential for fetal development. Specific embodiments of these polynucleotides are also as described above.

Furthermore, there is no limitation on the type of blastocyst into which the above-described polynucleotides are introduced. For example, the above-described blastocysts may be used.

In the methods of the present invention for producing blastocysts, there is no limitation on the polynucleotide to be introduced, blastocyst into which the polynucleotide is introduced, or combinations thereof. Those skilled in the art can produce and use appropriate combinations depending on the purpose.

The present invention further relates to methods for producing non-human animals and methods for rescuing non-human animals from embryonic lethality.

In the methods of the present invention for producing non-human animals, first, the zona pellucida is removed from blastocysts of a non-human animal. Any blastocysts can be used for this purpose. The blastocysts to be used in the methods of the present invention for producing non-human animals are preferably, but are not limited to, blastocysts of non-human animals having abnormality in a protein essential for fetal development or in the protein expression regulation thereof. Polynucleotides can be introduced into such blastocysts to generate non-human animals rescued from embryonic lethality due to placental abnormalit.

Such blastocysts can be obtained by the methods described above. The zona pellucida may also be removed by any methods, for example, the methods described above.

In the methods of the present invention for producing non-human animals, an arbitrary polynucleotide is then introduced into the above blastocysts. The polynucleotide can also be introduced by the methods described above.

In the methods of the present invention for producing non-human animals, there is no limitation on the type of polynucleotide to be introduced. In a preferred embodiment, the polynucleotide includes polynucleotides encoding a protein essential for fetal development or polynucleotides that normalize regulation of the expression of a protein essential for fetal development. Specific embodiments of the polynucleotide encoding a protein essential for fetal development are as described above. Furthermore, the polynucleotides that normalize regulation of the expression of a protein essential for fetal development include polynucleotides that can correct abnormalities in either or both of the following processes: transcription of a DNA encoding a protein essential for fetal development to RNA and translation of the RNA to protein. Herein, normalization means not only perfect correction of the abnormality, but also partial correction of the abnormality and reduction in the degree of abnormality.

In the methods of the present invention for producing non-human animals, the above blastocysts are finally transplanted into a recipient. The recipient is preferably the same animal or an animal belonging to the same animal species as the animal from which the blastocysts are derived. Those skilled in the art can routinely transplant blastocysts into recipients (Manipulating the mouse embryo, a laboratory manual, 3rd edition, p 263-271, Cold Spring Harbor Laboratory Press). Non-human animals to be produced according to the present invention include, but are not limited to, for example, mice, rats, rabbits, dogs, cats, bovines, horses, pigs, goats, sheep, monkeys, and the like.

Thus, non-human animals which are embryonic lethal can be produced by using methods of the present invention for introducing of polynucleotides specifically into trophectodermal cells. It should be noted that the non-human animals produced by the methods of the present invention are not chimeric animals because they do not carry in their bodies the polynucleotide introduced into the blastocysts.

The present invention further provides methods for rescuing non-human animals from embryonic lethality. In the methods of the present invention for rescuing non-human animals from embryonic lethality, first, the zona pellucida is removed from blastocysts of a non-human animal having abnormality in a protein essential for fetal development or in the protein expression regulation thereof. Embodiments of non-human animals having abnormality in a protein essential for fetal development and non-human animals having abnormality in the regulation of expression of the protein essential for fetal development are as described above. Such blastocysts can be obtained, for example, by the methods described above. The zona pellucida may also be removed by any methods and the methods described above.

In the methods of the present invention for rescuing non-human animals from embryonic lethality, polynucleotides encoding a protein essential for fetal development or polynucleotides that normalize regulation of expression of a protein essential for fetal development are then introduced into the above blastocysts. The polynucleotides can also be introduced by the methods described above.

In the methods of the present invention for rescuing non-human animals from embryonic lethality, the above blastocysts are transplanted into a recipient to give birth to newborn animals. The recipient is preferably the same animal or an animal belonging to the same animal species as the animal from which the blastocysts are derived. Those skilled in the art can transplant blastocysts into recipients and give birth to newborn animals using conventional methods. Furthermore, non-human animals to be rescued by the methods of the present invention include, but are not limited to, for example, mice, rats, rabbits, dogs, cats, bovines, horses, pigs, goats, sheep, monkeys, and the like.

Furthermore, the present invention provides methods of screening for polynucleotides that rescue embryonic lethality, which comprise the following steps:

(a) removing the zona pellucida from blastocysts of a non-human animal having abnormality in a protein essential for fetal development or in the protein expression regulation thereof;

(b) introducing arbitrary polynucleotides into the blastocysts obtained in step (a);

(c) transplanting the blastocysts obtained in step (b) into a recipient to give birth to newborn animal; and (d) selecting polynucleotides that have rescued embryonic lethality as compared to when no arbitrary polynucleotide has been introduced.

In the screening methods of the present invention, first, the zona pellucida is removed from blastocysts of a non-human animal having abnormality in a protein essential for fetal development or in the protein expression regulation thereof. Specific embodiments of non-human animals having abnormality in a protein essential for fetal development or in the protein expression regulation thereof are as described above. The removal from blastocysts can be achieved by the methods described above, but they are not limited thereto.

In the screening methods of the present invention, arbitrary polynucleotides are then introduced into blastocysts obtained as described above. Any polynucleotides may be introduced, and the length and origin thereof, and methods for obtaining them are not limited. Polynucleotides used in the screening methods of the present invention may be chemically synthesized, or derived from natural sources, for example, gene libraries such as cDNA libraries, and transcription products of the gene libraries. Furthermore, these polynucleotides can be used after appropriate labeling as needed. Such labeling includes, for example, radioactive labeling, fluorescent labeling, and the like. These polynucleotides can be introduced into blastocysts by the methods described above.

In the screening methods of the present invention, the above blastocysts introduced with an arbitrary polynucleotide are then transplanted into a recipient to give birth to newborn animals. As described above, blastocysts can be transplanted into recipients and newborn animals can be obtained by conventional methods used by those skilled in the art.

In the screening methods of the present invention, polynucleotides that have rescued embryonic lethality are selected as compared to when no arbitrary polynucleotide is introduced. The selected polynucleotides can serve as polynucleotides that normalize the regulation of expression of a protein essential for fetal development, and thus are useful in producing or rescuing non-human animals, which would naturally die due to embryonic lethality. Alternatively, these polynucleotides can be used as therapeutic agents for diseases caused by an abnormality in essential proteins for fetal development or in the expression regulation thereof.

All prior art documents cited herein are incorporated herein by reference.

EXAMPLES

Hereinbelow, the present invention will be described more specifically with reference to the Examples, but it is not limited thereto.

Materials and Methods (1) LV-Based Method of TG Production (Conventional Method)

PMSG (pregnant mare serum gonadotrophin) was administered to female BDF1 mice, and after about 48 hours, HCG was administered to induce superovulation. The mice were mated with male BDF1 mice. About 48 hours after mating, two- to four-cell stage embryos were washed out from the oviducts in FHM medium. The zona pellucida was removed by treatment with acidic Tyrode's solution. Then, the fertilized eggs were placed one by one in a spot of viral solution ($1\times10^8$ ng/ml) for infection. The eggs were cultured until they became blastocysts. After washing with kSOM medium, the blastocysts were transplanted into the uterus of a pseudopregnant mouse (on day 2.5 of pseudopregnancy).

(2) Tetraploid Rescue (Conventional Method)

Tetraploid refers to a tetraploid embryo. The embryo contributes mainly to the placenta which is an extraembryonic tissue. When an aggregation chimera is prepared with a tetraploid embryo and an embryo of a mutant mouse with placental abnormality, the mutant mouse can be developed in the placenta having normal functions.

PMSG was administered to female BDF1 mice, and after about 48 hours, HCG was administered to induce superovulation. The mice were mated with male BDF1 mice. About 48 hours after mating, two-cell stage embryos were washed out from the oviducts in FHM medium. Aggregation chimeras were produced by developing four-cell stage embryos from one tetraploid cell obtained by electrically fusing diploid two-cell stage embryos together; and placing them in close contact with eight-cell stage embryos obtained by superovulation treatment on the same schedule and mating of +/−heterozygotes, after zona pellucida was removed by treatment with acidic Tyrode's solution. The embryos were cultured in kSOM medium until they became blastocysts. The blastocysts were transplanted into the uterus of a pseudopregnant mouse (on day 2.5 of pseudopregnancy).

(3) Placenta-Specific Gene Transfer Method Using LV (Method of the Present Invention)

PMSG was administered to female +/−mice, and after about 48 hours, HCG was administered to induce superovulation. The mice were mated with male +/−mice. About 48 hours after mating, two- to four-cell stage embryos were washed out from the oviducts in FHM medium. The two- to four-cell stage embryos were cultured in kSOM medium for about 48 hours until they became blastocysts. After zona pellucida was removed by treatment with acidic Tyrode's solution, the blastocysts were placed one by one in a spot of viral solution ($1\times10^3$ ng/ml) for infection. The infection time was four to five hours. The blastocysts collected from the viral solution were washed once, and then the blastocysts were transplanted into the uterus of a pseudopregnant mouse (on day 2.5 of pseudopregnancy).

(4) Tissue Sections

Placentas were fixed with 4% paraformaldehyde at 4° C. for 12 hours, and then washed in PBS at 4° C. for two or three hours. PBS was replaced with acetone and after one or two hours, acetone was replaced with 1.5 ml/tissue of Technovit 8400 solution (0.06 g/10 ml). The tissues were fixed for about two hours. After the tissues precipitated, 501 of Technovit 8400 solution (small vial) was added. The tissues and resin were added inside the frame, covered, and then incubated at 4° C. for 12 hours for embedding. Thin sections were produced and observed.

(5) Western Blotting

Tails of the newborns were homogenized in lysis buffer using a homogenizer. The lysates were left on ice with occasional stirring for 1 hour, and then centrifuged at 13,000 rpm and 4° C. for 20 minutes. The resulting supernatants were used as extracts. The concentrations were determined, and adjusted to be constant. Then, the extracts were loaded and electrophoresed. After electrophoresis, the samples were transferred onto a PCDF membrane (Immobilon-P, Millipore, Bedford, Mass.). After blocking with TBS-T buffer containing 5% skim milk, the membrane was reacted with a primary antibody (ERK2, BD pan ERK #610123; p38α, Santa Cruz p38 (C-20) #sc-535) at 4° C. overnight. The membrane was washed three times with TBS-T buffer, and then incubated with an HRP-labeled anti-mouse antibody or anti-rabbit antibody at room temperature for one hour. After washing four times with TBS-T buffer, ECL™ (RPN2209) was used for color development and an image was developed.

(6) PCR

Genomic DNAs were extracted from a portion of the tissues of fetuses, placentas, and newborns to examine their genotypes by PCR method. Primers and PCR conditions used are shown below.

```
EGFP typing
Primer-1378:
gagctagccaccatggtgagcaagggcgag    (SEQ ID NO: 52)

Primer-1382:
tcaccttgatgccgttcttct             (SEQ ID NO: 53)
PCR condition: 940 C. for two minutes, 30 cycles
of (940 C. for 30 seconds, 650 C. for 30 seconds,
and 720 C. for 30 seconds), and 720 C. for two
minutes, followed by 40 .C

ERK2 typing
Primer-1331:
taactgggtcgagcacagtgatgc          (SEQ ID NO: 54)

Primer-1332:
tcagaattgatctggtcttcaagaccttg     (SEQ ID NO: 55)

Primer-1333:
atgtatgctatacgaagttattagggc       (SEQ ID NO: 56)
PCR condition: 950 C. for two minutes, 40 cycles
of (950 C. for 20 seconds and 640 C. for 40
seconds), and 720 C. for one minute, followed by
40 C,

p38 typing
Primer-1380:
ccctcgtggatggttgccagcagc          (SEQ ID NO: 57)

Primer-1343:
cttactttgcactgaacacacacatcc       (SEQ ID NO: 58)
```

PCR conditions: 94° C. for two minutes; 40 cycles of 94° C. for 30 seconds, 65° C. for 30 seconds, and 72° C. for one minute); and 72° C. for two minutes, followed by 4° C.

The resulting PCR products were treated with the restriction enzyme EcoRV. Genotyping was based on the differences in size between the wild and mutant types.

Example 1

Infection and Evaluation of LV-CAG-EGFP

Introduction of a lentivirus (LV) carrying the GFP gene (LV-CAG-EGFP, which was constructed by the method described in Molecular Therapy 2003, 8; 666-673; SIN lentivirus vector plasmid introduced with an EGFP-encoding cDNA under the control of a CAG promoter was constructed and combined with a packaging plasmid, Rev expression plasmid and VSVG expression plasmid; the mixture was introduced into 293T cells by the calcium phosphate method; viral particles released to the culture supernatant were collected and concentrated by ultracentrifugation; for the plasmids, see FIG. 1) was attempted using TG method and the method of the present invention. The gene used in this experiment was the GFP gene, and areas introduced with the gene emit green fluorescence. Subjects introduced with the gene by each method were examined for the infection site and evaluated for infection efficiency by microscopic observation, tissue sections, PCR, and such.

Figure 2:
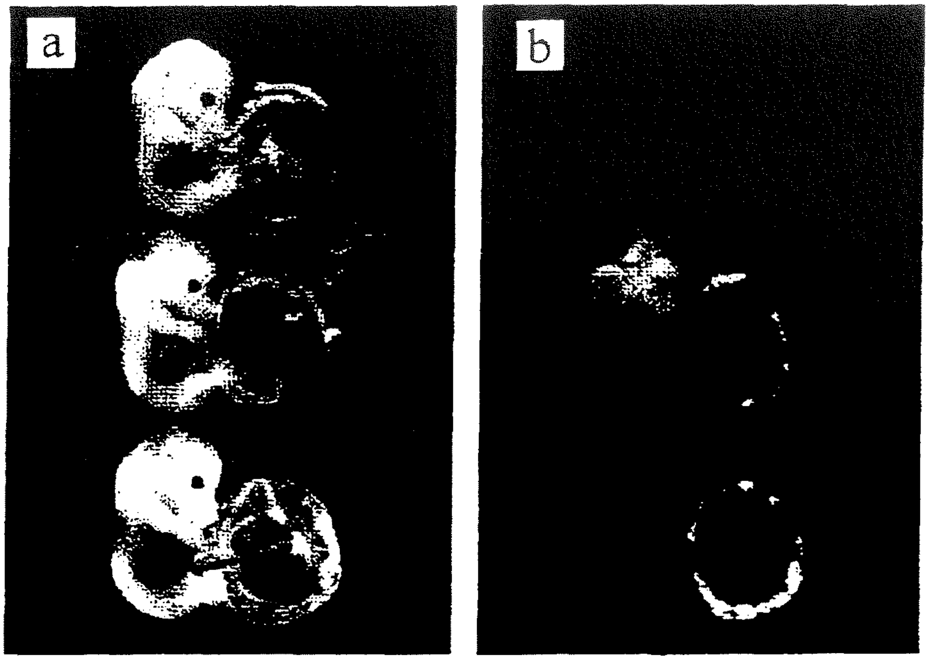
FIG. 2 shows photographs of fetuses and placentas of E13.5 embryos obtained by infection with an EGFP-expressing viral vector. The respective fetuses and placentas are: derived from non-treated embryo (top); obtained by TG method (middle); obtained by the method of the present invention (bottom). In the method of the present invention, expression of the introduced gene is found only in the placenta, while in the TG method, the gene expression is observed in both fetus and placenta.
Figure 3:
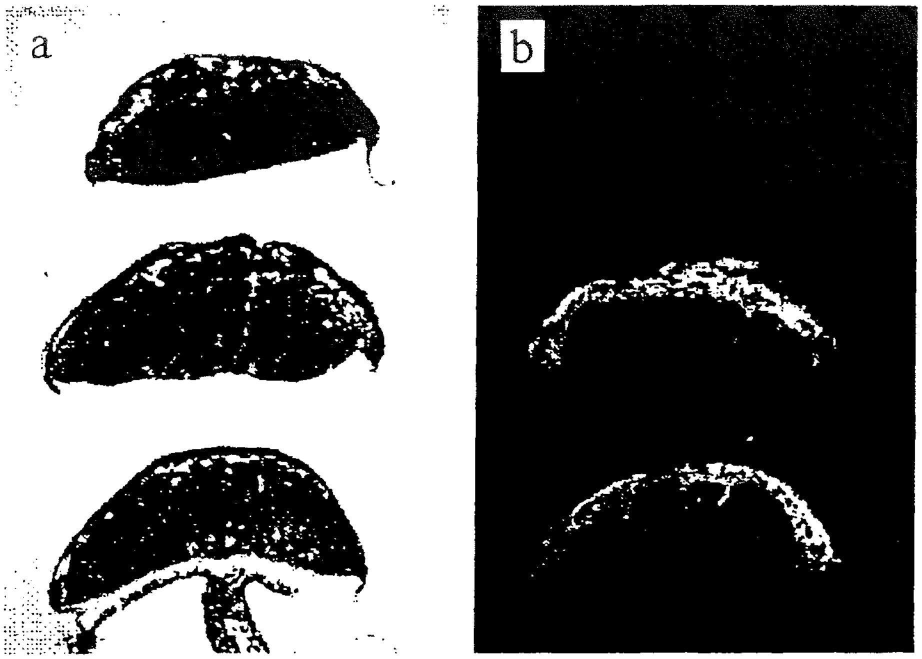
FIG. 3 shows photographs of sections of placentas from E13.5 embryos obtained by infection with an EGFP-expressing viral vector. The respective thin sections of placenta are: derived from non-treated embryo (top); obtained by TG method (middle); obtained by the method of the present invention (bottom). In the placenta treated by TG method and the method of the present invention, gene expression was observed in almost all cells, except for maternal cells, in the giant cell layer, spongiotrophoblast layer, and labyrinth layer. a is a photograph after HE stain; b is a photograph under fluorescent microscope.

With the TG method, both E13.5 fetus and placenta emitted green fluorescence, and the gene was introduced into both (FIG. 2). Meanwhile, with the method of the present invention, the gene was introduced into only the placenta and not into the fetus (FIG. 2). A comparison of the sections in untreated placenta and placenta introduced with the gene by the method of the present invention demonstrated that the gene was introduced into the whole area of the placenta that had the gene introduction by the method of the present invention (FIG. 3). Furthermore, introduction of the gene was examined by PCR. With the TG method, the gene was introduced into only the placenta in some cases; however, in about 60% of all cases (38 of 66 subjects), the gene was introduced into both the placenta and fetus (Table 1). In contrast, when the same viral vector was introduced by the method of the present invention, the gene was introduced into only the placenta in all 69 subjects, and not into any fetus (Table 1). Furthermore, 91 newborns were analyzed, and the result showed that they were all born normally and the gene was not introduced (Table 1). The findings described above demonstrate that placenta-specific gene transfer can be achieved by the method of the present invention.

TABLE 1

| Method | dpc | P + E | P | E | (—) | Total number |
|---|---|---|---|---|---|---|
| TG | 13.5 | 38 | 24 | 0 | 4 | 66 |
| method | 19.5 | ND | ND | 28 | 25 | 53 |
| Novel | 13.5 | 0 | 69 | 0 | 0 | 69 |
| method | 19.5 | ND | ND | 0 | 91 | 91 |

Screened by PCR However, E19.5 placenta was not analyzed.
ND: no data
P: Gene was introduced into only placenta
E: Gene was introduced into only embryo
(—): No gene was introduced Example 2

Rescue of ER 2- and p38α-Knockout Mice

Next, the present inventors speculated that introducing a gene of interest by the methods of the present invention into mutant mice that were originally embryonic lethal due to placental abnormality could allow their development and postnatal analysis. ER 2-knockout mice and p38α-knockout mice were used for these experiments.

Figure 4:
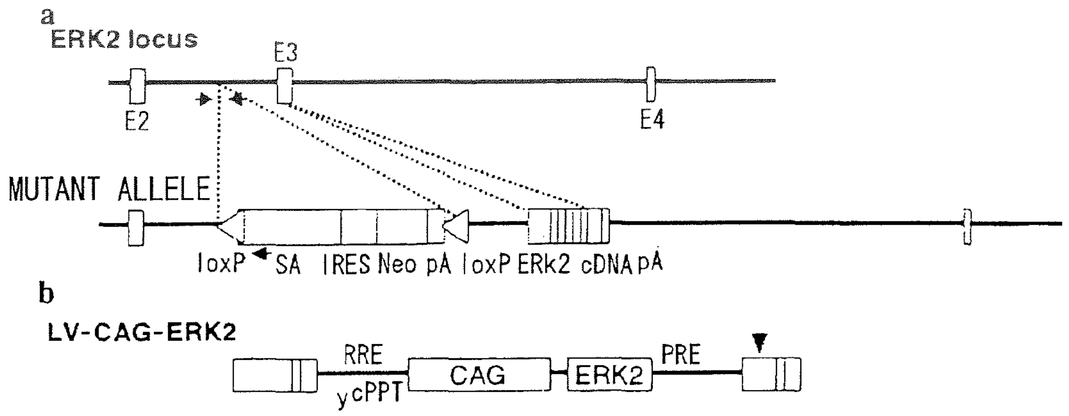
FIG. 4 shows diagrams and photographs illustrating rescue of erk2-knockout mice. a is a diagram illustrating the locus in erk2-knockout mice. The endogenous erk is not expressed, because a drug-resistance gene is inserted between exons 2 and 3. b is a diagram showing a lentivirus vector constructed to express erk2 under the control of a CAG promoter. c is a diagram showing genotypes of offsprings obtained by using the method of the present invention to transfer genes into blastocysts obtained by mating heterozygous mice. Homozygous mice are not born by natural mating; however, 16 homozygous mice were obtained by the placenta-specific gene transfer method of the present invention. d is a photograph showing PCR genotyping of the obtained offsprings. Homozygous mice were born, having only the mutant allele but no wild-type allele. e is a photograph showing erk2 wild-type mouse (left), heterozygous mouse (middle), and homozygous (right) newborn mouse born as a result of the treatment of the present invention. f is a photograph showing Western blot result. It was shown that the newborn expressed endogenous erk2 and homozygous mice did not express erk2.
Figure 4:
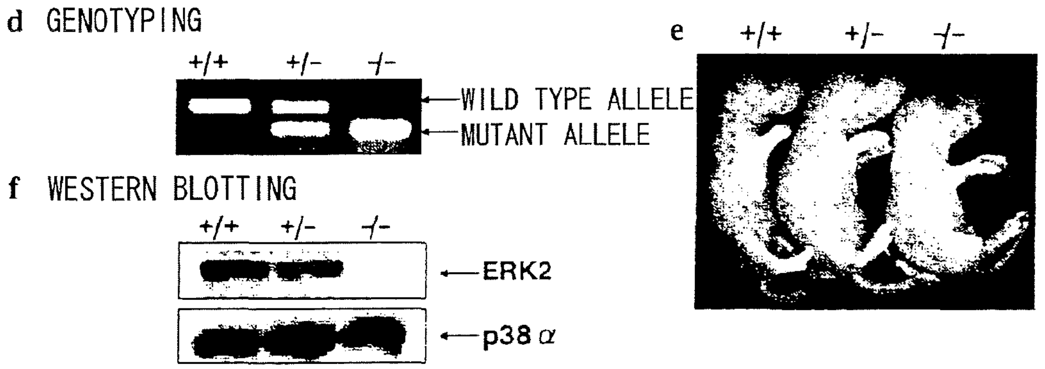

(1) ER 2-Knockout Mice (FIG. 4)

ER 2-knockout mice have been reported to be embryonic lethal around E10.5 due to placental abnormality (Hatano N. et al., Genes Cells. 2003 November; 8(11): 847-56). According to Hatano N. et al., labyrinthine layers are thin in the knockout placenta; the heart wall of the fetus becomes thinner and its development is retarded; and thus embryos after E1.5 are undetectable. The thinning of labyrinthine layers and heart wall abnormality were improved by the tetraploid rescue. Therefore, Hatano N. et al., argued that the heart wall thinning was a secondary abnormality as a result of the insufficient supply of oxygen and nutrient from the placenta.

A lentivirus vector was constructed to express ERK2 cDNA under the control of a CAG promoter (FIG. 3*b*). After zona pellucida was removed from the blastocysts obtained by mating ERK2+/− with ER 2+/−, the blastocysts were infected with the viral vector and transplanted into the uterus of a pseudopregnant mouse. Genotyping of the resulting offsprings by PCR showed 16 homozygous mice (FIGS. 4*c* and 4*d*). The homozygous newborns seemed to be slightly small but healthy, and were also observed to drink milk (FIG. 4*e*). Furthermore, Western blotting demonstrated that the ERK2 protein was absent in the mice (FIG. 4*f*).

Figure 5:
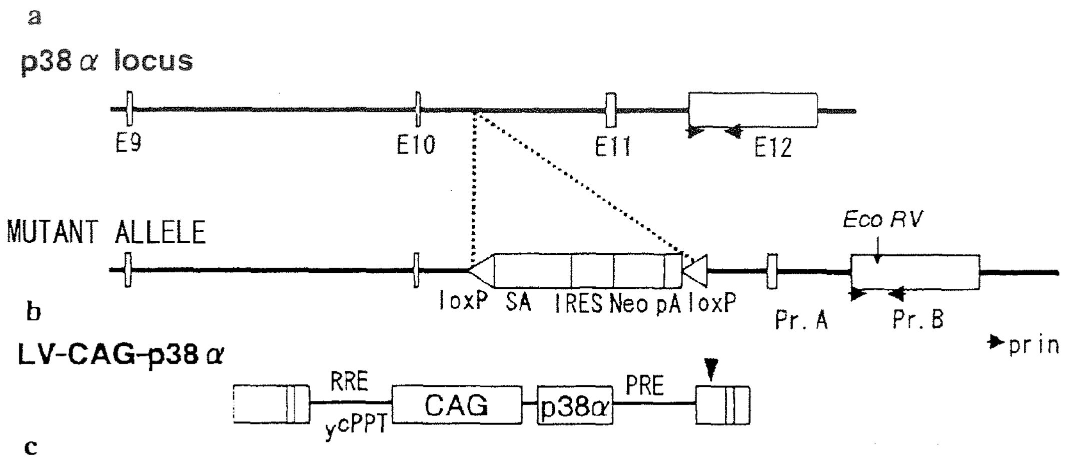
FIG. 5 shows diagrams and photographs illustrating rescue of p38α-knockout mice. a is a diagram illustrating the locus in p38α-knockout mice. The endogenous p38α is not expressed, because a drug-resistance gene is inserted between exons 10 and 11. b is a diagram showing a lentivirus vector constructed to express p38α under the control of a CAG promoter. c is a photograph showing genotypes of offsprings obtained by using the method of the present invention to transfer genes into blastocysts obtained by mating heterozygous mice. Homozygous mice are not born by natural mating; however, 34 homozygous mice were obtained by the placenta-specific gene transfer method of the present invention. d is a photograph showing PCR genotyping of the obtained offsprings. Homozygous mice were born, having only the mutant allele but no wild-type allele. e is a photograph showing p38α wild-type mouse (left), and homozygous (right) newborn mouse born as a result of the treatment of the present invention. f is a photograph showing Western blot result. It was shown that the newborn expressed endogenous p38α, and homozygous mice did not express p38α.
Figure 5:
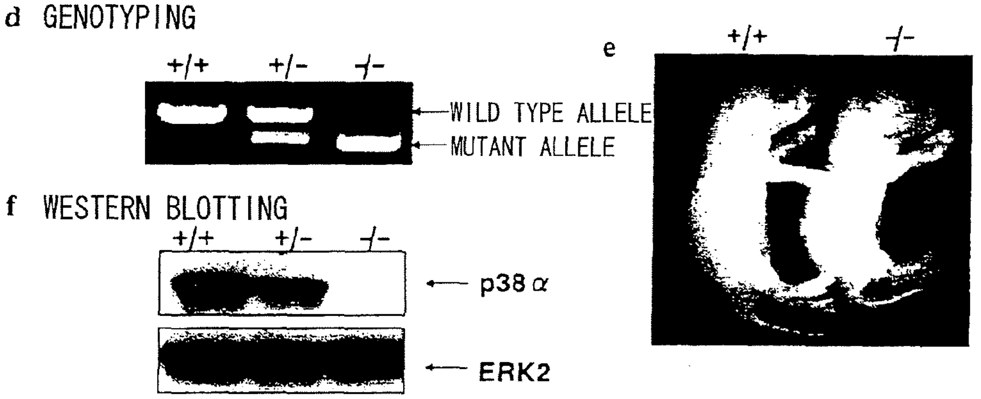

(2) p38α-Knockout Mice (FIG. 5)

p38α-knockout mice have been reported to be embryonic lethal around E10.5 due to placental abnormality (Adams R H et al., Mol Cell. 2000 July; 6(1): 109-16; Mudgett J S et al., Proc Natl Acad Sci USA. 2000 Sep. 12; 97(19): 10454-9). In p38α-knockout mice, placental labyrinthine layers and fetal heart wall are thin and imperfect, and aberrant cerebral angiogenesis is observed. When normal placenta was formed by tetraploid rescue in the mice, both of their heart wall and cerebral angiogenesis were normal. Adams R H et al. reported that non-placental abnormalities were assumed to be due to the insufficient supply of oxygen and nutrient from the placenta and thus the direct cause of embryonic lethality is placental abnormality.

In p38α-knockout mice, the gene was also introduced specifically into their placentas using a lentivirus vector (FIG. 5*b*) and their genotypes were determined by PCR. As a result, 34 homozygous mice were born (FIGS. 5*c* and 5*d*). The homozygous deletion newborns seemed to be slightly small but healthy, and were also observed to drink milk (FIG. 5*e*). Furthermore, Western blotting demonstrated that the p38α protein was absent in the mice (FIG. 5*f*).

As described above, a system for placenta-specific gene transfer was established, and it was demonstrated that knockout mice which are embryonic lethal due to placental abnormality can be born by using this system. Furthermore, the use of knockout mice also enables postnatal functional analyses.

Forty or more types of genetically mutant mice exhibiting placental abnormality had been reported as of 2001 (Rossant J, Cross J C., Nat Rev Genet. 2001 July; 2(7):538-48. Review). When mice are embryonic lethal due to placental abnormality, the gene cannot be analyzed for its function or such after birth. The methods of the present invention can be applied to rescue experiments of such mutant mice and thus enable postnatal gene functional analyses.

Although tetraploid rescue merely compensates for the abnormal placenta of an embryo and normalizes its function, the use of LV allows mutant genes to be expressed in a placenta-specific manner, and LV can also be used in combination with RNAi. For example, it is expected that the placenta-specific function of ERK2 can be analyzed when a mutant ERK2 gene functions as dominant-negative mutant in the placenta.

Alternatively, it is also expected that by using LV, not only can each gene be analyzed in detail, but the relationship of the gene to other members of the gene subfamily and to genes upstream or downstream of the signaling pathway can also be examined. Thus, it is expected that with further studies, development of the LV-based placenta-specific gene transfer method can lead to applied research such as gene therapy and gene function analysis at the individual level.

INDUSTRIAL APPLICABILITY

The present invention provides methods for introducing genes specifically into whole placenta. The gene transfer methods of the present invention impose only a small burden on mothers and fetuses, because they do not introduce genes directly into placenta. Furthermore, unlike the microinjection system, the present methods require neither expensive devices nor skillful techniques.

In addition, the methods of the present invention can be used to introduce various genes into the placenta; this not only complements placental function in mutant animals, but also allows functional analyses of these genes in the placenta. Thus, the methods of the present invention are also useful for studies that analyze gene functions in embryogenesis.

The invention claimed is:

1. A method for introducing a polynucleotide specifically into a trophectodermal cell, which comprises the steps of:

a) extracting a blastocyst from an mammal;

b) removing zona pellucida from the blastocyst; and c) introducing a polynucleotide into trophectodermal cells of the blastocyst by placing the blastocyst comprising trophectodermal cells obtained in step (b) in a solution comprising lentiviral vectors;

wherein the lentiviral vectors introduce the polynucleotide only into the trophectodermal cells of the blastocyst.

2. The method of claim 1, wherein the polynucleotide is a polynucleotide encoding a protein essential for fetal development or a polynucleotide that regulates expression of the protein.

3. The method of claim 2, wherein the polynucleotide encoding a protein essential for fetal development is a polynucleotide selected from the group consisting of: Dlx3, Fgfr2, Fra1, Fzd5, Gab1, Gcm1, Grb2 hypomorph, Gja7, Hgf, Hsp84-1, Itgav, Junb, Lifr, ERK1, ERK2, ERK5, MEK1, MEKk3, p38α, p38β, Met, Pdgfra, Pdgfb, Pparg, Rxra, Rxrb, Sos1, Vhlh, Wnt2, Ets2, Mash2, Egfr, Hsf1, Bmp5, Bmp7, Dnmt1, Itga4, Lhx1, Mrj, Tcf, Lef, Cdx2, Eomes, Fgf4, Esrrb, Hand1, Mdfi, Esx1, Arnt, Tcfeb, and Gjb2.

4. The method of claim 1, wherein the mammal possesses an abnormality in a protein essential for fetal development or in the regulation of expression of the protein.

* * * * *

SEQUENCE LISTING

<160> NUMBER OF SEQ ID NOS: 58

<210> SEQ ID NO 1
<211> LENGTH: 2631
<212> TYPE: DNA
<213> ORGANISM: Mus musculus

<400> SEQUENCE: 1

```
cgacaagagg taatccggga cgcggagaga ggcacgcagc gactgaccga cagccggcga     60
tggtctaagc gcccctcggc cacccccctcc cccagacgcg accgcgtcct gccctcgccc    120
tctggacaca cacccccacc tgggctcctc cgcccgttcg gcgctcctcg gaggaggccc    180
ggggtgttgc ggcgctcgcc agcatgagcg gctccttcga tcgcaagctc agcagcatcc    240
tcaccgacat ctccagctcg ctcagctgcc atgcgggctc caaggactcg cccaccctgc    300
ccgaatctac agtcactgac ctgggctatt acagcgctcc tcagcatgac tactactcgg    360
gccagcccta cggccagacg gtgaacccct acacctacca ccaccagttc aatctcaatg    420
ggctcgcagg caccggcgct tactcgccca agtcggaata tacctacggg ggatcctata    480
ggcagtacgg agcgtaccgg gagcagcctt tgcctgccca ggacccagtg tcggtgaaag    540
aggagccgga agccgaggtt cgcatggtga acggcaagcc caaaaaggtc cgaaagccgc    600
gaacgatcta ctccagctat cagctggctg ccctgcagcg ccgtttccag aaagcccagt    660
atctggcctt gcctgagcgc gccgagctag ctgcacagct gggcctcaca caaacacagg    720
tgaaaatctg gttccagaac cgccgctcca agttcaaaaa gctctataag aatggggagg    780
tgccgctgga acacagcccc aacaacagtg actccatggc ctgcaactca ccgccgtcac    840
cagcactctg ggacacatct tcccattcca cgccagcccc tgcccgcaat ccgctgcccc    900
caccgctccc atacagtgcc tcccccaact acctggacga ccccaccaac tcctggtacc    960
acacacagaa cctcagtgga ccccacttac agcagcagcc tcctcagccg gctaccctgc   1020
accatgcctc ccctgggccc ccgcctaacc ctggggctgt gtactgagta cccacctggc   1080
ctgcgcccct ccacgaagga ccccctccag gaccaggcag aaggtgccct gtcctagcga   1140
cactcaggaa tcattgaggg gcacaggggg aaagactccc ttccctctcc cttgtccctt   1200
cttccaggga cccaacaacc tccagataac aaatgcatgg accgaggatg ccccccaatc   1260
tccctcccct tgcttagact ggggtgccct ccagacggcg aggagttcta ccccagtggg   1320
gacagcacat gctctctgct ccaggaaccc ggattgcctc tagatggctc atcgctttcc   1380
agcttttcaa acacagtaga gacctccaaa atgggagcca gagtgtttgc aggtccacct   1440
gtgctggggc accaggcgcc acggattcca gcacagccag acctaaagca ccaaggggca   1500
actatacatt cttgagccac tctttaaaag acattggaca ttacatcatg gctgatcctc   1560
aagatggggg ggggctgacc tagtccccac tgttctccag ccctcattag gatttgaggg   1620
```

-continued tccaaaccaa agaaaactcc cccaaatgag ggaacctttg atatccaggg cttccaaggg 1680
aagacttaaa ggagccatcc ctccgcccct tccctgggga aaaggattgt ccatgtcctt 1740
ttccaaggac ctgtttctcc ttccatgtac aggactttgc acaagtctgg ttttaaaagc 1800
tgttgaaacc taggacgaca atgggcattg ttaacagtta ggaccaaatc cactcctctc 1860
tgggcgggca gctctgctct gccctgaccc tgctcacccc ttcgttttgt tttgttttgt 1920
ttttctccca gtaagtttgc agtcttgggg gacgggctca aaccccaact ctctacagag 1980
atagaccagg caagaccccc cccactcaga caccccccttc gtggcagctt tggaaacagg 2040
ttgtccgttc tgctgcagga ttcaagtgag gatccaggag acaagaggag gcctagaact 2100
cagtgcctta ggggtaaggc tgtcagcttg gacggctggt accagtgcct ctccctggcc 2160
caggcatccc ccaaagctaa ctttcttctg ccccctgatg tggtaaaaca tcgaagaaag 2220
gagaggtgac agactgtagt tatatatata tagtatggtt tttttttgtt gttgttgttt 2280
cttttttttt tttttttttt agagcaacca agagaagcag gtcccctccc ttgtggtttc 2340
ctatttatgt gaccctgttc ctcctggacc aatctccctg tgttgcaagt cgaaagaggg 2400
atgtgggctc ctgctggatt tgggtttcgt gggaagtgaa ggagtaagaa gagacagacg 2460
tggtgggtct ccgagtccca ccccaaaggg acaggactga agccagctcc cacccctccc 2520
cagccttctc atttctgctt tcttactgga ccagtcttta tatataatgt taataaaaat 2580
taaaaaaaaa gaagaaaaaa aaaaaaaaaa aaaaaaaaaa aaaaaaaaaa a 2631

<210> SEQ ID NO 2
<211> LENGTH: 232
<212> TYPE: DNA
<213> ORGANISM: Homo sapiens

<400> SEQUENCE: 2
tttacaaggg tcgcgctcca gcagtctcct ttgaagtcgt ttctgttatt catggggcca 60
cagtgttatt tcaaaggtgt cagccagcag gcttgaggct tttctggcat gaggtcactg 120
acagccctct ggacaacaca acttatttat tggtctctca ttctcccatc cccactcctc 180
ctttcttccc tctctccacc agagcgatcg cctcaccggc ccatcctcca ag 232

<210> SEQ ID NO 3
<211> LENGTH: 1551
<212> TYPE: DNA
<213> ORGANISM: Homo sapiens

<400> SEQUENCE: 3
cagaacccag cagccgtgta ccccgcagag ccgccagccc cgggcatgtt ccgagacttc 60
ggggaacccg gcccgagctc cgggaacggc ggcgggtacg gcggccccgc gcagcccccg 120
gccgcagcgc aggcagccca gcagaagttc cacctggtgc caagcatcaa caccatgagt 180
ggcagtcagg agctgcagtg gatggtacag cctcatttcc tggggcccag cagttacccc 240
aggcctctga cctaccctca gtacagcccc ccacaacccc ggccaggagt catccgggcc 300
ctggggccgc ctccaggggt acgtcgaagg ccttgtgaac agatcagccc ggaggaagag 360
gagcgccgcc gagtaaggcg cgagcggaac aagctggctg cggccaagtg caggaaccgg 420
aggaaggaac tgaccgactt cctgcaggcg gagactgaca aactggaaga tgagaaatct 480
gggctgcagc gagagattga ggagctgcag aagcagaagg agcgcctaga gctggtgctg 540
gaagcccacc gacccatctg caaaatcccg gaaggagcca aggaggggga cacaggcagt 600

-continued

```
accagtggca ccagcagccc accagccccc tgccgccctg taccttgtat ctccctttcc    660

ccagggcctg tgcttgaacc tgaggcactg cacaccccca cactcatgac cacaccctcc    720

ctaactcctt tcacccccag cctggtcttc acctacccca gcactcctga gccttgtgcc    780

tcagctcatc gcaagagtag cagcagcagc ggagacccat cctctgaccc ccttggctct    840

ccaaccctcc tcgctttgtg aggcgcctga gccctactcc ctgcagatgc caccctagcc    900

aatgtctcct ccccttcccc caccggtcca gctggcctgg acagtatccc acatccaact    960

ccagcaactt cttctccatc cctctaatga gactgaccat attgtgcttc acagtagagc   1020

cagcttgggg ccaccaaagc tgcccactgt ttctcttgag ctggcctctc tagcacaatt   1080

tgcactaaat cagagacaaa atatttccca tttgtgccag aggaatcctg gcagcccaga   1140

gactttgtag atccttagag gtcctctgga gccctaaccc cttccagatc actgccacac   1200

tctccatcac cctcttcctg tgatccaccc aaccctatct cctgacagaa ggtgccactt   1260

tacccaccta gaacactaac tcaccagccc cactgccagc agcagcaggt gattggacca   1320

ggccattctg ccgcccccctc ctgaaccgca cagctcagga ggcgcccttg gcttctgtga   1380

tgagctgatc tgcggatctc agctttgaga agccttcagc tccagggaat ccaagcctcc   1440

acagcgaggg cagctgctat ttattttcct aaagagagta tttttataca aacctaccaa   1500

aatggaataa aaggcttgaa gctgtgaaaa aaaaaaaaaa aaaaaaaaaa a             1551


<210> SEQ ID NO 4
<211> LENGTH: 1758
<212> TYPE: DNA
<213> ORGANISM: Homo sapiens

<400> SEQUENCE: 4

atggctcggc ctgacccatc cgcgccgccc tcgctgttgc tgctgctcct ggcgcagctg     60

gtgggccggg cggccgccgc gtccaaggcc ccggtgtgcc aggaaatcac ggtgcccatg    120

tgccgcggca tcggctacaa cctgacgcac atgcccaacc agttcaacca cgacacgcag    180

gacgaggcgg gcctggaggt gcaccagttc tggccgctgg tggagatcca atgctcgccg    240

gacctgcgct tcttcctatg cactatgtac acgcccatct gtctgcccga ctaccacaag    300

ccgctgccgc cctgccgctc ggtgtgcgag cgcgccaagg ccggctgctc gccgctgatg    360

cgccagtacg gcttcgcctg gcccgagcgc atgagctgcg accgcctccc ggtgctgggc    420

cgcgacgccg aggtcctctg catggattac aaccgcagcg aggccaccac ggcgcccccc    480

aggcctttcc cagccaagcc caccccttcca ggcccgccag gggcgccggc ctcgggggggc    540

gaatgccccg ctgggggccc gttcgtgtgc aagtgtcgcg agcccttcgt gcccattctg    600

aaggagtcac acccgctcta caacaaggtg cggacgggcc aggtgcccaa ctgcgcggta    660

ccctgctacc agccgtcctt cagtgccgac gagcgcacgt tcgccacctt ctggataggc    720

ctgtggtcgg tgctgtgctt catctccacg tccaccacag tggccacctt cctcatcgac    780

atggacacgt tccgctatcc tgagcgcccc atcatcttcc tgtcagcctg ctacctgtgc    840

gtgtcgctgg gcttcctggt gcgtctggtc gtgggccatg ccagcgtggc ctgcagccgc    900

gagcacaacc acatccacta cgagaccacg ggccctgcac tgtgcaccat cgtcttcctc    960

ctggtctact tcttcggcat ggccagctcc atctggtggg tcatcctgtc gctcacctgg   1020

ttcctggccg ccgcgatgaa gtggggcaac gaggccatcg cgggctacgg ccagtacttc   1080

cacctggctg cgtggctcat ccccagcgtc aagtccatca cggcactggc gctgagctcc   1140

gtggacgggg acccagtggc cggcatctgc tacgtgggca accagaacct gaactcgctg   1200
```

-continued

```
cggcgcttcg tgctgggccc gctggtgctc tacctgctgg tgggcacgct cttcctgctg   1260

gcgggcttcg tgtcgctctt ccgcatccgc agcgtcatca agcagggcgg caccaagacg   1320

gacaagctgg agaagctcat gatccgcatc ggcatcttca cgctgctcta cacggtcccc   1380

gccagcattg tggtggcctg ctacctgtac gagcagcact accgcgagag ctgggaggcg   1440

gcgctcacct gcgcctgccc gggccacgac accggccagc cgcgcgccaa gcccgagtac   1500

tgggtgctca tgctcaagta cttcatgtgc ctggtggtgg gcatcacgtc gggcgtctgg   1560

atctggtcgg gcaagacggt ggagtcgtgg cggcgtttca ccagccgctg ctgctgccgc   1620

ccgcggcgcg gccacaagag cgggggcgcc atggccgcag ggactaccc cgaggcgagc   1680

gccgcgctca caggcaggac cgggccgccg ggccccgccg ccacctacca caagcaggtg   1740

tccctgtcgc acgtgtag                                                 1758
```

```
<210> SEQ ID NO 5
<211> LENGTH: 4877
<212> TYPE: DNA
<213> ORGANISM: Mus musculus

<400> SEQUENCE: 5

ctgggctgaa gctagaggcg accgatcgtg ggaaggggag gcagaaaggc taggaggagg     60

agggccgggg cccaggccgc gcctccccga acccgccgcg cgcccccggg gtgggggagg    120

agcgcagggg acaggacaga ggggtccctc cccgaagcag agccgccctg cgcctcgtcc    180

ctgtgctgat ccccgccctc atccgaggct ggagcgcaga cccaccctcc caccgcggac    240

ccgcgacctc cccgacgccc ggcgacgccc tgaccctcgc tgctggtccg cgaactccct    300

aggctgatca ggacctgccc ctgtgccggc tgccacccgg acgccgcacg ccttcccagg    360

cgccctttc cgagcagagg gaaagagaag atcgagcccc tctcagtgtg aatgcgccaa    420

cgggcggagc ggagcggagc ggacaccgcg cgcgggcatt gtgtgtgcgc gtgcagcgtg    480

gggtccgcag cggggagcac ccgcgggagg tcccgtttcc aaggggcgga gcgcagggct    540

tccagttctg ggctccctgt ccggacagag tcccagcgga gcccgaccgc tgcctaggcg    600

gcgggacggc gcgcctggcg gccaggaggg cgcactgaaa gaaggtcggc gagccctggt    660

ccccgcggtt cccgatcgag ttcctcttca gtccgcgaat ctgcgggaga ggttcgatcg    720

ccgacacagg gcgcggggag ccgggccgcc ccgtcggggg aatctgagac gtcctctggg    780

ctgcgtttga ctgccgtgcc cgccgtgcac ggagcgcgtc cactgtgtcc accgacccct    840

ttggtgtctg gtcctcgagt cctcacggcg tgcaccatga gcggcggcga agtggtttgc    900

tcgggatggc tccgcaagtc gcccccggag aagaagttga agcgttatgc gtggaagaga    960

aggtggtttg tgttgcgcag tggccgtttg actggagacc cggatgtcct ggagtattac   1020

aaaaacgatc atgccaagaa gcctattcgg attattgatt taaatttatg tcagcaagtt   1080

gatgctgggt tgacattcaa caaaaaggag tttgaaaaca gctatatctt tgatatcaac   1140

accatcgacc ggattttcta cttggtggca gatagtgagg aagacatgaa caagtgggtc   1200

cgttgtatct gtgacatctg tggattcaat ccccacagaag aagatcctgt gaagccgctg   1260

actggctcct cacaagcacc cgtcgattca cctttcgcta taagtacagc accagcctcc   1320

agtcagatgg aagcttcttc agtcgcgcta cctcctcctt accaggtcat cagccttccg   1380

ccacacccag acaccctcgg cctccaggac gatccacaag actacctctt gctgatcaac   1440

tgtcaaagca agaagcctga acctaacaga accctctttg actctgccaa gcccaccttt   1500
```

-continued

```
tctgagacag actgcaatga caacgtccct tcccaccaga ctcctgcttc ctcccagagc   1560
aaacacggaa tgaatggctt tttccagcaa caaatgatgt atgactgccc accgtcccgg   1620
ctgacatctg tctcgggaga gtccagcctc tataacctgc ccaggagcta ttcccatgac   1680
gtgttgccaa aggaatcccc atcaagcacg gaggccgacg gggagctgta cacctttaac   1740
accccatctg ggactgcagg tgtagaaacg cagatgagac atgtatccat cagttacgac   1800
attccgccaa cacctggcaa cacttaccag atcccacgga catttccaga aagcacactg   1860
ggacagtcat caaagctgga caccattcct gatatccccc cacctcggcc accaaagcca   1920
catccaactc atgaccggtc tcctgtggaa acgtgtggag tcccacgcac ggcctcggac   1980
actgacagca gttactgtat ccctcctcca gcaggcatga cgccctcccg gagtaatacc   2040
atttccaccg tggatttgaa caagttgcgg aaagatgcta gttctcaaga ttgctatgat   2100
attccacgga cctttccgag cgatagatct agttccctgg aaggcttcca tagccagtat   2160
aaaatcaaaa gcgtgttgac agcgggaggt gtctcgggtg aagagctgga tgagaactac   2220
gttcccatga accccaactc gccacctcga caacattccg gcagctttac cgagccaatc   2280
caggagccaa actatgtgcc aatgacccca gggacctttg acttttcttc ctttggaatg   2340
caagtccctc ctcctgctca tatgggcttc aggtccagcc caaagacccc tcccaggagg   2400
ccagttcctg ttgctgactg tgaaccaccc ccggtggata ggaacctcaa gccagacaga   2460
aaagtcaagc cggcaccttt agacataaaa cctctgtcag aatgggaaga gctgcaagcc   2520
ccagtcagat ctcccatcac caggagcttc gctcgggact cctctaggtt tcccatgtcc   2580
cctcggcctg attctgtgca cagtacgaca tcgagcagcg actctcatga cagtgaagag   2640
aactatgtcc ccatgaatcc aaatctgtct ggcgaagacc cgaatctctt tgccagcaac   2700
agccttgatg gggaagcag cccgatgaat aaacccaaag gagacaaaca agtcgaatac   2760
ctggatttag acctagattc tgggaagtcc acgccaccac ggaagcaaaa gagcagtggt   2820
tctggcagca gcatggcaga cgagagggtg gattacgttg tggtggacca acagaagact   2880
ctggccctga agagtaccag agaagcttgg acggatggga ggcagtccac agagtccgag   2940
acacccacca agaatgtgaa gtgaagacat gccgtcgcct ctgccggcag acgagatctg   3000
agtggaaaga gagatgccaa gtgaagatgt tcccactctc agtggagcct cgagccagca   3060
ggggcagaga gaaggatctc tcacacatgt tcaagcaaat taggttgtga atggtgctgt   3120
gtggtattgg atttataacg tgtaaataac ccggggaaat agtgttttta gttcacagag   3180
aagcttctgt ccctaattaa cacacctgta gtattactat actgatgcac ttttcattta   3240
aaaccttggt ttgggtcttc ccgatctacc ttaacagact ttccttggga ggtcttttgg   3300
cctcctcaca ctactctata taacaatact aagtgaactg agctacttgt aattctggaa   3360
attccagttg aagctacagg gctaacacca ttaaaacaag aagtaagttg acacattcgc   3420
ttttctcttg aaggtggtag ccattagctt aagctgtaga acatagttgg acttgtcctt   3480
cgttgttttc caaaaattcc ggggatattg tatatagcag gtcaagacct agctctctga   3540
ctcatgtaca cttaggtttt aactgtagga ctttgttatt attatttttt ttgttaatga   3600
cagtgttggg ttcatcgtgt gaaggttctg ctgggtagga tcttgcacct ttcaaagact   3660
gcctcttagt tacactagta agcccccaaa tcatccacag catggactgc tggcctgctc   3720
ttactcctgt ttatgtgtta aacattatct gcaaaaggca gattatacga ctgaccaatc   3780
aggtacgtac aaggcactga tgtgctaata cagtgattgg gtcagacaaa gtgcttcagt   3840
tagtgtgcgt tcgtcctaat cttggtttag aattaatgaa acagttggcg ttcactgtca   3900
```

-continued gcagcatagt gtgattttga atgaattagg caggaattca agattactac tcttagctcg 3960
ctcgctctct ctctctctcc accgtagtgc tcttcctagg gttttctttc ttctacttaa 4020
tatcttcttg gccttatatt taaatcccta tgcaattaat gttttatatc tgcgttttta 4080
aaaaagaaat gtcattttaa gtgattcttg tatgtagcaa gcacctattg cttttgtgag 4140
taaatgaatt aagacttttg tactgtgatt tgtactcact gccccagttc cccaactgtt 4200
ggagccttgc tgctgtgaaa cgctgtagtc accatagttg tgtccaccac ccagccgggt 4260
ctgtgagtct cacctgtcac gtgacatcgt ctggtgtgga tgttggctct gaattagtgt 4320
cactgcagtt acacgtgtct gtctaggctt tgcaagatgc tgtagtcacc atagtcgtga 4380
ccaccaccta gccaggtctg tgagtctcac ctgtcacgtg ccatcatctg gtgtcactgc 4440
agttacacgt gtctgtctag gctttgccgc aaccttgaga agcagctagc attttccgtt 4500
gttcacacag taaggacaat gtctctgcat tgatctgagg ctcactggtg gcctggggaa 4560
gggacacaga gaacagaatg tctgcagctg aggcttgtct ctcttcgttc agacctctta 4620
cctgttgcct gagtacacaa tgcaccccgc tttctggccc actggccacg gtgctgtgcc 4680
taatctgagt tctcccctgg cttttccagt cagtttgaaa gctgtgttca taactagatg 4740
aagtgtagaa tagtaatatt agatgctttt aaatgttcgc ttctttttaa acaaaaacta 4800
aaacccagaa ctgaattttg aggtggattt ttaaataaaa aaagattgag tttgctgtga 4860
aaaaaaaaaa aaaaaaa 4877

<210> SEQ ID NO 6
<211> LENGTH: 2763
<212> TYPE: DNA
<213> ORGANISM: Homo sapiens

<400> SEQUENCE: 6
gagcctgctg ggacttgaac cagcagtaag attttcacga cacagtgctg tctgcttctc 60
cgtaagaagt tagaagccct agaaaacaat ctcctggtcc aaggtgcttg agtgggccga 120
tccagctata tcaagaacct ttgagaacaa aattctcaag catttctgag gggagtcgaa 180
taggtgaaaa ccttggctgg cctgacctta tcatggaacc tgacgacttt gattctgaag 240
acaaagagat attaagctgg gatattaatg atgtgaaact gccacagaac gtgaaaaaaa 300
ccgactggtt ccaggagtgg ccagattcct atgccaaaca catctacagc tcggaggaca 360
agaatgcgca gcggcacctg agcagctggg ccatgcgcaa taccaacaac cacaactccc 420
gcatcctcaa gaagtcctgc ctgggtgtgg tggtgtgcgg ccgcgactgt ctcgcagagg 480
aggggcgcaa gatctacctg agacctgcca tctgtgacaa ggcccggcag aagcagcagc 540
ggaaacgctg tcccaactgt gacgggcctc tgaagctcat cccttgccga ggtcatgggg 600
gcttcccggt caccaacttc tggaggcacg acggacgctt tatatttttc cagtcaaagg 660
gagagcatga tcatccaaaa ccagaaacca agttagaagc tgaggcaaga agagccatga 720
agaaagtgaa cacagcacct tcctccgtct cattgagcct gaaggggagc acagagacca 780
ggtctcttcc aggtgaaaca caaagtcagg ggagtttacc tttaacttgg tctttccagg 840
aaggcgtcca attgcctggt agttacagtg gacatttaat agctaacact cctcagcaga 900
actcactaaa tgattgcttt tccttctcca agagttatgg tctgggagga atcacagatc 960
tgactgacca gacttccact gtggacccca tgaagctcta tgaaaagcgc aaattgtcca 1020
gtagcagaac ctacagtagt ggagacctgc ttcctccttc tgcctccgga gtctactctg 1080

-continued atcatggcga tctacaagcg tggagtaaaa atgctgcttt ggggagaaat catcttgctg 1140
acaactgtta ttccaattat ccttttcctc tgaccagctg gccttgcagc ttctctcctt 1200
cccaaaactc ttcagaaccc ttttaccagc agcttccatt ggagccacct gcagccaaaa 1260
ctggctgtcc cccattatgg ccaaatccag cgggtaatct ttatgaagag aaagtacatg 1320
tggattttaa cagctacgtc cagtctcctg cataccattc acctcaagaa gacccctttc 1380
tcttcaccta cgcctctcat cctcatcagc aatattcact gccaagcaag agcagcaaat 1440
gggattttga ggaagaaatg acatacttgg gtttggatca ctgcaacaat gatatgcttc 1500
tgaacctgtg tcctttgaga tgacccaaat ctttcactat gtgcacccca gcccctcaaa 1560
aatggggaag ggctgaaaga atttccttag gaaataattt ttaaaacata accacagata 1620
aatgagaatc atgataagca gtagacaagg ctttttttctt tttcttttt ccttcttttt 1680 ttttttttt ttttttttga gacagagtct tgctcttttg cccaggcagg aatgcagtgg 1740
cgccatctcg gctcactgca acctctgcct cccgggtttg agtgattctc ctgcgtcagc 1800
ctcccgagta gctgggatta caggcacctg ccactgcgcc tggctaattt ttctattttt 1860
agtagagaca gggttttgcc atgttggtca ggctgctctc aaactcctga tctcaagtga 1920
tctgcccacc tcaccatccc aaagtgctgg gattacaggc gtgagccatt gtgcccggct 1980
gacaaggctt ttttcttcac atgagtaatt tttttggctt cttctcctcc actctagtat 2040
ttccaccctc agtaaggaat ggaaacctgt cccgtctggg gtgtgaagtg ccctctgctt 2100
tttcccccac attgtttggg gttcccagca cctcagccac attgcatgct gggttttcat 2160
tgtcattgtt gcaaatgaaa tggagtagac atgtgaaatg ctaacctatc taggacctga 2220
tctatgcctt cttgggaact gagaatgaag aaacagaaat agatggtgga agaactgcct 2280
aaggtgtgaa aagctgaaga ttctaccact gaagtactga atatgttgtc tagttgtgag 2340
actagtgtgt aaaatatatg ttttctagat gatttctgag acttgtgatg acaaggaacc 2400
tgacctaacc ccatttttca taaagacaaa gaacagcaat gttaaattgc catatgaaga 2460
gaaacactag tgatgtgcgt ggtctccttg cctcttgttt ccttccctct tcctcactga 2520 cttcccccttg cacaggggct tctgttttat cccatttatt atttgtggca cctatatcaa 2580
tgtggggttt gtaataggtg agaaatattt gcttggagaa gctcttgtgc aattagcctg 2640
gcaatgattg gccggccatg tttgaatgcc agtttctctt ctttgctgaa gtactttatg 2700
ataaaagtaa gcctagacat aaaatctgga gagaaccatg caataaacaa gtatttttga 2760
aat 2763

<210> SEQ ID NO 7
<211> LENGTH: 2641
<212> TYPE: DNA
<213> ORGANISM: Mus musculus

<400> SEQUENCE: 7
cgggaccctg gcgaggagcg gaagctaggt tgctctgttg cttctgcgat cgggcggcgg 60
cggcggcgag agcgagcggg gctgcggccg ggacggcggt cggggcagcg ggcgccgcag 120
tcagggagca gcagcgaggt tggcggctgc gggcggcagc gcagggcggg ccgggccggg 180
tgacggagtg gacggcgcgt cacgggtggc attgtgtgtc ccagtgtgca agaatagccc 240
cagaagagga aaggctgagc ccagagctct tcagcaggga agattccctt cccccctgct 300
tcaggctgct gagcactgag cggcgctcag aatggaagcc atcgccaaat atgacttcaa 360
agctactgct gacgatgagc tgagcttcaa aaggggggac atccttaagg ttttgaatga 420

-continued agaatgtgac cagaactggt ataaggcaga actcaatggg aaagatggct tcatccccaa 480
gaattacata gaaatgaaac cacatccgtg gtttttggc aaaatcccca gagccaaggc 540
agaagaaatg ctcagcaaac agcggcatga cggggccttc ctgatccgag agagcgagag 600
cgctcctggg gacttctccc tgtccgtcaa gtttggaaat gatgtgcagc acttcaaggt 660
gctccgcgac ggagccggga agtatttcct gtgggtggtg aagtttaatt ctttgaatga 720
gctggtagat taccacagat caacatccgt gtccaggaac cagcagatat tcttacggga 780
catagaacag atgccacagc agccaaccta cgtccaggcg ctctttgact ttgaccccca 840
ggaggatggc gagctgggct ttcgcagagg agacttcatt catgtcatgg ataactcaga 900
tcccaattgg tggaaagggg cctgccacgg gcagaccggc atgtttcccc gcaattatgt 960
caccccagtg aaccggaacg tctaagaagc aaaagagatt atttaaagaa agtgaaaagt 1020
taagaccgtt cacaagaatt acacccacac gctgcctgtc acagcctgtg agggaacgca 1080
gaacacctgg ctgggtccca cgggtgaccc tctcattggg ttgcaacttt ggggggtggg 1140
gaggggtgtt tgatttcata atgccaaaac ttaacctatt gaatgaatta cagtttttat 1200
tacggaatct cgccgctacc cctgttcccc tcctgtgtcc tttttctcgt tctttctttc 1260
ctgtccagtg catgatgttt aaggccacat atagtccagc tgatgccaat aataaaagac 1320
aagaaaccaa gtgggctggt attttctcta tgcaaaatgt ctgtggagat ggatggactg 1380
aaagagccgg attcctcaca cacaggggca gccagtgctt ctggggccct ggttggggtt 1440
cacccgagat gcccaggggt accgcctcca gcctcaggcc tggagcattc catcaaagtt 1500
ggaattaggg gaaggaggcc cactgtcctc cccggtctcc tgagagtcag actgcaggcc 1560
ctcccctctc ccactgcttc ccttcaggtg ttttgacgtt tttttgtttg tttgtttgtt 1620
ttttttaaat agtgcctttg tcttatttca agggtgttca taaatggtat ttgtaccatt 1680
ttttttttt aataagttaa agacagtcca gagcttttca gttgattcgt ctcctatcct 1740
gtgtaaatat tttcctctca gggcagggga aagaggacag agaaaggagc tggtagaagc 1800
agagagtgta tttcccatct tgaatgggcc ggaggtctcg aagcctcagc ttttactttg 1860
tgagctgcaa cactcgcttc agctcagact cagtggacat cagagtctct gtctccgtgt 1920
ctcagttatg gtctgctctc tctatgcctg gagctactga tccaaacaca agacggtcag 1980
aggagccctg gcatccttca ctcttatagg cctacatgca gatgggcttg aagagaattg 2040
gcctttcatt tttcacgctc gtatttcccc acctgtccaa gggtgcagat agcaggattg 2100
tggggtcggc cgcatttctc ttggcagtgg gttgtgctgc cctccccccc accccacccc 2160
tccatcccac aaagcctttc gaggtaggag agaccaagac cagtgcacag ctttttaact 2220
cttgtcttct gtgagttttc cgtcctctgt agtcacgtgc ctgcacaccg ttctctccac 2280
cctgcctcct tcccacagca gaagcagggc tccacccagg ccttcccttg gagtcggtgc 2340
atccatgggc tgctagactc ttgcgggtag agtctcccct ggacttagca ttgtgagatg 2400
gactcagctc agggcgcccc taaggctcgg aggcggcctt ctgggtcccc acctctcctg 2460
gttccgctgc tgctctccct gctgatgata aagtaatctc tggagtcaca cctgggccat 2520
gtgattgttt tattttggaa ttggtgtata tcatgaagcc ttgctgaact aagttttgtg 2580
tgtatatatt taaagatcag tgtttaaata aaaaaaaaaa aaaaaaaaaa aaaaaaaaaa 2640
a 2641

<210> SEQ ID NO 8

-continued

<211> LENGTH: 2074
<212> TYPE: DNA
<213> ORGANISM: Mus musculus

<400> SEQUENCE: 8

```
agagacaggg tttctctgtg tagccctgga gtgctgggtt taaaggcata cctagtcctg     60
gttctgaact cttttttttt cttttaaaca tgtatgagtg ttttccctgc ttgtatgtct    120
ccatacagtc tatacacctg gcgccaggga aggccagaag aggatgttga ttcccctgga    180
actggagtta cagatggttg tgagacgcta tgtggatact gcaaattaaa cccaagtcct    240
cctaaaagca gcagcacctg ctctaaacca ctgcaccagc tctccagccc ctggtcctga    300
cctcctgatc accctgcctt gtcacctact agtttagcgt catgtctcag cttttcacat    360
agagaatttg ggaaagcaac aaacaaagta cagaatctga aagaaggttt tgggtaacag    420
gagttctggt gaacagggca aaccaattcc accaccatga gttggagctt cctgactcgc    480
ctgctagagg agatccacaa ccattcgaca tttgtaggga agatctggct cactgtgctg    540
attgtctttc gaattgtcct aactgctgta ggaggagagt ccatctacta tgatgaacaa    600
agcaaatttg tgtgcaacac agagcagccg ggctgtgaga atgtctgcta tgatgccttt    660
gccccgctct cccacgtgcg cttctgggta ttccagatca tcctggttgc aactccctct    720
gtgatgtacc tgggatatgc tattcataag attgccaaaa tggagcatgg tgaggcagac    780
aagaaggcag ctcggagcaa accctatgcc atgcgttgga aacagcaccg ggctctggaa    840
gaaacggaag aggaccatga agaggatcct atgatgtatc cagagatgga gttagaaagc    900
gaaaaagaaa ataaagagca gagccaacca aaacctaagc atgatggccg acgacgaatt    960
cgagaggatg ggctcatgaa aatctatgtg ttgcagctgc tggccaggac tgtgtttgag   1020
gtgggctttc taatagggca gtatttcctg tatggcttcc aagtccaccc attttatgtg   1080
tgcagcagac ttccttgccc tcataagata gactgcttta tttctagacc cactgaaaag   1140
accatcttcc ttctgataat gtatggtgtc acaggcctct gcctattgct taacatttgg   1200
gagatgcttc acttagggtt tgggacaatt cgagactcac taaacagtaa aaggagggaa   1260
cttgatgatc cgggtgctta taattatcct ttcacttgga acacaccctc tgctccccct   1320
ggctataaca ttgctgtcaa accagatcag atccagtaca ctgagctgtc caatgctaag   1380
attgcctaca agcaaaacaa agccaatatt gcccaggaac agcagtacgg cagccacgag   1440
gaacacctcc cggctgatct ggagactctg cagcgggaga tcagaatggc tcaggaacga   1500
ttggacctag caatccaggc ctaccatcac caaaacaacc cccatggtcc tcgggaaaag   1560
aaggccaaag tggggtccaa atctgggtcc aacaaaagca gtattagtag caaatcaggg   1620
gatgggaaga cctccgtctg gatttaatct tggttgggct taaaacttgg gttttcatag   1680
tttatggtaa gcagcaactt gctgaataat gacttccatt gagtaaacat ttggctctgg   1740
ttatcttcag ggatgctgtt ggctcatgat ccaaactcag gggactctga aggtggagct   1800
gggatgagtc gggagaggga aacacagtgt tcccaggcac atgttctcag caataatgca   1860
gttgcagaac tttcaggttg tgtcttccag atccagagaa gaactgatat atttaaatca   1920
ttcttgttgg acagtttttg tatgtacagt attatggtac agttttttta gtatgataaa   1980
ttttttttt gtatttgtac attggactgc tgtagttaca ctttttata ttaaaggaaa   2040
aaatccttgt aaataaaaaa aaaaaaaaaa aaaa                               2074
```

<210> SEQ ID NO 9
<211> LENGTH: 2281

-continued

<212> TYPE: DNA
<213> ORGANISM: Mus sp.

<400> SEQUENCE: 9

```
atgatgtggg ggaccaaact tctgccggtc ctgttgctgc agcatgtcct cctgcacctc     60

ctcctgcttc atgtcgccat cccctatgca gaaggacaga agaaaagaag aaatacactt    120

catgaattta aaaagtcagc aaaaactact cttaccaagg aagacccatt actgaagatt    180

aaaaccaaaa aagtgaactc tgcagatgag tgtgccaaca ggtgtatcag gaacaggggc    240

tttacgttca cttgcaaggc cttcgttttt gataagtcaa gaaaacgatg ctactggtat    300

cctttcaata gtatgtcaag tggagtgaaa aaagggtttg gccatgaatt tgacctctat    360

gaaaacaaag actatattag aaactgcatc attggtaaag gaggcagcta taaagggacg    420

gtatccatca ctaagagtgg catcaaatgc cagccttgga attccatgat cccccatgaa    480

cacagctttt tgccttcgag ctatcgcggt aaagacctac aggaaaacta ctgtcgaaat    540

cctcgagggg aagaaggggg accctggtgt ttcacaagca atccagaggt acgctacgaa    600

gtctgtgaca ttcctcagtg ttcagaagtt gaatgcatga cctgcaatgg tgaaagctac    660

agaggtccca tggatcacac agaatcaggc aagacttgtc agcgctggga ccagcagaca    720

ccacaccggc acaagttctt gccagaaaga tatcccgaca agggctttga tgataattat    780

tgccgcaatc ctgatggcaa gccgaggcca tggtgctaca ctcttgaccc tgacacccct    840

tgggagtatt gtgcaattaa aacgtgcgct cacagtgctg tgaatgagac tgatgtccct    900

atggaaacaa ctgaatgcat tcaaggccaa ggagaaggtt acaggggaac cagcaatacc    960

atttggaatg gaattccctg tcagcgttgg gattcgcagt accctcacaa gcatgatatc   1020

actcccgaga agttcaaatg caaggacctt agagaaaatt attgccgcaa tccagatggg   1080

gctgaatcac catggtgttt taccactgac ccaaacatcc gagttggcta ctgctctcaa   1140

attcccaagt gtgacgtgtc aagtggacaa gattgttatc gtggcaatgg gaaaaactac   1200

atgggcaact tatccaaaac aaggtctgga cttacatgtt ccatgtggga caagaatatg   1260

gaggatttac accgtcatat cttctgggag ccagatgcta gcaaattgaa taagaattac   1320

tgccggaatc ctgatgatga tgcccatgga ccttggtgct acacggggaa tcctcttatt   1380

ccttgggatt attgccctat ttcccgttgt gaaggagata ctacacctac aattctgaat   1440

ttggaccatc ctgtaatatc ctgtgccaaa acaaaacaac tgcgggttgt aaatggcatt   1500

ccaacacaaa caacagtagg gtggatggtt agtttgaaat acagaaataa acatatctgt   1560

ggaggatcat tgataaagga aagttgggtt cttactgcaa gacaatgttt tccagccaga   1620

aacaaagact tgaaagacta tgaagcttgg cttggcatcc acgatgttca tgagagaggc   1680

gaggagaagc gcaagcagat cttaaacatt tcccagctgg tctatggtcc tgaaggctca   1740

gacttggttt tactgaagct tgctcgacct gcaatcctgg ataactttgt cagtacaatt   1800

gatttaccta gttatggttg tacaatccct gaaaagacca cttgcagtat ttacggctgg   1860

ggctacactg gattgatcaa cgcggatggt ttattacgag tagctcatct gtatattatg   1920

gggaatgaga aatgcagtca gcaccatcaa ggcaaggtga ctttgaatga gtctgagtta   1980

tgtgctgggg ctgaaaagat tggatcagga ccatgtgagg gagattatgg tggcccactc   2040

atttgtgaac aacacaaaat gagaatggtt cttggtgtca ttgttcctgg tcgtggatgt   2100

gccatcccaa atcgtcctgg tatttttgtt cgagtagcat attatgcaaa atggatacac   2160

aaagtaattt tgacatacaa gttgtaatag ccatagaaga ggccagtgtg tttgaagcat   2220
```

-continued

```
ccatggatac atgaggattt ccaagacttc aggattaaaa tgtcacctaa aacaatccta   2280

a                                                                   2281


<210> SEQ ID NO 10
<211> LENGTH: 2525
<212> TYPE: DNA
<213> ORGANISM: Mus musculus

<400> SEQUENCE: 10

gagtcacccc cgcgcagcct aggcttgccg tgcgagtcgg acttggtccg ggcccaccgc     60

cctgctctgt actactactc ggctttctcg tcaagatgcc tgaggaagtg caccatggag    120

aggaggaggt ggagaccttt gcctttcagg cagaaattgc ccagctcatg tccctcatca    180

tcaacacttt ctattcaaac aaggagattt tcctccgcga gttgatctct aatgcttcag    240

atgccctgga caagattcga tatgagagcc tgacggaccc ttctaagttg gacagtggga    300

aagagctgaa aattgacatc atccccaacc ctcaggagcg cacgctgact ttggtggaca    360

caggcattgg catgaccaag gctgacctca ttaataacct gggaaccatt gctaagtctg    420

gcacgaaggc gttcatggag gctctccagg ctggtgcaga catctccatg atcgggcagt    480

ttggtgtcgg attctactcg gcctatctag ttgcagagaa agtggttgtg atcacgaagc    540

acaatgatga tgagcagtat gcctgggagt cgtctgcggg tggctccttc accgtccggg    600

cagaccatgg tgagcccatt ggccggggta ccaaagtgat ccttcacctc aaagaagacc    660

agacagagta cttggaggag aggagggtca aggaagtggt gaagaaacat tcgcagttca    720

taggctatcc catcaccctc tatttggaga aggaacggga gaaggagatc agtgatgatg    780

aggcagagga agagaaaggt gagaaagagg aggaagataa ggaggatgag gagaagccta    840

agattgaaga tgtgggatcc gatgaggaag atgacagcgg caaagacaag aaaaagaaaa    900

caaagaagat caaagagaag tacattgacc aggaggagct gaacaagaca aagcctatct    960

ggaccagaaa cccggatgac atcacgcagg aggagtatgg cgaattctat aagagcctca   1020

ccaatgactg ggaggaccac ttggcagtca agcacttctc tgtagaaggt cagttggaat   1080

tcagggcatt gctcttcatt ccccggcggg ctcccttcga cctttttgag aacaagaaga   1140

agaagaacaa catcaaattg tatgtccgcc gtgtgttcat catggacagc tgtgacgagc   1200

tgatacctga gtacctcaac tttatccgcg gtgtggttga ctccgaggac ctgcccctga   1260

acatctcccg ggagatgctg cagcagagca agatcctgaa ggtcatccgc aagaacatcg   1320

tcaagaagtg cctggagctc ttctccgagc tggctgagga caaggagaac tacaagaagt   1380

tctatgaggc cttctccaaa aatttaaagc ttggaattca tgaagattcc actaaccgac   1440

gccgcctctc tgagctcctt cgctatcaca cctctcagtc tggagatgag atgacctcct   1500

tgtcagagta tgtgtctcgc atgaaggaga cccagaagtc catctactat atcactggtg   1560

agagcaaaga gcaagtggcc aactctgcct ttgtggagcg agtgcggaag cggggcttcg   1620

aggtggtgta tatgactgag cctattgacg agtactgcgt gcagcagctc aaggagtttg   1680

atgggaagag cctggtctca gtgactaagg agggcctgga gctaccagag gacgaggaag   1740

agaagaagaa aatggaggag agcaaggcaa agtttgagaa tctctgcaag ctcatgaagg   1800

agatcttgga caagaaggtt gaaaaggtga caatctccaa taggcttgtg tcttcaccct   1860

gctgcattgt gacaagcacc tatggctgga cagccaacat ggaacggatc atgaaggccc   1920

aggcactgcg agacaactct acaatgggct acatgatggc caaaaaacac ctggagatca   1980

accctgacca ccccatcgtg gagaccctgc ggcagaaggc tgaggcagac aaaaacgaca   2040
```

aagctgtcaa ggacctggtg gtgctgctgt ttgaaactgc tctgctctcc tctggtttct 2100
cacttgagga tccccaaacc cactccaacc gcatctaccg catgattaaa ctaggcctgg 2160
gcatcgatga agatgaggtc actgcagagg agcccagtgc tgctgttcct gatgagatcc 2220
cccctctgga aggcgatgag gatgcctcgc gcatggaaga ggtggattaa agcctcctgg 2280
aagaagccct gccctctgta tagtatcccc gtggctcccc cagcagccct gacccacctg 2340
gctctctgct catgtctaca agaatcttct atcctgtcct gtgccttaag gcaggaagat 2400
cccctcccac agatagcagg gttgggtgtt atgtattgtg gtttttttgt ttgttttatt 2460
ttgttctaaa attaaaagta tgcaaaataa agaagatgca gttttaaaaa aaaaaaaaaa 2520
aaaaa 2525

<210> SEQ ID NO 11
<211> LENGTH: 7037
<212> TYPE: DNA
<213> ORGANISM: Homo sapiens

<400> SEQUENCE: 11
gctgcgtgga gcggcggagc cggagggaag caaaggaccg tctgcgctgc tgtccccgcc 60
ccgcgcgctc tgcgcccctc gtccctggcg gtcgctccga agctcagccc tcttgcctgc 120
cccggagctg tcccgggcta gccgagaaga gagcggccgg caagtttggg cgcgcgcagg 180
cggcgggccg cgggcactgg gcgcctcgct ggggcggggg gaggtggcta ccgctcccgg 240
cttggcgtcc cgcgcgcact tcggcgatgg cttttccgcc gcggcgacgg ctgcgcctcg 300
gtccccgcgg cctcccgctt cttctctcgg gactcctgct acctctgtgc cgcgccttca 360
acctagacgt ggacagtcct gccgagtact ctggccccga gggaagttac ttcggcttcg 420
ccgtggattt cttcgtgccc agcgcgtctt cccggatgtt tcttctcgtg ggagctccca 480
aagcaaacac cacccagcct gggattgtgg aaggagggca ggtcctcaaa tgtgactggt 540
cttctacccg ccggtgccag ccaattgaat ttgatgcaac aggcaataga gattatgcca 600
aggatgatcc attggaattt aagtcccatc agtggtttgg agcatctgtg aggtcgaaac 660
aggataaaat tttggcctgt gccccattgt accattggag aactgagatg aaacaggagc 720
gagagcctgt tggaacatgc tttcttcaag atggaacaaa gactgttgag tatgctccat 780
gtagatcaca agatattgat gctgatggac agggattttg tcaaggagga ttcagcattg 840
attttactaa agctgacaga gtacttcttg gtggtcctgg tagcttttat tggcaaggtc 900
agcttatttc ggatcaagtg gcagaaatcg tatctaaata cgaccccaat gtttacagca 960
tcaagtataa taaccaatta gcaactcgga ctgcacaagc tatttttgat gacagctatt 1020
tgggttattc tgtggctgtc ggagatttca atggtgatgg catagatgac tttgtttcag 1080
gagttccaag agcagcaagg actttgggaa tggtttatat ttatgatggg aagaacatgt 1140
cctccttata caattttact ggcgagcaga tggctgcata tttcggattt tctgtagctg 1200
ccactgacat taatggagat gattatgcag atgtgtttat tggagcacct ctcttcatgg 1260
atcgtggctc tgatggcaaa ctccaagagg tggggcaggt ctcagtgtct ctacagagag 1320
cttcaggaga cttccagacg acaaagctga atggatttga ggtctttgca cggtttggca 1380
gtgccatagc tcctttggga gatctggacc aggatggttt caatgatatt gcaattgctg 1440
ctccatatgg gggtgaagat aaaaaaggaa ttgtttatat cttcaatgga agatcaacag 1500
gcttgaacgc agtcccatct caaatccttg aagggcagtg ggctgctcga agcatgccac 1560

-continued

```
caagctttgg ctattcaatg aaaggagcca cagatataga caaaaatgga tatccagact   1620
taattgtagg agcttttggt gtagatcgag ctatcttata cagggccaga ccagttatca   1680
ctgtaaatgc tggtcttgaa gtgtacccta gcattttaaa tcaagacaat aaaacctgct   1740
cactgcctgg aacagctctc aaagtttcct gttttaatgt taggttctgc ttaaaggcag   1800
atggcaaagg agtacttccc aggaaactta atttccaggt ggaacttctt ttggataaac   1860
tcaagcaaaa gggagcaatt cgacgagcac tgtttctcta cagcaggtcc ccaagtcact   1920
ccaagaacat gactatttca aggggggac tgatgcagtg tgaggaattg atagcgtatc    1980
tgcgggatga atctgaattt agagacaaac tcactccaat tactattttt atggaatatc   2040
ggttggatta tagaacagct gctgatacaa caggcttgca acccattctt aaccagttca   2100
cgcctgctaa cattagtcga caggctcaca ttctacttga ctgtggtgaa gacaatgtct   2160
gtaaacccaa gctggaagtt tctgtagata gtgatcaaaa gaagatctat attggggatg   2220
acaaccctct gacattgatt gttaaggctc agaatcaagg agaaggtgcc tacgaagctg   2280
agctcatcgt ttccattcca ctgcaggctg atttcatcgg ggttgtccga aacaatgaag   2340
ccttagcaag actttcctgt gcatttaaga cagaaaacca aactcgccag gtggtatgtg   2400
accttggaaa cccaatgaag gctggaactc aactcttagc tggtcttcgt ttcagtgtgc   2460
accagcagtc agagatggat acttctgtga aatttgactt acaaatccaa agctcaaatc   2520
tatttgacaa agtaagccca gttgtatctc acaaagttga tcttgctgtt ttagctgcag   2580
ttgagataag aggagtctcg agtcctgatc atatctttct tccgattcca aactgggagc   2640
acaaggagaa ccctgagact gaagaagatg ttgggccagt tgttcagcac atctatgagc   2700
tgagaaacaa tggtccaagt tcattcagca aggcaatgct ccatcttcag tggccttaca   2760
aatataataa taacactctg ttgtatatcc ttcattatga tattgatgga ccaatgaact   2820
gcacttcaga tatggagatc aaccctttga gaattaagat ctcatctttg caaacaactg   2880
aaaagaatga cacggttgcc gggcaaggtg agcgggacca tctcatcact aagcgggatc   2940
ttgccctcag tgaaggagat attcacactt tgggttgtgg agttgctcag tgcttgaaga   3000
ttgtctgcca agttgggaga ttagacagag gaaagagtgc aatcttgtac gtaaagtcat   3060
tactgtggac tgagactttt atgaataaag aaaatcagaa tcattcctat tctctgaagt   3120
cgtctgcttc atttaatgtc atagagtttc cttataagaa tcttccaatt gaggatatca   3180
ccaactccac attggttacc actaatgtca cctggggcat tcagccagcg cccatgcctg   3240
tgcctgtgtg ggtgatcatt ttagcagttc tagcaggatt gttgctactg gctgttttgg   3300
tatttgtaat gtacaggatg ggctttttta aacgggtccg gccacctcaa gaagaacaag   3360
aaagggagca gcttcaacct catgaaaatg gtgaaggaaa ctcagaaact taactgcagt   3420
ttttaagtta tgctacatct tgacccacta gaattagcaa ctttattata gatttaaact   3480
ttcttcatga ggagtaaaaa tccaaggctt tactgctgat agtgctaatt ggcattaacc   3540
acaaaatgag aattatattt gtcaaccttc tccttataaa taagttcaga catacattta   3600
ataacatagg gtgacttgtg tttttaggta tttaaataat aaaatttcaa gggatagttt   3660
ttattcaatg tatataagac aggtagtgcc tgatttacta ctttatataa aatagtacct   3720
ccttcagtta ctgtttctga tttaatgtac ggaactttat ttgttgttgt tgttgttgtt   3780
gttgttgttg ttttaaagca gtccaaattt ggaccttagc aatcatgtct tttgtatagg   3840
tacttaatgt taatacatat tacactacag tttacttttc agaatactaa agactttata   3900
actgcatgaa cttggatttt tttaatcact catatggtag aattttataa acacatacat   3960
```

-continued

```
gataccatcc aaattcttgc ttttaataac aaaggtacaa tattttgttt tagtatgaaa   4020
atctggtaga tcctattaca cttctgttta tattaaatcc acaatatttt attacatttt   4080
taacttgtat aaattttagg tcaaatcctt caagccaacc tatactaaaa attagttcca   4140
taatcacaaa tggctctttt gtgtaattgt ttaatttcac ctgaatatca taatgcttaa   4200
agccatatgg agttggaaat tatttccaaa gcatatttat tccattgttt tagtctggct   4260
atttacagta taaaaaaagc atttttatta aaatactgtg tagttctttg agatagttgc   4320
ttatgcatat agtaagtatt acattcttag agtagagcag agtttttagt tagtattaat   4380
ttattttcct ccattcatgt acttttcctt atatttccaa aactgttact gagaatgggt   4440
caagatcagt gagaaatctt tacagttgac aggaacctgg accccttacc ccaactttat   4500
gagtaatgct tggaataaaa actcttaagg caactcactg atttacttct agcaatagca   4560
tgatgttaca ggaatattac ctctgtttaa gcaaggtaat gtgtaaaatc agtctcggct   4620
gtcagaataa cttctaaaag gtatttttat aagcagttca agttactgaa aacctttttaa   4680
acctttctga agttcgttag tataaattac ttttctagga ttattaataa aagccacata   4740
ggtggcaagt tgtagtttta tatggctctg tagagtggtg aaccttctag aggaatatat   4800
gatttattca cagttcctca aggcctgggg atgatgatca gttataccta tttttgtgca   4860
attacatcat gttgtacatt agaaatggag agtttaatag ctctttaact gctgtcctca   4920
ttaggtaatg ataaatattt cccttaaata attgactatt ttgctgtgtt ttaaaaatga   4980
ttgaaattta tcttgccata tctcataatt tcatgcacaa gttgactgag ctaatcttga   5040
gaatatattc gtaaaatagg agcacattta gttgaggtat acaaggtagg actctagaca   5100
aaaccttcta ttttagcttt agtgaatttc aaaagtaatg ggtcttggag tatagatttt   5160
tattagtagc ttgaaagagc ttaatcatat gcagtaagta tttttattac caataaattt   5220
aaaatttttt aagaaaaata tttttatcct agggccaagt gttgcctgcc accaatcagt   5280
aagttagtct ataacaaatt ttaccctaac agttttacca cctagtaaca gtcatttctg   5340
aaaatatgtt ggatagaaag tcactctttg gcaaaagtgt tagaatttgc ttttgtgcca   5400
tctattcctt ttatggcatc tatcttgaaa gtaatcttgt attggagatt gaaagatgct   5460
gtaatttaga aattaacatg atatcttaaa ttacctttat gaaatatagt tttgtataat   5520
agcatagatt ttccttcaaa aaatgaacat ttatatatct acaaaaaatat ggagaagagt   5580
aatttgaaag cctactttct gaagaaaatg gtgggatttt tttttatcat gattaaatat   5640
caaaaaattg ccctatgaaa actttaaatc tctaaaacat ttgaaatact accatatttg   5700
tgatttattg agaataaaaa tccattttga aatgtaaaat ttttatgatc tgattcagtt   5760
ttaagaaaac atgaatgaac tagaagatat taaaaacatt tgacattggt aagaaatatt   5820
gatactgata ttgattttta tataggtatt tatttcagaa ttgatatttt gagaaaaata   5880
catgtgagtc atttttttctg tttctctttt ctcttaacga ttatcactgt aattctgaat   5940
ctgaaaggta aaacaattag tcaaaatatt attgccatca ttctacctgt gttatgaaac   6000
tacttattca tagttaattc tcattaacac ttacatttcc ataaagaaaa ctcaagtatt   6060
aataaaagag actttactgg cttaagaggg ctgtgaaaga tttttgatag tgaatcatga   6120
ccctaaggga gagatttgtg tgataaaagt attgtatata atagatcagc gatttttgta   6180
aggcaaacag aatttgtaag ttggcagatc ttcctaagtt gcaaaatgta atgatgagct   6240
tggtggagaa gaatgagtcg ttcttggaat acctatgtgc agccactacc catctcaatg   6300
```

-continued

```
tcaccttgtt tgcattcttg gatagcttgt atatgtagta gtttgatgaa taatttaaag   6360

aaaaacacct aaaatttgaa aaatgattgt aggatcaaaa aaggcagatg aaattactta   6420

atactcagtg ttttggagag tattcctttt agtttgttgg ttggctggtt tgaacgatag   6480

aaatatgcag catgcaatat atgcttatat ttcattttaa tttctgatat ataatgaact   6540

tcttgggaga ggtactgaat ctttgatgtt ttttgtcatt gttctcaagt gcaatataac   6600

aatgtaacca aatctagata atttcaaagt tgtcattaat ttagtaagcc taatataaac   6660

aaatatttgt attatttttg ttagcaggaa agagtgatta agtgaggtta tttacccccta   6720

aatggtccat tctgcattgt atttcaggct ggaaatgaat tattctttac cagttttgaa   6780

acactttgaa atatcctaag gtaacttgga agctgtgtag tatatcaaat taatttgcta   6840

cctaataaca tagaaagtaa atatctttgt ggtcacccac attgggtgag acagaaaatg   6900

aatctgttct aaaatttgta atttgctaac ttgatttgag ttagtgaaaa ctggtacagt   6960

gttctgcttg atttacaaca tgtaacttgt gactgtacaa taaacataag catatggtac   7020

caaaaaaaaa aaaaaaa                                                   7037
```

<210> SEQ ID NO 12
<211> LENGTH: 1572
<212> TYPE: DNA
<213> ORGANISM: Danio rerio

<400> SEQUENCE: 12

```
gccagaagag ctgtttgtaa ataaccgtct gggaagacac tttttggacg tcagctgtca     60

agagaaaaca cctgtcgaat tggtacagta aactattttg gaagtttctt cttttttttgc   120

tctcttttgc ctgatgtaat ataacggaga gaacttgcgg actttagtca gcttcagtac    180

gtcccaacgt aatctctgtt cacatgtcaa caaaaatgga gcaaccgttt tatgacgact    240

cgtttctttc tgcttatggt catccagacg ctgccctgca cgactacaag ctcctaaagc    300

agaacatgag cgtgagcttc gccgaaccct accggaacct caagaccctc cgctccgaaa    360

tcgacttcta cacagcggcg accggagacg tgggctcgct gaaactcgcc tctccggagc    420

tggagagact catcatccag aacggtaacg gcgtcatcac atcacccacg ccggggcagt    480

atttgtacgg tcggagcatc acagaggagc aagagggctt cgcggacgga ttcgtcaaag    540

cgctggacga gctccacaaa atgaaccaaa tgccccccgcc gaacgtgtcc atcggagccc   600

ccggggtgtc gagttgttcg gtggcgtcgt cagtcttcgg cgcctcctta ccgcccgaga    660

ctccggtgta caccaccctg aacagctgca atcctaacac taacctcaca cctgcagcca    720

actacccgac agccaccatc agctacctgc ctcaccatca ccaccaccag cagtaccacc    780

accatcacca ccagcccacg ccgcatcctc atcacttcca gcactcgctc catccgcagc    840

ggctcgttac tctgaaagag gagccacaga ccgtccccga cctgcagagc agcgatggtt    900

ctcctcccat gtcgcccatc gacatggagg accaggagcg catcaaagcg gagcgcaaga    960

ggctccggaa ccgactggcg gccaccaagt gccggcgacg gaagctggag cgcatctccc   1020

ggctggagga caaagtgaaa gtgctcaagt cggataacgc cggactgtcc agcactgcgt   1080

ccctgctgag ggagcaggta gctcagctta agcagaaggt catgacccat gtgagcagcg   1140

ggtgccagct gatgctgacg cccaagatca agtcgtttta ggggggagag ggatgctacg   1200

gactctggga aacactggaa gagcagatcc tgtttgtgat gatgttattg tcgcagcact   1260

gagtacgagc gttgtatatt tcttaagtgt tttcttgtag aaaactttaa tgttattgtt   1320

gttttccaaa gataaggtac tttcagccga acggacaatg gactaaactt ttgaagtgaa   1380
```

-continued

```
cagttttggt tttgttgtta agtgctgccc tttgaaaaca ttccagtaag ttattgatat   1440

tgtgagtcag gttgagccag acctttaact gtttttctgt ttgtttgttt ttgtttattt   1500

tttatattta agtaaaaatg ttgaaaatga aaaaaaaaaa aaaaaaaaaa aaaaaaaaaa   1560

aaaaaaaaaa aa                                                       1572
```

```
<210> SEQ ID NO 13
<211> LENGTH: 5252
<212> TYPE: DNA
<213> ORGANISM: Homo sapiens

<400> SEQUENCE: 13

ctctctccca gaacgtgtct ctgctgcaag gcaccgggcc ctttcgctct gcagaactgc     60

acttgcaaga ccattatcaa ctcctaatcc cagctcagaa agggagcctc tgcgactcat    120

tcatcgccct ccaggactga ctgcattgca cagatgatgg atatttacgt atgtttgaaa    180

cgaccatcct ggatggtgga caataaaaga atgaggactg cttcaaattt ccagtggctg    240

ttatcaacat ttattcttct atatctaatg aatcaagtaa atagccagaa aaagggggct    300

cctcatgatt tgaagtgtgt aactaacaat ttgcaagtgt ggaactgttc ttggaaagca    360

ccctctggaa caggccgtgg tactgattat gaagtttgca ttgaaaacag gtcccgttct    420

tgttatcagt tggagaaaac cagtattaaa attccagctc tttcacatgg tgattatgaa    480

ataacaataa attctctaca tgattttgga agttctacaa gtaaattcac actaaatgaa    540

caaaacgttt ccttaattcc agatactcca gagatcttga atttgtctgc tgatttctca    600

acctctacat tatacctaaa gtggaacgac aggggttcag tttttccaca ccgctcaaat    660

gttatctggg aaattaaagt tctacgtaaa gagagtatgg agctcgtaaa attagtgacc    720

cacaacacaa ctctgaatgg caaagataca cttcatcact ggagttgggc ctcagatatg    780

cccttggaat gtgccattca ttttgtggaa attagatgct acattgacaa tcttcatttt    840

tctggtctcg aagagtggag tgactggagc cctgtgaaga acatttcttg gatacctgat    900

tctcagacta aggtttttcc tcaagataaa gtgatacttg taggctcaga cataacattt    960

tgttgtgtga gtcaagaaaa agtgttatca gcactgattg gccatacaaa ctgccccttg   1020

atccatcttg atggggaaaa tgttgcaatc aagattcgta atatttctgt ttctgcaagt   1080

agtggaacaa atgtagtttt tacaaccgaa gataacatat ttggaaccgt tatttttgct   1140

ggatatccac cagatactcc tcaacaactg aattgtgaga cacatgattt aaaagaaatt   1200

atatgtagtt ggaatccagg aagggtgaca gcgttggtgg gcccacgtgc tacaagctac   1260

actttagttg aaagtttttc aggaaaatat gttagactta aaagagctga agcacctaca   1320

aacgaaagct atcaattatt atttcaaatg cttccaaatc aagaaatata taattttact   1380

ttgaatgctc acaatccgct gggtcgatca caatcaacaa ttttagttaa tataactgaa   1440

aaagtttatc cccatactcc tacttcattc aaagtgaagg atattaattc aacagctgtt   1500

aaactttctt ggcatttacc aggcaacttt gcaaagatta attttttatg tgaaattgaa   1560

attaagaaat ctaattcagt acaagagcag cggaatgtca caatcaaagg agtagaaaat   1620

tcaagttatc ttgttgctct ggacaagtta aatccataca ctctatatac ttttcggatt   1680

cgttgttcta ctgaaacttt ctggaaatgg agcaaatgga gcaataaaaa acaacattta   1740

acaacagaag ccagtccttc aaaggggcct gatacttgga gagagtggag ttctgatgga   1800

aaaaatttaa taatctattg gaagccttta cccattaatg aagctaatgg aaaaatactt   1860
```

-continued

```
tcctacaatg tatcgtgttc atcagatgag gaaacacagt ccctttctga aatccctgat   1920
cctcagcaca aagcagagat acgacttgat aagaatgact acatcatcag cgtagtggct   1980
aaaaattctg tgggctcatc accaccttcc aaaatagcga gtatggaaat tccaaatgat   2040
gatctcaaaa tagaacaagt tgttgggatg ggaaagggga ttctcctcac ctggcattac   2100
gaccccaaca tgacttgcga ctacgtcatt aagtggtgta actcgtctcg gtcggaacca   2160
tgccttatgg actggagaaa agttccctca aacagcactg aaactgtaat agaatctgat   2220
gagtttcgac caggtataag atataatttt ttcctgtatg gatgcagaaa tcaaggatat   2280
caattattac gctccatgat tggatatata gaagaattgg ctcccattgt tgcaccaaat   2340
tttactgttg aggatacttc tgcagattcg atattagtaa aatgggaaga cattcctgtg   2400
gaagaactta gaggcttttt aagaggatat ttgttttact ttggaaaagg agaaagagac   2460
acatctaaga tgagggtttt agaatcaggt cgttctgaca taaaagttaa gaatattact   2520
gacatatccc agaagacact gagaattgct gatcttcaag gtaaaacaag ttaccacctg   2580
gtcttgcgag cctatacaga tggtggagtg ggcccggaga agagtatgta tgtggtgaca   2640
aaggaaaatt ctgtgggatt aattattgcc attctcatcc cagtggcagt ggctgtcatt   2700
gttggagtgg tgacaagtat cctttgctat cggaaacgag aatggattaa agaaaccttc   2760
taccctgata ttccaaatcc agaaaactgt aaagcattac agtttcaaaa gagtgtctgt   2820
gagggaagca gtgctcttaa aacattggaa atgaatcctt gtaccccaaa taatgttgag   2880
gttctggaaa ctcgatcagc atttcctaaa atagaagata cagaaataat ttccccagta   2940
gctgagcgtc ctgaagatcg ctctgatgca gagcctgaaa accatgtggt tgtgtcctat   3000
tgtccaccca tcattgagga agaaatacca aacccagccg cagatgaagc tggagggact   3060
gcacaggtta tttacattga tgttcagtcg atgtatcagc ctcaagcaaa accagaagaa   3120
gaacaagaaa atgaccctgt aggaggggca ggctataagc cacagatgca cctccccatt   3180
aattctactg tggaagatat agctgcagaa gaggacttag ataaaactgc gggttacaga   3240
cctcaggcca atgtaaatac atggaattta gtgtctccag actctcctag atccatagac   3300
agcaacagtg agattgtctc atttggaagt ccatgctcca ttaattcccg acaatttttg   3360
attcctccta aagatgaaga ctctcctaaa tctaatggag gagggtggtc ctttacaaac   3420
tttttcaga acaaaccaaa cgattaacag tgtcaccgtg tcacttcagt cagccatctc   3480
aataagctct tactgctagt gttgctacat cagcactggg cattcttgga gggatcctgt   3540
gaagtattgt taggaggtga acttcactac atgttaagtt acactgaaag ttcatgtgct   3600
tttaatgtag tctaaaagcc aaagtatagt gactcagaat cctcaatcca caaaactcaa   3660
gattgggagc tctttgtgat caagccaaag aattctcatg tactctacct tcaagaagca   3720
tttcaaggct aatacctact tgtacgtaca tgtaaaacaa atcccgccgc aactgttttc   3780
tgttctgttg tttgtggttt tctcatatgt atacttggtg gaattgtaag tggatttgca   3840
ggccagggag aaaatgtcca agtaacaggt gaagtttatt tgcctgacgt ttactccttt   3900
ctagatgaaa accaagcaca gattttaaaa cttctaagat tattctcctc tatccacagc   3960
attcacaaaa attaatataa tttttaatgt agtgacagcg atttagtgtt ttgtttgata   4020
aagtatgctt atttctgtgc ctactgtata atggttatca aacagttgtc tcaggggtac   4080
aaactttgaa aacaagtgtg acactgacca gcccaaatca taatcatgtt ttcttgctgt   4140
gataggtttt gcttgccttt tcattatttt ttagctttta tgcttgcttc cattatttca   4200
gttggttgcc ctaatattta aaatttacac ttctaagact agagacccac atttttttaaa   4260
```

-continued

```
aatcatttta ttttgtgata cagtgacagc tttatatgag caaattcaat attattcata   4320

agcatgtaat tccagtgact tactatgtga gatgactact aagcaatatc tagcagcgtt   4380

agttccatat agttctgatt ggatttcgtt cctcctgagg agaccatgcc gttgagcttg   4440

gctacccagg cagtggtgat ctttgacacc ttctggtgga tgttcctccc actcatgagt   4500

cttttcatca tgccacatta tctgatccag tcctcacatt tttaaatata aaactaaaga   4560

gagaatgctt cttacaggaa cagttaccca agggctgttt cttagtaact gtcataaact   4620

gatctggatc catgggcata cctgtgttcg aggtgcagca attgcttggt gagctgtgca   4680

gaattgattg ccttcagcac agcatcctct gcccaccctt gtttctcata agcgatgtct   4740

ggagtgattg tggttcttgg aaaagcagaa ggaaaaacta aaaagtgtat cttgtatttt   4800

ccctgccctc aggttgccta tgtattttac cttttcatat ttaaggcaaa agtacttgaa   4860

aattttaagt gtccgaataa gatatgtctt ttttgtttgt ttttttggt tggttgtttg   4920

ttttttatca tctgagattc tgtaatgtat ttgcaaataa tggatcaatt aatttttttt   4980

gaagctcata ttgtatcttt ttaaaaacca tgttgtggaa aaaagccaga gtgacaagtg   5040

acaaaatcta tttaggaact ctgtgtatga atcctgattt taactgctag gattcagcta   5100

aatttctgag ctttatgatc tgtggaaatt tggaatgaaa tcgaattcat tttgtacata   5160

catagtatat taaaactata taatagttca tagaaatgtt cagtaatgaa aaaatatatc   5220

caatcagagc catcccgaaa aaaaaaaaaa aa                                 5252
```

```
<210> SEQ ID NO 14
<211> LENGTH: 1718
<212> TYPE: DNA
<213> ORGANISM: Mus musculus

<400> SEQUENCE: 14

gcggcggcgg ctccgggggg cgggggcggg gagcccaggg gaactgctgg ggtcgtcccg     60

gtggtccccg gggaggtgga ggtggtgaag gggcagccat tcgatgtggg cccacgctac    120

acgcagctgc agtacatcgg cgagggcgcg tacggcatgg tcagctcagc ttatgaccac    180

gtgcgcaaga ccagagtggc catcaagaag atcagcccct ttgagcatca aacctactgt    240

cagcgcacgc tgagggagat ccagatcttg ctgcgattcc gccatgagaa tgttataggc    300

atccgagaca tcctcagagc gcccaccctg gaagccatga gagatgttta cattgttcag    360

gacctcatgg agacagacct gtacaagctg cttaaaagcc agcagctgag caatgaccac    420

atctgctact tcctctacca gatcctccgg ggcctcaagt atatacactc agccaatgtg    480

ctgcaccggg acctgaagcc ttccaatctg cttatcaaca ccacctgcga ccttaagatc    540

tgtgattttg gcctggcccg gattgctgac cctgagcacg accacactgg ctttctgacg    600

gagtatgtgg ccacacgctg gtaccgagcc ccagagatca tgcttaattc caagggctac    660

accaaatcca tcgacatctg gtctgtgggc tgcattctgg ctgagatgct ctccaaccgg    720

cccatcttcc ccggcaagca ctacctggac cagctcaacc acattctagg tatcttgggt    780

tccccatccc aggaggacct taattgcatc attaacatga aggcccgaaa ctacctgcag    840

tctctgccct cgaaaaccaa ggtggcttgg gccaagctct ttcctaaatc tgactccaaa    900

gctcttgacc tgctggaccg gatgttaacc ttcaacccaa acaagcgcat cacagtagag    960

gaagcgctgg ctcaccctta cctggaacag tactacgatc cgacagatga gccagtggcc   1020

gaggagccat tcaccttcga catggagctg gatgacctcc ccaaggagcg gctgaaggag   1080
```

ttgatcttcc aggagacagc ccgcttccag ccaggggcgc cagagggccc ctaacaagaa 1140
cagacacccc tgtccttttg gatctggtcc tgctcctacc tgctccttct ctgcagattg 1200
ttagaaagtg aactttgctc aacccagacc ccggcagccc aggctggacc aagggtgggc 1260
ctggccacct tctctcactt tgctggggtc tcctgcttca agcaggcttc tcccactcca 1320
tcccctgccc catctcccca tagcctgagt gatgaggtgg ccccagagct gatctctgct 1380
gctgtgtctt atctaccctt gctagccccg gctctggtag accgttctgg aatggagggg 1440
ctatgatcgt cctaggacct gtgctacgga ggggtggagg gcactgagta gggctctgcc 1500
ctatttcatc ttgttggaac cccaccccat tttccctgac agaacattcc taagtctcaa 1560
gggctagttt ccctgaggag cccaggccta accctctctc tctcaagctg ccacatgtaa 1620
cgcccttgct gcttctgtgt gtgggtgatt ggatgtgggg gtggggcccg tggagagccg 1680
gtgcccctcc ccatctcccc gtgcctgcct gtatctaa 1718

<210> SEQ ID NO 15
<211> LENGTH: 1272
<212> TYPE: DNA
<213> ORGANISM: Bos taurus

<400> SEQUENCE: 15
ggcgtccccg gctctcccga gcggcggcct ccccgctcct ttccggccag cggaggcagc 60
ttgcggcggc cggtcccccg gaggcgcggc gtcggccgag cggcggcgcg gagcgtcgag 120
cgcagcgcgg cggcggcggc ggcccggcag ccaacatggc ggcggcggcg gcggcgggcg 180
cgggcccgga gatggtccgc gggcaggtgt tcgacgtggg gccgcgctac accaatctct 240
cgtacatcgg cgagggcgcc tacggcatgg tgtgctctgc ttatgacaat gtcaacaaag 300
tccgagtcgc catcaagaaa atcagccctt ttgagcacca gacgtactgc cagagaacgc 360
tgagagagat aaagatctta ctgcgcttca gacatgagaa catcatcgga atcaatgaca 420
ttattcgagc accgaccatc gagcagatga aagatgtgta tatagtacag gacctcatgg 480
aaacagatct ctacaagctc ttgaagacgc aacacctcag caacgaccac atctgctatt 540
ttctctacca gatcctcaga gggttaaagt atattcattc agccaacgtg ctgcaccgtg 600
acctcaaacc ttccaacctg ctgctcaaca ccacctgcga tctcaagatc tgtgactttg 660
gcttggcccg tgttgcagat ccagaccacg accacacagg gttcttgaca gagtacgtgg 720
ccactcgctg gtaccgggct ccagaaatca tgttgaattc caagggctac accaagtcca 780
tcgacatctg gtccgtcggc tgcatcctcg cggagatgct ctccaacagg cccatcttcc 840
ccgggaagca ctaccttgac cagctgaacc acattctggg tattcttgga tccccgtcgc 900
aggaagacct gaattgtata ataaatttaa aagctagaaa ctacctgctc tctcttccac 960
acaaaaataa ggtgccatgg aacaggctgt tcccgaacgc ggactccaaa gctctggatc 1020
tactggacaa aatgttgacg ttcaaccctc acaagaggat cgaggtggag caggctctgg 1080
cccatcctta cctggagcag tactacgacc cgagcgatga gcccgtcgcc gaagcaccct 1140
tcaagtttga catggaattg gatgacttgc ccaaggaaaa gctcaaagaa ctcatttttg 1200
aagagactgc tcgattccag ccgggatacc gatcttaaat ttgtcaggac acgggctcag 1260
agcacggcac gc 1272

<210> SEQ ID NO 16
<211> LENGTH: 2945
<212> TYPE: DNA
<213> ORGANISM: Mus musculus -continued

<400> SEQUENCE: 16
tgccgctcgt gccgctttgg tggtggccgc ggttcttgtt aagtgagcga gcccggggga 60
acactcatca ctgggttggc aagactcagg aatcccaaat tcccgaggag gcgtggcggc 120
ggggtgccgg ccggtcggtc ctgcctccaa acccacagag gcggaactga gaggccctca 180
ggacgatctt ctcatcagcg cttcgtacag accatggccg aaccgctgaa ggaggaggac 240
ggcgaagatg gctctgggga gccccctggg agggtgaagg cagaacccgt tcacaccgct 300
gcctctgtgg tggccaagaa cctggccctg ctcaaagccc gctccttcga cgtgaccttt 360
gacgtggggg acgagtacga gatcatcgag accataggca atggggccta cggggtggtg 420
tcttcggcgc gccgccgcct cacgggccag caggtggcca tcaagaagat acctaatgct 480
tttgatgtgg tgaccaatgc caaacggacc ctcagggagc tgaagatcct caaacacttc 540
aaacacgaca atatcatcgc catcaaggac atcctgaagc ctactgtgcc ctatggagaa 600
ttcagatctg tctatgtggt actggacctc atggagagcg acctacacca gatcattcac 660
tcttcacagc cgctcaccct ggaacatgtg agatacttcc tgtaccagct gcttcggggc 720
ctcaaataca tgcactctgc tcaggtcatc caccgtgatc ttaaaccctc taaccttctg 780
gtcaatgaga actgtgagct caagatcggt gactttggaa tggcccgtgg cctctgtact 840
tcccctgccg agcaccagta cttcatgact gagtatgtgg ctactcgctg gtaccgtgcc 900
ccggagctca tgctttccct gcacgagtat acgcaggcaa tcgacctctg gtctgtgggc 960
tgcatctttg gtgagatgct ggctcggcgc cagctcttcc caggcaaaaa ctacgtgcac 1020
cagttacagc tgatcatgat ggtgttggga actccgtcac cagctgtgat tcaggctgtg 1080
ggggctgaaa gggtgcgagc ctatatccag agcctgccac caaggcaacc tgtgccttgg 1140
gagacagtat acccaggtgc tgaccgccag gccctctccc tgctgggacg catgttgcga 1200
tttgaaccca gtgcccgaat ctcagctgct gctgcccttc gccacccctt cctggctaag 1260
taccatgacc ctgatgatga gcctgattgc gccccacctt ttgactttgc ttttgaccgt 1320
gaagccctta ccagggagcg cattaaggag gccattgtgg ctgagattga ggacttccat 1380
gcacgacggg agggcatccg ccaacaaatc cgcttccagc cttctctgca gcctgtggct 1440
agtgagcctg tgtgtccaga tgttgagatg cccagtccct gggctccaag tggagactgt 1500
gccatggagt cgcctcctcc agcactgcca ccatgctctg atcctgcacc tgacaccgtt 1560
gatctgactc tgcagcctgc cccgccggcc agtgagcttg ctccaccaaa aagagagggt 1620
gccatctccg acaataccaa agcagccctc aaagctgccc tgctcaagtc cctaaggagc 1680
aggctcagag atgggcccag tgcacccttg gaggcgcctg agcctcgaaa gcccgtgaca 1740
gctcaggaac gccagcgaga acgagaagag aagcgcagga ggcgacaaga gagagccaag 1800
gagcgggaga agcgacgaca agagagagaa cgcaaggaga gggggggctgg taccttgggg 1860
ggcccctcta ctgaccctct ggctggactg gtgctcagtg acaatgaccg aagcctgcta 1920
gagcggtgga ctcgcatggc taggcctcct gcccctgccc ctgccccagc gccagcacca 1980
gcgccagcac cgtcctctgc ccagcccact agtactccta ctggccccgt atctcagtct 2040
actggtcctc tacagcctgc aggctctatt ccgggtcctg cctcccagcc tgtttgccca 2100
ccccctggcc ctgttcccca gcctgctggc cctatccctg ctccgctcca gactgcccct 2160
tccactagcc ttttggcctc ccagtcactt gtgccaccta gtgggttgcc tggttctggt 2220
gccccagaag ttctgcctta cttcccatct ggcccaccac ctccagatcc tgggctcacc 2280

-continued

```
cctcagcctt ctacatcaga gtcacctgat gtcaacctgg tgactcagca gctgtccaag   2340

tctcaggtgg aggaccccct gcctcctgtg ttctctggca ctccaaaggg cagtggggct   2400

ggctacggag ttggctttga tctggaggaa ttcttaaatc aatcttttga tatgggtgtg   2460

gctgatgggc cacaggatgg ccaggcagac tcagcctcac tctcagcctc tctccttgct   2520

gactggcttg agggccatgg catgaaccct gctgacattg agtctctgca gcgtgagatc   2580

cagatggact ccccaatgct gctgtctgac ctgcctgacc tccaagagcc ctgaaaccca   2640

cagcttgtgc cttgctgcca ggatagaccc agcatcaagg tccaggggtg cgatccaaag   2700

ggctgcaccc tgggcctggc aggtgaggct tggcttgagt tactctgcag gttcatctca   2760

gacccacctt tcagccttaa gcagccacct gagccaccac cgagccataa caggaccagg   2820

agactctact cctccctgag cagtcttctc cagtattgta tttttatta ttgttgtaat   2880

atgcatttgt tttgccatca aaatgaggcc tgtgaaatac aaggttttct ttaacctgaa   2940

aaaaa                                                                2945
```

<210> SEQ ID NO 17
<211> LENGTH: 360
<212> TYPE: PRT
<213> ORGANISM: Homo sapiens

<400> SEQUENCE: 17

```
Met Ala Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
    50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
    210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255
```

```
Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285

Leu Leu Asp Lys Met Leu Thr Phe Asn Pro His Lys Arg Ile Glu Val
    290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
        355                 360


<210> SEQ ID NO 18
<211> LENGTH: 626
<212> TYPE: PRT
<213> ORGANISM: Homo sapiens

<400> SEQUENCE: 18

Met Asp Glu Gln Glu Ala Leu Asn Ser Ile Met Asn Asp Leu Val Ala
1               5                   10                  15

Leu Gln Met Asn Arg Arg His Arg Met Pro Gly Tyr Glu Thr Met Lys
            20                  25                  30

Asn Lys Asp Thr Gly His Ser Asn Arg Gln Ser Asp Val Arg Ile Lys
        35                  40                  45

Phe Glu His Asn Gly Glu Arg Arg Ile Ile Ala Phe Ser Arg Pro Val
    50                  55                  60

Lys Tyr Glu Asp Val Glu His Lys Val Thr Thr Val Phe Gly Gln Pro
65                  70                  75                  80

Leu Asp Leu His Tyr Met Asn Asn Glu Leu Ser Ile Leu Leu Lys Asn
                85                  90                  95

Gln Asp Asp Leu Asp Lys Ala Ile Asp Ile Leu Asp Arg Ser Ser Ser
            100                 105                 110

Met Lys Ser Leu Arg Ile Leu Leu Leu Ser Gln Asp Arg Asn His Asn
        115                 120                 125

Ser Ser Ser Pro His Ser Glu Val Ser Arg Gln Val Arg Ile Lys Ala
    130                 135                 140

Ser Gln Ser Ala Gly Asp Ile Asn Thr Ile Tyr Gln Pro Pro Glu Pro
145                 150                 155                 160

Arg Ser Arg His Leu Ser Val Ser Ser Gln Asn Pro Gly Arg Ser Ser
                165                 170                 175

Pro Pro Pro Gly Tyr Val Pro Glu Arg Gln Gln His Ile Ala Arg Gln
            180                 185                 190

Gly Ser Tyr Thr Ser Ile Asn Ser Glu Gly Glu Phe Ile Pro Glu Thr
        195                 200                 205

Ser Glu Gln Cys Met Leu Asp Pro Leu Ser Ser Ala Glu Asn Ser Leu
    210                 215                 220

Ser Gly Ser Cys Gln Ser Leu Asp Arg Ser Ala Asp Ser Pro Ser Phe
225                 230                 235                 240

Arg Lys Ser Arg Met Ser Arg Ala Gln Ser Phe Pro Asp Asn Arg Gln
                245                 250                 255

Glu Tyr Ser Asp Arg Glu Thr Gln Leu Tyr Asp Lys Gly Val Lys Gly
```

```
            260                 265                 270

Gly Thr Tyr Pro Arg Arg Tyr His Val Ser Val His His Lys Asp Tyr
        275                 280                 285

Ser Asp Gly Arg Arg Thr Phe Pro Arg Ile Arg Arg His Gln Gly Asn
    290                 295                 300

Leu Phe Thr Leu Val Pro Ser Ser Arg Ser Leu Ser Thr Asn Gly Glu
305                 310                 315                 320

Asn Met Gly Leu Ala Val Gln Tyr Leu Asp Pro Arg Gly Arg Leu Arg
                325                 330                 335

Ser Ala Asp Ser Glu Asn Ala Leu Ser Val Gln Glu Arg Asn Val Pro
            340                 345                 350

Thr Lys Ser Pro Ser Ala Pro Ile Asn Trp Arg Arg Gly Lys Leu Leu
        355                 360                 365

Gly Gln Gly Ala Phe Gly Arg Val Tyr Leu Cys Tyr Asp Val Asp Thr
    370                 375                 380

Gly Arg Glu Leu Ala Ser Lys Gln Val Gln Phe Asp Pro Asp Ser Pro
385                 390                 395                 400

Glu Thr Ser Lys Glu Val Ser Ala Leu Glu Cys Glu Ile Gln Leu Leu
                405                 410                 415

Lys Asn Leu Gln His Glu Arg Ile Val Gln Tyr Tyr Gly Cys Leu Arg
            420                 425                 430

Asp Arg Ala Glu Lys Thr Leu Thr Ile Phe Met Glu Tyr Met Pro Gly
        435                 440                 445

Gly Ser Val Lys Asp Gln Leu Lys Ala Tyr Gly Ala Leu Thr Glu Ser
    450                 455                 460

Val Thr Arg Lys Tyr Thr Arg Gln Ile Leu Glu Gly Met Ser Tyr Leu
465                 470                 475                 480

His Ser Asn Met Ile Val His Arg Asp Ile Lys Gly Ala Asn Ile Leu
                485                 490                 495

Arg Asp Ser Ala Gly Asn Val Lys Leu Gly Asp Phe Gly Ala Ser Lys
            500                 505                 510

Arg Leu Gln Thr Ile Cys Met Ser Gly Thr Gly Met Arg Ser Val Thr
        515                 520                 525

Gly Thr Pro Tyr Trp Met Ser Pro Glu Val Ile Ser Gly Glu Gly Tyr
    530                 535                 540

Gly Arg Lys Ala Asp Val Trp Ser Leu Gly Cys Thr Val Val Glu Met
545                 550                 555                 560

Leu Thr Glu Lys Pro Pro Trp Ala Glu Tyr Glu Ala Met Ala Ala Ile
                565                 570                 575

Phe Lys Ile Ala Thr Gln Pro Thr Asn Pro Gln Leu Pro Ser His Ile
            580                 585                 590

Ser Glu His Gly Arg Asp Phe Leu Arg Arg Ile Phe Val Glu Ala Arg
        595                 600                 605

Gln Arg Pro Ser Ala Glu Glu Leu Leu Thr His His Phe Ala Gln Leu
    610                 615                 620

Met Tyr
625


<210> SEQ ID NO 19
<211> LENGTH: 1064
<212> TYPE: DNA
<213> ORGANISM: Homo sapiens

<400> SEQUENCE: 19
```

-continued

```
atgtctcagg agaggcccac gttctaccgg caggagctga acaagacaat ctgggaggtg     60
cccgagcgtt accagaacct gtctccagtg ggctctggcg cctatggctc tgtgtgtgct    120
gcttttgaca caaaaacggg gttacgtgtg gcagtgaaga agctctccag accatttcag    180
tccatcattc atgcgaaaag aacctacaga gaactgcggt tacttaaaca tatgaaacat    240
gaaaatgtga ttggtctgtt ggacgttttt acacctgcaa ggtctctgga ggaattcaat    300
gatgtgtatc tggtgaccca tctcatgggg gcagatctga acaacattgt gaaatgtcag    360
aagcttacag atgaccatgt tcagttcctt atctaccaaa ttctccgagg tctaaagtat    420
atacattcag ctgacataat tcacagggac ctaaaaccta gtaatctagc tgtgaatgaa    480
gactgtgagc tgaagattct ggattttgga ctggctcggc acacagatga tgaaatgaca    540
ggctacgtgg ccactaggtg gtacagggct cctgagatca tgctgaactg gatgcattac    600
aaccagacag ttgatatttg gtcagtggga tgcataatgg ccgagctgtt gactggaaga    660
acattgtttc ctggtacaga ccatattgat cagttgaagc tcattttaag actcgttgga    720
accccagggg ctgagctttt gaagaaaatc tcctcagagt ctctgtcgac ttgctggaga    780
agatgcttgt attggactca gataagagaa ttacagcggc ccaagccctt gcacatgcct    840
actttgctca gtaccacgat cctgatgatg aaccagtggc cgatccttat gatcagtcct    900
ttgaaagcag ggacctcctt atagatgagt ggaaaagcct gacctatgat gaagtcatca    960
gctttgtgcc accacccctt gaccaagaag agatggagtc ctgagcacct ggtttctgtt   1020
ctgttgatcc cacttcactg aggggaaggc cttttcacgg gaac                    1064
```

<210> SEQ ID NO 20
<211> LENGTH: 3352
<212> TYPE: DNA
<213> ORGANISM: Mus musculus

<400> SEQUENCE: 20

```
aggaggaccg cggcgggagc agcctcgagc cgtgcagccg gctccggcac cttgccgacg     60
ctcgtaggag ccgccgcggc tgacaggggc ggcgggtcgc agcctccaca cctgcgcggg    120
tggcgggcgc ggggtccggt ctgccgcggg cgggcgcaga ggagagcgtg cggctgcagg    180
caggagcccc cgctcggcca cctcctcgcc ccgctgctgc cgctggaaga tgtcgcagga    240
gaggcccacg ttctaccggc aggagctgaa caagaccatc tgggaggtgc ccgaacgata    300
ccagaacctg tccccggtgg gctcgggcgc ctatggctcg gtgtgtgctg cttttgatac    360
aaagacgggg catcgtgtgg cagttaagaa gctgtcgaga ccgtttcagt ccatcattca    420
cgccaaaagg acctaccgag agttgcgtct gctgaagcac atgaaacacg aaaatgtgat    480
tggtctgttg gatgtgttca cacccgcaag gtcactggag gaattcaatg acgtgtacct    540
ggtgacccat ctcatggggg cggacctgaa caacatcgtg aagtgccaga agctgaccga    600
cgaccacgtt cagtttctca tctaccagat cctccgaggg ctgaagtata tacattcggc    660
tgacataatt cacagggacc taaagcccag caacctagct gtgaacgaag actgtgagct    720
caagattctg gattttgggc tggctcggca cactgatgat gagatgacag gctacgtggc    780
taccaggtgg taccgagccc cagagatcat gctgaattgg atgcactata accagacagt    840
ggatatttgg tccgtgggct gcatcatggc tgagctgttg accggaagaa cgttgtttcc    900
tggtacagac catattaacc agcttcagca gataatgcgt atgacgggga cacccccctgc   960
ttatctcatt aacaggatgc caagccatga ggcaagaaac tacattcagt ctctggccca   1020
gatgccgaag atgaacttcg caaatgtatt tattggtgcc aatcccctgg ctgtcgacct   1080
```

-continued

```
actggagaag atgctcgttt tggactcaga taagaggatc acagcagccc aagctcttgc   1140
gcatgcctac tttgctcagt accacgaccc tgatgatgag cctgttgctg acccttatga   1200
ccagtccttt gaaagcaggg accttctcat agatgagtgg aagagcctga cctatgatga   1260
agtcatcagc tttgtgccac cacccttga ccaagaagaa atggagtcct gagcacctgg   1320
tttctgttct gtctatctca cttcactgtg aggggaagac cttctcatgg gaactctcca   1380
aataccattc aagtgcctct tgttgaaaga ttccttcatg gtggaagggg gtgcatgtat   1440
gtgttagtgt ttgtgtgtgt gtgtgtgtct gtctgttcgt ctgtccacct atctttgtgg   1500
aagtcactgt gatggtagtg actttatgag ttgtgaatgg tccttggcag tctgcctgct   1560
ttctcagagt ctgggcaggc cgatgggaac tgtcatctcc ttagggatgt gtgtgttcag   1620
tgcaaagtaa gaaatatgaa aatatccctg ttcttagtta ccttgccact ttggcttctc   1680
ctgtggccct gcctttacca tatcagtgac agagagaggc tgcttcaggt ctgaggctat   1740
ccctcagcca tgcataaagt ccaagagaac caactggctc ctggtctcta gcctgtgacc   1800
ggcttgctta atgtcctcag aacctgacag gtatgttcaa aactgtcagt ctgtttgtgc   1860
cttaaaaggg tgagaagggc gcgtagatag ttacagagtc tcagctgctg acgttctgag   1920
ccaggcaagt gcacggggct gttggatggc cagtggggag ctggaaaaaa caaggcagcc   1980
tttaggaagg ccatggtgca tgtgtgtgca tgcgtgtatg tgcagccgcc ctccctcact   2040
tcaggagcaa gctgtttgct gtgcttaccc ttcacctcag tgcagaggtc tccagtgccg   2100
agcacaggca cctgccatca gtagttcctg tgtcatcttc acatctagca gagcacggat   2160
gtgtttgcat gctgtgctct tggagcttgt cctgtcttct ggaagccctg gacaaggcgt   2220
gtgaaggctt cccagaagtt cctgtccaca ttgcctccgc ccaccgacgc catgggcaca   2280
ctgctccctc ctcctcctcc agctactttg tgttgaacac aattgattct ccaggtgctc   2340
atggtgcagg aaaacaggac agacagagag cactgaaccc ttgccatctg atgtcaccaa   2400
ttcaggaaaa cgagtcctct cctaggacta tccccggttc tggaaatcat gttctcctca   2460
ctcatggtga caagctaaga aagctgaaca aagggagaga cgagagcgcc tgaagccagg   2520
agctccttta ctatctttct caaaagggtt gttagacaca aaccaagtca tcaaggcccc   2580
gctcctctcc tcggaagggt cccccacccc ccggcagctt gacactgaat ccagtgtcaa   2640
tttggggaga aagcagtttt gtcttggaat tttgtatgtt gtaggaatcc ttagagagtg   2700
tggttccttc tgatggggag aaagggcaaa ttattttaat attttgtatt ttcaccttta   2760
taaacatgaa tcctcagggg tgaagaactg tttgcataat tttctgaatt ttgagcactt   2820
tgtgctatat aaggacccat atttaagctt tgtgtgcagt aagaaagtgt aaagccaatt   2880
ccagtgttgg acgtgacagg tcttgtgttt aggtcaaggt gtctcctctc agtgcaggga   2940
catgcctgct ctgtggggca ggcgaggacc ctgaatcatt tggagcccag aaggaggcag   3000
actggccagg tctcaccacc tcagtgtgca gttcaactcc atgccatccc atcaagatgg   3060
gttagtagca gtgtctgttt ttgaatgcca agtgtgattt ccaacaattc tgctctggtt   3120
atttcattga agacatcttt gcacatgtga ccatgctgtg ttaggggctg tgttccaggg   3180
actggactcg aagctagaac tggcagaaga gttctggcat ccacagcgca atgctgccac   3240
cacccagttt cttcatcaga agacaaggga acgagaaaac tgctgttcgt ttgtatttgt   3300
gaacttggct gtaatctggt atgccatagg atgtcagata ataccactgg tt           3352
```

<210> SEQ ID NO 21

<211> LENGTH: 6641
<212> TYPE: DNA
<213> ORGANISM: Homo sapiens

<400> SEQUENCE: 21
gccctcgccg cccgcggcgc cccgagcgct ttgtgagcag atgcggagcc gagtggaggg 60
cgcgagccag atgcggggcg acagctgact tgctgagagg aggcggggag gcgcggagcg 120
cgcgtgtggt ccttgcgccg ctgacttctc cactggttcc tgggcaccga aagataaacc 180
tctcataatg aaggcccccg ctgtgcttgc acctggcatc ctcgtgctcc tgtttacctt 240
ggtgcagagg agcaatgggg agtgtaaaga ggcactagca aagtccgaga tgaatgtgaa 300
tatgaagtat cagcttccca acttcaccgc ggaaacaccc atccagaatg tcattctaca 360
tgagcatcac attttccttg gtgccactaa ctacatttat gttttaaatg aggaagacct 420
tcagaaggtt gctgagtaca agactgggcc tgtgctggaa cacccagatt gtttcccatg 480
tcaggactgc agcagcaaag ccaatttatc aggaggtgtt tggaaagata acatcaacat 540
ggctctagtt gtcgacacct actatgatga tcaactcatt agctgtggca gcgtcaacag 600
agggacctgc cagcgacatg tctttcccca caatcatact gctgacatac agtcggaggt 660
tcactgcata ttctccccac agatagaaga gcccagccag tgtcctgact gtgtggtgag 720
cgccctggga gccaaagtcc tttcatctgt aaaggaccgg ttcatcaact tctttgtagg 780
caataccata aattcttctt atttcccaga tcatccattg cattcgatat cagtgagaag 840
gctaaaggaa acgaaagatg gttttatgtt tttgacggac cagtcctaca ttgatgtttt 900
acctgagttc agagattctt accccattaa gtatgtccat gcctttgaaa gcaacaattt 960
tatttacttc ttgacggtcc aaagggaaac tctagatgct cagacttttc acacaagaat 1020
aatcaggttc tgttccataa actctggatt gcattcctac atggaaatgc ctctggagtg 1080
tattctcaca gaaaagagaa aaaagagatc cacaaagaag gaagtgttta atatacttca 1140
ggctgcgtat gtcagcaagc ctggggccca gcttgctaga caaataggag ccagcctgaa 1200
tgatgacatt cttttcgggg tgttcgcaca aagcaagcca gattctgccg aaccaatgga 1260
tcgatctgcc atgtgtgcat tccctatcaa atatgtcaac gacttcttca acaagatcgt 1320
caacaaaaac aatgtgagat gtctccagca tttttacgga cccaatcatg agcactgctt 1380
taataggaca cttctgagaa attcatcagg ctgtgaagcg cgccgtgatg aatatcgaac 1440
agagtttacc acagctttgc agcgcgttga cttattcatg ggtcaattca gcgaagtcct 1500
cttaacatct atatccacct tcattaaagg agacctcacc atagctaatc ttgggacatc 1560
agagggtcgc ttcatgcagg ttgtggtttc tcgatcagga ccatcaaccc ctcatgtgaa 1620
ttttctcctg gactcccatc cagtgtctcc agaagtgatt gtggagcata cattaaacca 1680
aaatggctac acactggtta tcactgggaa gaagatcacg aagatcccat tgaatggctt 1740
gggctgcaga catttccagt cctgcagtca atgcctctct gccccaccct ttgttcagtg 1800
tggctggtgc cacgacaaat gtgtgcgatc ggaggaatgc ctgagcggga catggactca 1860
acagatctgt ctgcctgcaa tctacaaggt tttcccaaat agtgcacccc ttgaaggagg 1920
gacaaggctg accatatgtg gctgggactt tggatttcgg aggaataata aatttgattt 1980
aaagaaaact agagttctcc ttggaaatga gagctgcacc ttgactttaa gtgagagcac 2040
gatgaataca ttgaaatgca cagttggtcc tgccatgaat aagcatttca atatgtccat 2100
aattatttca aatggccacg ggacaacaca atacagtaca ttctcctatg tggatcctgt 2160
aataacaagt atttcgccga aatacggtcc tatggctggt ggcactttac ttactttaac 2220

-continued

```
tggaaattac ctaaacagtg ggaattctag acacatttca attggtggaa aaacatgtac   2280
tttaaaaagt gtgtcaaaca gtattcttga atgttatacc ccagcccaaa ccatttcaac   2340
tgagtttgct gttaaattga aaattgactt agccaaccga gagacaagca tcttcagtta   2400
ccgtgaagat cccattgtct atgaaattca tccaaccaaa tcttttatta gtggtgggag   2460
cacaataaca ggtgttggga aaaacctgaa ttcagttagt gtcccgagaa tggtcataaa   2520
tgtgcatgaa gcaggaagga actttacagt ggcatgtcaa catcgctcta attcagagat   2580
aatctgttgt accactcctt ccctgcaaca gctgaatctg caactccccc tgaaaaccaa   2640
agccttttc atgttagatg ggatcctttc caaatacttt gatctcattt atgtacataa   2700
tcctgtgttt aagccttttg aaaagccagt gatgatctca atgggcaatg aaaatgtact   2760
ggaaattaag ggaaatgata ttgaccctga agcagttaaa ggtgaagtgt taaaagttgg   2820
aaataagagc tgtgagaata tacacttaca ttctgaagcc gttttatgca cggtccccaa   2880
tgacctgctg aaattgaaca gcgagctaaa tatagagtgg aagcaagcaa tttcttcaac   2940
cgtccttgga aaagtaatag ttcaaccaga tcagaatttc acaggattga ttgctggtgt   3000
tgtctcaata tcaacagcac tgttattact acttgggttt ttcctgtggc tgaaaaagag   3060
aaagcaaatt aaagatctgg gcagtgaatt agttcgctac gatgcaagag tacacactcc   3120
tcatttggat aggcttgtaa gtgcccgaag tgtaagccca actacagaaa tggtttcaaa   3180
tgaatctgta gactaccgag ctacttttcc agaagatcag tttcctaatt catctcagaa   3240
cggttcatgc cgacaagtgc agtatcctct gacagacatg tcccccatcc taactagtgg   3300
ggactctgat atatccagtc cattactgca aaatactgtc cacattgacc tcagtgctct   3360
aaatccagag ctggtccagg cagtgcagca tgtagtgatt gggcccagta gcctgattgt   3420
gcatttcaat gaagtcatag gaagagggca ttttggttgt gtatatcatg ggactttgtt   3480
ggacaatgat ggcaagaaaa ttcactgtgc tgtgaaatcc ttgaacagaa tcactgacat   3540
aggagaagtt tcccaatttc tgaccgaggg aatcatcatg aaagatttta gtcatcccaa   3600
tgtcctctcg ctcctgggaa tctgcctgcg aagtgaaggg tctccgctgg tggtcctacc   3660
atacatgaaa catggagatc ttcgaaattt cattcgaaat gagactcata atccaactgt   3720
aaaagatctt attggctttg gtcttcaagt agccaaaggc atgaaatatc ttgcaagcaa   3780
aaagtttgtc cacagagact tggctgcaag aaactgtatg ctggatgaaa aattcacagt   3840
caaggttgct gattttggtc ttgccagaga catgtatgat aaagaatact atagtgtaca   3900
caacaaaaca ggtgcaaagc tgccagtgaa gtggatggct ttggaaagtc tgcaaactca   3960
aaagtttacc accaagtcag atgtgtggtc ctttggcgtg ctcctctggg agctgatgac   4020
aagaggagcc ccaccttatc ctgacgtaaa cacctttgat ataactgttt acttgttgca   4080
agggagaaga ctcctacaac ccgaatactg cccagacccc ttatatgaag taatgctaaa   4140
atgctggcac cctaaagccg aaatgcgccc atccttttct gaactggtgt cccggatatc   4200
agcgatcttc tctactttca ttggggagca ctatgtccat gtgaacgcta cttatgtgaa   4260
cgtaaaatgt gtcgctccgt atccttctct gttgtcatca gaagataacg ctgatgatga   4320
ggtggacaca cgaccagcct ccttctggga gacatcatag tgctagtact atgtcaaagc   4380
aacagtccac actttgtcca atggtttttt cactgcctga cctttaaaag gccatcgata   4440
ttctttgctc ttgccaaaat tgcactatta taggacttgt attgttattt aaattactgg   4500
attctaagga atttcttatc tgacagagca tcagaaccag aggcttggtc ccacaggcca   4560
```

cggaccaatg gcctgcagcc gtgacaacac tcctgtcata ttggagtcca aaacttgaat 4620
tctgggttga attttttaaa aatcaggtac cacttgattt catatgggaa attgaagcag 4680
gaaatattga gggcttcttg atcacagaaa actcagaaga gatagtaatg ctcaggacag 4740
gagcggcagc cccagaacag gccactcatt tagaattcta gtgtttcaaa acacttttgt 4800
gtgttgtatg gtcaataaca tttttcatta ctgatggtgt cattcaccca ttaggtaaac 4860
attccctttt aaatgtttgt ttgtttttttg agacaggatc tcactctgtt gccagggctg 4920
tagtgcagtg gtgtgatcat agctcactgc aacctccacc tcccaggctc aagcctcccg 4980
aatagctggg actacaggcg cacaccacca tccccggcta atttttgtat tttttgtaga 5040
gacggggttt tgccatgttg ccaaggctgg tttcaaactc ctggactcaa gaaatccacc 5100
cacctcagcc tcccaaagtg ctaggattac aggcatgagc cactgcgccc agcccttata 5160
aatttttgta tagacattcc tttggttgga agaatattta taggcaatac agtcaaagtt 5220
tcaaaatagc atcacacaaa acatgtttat aaatgaacag gatgtaatgt acatagatga 5280
cattaagaaa atttgtatga aataatttag tcatcatgaa atatttagtt gtcatataaa 5340
aacccactgt ttgagaatga tgctactctg atctaatgaa tgtgaacatg tagatgtttt 5400
gtgtgtattt ttttaaatga aaactcaaaa taagacaagt aatttgttga taaatatttt 5460
taaagataac tcagcatgtt tgtaaagcag gatacatttt actaaaaggt tcattggttc 5520
caatcacagc tcataggtag agcaaagaaa gggtggatgg attgaaaaga ttagcctctg 5580
tctcggtggc aggttcccac ctcgcaagca attggaaaca aaacttttgg ggagttttat 5640
tttgcattag ggtgtgtttt atgttaagca aaacatactt tagaaacaaa tgaaaaaggc 5700
aattgaaaat cccagctatt tcacctagat ggaatagcca ccctgagcag aactttgtga 5760
tgcttcattc tgtggaattt tgtgcttgct actgtatagt gcatgtggtg taggttactc 5820
taactggttt tgtcgacgta aacatttaaa gtgttatatt ttttataaaa atgtttattt 5880
ttaatgatat gagaaaaatt ttgttaggcc acaaaaacac tgcactgtga acattttaga 5940
aaaggtatgt cagactggga ttaatgacag catgattttc aatgactgta aattgcgata 6000
aggaaatgta ctgattgcca atacacccca ccctcattac atcatcagga cttgaagcca 6060
agggttaacc cagcaagcta caaagagggt gtgtcacact gaaactcaat agttgagttt 6120
ggctgttgtt gcaggaaaat gattataact aaaagctctc tgatagtgca gagacttacc 6180
agaagacaca aggaattgta ctgaagagct attacaatcc aaatattgcc gtttcataaa 6240
tgtaataagt aatactaatt cacagagtat tgtaaatggt ggatgacaaa agaaaatctg 6300
ctctgtggaa agaaagaact gtctctacca gggtcaagag catgaacgca tcaatagaaa 6360
gaactcgggg aaacatccca tcaacaggac tacacacttg tatatacatt cttgagaaca 6420
ctgcaatgtg aaaatcacgt ttgctattta taaacttgtc cttagattaa tgtgtctgga 6480
cagattgtgg gagtaagtga ttcttctaag aattagatac ttgtcactgc ctatacctgc 6540
agctgaactg aatggtactt cgtatgttaa tagttgttct gataaatcat gcaattaaag 6600
taaagtgatg caacatcttg taaaaaaaaa aaaaaaaaaa a 6641

<210> SEQ ID NO 22
<211> LENGTH: 3843
<212> TYPE: DNA
<213> ORGANISM: Danio rerio

<400> SEQUENCE: 22
atggggggtg cgcgccgaat atgtgcggac gctcccgaca ccgctggctg ggcagatgag 60

-continued

```
cggtaccaaa cgcgcaccag tctgccatta cacaaaggat tcccacggca atccgatgga    120
ctctgcacag aaaggggtcg actaattaca gtcttactcg acacccccgg attcaccaag    180
gataactggc ttgagaggga tgacacgact gagcacaatc tacgtgacat gggattcctg    240
aagacacatc tcgtttttgg gattgtctta ctaggggtgt tttcagatgt ctcgaagcca    300
tggctagtta cggataaaga gaaagaggaa ttcatgctga caccacattc cgactttaac    360
atcacttgct ttggaatgag gagagtaact tgggtcgaac cattaccgtt caacatcaaa    420
gttcattctg gatttaacta cagtacttta atgatcactg atgcggtggc ctctaacact    480
cgtttctaca cctgccagca tgaggatcat tctgaaactg aaactgatat ctacattttt    540
gttcaagatc ccgatgttcc atttgtgtct gaacacgatg ctgagacaga tgaaataggc    600
acaacaatcc cctgccacgt aacaaaccca cattctgaag tgatgctcag agatctgcag    660
agcggggatg aggttactgt gctttatgac ccccaaacttg gcttttttgg tacaataccg    720
ccaggacaat acgtctgtga gacaactgtg aatggcaaaa cagtgcggag catcgtttat    780
aatgtgacaa atgacatggc tactgacgtt cctgaggttg tagaccagaa cttcagcatc    840
cagctgagcg ccagtatgga ggatttgaaa gagggagatt cagtcaacct cacctgtgag    900
actcctgctg gaatggcttt ccaccagcag tggctgcatc cccaaaaaca ggccaaagac    960
ggggtcccaa taaagttaac tctccaagat aagatccagt acatcctcaa catcccaaaa   1020
gcttctgtgg aagacaccgg acgctatgag tgttctgtga caaaccagct tactagacaa   1080
accaggtcca aaagcctggg catcacagtt cacgagagct catttgtgga aattatatct   1140
aatggtattg ggccagtgga ggttgtgtct cttctggagg aaaaagagtt cactatttac   1200
attgatgctg accctgagcc aaaggtcaca tggtttaaag atggacagcc attggaggac   1260
agctacatct tctctaagac cactcatcta gaaaacctca ggtatgaaaa tattctgatt   1320
ctccgacacc ctgtagaaga agacagcggc atttatgaga tcgttgcttc caccggctcc   1380
aggacttcac aattttcatt caaactcctc attgaagtca tgttcccggt gctgccacag   1440
tcagttcagg ctccactgat ttggccccag agggagagta tggaggtgtc tctgcactcc   1500
actttcagac tcacatgtcg aggtcaagcc gagctctcct ggaatggccc tgtttttatt   1560
gatgaccaga ccaacagtgt aaagaaagga ctctttatta gcactgtgac aattagcaat   1620
gccacagctg tccatacagg agagtacgtc tgctcttctg aacccttcaa cagcactgag   1680
tcaaccatct atatttatgt gccagatcca caaaccccat ttgtgccgtc catgaccccg   1740
tttgaaaacc acgtgctgac gagttatgat gaaatggaga ttccctgccg tgtgacggat   1800
cccagtgcca gcgtctctct catccacatg gagaccgatc aagttatgcc cagcgcctac   1860
gacagcaaga gaggattcat cgggctcttc ggcgctggga cgtatgtctg ccgagccctc   1920
attcatggac agaatcatga cagcattgag tacattgttc atggatggac aggagggtct   1980
gatttgcgag tggagctgcg ggcagtgaag agaactctgc tggtgggtga gactatcact   2040
gttgactgtg tagccaaagg cagtgagatg ctggaggacc actggaaata ccctggcaaa   2100
ctggctaatc gtggaacaaa gactgtaaag gagaataagc taaatctgga gatctattat   2160
actctgacag tgactaatgc ctcaccaaaa gacagcggca tctatgcctg ctccatcact   2220
gacatcatga gcaacgagag ccaaaccaaa gagctgacta ttactgtcta tgatcatgaa   2280
tttgtccaca tcaatccatt gatcggtcca gtggaaactg ccaggctgga cgaggtgcca   2340
gagtttaaag tggacataga gtctttccct gcacccaaag ttacatggtt aaaggacagc   2400
```

-continued

```
gctgtcctgg gagatgatac tgcagagatc agcaccaacc tcctcaaaat cggcgagacc   2460
agttacaagg gtgtgttgaa cctgatcaga gctaaagcag aggacagtgg aaactacacc   2520
gtcaaggcag aaataggcag cataagtacc agctacagtt tctaccttca ggttaaagtt   2580
ccccctgtga ttgtggacct gatggacgtc catcatggtt ctgctgcggg tcaggaagtg   2640
gtatgcactg ctggcggctc ccccattccct gaagtggact ggtatatctg caaaaacctt   2700
aaacactgtg ccaatgattc ctcccagtgg atgccacttc cgatcaactc gacggacatc   2760
acagtggaac tgcaaatgaa tgtggacaac cacattgaga gccacattat tttccaccat   2820
cttgagggca cagtcgctgt gcgctgtctg gccaggaatg acatgggtgt tgtttcacgg   2880
gaggttaaac tcatgtcaag tggtccgcat tcggagctca ctgtggctgc tgcggttctg   2940
gtgctgctgg tcattgtcat catctcactc attgtgctgg tcattatatg gaaacagaaa   3000
ccacgttatg agattagatg gcgcgtgatt gaatcagtca gtccggatgg gcacgagtac   3060
atctatgtcg atcccatgca gcttccatat gattcccgct gggagttccc tcgggatgga   3120
ctcgttctgg gtcgcgtcct gggttcagga gcttttggta aagtggtgga gggtactgct   3180
tatggactaa gccgttctca gcctgtgatg aaagttgctg tgaaaatgct taagccgacc   3240
gcccgttcca gtgagaaaca agctttgatg tcagagctga aaatcatgac ccatctgggc   3300
cctcacctaa acattgttaa ccttctggga gcgtgtacca aatcaggacc aatctacatt   3360
ataacagagt attgtttcta tggagatctg gtgaattacc ttcataagaa cagagatggg   3420
tttctcagcc ggcacacaga aaagggaaag aaagatctag acatctttgg catcaaccca   3480
gccgatgaga gcagcaggag ctatgtcatc ctgtctttcg aggggaaagg tgattatatg   3540
gacatgaagc aggcagacac catgcagtac gtccccatgc tggaaatgaa tgaagcctca   3600
aaatactctc ccatccagag atcagactac gaccatcctc cctctcacag acaattcaat   3660
ggagaagctg taaggggcca gtgcattgtg gaattaggtg gtggtcgaag ctgtgatgca   3720
acacctgtgg tgccttttgt ggacacaaac ccggtggtgg acaccgatag taagggatgc   3780
tgtcaagctg aaggaggagt cttaccaggc ttgattggct tgtgggactc cagaggcatc   3840
tga                                                                 3843
```

<210> SEQ ID NO 23
<211> LENGTH: 5718
<212> TYPE: DNA
<213> ORGANISM: Homo sapiens

<400> SEQUENCE: 23

```
ctcctgaggc tgccagcagc cagcagtgac tgcccgccct atctgggacc caggatcgct     60
ctgtgagcaa cttggagcca gagaggagat caacaaggag gaggagagag ccggcccctc    120
agccctgctg cccagcagca gcctgtgctc gccctgccca acgcagacag ccagacccag    180
ggcggcccct ctggcggctc tgctcctccc gaaggatgct tggggagtga ggcgaagctg    240
ggccgctcct ctcccctaca gcagccccct tcctccatcc ctctgttctc ctgagccttc    300
aggagcctgc accagtcctg cctgtccttc tactcagctg ttacccactc tgggaccagc    360
agtctttctg ataactggga gagggcagta aggaggactt cctggagggg gtgactgtcc    420
agagcctgga actgtgccca caccagaagc catcagcagc aaggacacca tgcggcttcc    480
gggtgcgatg ccagctctgg ccctcaaagg cgagctgctg ttgctgtctc tcctgttact    540
tctggaacca cagatctctc agggcctggt cgtcacaccc ccggggccag agcttgtcct    600
caatgtctcc agcaccttcg ttctgacctg ctcgggttca gctccggtgg tgtgggaacg    660
```

-continued

```
gatgtcccag gagcccccac aggaaatggc caaggcccag gatggcacct tctccagcgt    720
gctcacactg accaacctca ctgggctaga cacgggagaa tacttttgca cccacaatga    780
ctcccgtgga ctggagaccg atgagcggaa acggctctac atctttgtgc cagatcccac    840
cgtgggcttc ctccctaatg atgccgagga actattcatc tttctcacgg aaataactga    900
gatcaccatt ccatgccgag taacagaccc acagctggtg gtgacactgc acgagaagaa    960
aggggacgtt gcactgcctg tcccctatga tcaccaacgt ggcttttctg gtatctttga   1020
ggacagaagc tacatctgca aaaccaccat tggggacagg gaggtggatt ctgatgccta   1080
ctatgtctac agactccagg tgtcatccat caacgtctct gtgaacgcag tgcagactgt   1140
ggtccgccag ggtgagaaca tcaccctcat gtgcattgtg atcgggaatg aggtggtcaa   1200
cttcgagtgg acatacccccc gcaaagaaag tgggcggctg gtggagccgg tgactgactt   1260
cctcttggat atgccttacc acatccgctc catcctgcac atccccagtg ccgagttaga   1320
agactcgggg acctacacct gcaatgtgac ggagagtgtg aatgaccatc aggatgaaaa   1380
ggccatcaac atcaccgtgg ttgagagcgg ctacgtgcgg ctcctgggag aggtgggcac   1440
actacaattt gctgagctgc atcggagccg gacactgcag gtagtgttcg aggcctaccc   1500
accgcccact gtcctgtggt tcaaagacaa ccgcaccctg ggcgactcca gcgctggcga   1560
aatcgccctg tccacgcgca acgtgtcgga gacccggtat gtgtcagagc tgacactggt   1620
tcgcgtgaag gtggcagagg ctggccacta caccatgcgg gccttccatg aggatgctga   1680
ggtccagctc tccttccagc tacagatcaa tgtccctgtc cgagtgctgg agctaagtga   1740
gagccaccct gacagtgggg aacagacagt ccgctgtcgt ggccggggca tgccccagcc   1800
gaacatcatc tggtctgcct gcagagacct caaaaggtgt ccacgtgagc tgccgcccac   1860
gctgctgggg aacagttccg aagaggagag ccagctggag actaacgtga cgtactggga   1920
ggaggagcag gagtttgagg tggtgagcac actgcgtctg cagcacgtgg atcggccact   1980
gtcggtgcgc tgcacgctgc gcaacgctgt gggccaggac acgcaggagg tcatcgtggt   2040
gccacactcc ttgcccttta aggtggtggt gatctcagcc atcctggccc tggtggtgct   2100
caccatcatc tcccttatca tcctcatcat gctttggcag aagaagccac gttacgagat   2160
ccgatggaag gtgattgagt ctgtgagctc tgacggccat gagtacatct acgtggaccc   2220
catgcagctg ccctatgact ccacgtggga gctgccgcgg gaccagcttg tgctgggacg   2280
caccctcggc tctggggcct ttgggcaggt ggtggaggcc acggctcatg gcctgagcca   2340
ttctcaggcc acgatgaaag tggccgtcaa gatgcttaaa tccacagccc gcagcagtga   2400
gaagcaagcc cttatgtcgg agctgaagat catgagtcac cttgggcccc acctgaacgt   2460
ggtcaacctg ttgggggcct gcaccaaagg aggacccatc tatatcatca ctgagtactg   2520
ccgctacgga gacctggtgg actacctgca ccgcaacaaa cacaccttcc tgcagcacca   2580
ctccgacaag cgccgcccgc ccagcgcgga gctctacagc aatgctctgc ccgttgggct   2640
ccccctgccc agccatgtgt ccttgaccgg ggagagcgac ggtggctaca tggacatgag   2700
caaggacgag tcggtggact atgtgcccat gctggacatg aaaggagacg tcaaatatgc   2760
agacatcgag tcctccaact acatggcccc ttacgataac tacgttccct ctgcccctga   2820
gaggacctgc cgagcaactt tgatcaacga gtctccagtg ctaagctaca tggacctcgt   2880
gggcttcagc taccaggtgg ccaatggcat ggagtttctg gcctccaaga actgcgtcca   2940
cagagacctg gcggctagga acgtgctcat ctgtgaaggc aagctggtca agatctgtga   3000
```

-continued

```
ctttggcctg gctcgagaca tcatgcggga ctcgaattac atctccaaag gcagcacctt   3060
tttgccttta aagtggatgg ctccggagag catcttcaac agcctctaca ccaccctgag   3120
cgacgtgtgg tccttcggga tcctgctctg ggagatcttc accttgggtg gcacccctta   3180
cccagagctg cccatgaacg agcagttcta caatgccatc aaacggggtt accgcatggc   3240
ccagcctgcc catgcctccg acgagatcta tgagatcatg cagaagtgct gggaagagaa   3300
gtttgagatt cggcccccct tctcccagct ggtgctgctt ctcgagagac tgttgggcga   3360
aggttacaaa aagaagtacc agcaggtgga tgaggagttt ctgaggagtg accacccagc   3420
catccttcgg tcccaggccc gcttgcctgg gttccatggc ctccgatctc ccctggacac   3480
cagctccgtc ctctatactg ccgtgcagcc caatgagggt gacaacgact atatcatccc   3540
cctgcctgac cccaaacccg aggttgctga cgagggccca ctggagggtt cccccagcct   3600
agccagctcc accctgaatg aagtcaacac ctcctcaacc atctcctgtg acagcccccct   3660
ggagccccag gacgaaccag agccagagcc ccagcttgag ctccaggtgg agccggagcc   3720
agagctggaa cagttgccgg attcggggtg ccctgcgcct cgggcggaag cagaggatag   3780
cttcctgtag gggggctggcc cctaccctgc cctgcctgaa gctccccccc tgccagcacc   3840
cagcatctcc tggcctggcc tgaccgggct tcctgtcagc caggctgccc ttatcagctg   3900
tccccttctg gaagctttct gctcctgacg tgttgtgccc caaaccctgg ggctggctta   3960
ggaggcaaga aaactgcagg ggccgtgacc agccctctgc ctccagggag gccaactgac   4020
tctgagccag ggttccccca gggaactcag ttttcccata tgtaagatgg gaaagttagg   4080
cttgatgacc cagaatctag gattctctcc ctggctgaca ggtggggaga ccgaatccct   4140
ccctgggaag attcttggag ttactgaggt ggtaaattaa ctttttctg ttcagccagc   4200
taccccctcaa ggaatcatag ctctctcctc gcacttttat ccacccagga gctagggaag   4260
agaccctagc ctccctggct gctggctgag ctagggccta gccttgagca gtgttgcctc   4320
atccagaaga aagccagtct cctccctatg atgccagtcc ctgcgttccc tggcccgagc   4380
tggtctgggg ccattaggca gcctaattaa tgctggaggc tgagccaagt acaggacacc   4440
cccagcctgc agcccttgcc cagggcactt ggagcacacg cagccatagc aagtgcctgt   4500
gtccctgtcc ttcaggccca tcagtcctgg ggctttttct ttatcaccct cagtcttaat   4560
ccatccacca gagtctagaa ggccagacgg gccccgcatc tgtgatgaga atgtaaatgt   4620
gccagtgtgg agtggccacg tgtgtgtgcc agtatatggc cctggctctg cattggacct   4680
gctatgaggc tttggaggaa tccctcaccc tctctgggcc tcagtttccc cttcaaaaaa   4740
tgaataagtc ggacttatta actctgagtg ccttgccagc actaacattc tagagtattc   4800
caggtggttg cacatttgtc cagatgaagc aaggccatat accctaaact tccatcctgg   4860
gggtcagctg ggctcctggg agattccaga tcacacatca cactctgggg actcaggaac   4920
catgcccctt ccccaggccc ccagcaagtc tcaagaacac agctgcacag gccttgactt   4980
agagtgacag ccggtgtcct ggaaagcccc cagcagctgc cccagggaca tgggaagacc   5040
acgggacctc tttcactacc cacgatgacc tccgggggta tcctgggcaa aagggacaaa   5100
gagggcaaat gagatcacct cctgcagccc accactccag cacctgtgcc gaggtctgcg   5160
tcgaagacag aatggacagt gaggacagtt atgtcttgta aaagacaaga agcttcagat   5220
gggtacccca agaaggatgt gagaggtggg cgctttggag gtttgcccct cacccaccag   5280
ctgccccatc cctgaggcag cgctccatgg gggtatggtt ttgtcactgc ccagacctag   5340
cagtgacatc tcattgtccc cagcccagtg ggcattggag gtgccagggg agtcagggtt   5400
```

gtagccaaga cgcccccgca cggggagggt tgggaagggg gtgcaggaag ctcaacccct 5460
ctgggcacca accctgcatt gcaggttggc accttacttc cctgggatcc ccagagttgg 5520
tccaaggagg gagagtgggt tctcaatacg gtaccaaaga tataatcacc taggtttaca 5580
aatattttta ggactcacgt taactcacat ttatacagca gaaatgctat tttgtatgct 5640
gttaagtttt tctatctgtg tacttttttt taagggaaag attttaatat taaacctggt 5700
gcttctcact cacaaaaa 5718

<210> SEQ ID NO 24
<211> LENGTH: 1883
<212> TYPE: DNA
<213> ORGANISM: Homo sapiens

<400> SEQUENCE: 24
cccgcccccg cgccgggccc ggctcggccc gacccggctc cgccgcgggc aggcggggcc 60
cagcgcactc ggagcccgag cccgagccgc agccgccgcc tggggcgctt gggtcggcct 120
cgaggacacc ggagaggggc gccacgccgc cgtggccgca gatttgaaag aagccaacac 180
taaaccacaa atatacaaca aggccatttt ctcaaacgag agtcagcctt taacgaaatg 240
accatggttg acacagagat gccattctgg cccaccaact ttgggatcag ctccgtggat 300
ctctccgtaa tggaagacca ctcccactcc tttgatatca agcccttcac tactgttgac 360
ttctccagca tttctactcc acattacgaa gacattccat tcacaagaac agatccagtg 420
gttgcagatt acaagtatga cctgaaactt caagagtacc aaagtgcaat caaagtggag 480
cctgcatctc caccttatta ttctgagaag actcagctct acaataagcc tcatgaagag 540
ccttccaact ccctcatggc aattgaatgt cgtgtctgtg gagataaagc ttctggattt 600
cactatggag ttcatgcttg tgaaggatgc aagggtttct tccggagaac aatcagattg 660
aagcttatct atgacagatg tgatcttaac tgtcggatcc acaaaaaaag tagaaataaa 720
tgtcagtact gtcggtttca gaaatgcctt gcagtgggga tgtctcataa tgccatcagg 780
tttgggcgga tgccacaggc cgagaaggag aagctgttgg cggagatctc cagtgatatc 840
gaccagctga atccagagtc cgctgacctc cgggccctgg caaaacattt gtatgactca 900
tacataaagt ccttcccgct gaccaaagca aaggcgaggg cgatcttgac aggaaagaca 960
acagacaaat caccattcgt tatctatgac atgaattcct taatgatggg agaagataaa 1020
atcaagttca aacacatcac cccccctgcag gagcagagca aagaggtggc catccgcatc 1080
tttcagggct gccagtttcg ctccgtggag gctgtgcagg agatcacaga gtatgccaaa 1140
agcattcctg gttttgtaaa tcttgacttg aacgaccaag taactctcct caaatatgga 1200
gtccacgaga tcatttacac aatgctggcc tccttgatga ataaagatgg ggttctcata 1260
tccgagggcc aaggcttcat gacaagggag tttctaaaga gcctgcgaaa gccttttggt 1320
gactttatgg agcccaagtt tgagtttgct gtgaagttca atgcactgga attagatgac 1380
agcgacttgg caatatttat tgctgtcatt attctcagtg gagaccgccc aggtttgctg 1440
aatgtgaagc ccattgaaga cattcaagac aacctgctac aagccctgga gctccagctg 1500
aagctgaacc accctgagtc ctcacagctg tttgccaagc tgctccagaa aatgacagac 1560
ctcagacaga ttgtcacgga acacgtgcag ctactgcagg tgatcaagaa gacggagaca 1620
gacatgagtc ttcacccgct cctgcaggag atctacaagg acttgtacta gcagagagtc 1680
ctgagccact gccaacattt cccttcttcc agttgcacta ttctgaggga aaatctgaca 1740
cctaagaaat ttactgtgaa aaagcatttt aaaaagaaaa ggttttagaa tatgatctat 1800
tttatgcata ttgtttataa agacacattt acaatttact tttaatatta aaaattacca 1860
tattatgaaa aaaaaaaaaa aaa 1883

<210> SEQ ID NO 25
<211> LENGTH: 5449
<212> TYPE: DNA
<213> ORGANISM: Homo sapiens

<400> SEQUENCE: 25
gcgccggggg ccgccgcgcc cgccgcccgc tgcctgcgcc gccggccggg catgagttag 60
tcgcagacat ggacaccaaa catttcctgc cgctcgattt ctccacccag gtgaactcct 120
ccctcacctc cccgacgggg cgaggctcca tggctgcccc ctcgctgcac ccgtccctgg 180
ggcctggcat cggctccccg ggacagctgc attctcccat cagcaccctg agctccccca 240
tcaacggcat gggcccgcct ttctcggtca tcagctcccc catgggcccc cactccatgt 300
cggtgcccac cacacccacc ctgggcttca gcactggcag cccccagctc agctcaccta 360
tgaaccccgt cagcagcagc gaggacatca agccccccct gggcctcaat ggcgtcctca 420
aggtccccgc ccacccctca ggaaacatgg cttccttcac caagcacatc tgcgccatct 480
gcggggaccg ctcctcaggc aagcactatg gagtgtacag ctgcgagggg tgcaagggct 540
tcttcaagcg gacggtgcgc aaggacctga cctacacctg ccgcgacaac aaggactgcc 600
tgattgacaa gcggcagcgg aaccggtgcc agtactgccg ctaccagaag tgcctggcca 660
tgggcatgaa gcgggaagcc gtgcaggagg agcggcagcg tggcaaggac cggaacgaga 720
atgaggtgga gtcgaccagc agcgccaacg aggacatgcc ggtggagagg atcctggagg 780
ctgagctggc cgtggagccc aagaccgaga cctacgtgga ggcaaacatg gggctgaacc 840
ccagctcgcc gaacgaccct gtcaccaaca tttgccaagc agccgacaaa cagcttttca 900
ccctggtgga gtgggccaag cggatcccac acttctcaga gctgcccctg gacgaccagg 960
tcatcctgct gcgggcaggc tggaatgagc tgctcatcgc ctccttctcc caccgctcca 1020
tcgccgtgaa ggacgggatc ctcctggcca ccgggctgca cgtccaccgg aacagcgccc 1080
acagcgcagg ggtgggcgcc atctttgaca gggtgctgac ggagcttgtg tccaagatgc 1140
gggacatgca gatggacaag acggagctgg gctgcctgcg cgccatcgtc ctctttaacc 1200
ctgactccaa ggggctctcg aacccggccg aggtggaggc gctgagggag aaggtctatg 1260
cgtccttgga ggcctactgc aagcacaagt acccagagca gccgggaagg ttcgctaagc 1320
tcttgctccg cctgccggct ctgcgctcca tcgggctcaa atgcctggaa catctcttct 1380
tcttcaagct catcggggac acacccattg acaccttcct tatggagatg ctggaggcgc 1440
cgcaccaaat gacttaggcc tgcgggccca tcctttgtgc ccacccgttc tggccaccct 1500
gcctggacgc cagctgttct tctcagcctg agccctgtcc ctgcccttct ctgcctggcc 1560
tgtttggact ttggggcaca gcctgtcact gctctgccta agagatgtgt tgtcaccctc 1620
cttatttctg ttactacttg tctgtggccc agggcagtgg ctttcctgag gcagcagcct 1680
tcgtggcaag aactagcgtg agcccagcca ggcgcctccc caccgggctc tcaggacacc 1740
ctgccacacc ccacggggct tgggcgacta cagggtcttc gggccccagc cctggagctg 1800
caggagttgg gaacggggct tttgtttccg ttgctgttta tcgatgctgg ttttcagaat 1860
tcctgtgtgg ccctcctgtc tggagtgaca tcttcatctg ctctgaatac tggtgcccag 1920
ccagcccgtg acagcttccc cctaatcagg aggggacagc tgggggcgca agctggtgtg 1980

-continued

```
tcatcagcaa agacctcagc cgcctcgggg atgagagggg actcgtgggg caagcaagct   2040
gccctgtgct ctgagtgagg gggaaggtag ccccttttc caaagataac tcacagtttt   2100
gccctcgagc caatgagaac atgagctgcc ctctgtgcaa ggtttcgggg ccacctccag   2160
gctgcagggg cgggtcactc acccccctgt tttctctctg ccttggtgtt ctggtttcag   2220
actcccgact ccccgttcag accagagtgc cccggcccct ccccagcctg agtcttctcc   2280
ttgctctgcg gggtgggctg aggcttgtcc ttgtttcctg cagggctggc cctggctcgg   2340
gcagggtggg gcatcaccac ctcactggcc ttgctggagg cacagggctc tgcggacctg   2400
cagccatctg tgaggcccgc ggggatggga ggggaggagg gtggcctgtt ggtttccctc   2460
agaggggggca ggtggcctgg agagagaggg gctcaggaac tgggagcctc gtgggtgggg   2520
cagatgctcc gcggcctgga gtggctctgc cggggcattg gtgggacccc tgctcaggcc   2580
ttctctctgg ctgccagttg tgtctaaaag actcttggaa tctgagaacc cggagtcgca   2640
gcgccctcgg gcctgggcca cacgcaggcc ctggtgggac cacccagcct ggtattgtcc   2700
acggacagcg ttgttcaccc agagccttac ttgggagcct cactgaacgc ctgctctggt   2760
tgaaggtggg gtgggggcgg ggcttggggc ctccctggct cagcccagtg cggcctggcg   2820
ctcctcccgc aggctctgcc cccgggctcc ggtggtgcgg ggccctctca ggttgaactc   2880
gcctcttttg cactggaagg ccctcccttt ggcctgagta cttttcccgt tcacgcctca   2940
gtcccgtgga cccagccttt gtcagtggca ggtgcctgaa cagagggtgg atggggggga   3000
taccggaggg ggtcttgtct tcccagccgc agtctaggaa tgatgcgggg gggtggacgc   3060
cttctccata gtctttcccc acctggagca ggggcttcct cagtggtgag gggagctgcc   3120
tacaggttgg accgggaggc agtggcttgg agaggcagct ttccagcctt ggtggggaag   3180
aaagtgtcca ttctttgcct tcctggagct cccagccaga gctgagctta ggcacccgag   3240
tggagcctgc agctgagtct gtgcccgaga caggctgtca gagattccag aagcctctcc   3300
tccccgccgc cctccacccc tgcctttcag cgttgtggat ccctagaggt ggccccctgc   3360
ccgatccacc gtcctgaggc agagtgttga gcctcatacc tgtaccaggt ccccggccag   3420
ctgggcccct cccaggcact gccaggaagc cccagctgcc cctggcgggt gtggtggaaa   3480
tggcaggagg gtgcaggtac tcttggggcc ccagcggtgg gagtgcaaaa gacccaacgc   3540
caacacctgg tgccttttgc agccagcgcc cacccatccg tgcccggacc cttgggaatg   3600
cccgcggctc cagaggaaaa agcccaggga cggggcctcc gttgcggggg gtcggctgct   3660
tcttgggaac tttgtcgttt ccggcgctgg ctggctggct ggctgtaaag cactgaagcc   3720
ccccggccgc caacccctga aagcagaacc tggcctccct ggccacagca gccttaccca   3780
ccgctctacg tgtcccgggc acttcccgca gccttcccgt ccctttctca tcggccttgt   3840
agttgtacag tgctgttggt ttgaaaaggt gatgtgtggg gagtgcggct catcactgag   3900
tagagaggta gaatttctat ttaaccagac ctgtagtagt attaccaatc cagttcaatt   3960
aaggtgattt tttgtaatta ttattatttt ggtgggacaa tctttaattt tctaaagata   4020
gcactaacat cagctcatta gccacctgtg cctgtccccg ccttggcccg gctggatgaa   4080
gcggcttccc cgcagggccc ccacttccca gtggctgctt cctggggacc cagggcaccc   4140
cggcaccttc aggcacgctc ctcagctggt cacctcccgg ctttgccgtt cagatggggc   4200
tcctgaggct caggagtgaa gatgccacag agccgggctc ccctaggctg cgtcgggcat   4260
gcttggaagc tggcctgcca ggaccttcca ccctggggcc tgtgtcagcc gccggccctc   4320
```

-continued

```
cgcaccctgg aagcacacgg cctctgggaa ggacagccct gaccttcggt tttccgagca   4380

cggtgtttcc caagaattct gggctggcgg cctggtggca gtgctggaga tgaccccgag   4440

cccctccccg tggggcaccc aggagggccc tgccggaatg tgcagcctgt gggtagtcgg   4500

ctggtgtccc tgtcgtggag ctggggtgcg tgatctggtg ctcgtccacg caggtgtgtg   4560

gtgtaaacat gtatgtgctg tacagagaga cgcgtgtgga gagagccgca caccagcgcc   4620

acccaggaaa ggcggagcgg ttaccagtgt tttgtgttta tttttaatca agacgtttcc   4680

cctgttttcc tataaatttg cttcgtgtaa gcaagtacat aaggaccctc ctttggtgaa   4740

atccgggttc gaatgaatat ctcaaggcag gagatgcatc tattttaaga tgctttggag   4800

cagacagctt tagccgttcc caatccttag caatgcctta gctgggacgc atagctaata   4860

ctttagagag gatgacagat ccataaagag agtaaagata agagaaaatg tctaaagcat   4920

ctggaaaggt aaaaaaaaaa aatctatttt tgtacaaatg taattttatc cctcatgtat   4980

acttggatat ggcgggggga gggctgggac tgtttcgttt ctgcttctag agattgaggt   5040

gaaagcttcg tccgagaaac gccaggacag acgatggcag aggagagggc tcctgtgacg   5100

gcggcgaggc ttgggaggaa accgccgcaa tgggggtgtc ttccctcggg gcaggagggt   5160

gggcctgagg ctttcaaggg ttttcttccc tttcgagtaa tttttaaagc cttgctctgt   5220

tgtgtcctgt tgccggctct ggccttcctg tgactgactg tgaagtggct tctccgtacg   5280

attgtctctg aaacatcgtg gcctcaggtg ccagggtttg atggacagta gcattagaat   5340

tgtggaaaag gaacacgcaa agggagaagt gtgagaggag aaacaaaata tgagcgttta   5400

aaatacatcg ccattcagtt cgttaaaaaa aaaaaaaaaa aaaaaaaaa              5449
```

```
<210> SEQ ID NO 26
<211> LENGTH: 2892
<212> TYPE: DNA
<213> ORGANISM: Homo sapiens

<400> SEQUENCE: 26

caaagatggc tgccacattg gcgctgtcat tttggtactg agcagagcga cgggcttaat     60

tcgacccaat ccaggccaga gtctttctct caggggcttc ctcgtgctca gctaatcctc    120

cgatcaatcc ttgggaatcc ctgggacctc ttcggtatcc ctactctcag ccagggatca    180

tgtcttgggc cgctcgcccg cccttcctcc ctcagcggca tgccgcaggg cagtgtgggc    240

cggtgggggt gcgaaaagaa atgcattgtg gggtcgcgtc ccggtggcgg cggcgacggc    300

cctggctgga tcccgcagcg gcggcggcgg cggcggtggc aggcggagaa caacaaaccc    360

cggagccgga gccaggggag gctggacggg acgggatggg cgacagcggg cgggactccc    420

gaagcccaga cagctcctcc ccaaatcccc ttccccaggg agtccctccc ccttctcctc    480

ctgggccacc cctaccccct tcaacagctc catcccttgg aggctctggg gccccacccc    540

cacccccgat gccaccaccc ccactgggct ctccctttcc agtcatcagt tcttccatgg    600

ggtcccctgg tctgccccct ccagctcccc caggattctc cgggcctgtc agcagccccc    660

agattaactc aacagtgtca ctccctgggg gtgggtctgg ccccccctgaa gatgtgaagc    720

caccagtctt aggggtccgg ggcctgcact gtccaccccc tccaggtggc cctggggctg    780

gcaaacggct atgtgcaatc tgcggggaca gaagctcagg caaacactac ggggtttaca    840

gctgtgaggg ttgcaagggc ttcttcaaac gcaccatccg caaagacctt acatactctt    900

gccgggacaa caaagactgc acagtggaca agcgccagcg gaaccgctgt cagtactgcc    960

gctatcagaa gtgcctggcc actggcatga agagggaggc ggtacaggag gagcgtcagc   1020
```

```
ggggaaagga caaggatggg gatggggagg gggctggggg agcccccgag gagatgcctg   1080
tggacaggat cctggaggca gagcttgctg tggaacagaa gagtgaccag ggcgttgagg   1140
gtcctggggg aaccgggggt agcggcagca gcccaaatga ccctgtgact aacatctgtc   1200
aggcagctga caaacagcta ttcacgcttg ttgagtgggc gaagaggatc ccacactttt   1260
cctccttgcc tctggatgat caggtcatat tgctgcgggc aggctggaat gaactcctca   1320
ttgcctcctt ctcacaccga tccattgatg ttcgagatgg catcctcctt gccacaggtc   1380
ttcacgtgca ccgcaactca gcccattcag caggagtagg agccatcttt gatcgggtgc   1440
tgacagagct agtgtccaaa atgcgtgaca tgaggatgga caagacagag cttggctgcc   1500
tgagggcaat cattctgttt aatccagatg ccaagggcct ctccaaccct agtgaggtgg   1560
aggtcctgcg ggagaaagtg tatgcatcac tggagaccta ctgcaaacag aagtaccctg   1620
agcagcaggg acggtttgcc aagctgctgc tacgtcttcc tgccctccgg tccattggcc   1680
ttaagtgtct agagcatctg tttttcttca agctcattgg tgacaccccc atcgacacct   1740
tcctcatgga gatgcttgag gctccccatc aactggcctg agctcagacc cagacgtggt   1800
gcttctcaca ctggaggagc acacatccaa gagggactcc aagccctggg gcagggtggg   1860
gggccatgtt cccagaacct tgatggggtg agaagtacag ggcagaacca agaacataaa   1920
ccctccaagg gatctgcttg atatcccaag ttggaaggga ccccagatac ctgtgaggac   1980
tggttgtctc tcttcggtgg ccttgagtct ctgaatttgt cgggttctcc catgatttgg   2040
ggtgatttct caccctctgt ccttccccca gcacaaagca ctggccttgc ctccaggacc   2100
ttgcttcctt ctcatcttgc ctcattttgc ttcccatctg aagagtggaa atggggaact   2160
cccccagagg tggatactgg ggggcaggcc tcccaagctg atggacatga gagtagggcc   2220
ctgacaggcc ttcctcctct caaacctggc agatgggggc ctctctggaa gagggagggg   2280
ccctgtcact gtccagagtc tctttttaca cttcacctcc ttctgcagtc agactgaaat   2340
ataaaaaagg tggtggtggt ggtgaagggg ctggtggaga tgtaggaacc gatctgctat   2400
ttttaatttc ctgtgaggat agagacttgc agttagactc aaagaagtac tgtactttcc   2460
caggttgact aagaaatgcc agtggtggag gtgggtgttt gggaaaggca gggccctgaa   2520
atggcctgtc cctagggctc tccaagcact agccttccca gcttcccgcc gcccccccta   2580
tctcttcctg tctaacttgg ggaaggggcc tgggctgtga ggacagggcc cccacagggg   2640
atggtttcac gagtgtagtc ccggaggcct tccctttaca gctctcctcc agccctgggc   2700
acatagcata ggctggggac acaggatcct ggcctgagaa ttgaggggag gtggccagcc   2760
cgcagaggtg gggtgctggg gctgcatgat ttttgccctg cgtcccttct ctttggggct   2820
cctttcccct ctcatacata aaatcgcttt caaattaaaa tcgctgtttt ctggaaaaaa   2880
aaaaaaaaaa aa                                                       2892
```

```
<210> SEQ ID NO 27
<211> LENGTH: 3915
<212> TYPE: DNA
<213> ORGANISM: Homo sapiens
<220> FEATURE:
<221> NAME/KEY: misc_feature
<222> LOCATION: (106)..(126)
<223> OTHER INFORMATION: n is a, c, g, or t
<220> FEATURE:
<221> NAME/KEY: misc_feature
<222> LOCATION: (1656)..(1853)
<223> OTHER INFORMATION: n is a, c, g, or t
<220> FEATURE:
```

<221> NAME/KEY: misc_feature
<222> LOCATION: (2304)..(2423)
<223> OTHER INFORMATION: n is a, c, g, or t

<400> SEQUENCE: 27

```
gtccaggggc aagttcatcc tactctcgag tctaatgatg atgctcttca gtatgttgaa     60
gaattaattt tgcaattatt aaatatgcta tgccaagctc agcccnnnnn nnnnnnnnnn    120
nnnnnngaac gtgttcaaaa aagtttccct catccaattg ataaatgggc aatagctgat    180
gcccaatcag ctattgaaaa gaggaagcga agaaaccctt tatctctccc agtagaaaaa    240
attcatcctt tattaaagga ggtcctaggt tataaaattg accaccaggt ttctgtttac    300
atagtagcag tcttagaata catttctgca gacattttaa agctggttgg gaattatgta    360
agaaatatac ggcattatga aattacaaaa caagatatta aagtggcaat gtgtgctgac    420
aaggtattga tggatatgtt tcatcaagat gtagaagata ttaatatatt atctttaact    480
gacgaagagc cttccacctc aggagaacaa acttactatg atttggtaaa agcatttatg    540
gcagaaattc gacaatatat aagggaacta aatctaatta taaaagtttt tagagagccc    600
tttgtctcca attcaaaatt gttttcagct aatgatgtag aaaatatatt tagtcgcata    660
gtagatatac atgaacttag tgtaaagtta ctgggccata tagaagatac agtagaaatg    720
acagatgaag gcagtcccca tccactagta ggaagctgct ttgaagactt agcagaggaa    780
ctggcatttg atccatatga atcgtatgct cgagatattt tgcgacctgg ttttcatgat    840
cgtttcctta gtcagttatc aaagcctggg gcagcacttt atttgcagtc aataggcgaa    900
ggtttcaaag aagctgttca atatgtttta cccaggctgc ttctggcccc tgtttaccac    960
tgtctccatt actttgaact tttgaagcag ttagaagaaa aaagtgaaga tcaagaagac   1020
aaggaatgtt taaaacaagc aataacagct ttgcttaatg ttcagagtgg tatggaaaaa   1080
atatgttcta aaagtcttgc aaaacgaaga ctgagtgaat ctgcatgtcg gttttatagt   1140
cagcaaatga aggggaaaca actagcaatc aagaagatga acgagattca gaagaatatt   1200
gatggttggg agggaaaaga cattggacag tgttgtaatg aatttataat ggaaggaact   1260
cttacacgtg taggagccaa acatgagaga cacatatttc tctttgatgg cttaatgatt   1320
tgctgtaaat caaatcatgg gcagccaaga cttcctggtg ctagcaatgc agaatatcgt   1380
cttaaagaaa agtttttat gcgaaaggta caaattaatg ataaagatga caccaatgaa     1440
tacaagcatg cttttgaaat aattttaaaa gatgaaaata gtgttatatt ttctgccaag   1500
tcagctgaag agaaaaacaa ttggatggca gcattgatat ctttacagta ccggagtaca   1560
ctggaaagga tgcttgatgt aacaatgcta caggaagaga aagaggagca gatgaggctg   1620
cctagtgctg atgtttatag atttgcagag cctgannnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnnnnnn nnnnnnnnnn nnnnnnnnnn nnnnnnnnnn nnnnnnnnnn nnngtttgaa   1860
attccagagc ctgagccaac agaagctgat cgcatagcta tagagaatgg agatcaaccc   1920
ttgagtgcag aactgaaaag atttagaaaa gaatatatac agcctgtgca actgcgagta   1980
ttaaatgtat gtcggcactg ggtagagcac cacttctatg attttgaaag agatgcatat   2040
cttttgcaac gaatggaaga atttattgga acagtaagag gtaaagcaat gaaaaaatgg   2100
gttgaatcca tcactaaaat aatccaaagg aaaaaaattg caagagacaa tggaccaggt   2160
cataatatta catttcagag ttcacctccc acagttgagt ggcatataag cagacctggg   2220
```

-continued

```
cacatagaga cttttgacct gctcacctta cacccaatag aaattgctcg acaactcact   2280
ttacttgaat cagatctata ccgnnnnnnn nnnnnnnnnn nnnnnnnnnn nnnnnnnnnn   2340
nnnnnnnnnn nnnnnnnnnn nnnnnnnnnn nnnnnnnnnn nnnnnnnnnn nnnnnnnnnn   2400
nnnnnnnnnn nnnnnnnnnn nnnatgtatt gtagaaactg aaaatttaga agaaagagta   2460
gctgtggtga gtcgaattat tgagattcta caagtctttc aagagttgaa caactttaat   2520
ggtgtccttg aggttgtcag tgctatgaat tcatcacctg tttacagact agaccacaca   2580
tttgagcaaa taccaagtcg ccagaagaaa attttagaag aagctcatga attgagtgaa   2640
gatcactata agaaatattt ggcaaaactc aggtctatta atccaccatg tgtgcctttc   2700
tttggaattt atctcactaa tatcttgaaa acagaagaag gcaaccctga ggtcctaaaa   2760
agacatggaa aagagcttat aaactttagc aaaaggagga aagtagcaga aataacagga   2820
gagatccagc agtaccaaaa tcagccttac tgtttacgag tagaatcaga tatcaaaagg   2880
ttctttgaaa acttgaatcc gatgggaaat agcatggaga aggaatttac agattatctt   2940
ttcaacaaat ccctagaaat agaaccacga aaccctaagc ctctcccaag atttccaaaa   3000
aaatatagct atcccctaaa atctcctggt gttcgtccat caaacccaag accaggtacc   3060
atgaggcatc ccacacctct gcagcaggag ccaaggaaaa ttagttatag taggatccct   3120
gaaagtgaaa cagaaagtac agcatctgca ccaaattctc caagaacacc gttaacacct   3180
ccgcctgctt ctggtgcttc cagtaccaca gatgtttgca gtgtatttga ttccgatcat   3240
tcgagccctt ttcactcaag caatgatacc gtctttatcc aagttactct gccccatggc   3300
ccaagatctg cttctgtatc atctataagt ttaaccaaag gcactgatga agtgcctgtc   3360
cctcctcctg ttcctccacg aagacgacca gaatctgccc cagcagaatc ttcaccatct   3420
aagattatgt ctaagcattt ggacagtccc ccagccattc ctcctaggca acccacatca   3480
aaagcctatt caccacgata ttcaatatca gaccggacct ctatctcaga ccctcctgaa   3540
agccctccct tattaccacc acgagaacct gtgaggacac ctgatgtttt ctcaagctca   3600
ccactacatc tccaacctcc ccctttgggc aaaaaaagtg accatggcaa tgccttcttc   3660
ccaaacagcc cttccccctt tacaccacct cctcctcaaa caccttctcc tcacggcaca   3720
agaaggcatc tgccatcacc accattgaca caagaagtgg accttcattc cattgctggg   3780
ccgcctgttc ctccacgaca aagcacttct caacatatcc ctaaactccc tccaaaaact   3840
tacaaaaggg agcacacaca cccatccatg cacagagatg gaccaccact gttggagaat   3900
gcccattctt cctga                                                    3915
```

<210> SEQ ID NO 28
<211> LENGTH: 2757
<212> TYPE: DNA
<213> ORGANISM: Mus musculus

<400> SEQUENCE: 28

```
cgccttcaag ttgcccggag cgcgtctggg accggcagac ctgtcccgga gcgcgtagat     60
ccgcacgcac gcacgcgccg cccacgtcca gcttgcgaat ccgagggacc cgttccaata    120
atgccccgga aggcagccag tccagaggag gcggcggggg agcccggtcc tgaggagatg    180
gaggctgggc ggccgcggcc ggtgctgcgc tcggtgaact cgcgcgagcc ctctcaggtc    240
atcttctgca atcgcagtcc gcgcgtcgtg ctgcctttgt ggctcaactt cgacggtgag    300
cctcagccct acccgatctt accaccgggc accggtcgcc gcatccacag ctaccgaggt    360
```

-continued

```
catctttggc tcttcaggga tgcggggacc catgatggac ttctggttaa ccaaacggag    420
ctgtttgtgc catccctcaa tgtcgatgga cagcctattt ttgccaacat cacattgcca    480
gtgtataccc tgaaagagcg gtgccttcag gttgtgcgga gcctggtcaa gcctgagaac    540
tacaggagac tggacatcgt caggtcactc tatgaggatt tggaggacta cccaagtgtg    600
cggaaggaca tacagcgact gagccaagag caccttgaga gtcagcacct ggaagaggag    660
ccttgaagga gtccatggag attaagtgtt cctgagtttc acccttgatg gtccgagatt    720
gatctacaca taggacaggt cactttcttt cagttttaaa atggttcatt cttggagtaa    780
aactatccat cacgtaaaag aaagttaact aacatccctg ggctttgtag tgtttaagaa    840
taaacatgca aagtgccact gcgtctgccc tttgtagagc actcacccga gggaggaaga    900
cgttttcagt tttgcttcct ggtgagctgg aagttgagtg taaggatgac tgtgtaataa    960
agctcagcag caggagttgt actgtgtcct ttcatttgag cagagggctc ttgcttggga   1020
aggcagagaa ggcccttccc aaacgctggg acagacctcc tgtggaggcc cgctgcctaa   1080
agcgtggagt cttcagtcat gaatgttgga cgaagaaacc attggatgct tggtgggaga   1140
gttgggaggg cctggctctt tgtctgagga gagccttaag tgttcatgta aggaacagct   1200
tagcagcttc tgattttccc acgtcccagc actttctctc tgttttttat tttatttttg   1260
agacttttgt atagcccagc cagcctcagt cactcagcag aggattcctg acctgtctgg   1320
gattatgtct cctgacattg ggaacacatg tgtgcacaca gcctgctctg ctcttccttt   1380
tcccatgttg agacgggctc ctgctgtagt cctgcctggc ctgagctgga gtcggtcctg   1440
cctcctgacc gaccgtctgg ctgctttcta agctgggtag acttcccata ctcactgtta   1500
cagacagtta cagcagagaa gaaccatcct tgtgtaagtc tggttttgag agctcctgtc   1560
tctgaggaaa ggaaactgtt ggcaggagca gggatttctg ttccttcttg tcaaccccta   1620
gcattccact ttgttttggc aggcgctggt tctgctttgt aggtggaagt gaagcttcca   1680
ctcagccaca gactccagac agtgggtcac agagcagtct ggaatgtgta gcagtcttat   1740
ggatggtcac agcttttctt acatattcat attctatcaa acgttttgta aagtataatt   1800
ttttatttat ttttaatccc cttagagaaa aagtaaaagt agagaagcct gggtattgtg   1860
tacacaacag aaaggacagt caaggaaagg gaagcagaaa ggctcttatg tactctcagc   1920
tccatgcaac ccctgtaact ggcgcatatg tagggcatat tttaattggt taaagcagtt   1980
tgttgtggct gaggtcataa gatatataca gttttgtatc ctgatttttc actgaacttc   2040
attgtttttt gtttgcttgc ttttcccttc ttctttgttt tttactttat tgagataggg   2100
tttctctgta gcccaggctg tcctagaact ccctttgtag accaaacatc tgattactga   2160
cctcacatgg agagatctgt ctcttacttt ccagcgctgg gattgaagta ggcctaatct   2220
tcatctaact tcttagcttg tcttttccat gttactacac acactgtgta aataccagtg   2280
tgctaccctc cttctttgag ggtgactgtt gggagtattt gtccaaatcc tgggcacctt   2340
gagtgcagac tgatgctcta agatcagcaa aatgactgaa ctacatccta acacttccca   2400
gtgtcctctc agtgtctctt cttatctgca gcattgcagg agtgaagtgg ccacagacca   2460
gtgtggaggc ctgtgtgtgg gaagtcagca ggtgccaagc tattgaaaca ttggttttat   2520
ttttttaaac cgatctctgt ctctaaaaga tgtgtatgtt tgtgttattc agctggaagt   2580
ttgaatactg ttctctgtgc tgtccaacaa gtgaagagtt atgaaatgag ccacttgtcc   2640
tgggacatcc tgtaatgagt tcctcgggct tttctcctgt gagttttctg aaaaaagctg   2700
acctttttag tacaataaac ggtgctaatt gaaggaaaaa aaaaaaaaaa aaaaaaa      2757
```

<210> SEQ ID NO 29
<211> LENGTH: 2301
<212> TYPE: DNA
<213> ORGANISM: Homo sapiens

<400> SEQUENCE: 29

```
agcagagcgg acgggcgcgc gggaggcgcg cagagctttc gggctgcagg cgctcgctgc     60
cgctggggaa ttgggctgtg ggcgaggcgg tccgggctgg cctttatcgc tcgctgggcc    120
catcgtttga aactttatca gcgagtcgcc actcgtcgca ggaccgagcg gggggcgggg    180
gcgcggcgag gcggcggccg tgacgaggcg ctcccggagc tgagcgcttc tgctctgggc    240
acgcatggcg cccgcacacg gagtctgacc tgatgcagac gcaagggggt taatatgaac    300
gcccctctcg gtggaatctg gctctggctc cctctgctct tgacctggct cacccccgag    360
gtcaactctt catggtggta catgagagct acaggtggct cctccagggt gatgtgcgat    420
aatgtgccag gcctggtgag cagccagcgg cagctgtgtc accgacatcc agatgtgatg    480
cgtgccatta gccagggcgt ggccgagtgg acagcagaat gccagcacca gttccgccag    540
caccgctgga attgcaacac cctggacagg gatcacagcc tttttggcag ggtcctactc    600
cgaagtagtc gggaatctgc ctttgtttat gccatctcct cagctggagt tgtatttgcc    660
atcaccaggg cctgtagcca aggagaagta aaatcctgtt cctgtgatcc aaagaagatg    720
ggaagcgcca aggacagcaa aggcattttt gattggggtg gctgcagtga taacattgac    780
tatgggatca aatttgcccg cgcatttgtg gatgcaaagg aaaggaaagg aaaggatgcc    840
agagccctga tgaatcttca caacaacaga gctggcagga aggctgtaaa gcggttcttg    900
aaacaagagt gcaagtgcca cggggtgagc ggctcatgta ctctcaggac atgctggctg    960
gccatggccg acttcaggaa aacgggcgat tatctctgga ggaagtacaa tggggccatc   1020
caggtggtca tgaaccagga tggcacaggt ttcactgtgg ctaacgagag gtttaagaag   1080
ccaacgaaaa atgacctcgt gtattttgag aattctccag actactgtat cagggaccga   1140
gaggcaggct ccctgggtac agcaggccgt gtgtgcaacc tgacttcccg gggcatggac   1200
agctgtgaag tcatgtgctg tgggagaggc tacgacacct cccatgtcac ccggatgacc   1260
aagtgtgggt gtaagttcca ctggtgctgc gccgtgcgct gtcaggactg cctggaagct   1320
ctggatgtgc acacatgcaa ggcccccaag aacgctgact ggacaaccgc tacatgaccc   1380
cagcaggcgt caccatccac cttcccttct acaaggactc cattggatct gcaagaacac   1440
tggacctttg ggttctttct ggggggatat ttcctaaggc atgtggcctt tatctcaacg   1500
gaagcccccct cttcctccct gggggcccca ggatgggggg ccacacgctg cacctaaagc   1560
ctaccctatt ctatccatct cctggtgttc tgcagtcatc tcccctcctg gcgagttctc   1620
tttggaaata gcatgacagg ctgttcagcc gggagggtgg tgggcccaga ccactgtctc   1680
cacccacctt gacgtttctt ctttctagag cagttggcca agcagaaaaa aaagtgtctc   1740
aaaggagctt tctcaatgtc ttcccacaaa tggtcccaat taagaaattc catacttctc   1800
tcagatggaa cagtaaagaa agcagaatca actgcccctg acttaacttt aacttttgaa   1860
aagaccaaga cttttgtctg tacaagtggt tttacagcta ccacccttag ggtaattggt   1920
aattacctgg agaagaatgg ctttcaatac ccttttaagt ttaaaatgtg tatttttcaa   1980
ggcatttatt gccatattaa aatctgatgt aacaaggtgg ggacgtgtgt cctttggtac   2040
tatggtgtgt tgtatctttg taagagcaaa agcctcagaa agggattgct ttgcattact   2100
```

```
gtccccttga tataaaaaat ctttagggaa tgagagttcc ttctcactta gaatctgaag   2160

ggaattaaaa agaagatgaa tggtctggca atattctgta actattgggt gaatatggtg   2220

gaaaataatt tagtggatgg aatatcagaa gtatatctgt acagatcaag aaaaaaagga   2280

agaataaaat tcctatatca t                                               2301
```

<210> SEQ ID NO 30
<211> LENGTH: 3672
<212> TYPE: DNA
<213> ORGANISM: Homo sapiens

<400> SEQUENCE: 30

```
gcccggttac ttcctccaga gactgacgag tgcggtgtcg ctccagctca gagctcccgg     60

agccgcccgg ccagcgtccg gcctccctga tcgtctctgg ccggcgccct cgccctcgcc    120

cggcgcgcac cgagcagccg cgggcgccga gcagccaccg tcccgaccaa gcgccggccc    180

tgcccgcagc ggcaggatga atgatttcgg aatcaagaat atggaccagg tagcccctgt    240

ggctaacagt tacagaggga cactcaagcg ccagccagcc tttgacacct ttgatgggtc    300

cctgtttgct gtttttcctt ctctaaatga agagcaaaca ctgcaagaag tgccaacagg    360

cttggattcc atttctcatg actccgccaa ctgtgaattg cctttgttaa ccccgtgcag    420

caaggctgtg atgagtcaag ccttaaaagc taccttcagt ggcttcaaaa aggaacagcg    480

gcgcctgggc attccaaaga acccctggct gtggagtgag caacaggtat gccagtggct    540

tctctgggcc accaatgagt tcagtctggt gaacgtgaat ctgcagaggt tcggcatgaa    600

tggccagatg ctgtgtaacc ttggcaagga acgctttctg gagctggcac ctgactttgt    660

gggtgacatt ctctgggaac atctggagca aatgatcaaa gaaaaccaag aaaagacaga    720

agatcaatat gaagaaaatt cacacctcac ctccgttcct cattggatta acagcaatac    780

attaggtttt ggcacagagc aggcgcccta tggaatgcag acacagaatt accccaaagg    840

cggcctcctg gacagcatgt gtccggcctc cacacccagc gtactcagct ctgagcagga    900

gtttcagatg ttccccaagt ctcggctcag ctccgtcagc gtcacctact gctctgtcag    960

tcaggacttc ccaggcagca acttgaattt gctcaccaac aattctggga ctcccaaaga   1020

ccacgactcc cctgagaacg gtgcggacag cttcgagagc tcagactccc tcctccagtc   1080

ctggaacagc cagtcgtcct tgctggatgt gcaacgggtt ccttccttcg agagcttcga   1140

agatgactgc agccagtctc tctgcctcaa taagccaacc atgtctttca aggattacat   1200

ccaagagagg agtgacccag tggagcaagg caaaccagtt atacctgcag ctgtgctggc   1260

cggcttcaca ggaagtggac ctattcagct gtggcagttt ctcctggagc tgctatcaga   1320

caaatcctgc cagtcattca tcagctggac tggagacgga tgggagttta agctcgccga   1380

ccccgatgag gtggcccgcc ggtggggaaa gaggaaaaat aagcccaaga tgaactacga   1440

gaagctgagc cggggcttac gctactatta cgacaagaac atcatccaca agacgtcggg   1500

gaagcgctac gtgtaccgct tcgtgtgcga cctccagaac ttgctggggt tcacgcccga   1560

ggaactgcac gccatcctgg gcgtccagcc cgacacggag gactgaggtc gccgggacca   1620

ccctgagccg gccccaggct cgtggactga gtgggaagcc catcctgacc agctgctccg   1680

aggacccagg aaaggcagga ttgaaaatgt ccaggaaagt ggccaagaag cagtggcctt   1740

attgcatccc aaaccacgcc tcttgaccag gctgcctccc ttgtggcagc aacggcacag   1800

ctaattctac tcacagtgct tttaagtgaa aatggtcgag aaagaggcac caggaagccg   1860

tcctggcgcc tggcagtccg tgggacggga tggttctggc tgtttgagat tctcaaagga   1920
```

-continued gcgagcatgt cgtggacaca cacagactat ttttagattt tcttttgcct tttgcaacca 1980
ggaacagcaa atgcaaaaac tctttgagag ggtaggaggg tgggaaggaa acaaccatgt 2040
catttcagaa gttagtttgt atatattatt ataatcttat aattgttctc agaatccctt 2100
aacagttgta tttaacagaa attgtatatt gtaatttaaa ataattatat aactgtattt 2160
gaaataagaa ttcagacatc tgaggtttta tttcattttt caatagcaca tatggaattt 2220
tgcaaagatt taatctgcca agggccgact aagagaagtt gtaaagtatg tattatttac 2280
atttaataga cttacaggga taaggcctgt ggggggtaat ccctgctttt tgtgtttttt 2340
tgtttgtttg tttgtttgtt tttggggggt tttcttgcct tggttgtctg gcaaggactt 2400
tgtacatttg ggagttttta tgagaaactt aaatgttatt atctgggctt atatctggcc 2460
tctgctttct cctttaattg taaagtaaaa gctataaagc agtatttttc ttgacaaatg 2520
gcatatgttt tccacttctt tgcatgcgtt taagtcagtt tatacacaaa atggatttta 2580
ttttttagtt taactgtgtt tctccgacag ctcacctctc tctgaccacc cagccatttc 2640
cttcctgtgc tccacgttct tctgtgtgat taaaataaga atattatttt tggaaatatg 2700
caactccttt tcagagatca ggagggattt atgtagcagc tatttttact gcaaaagtaa 2760
ttcactggaa aaaaaatgta atttgtaaga aagctttatt tttatctcag ctctatgtaa 2820
agttaaagtt actgtacaga gctgaaggac ggggggcggt aggggtcttg atgaaacctc 2880
ttgaacgaag cacagtttgt cccatctttg ttcactcgtg tgtctcaacc atcttaatag 2940
catgctgctc ctttttgctc agtgtccaca gcaagatgac gtgattctta ttttcttgga 3000
cacagactat tctgaggcac agagcgggga cttaagatgg gaaagagaaa gcatcggagc 3060
cattcattcg gagaaaacgt tttgatcaaa atggagactt ttgtagtcgt ttcaaaagag 3120
cacctgagtc atgtgtattc ccggccttta taaatgaccc ggtcaagttg gtttcaaagt 3180
ccgacaggct tgtctgttta ctagctgcgt ggccttggac gggtggctga catctgtaaa 3240
gaatcctcct gtgatgaaac tgaggaatcg ggtggccggg caagctggga agagcaaagc 3300
cagagctgcg ctgcctcaat acccacaaaa gaccattccc agtatacata agcacaggat 3360
gtttttctca agagggatgt atttatcact tggacatctg tttataatat aaacagacat 3420
gtgactggga acatcttgct gccaaaagaa tcctaggcag tggctcattg tatgtgaggt 3480
tgaaccacgt gaaattgcca atattaggct ggcttttatc tacaaagaag gagtttcatg 3540
gggttcagcc taacagttat ggaaactaca gtccttataa accattggca tggtaataaa 3600
cagatcttaa gtataaaaat tttgtaattg ggcctttact ctctcaataa taaagtattt 3660
tgtttatata aa 3672

<210> SEQ ID NO 31
<211> LENGTH: 16479
<212> TYPE: DNA
<213> ORGANISM: Mus musculus

<400> SEQUENCE: 31
tctagaggtg tgaccgggcg cgtgagacca caggggagcc agacaaacgc ttgcttcctt 60
aagttgcttc ttggcagaca cttgggcata acagtaaggc aattatctgg tactcatccc 120
accttatgtg tccttgaata tgatggctct agggacctca tagagactga gtcacatggt 180
accttccccc tttattttga gaatttattt tgtagaaaaa acgcaaataa aaataagtaa 240
ataaaattta tttttgtgt tctatcatct atctatctat ctatctatct atctatctat 300

-continued

```
ctatccttcc ttccatctat ctatttttac tccatccatc catccatcca tccatccatc    360
catccatcca tctacctatc tatttttact tgggcctgtc agtccccatg gaactagact    420
tgtacatgag ggtgggctat ttgagcgggt gctgggtggg agtcaaactt gggtgaagag    480
caagtgctct taaccactga gtcatctctc tagtgcttgg cctttttggg attagctttt    540
tgcattgagt attgtgtcct aaaagcctat caatttccca catttttcct ctctcttctt    600
tctttcttct gcctcactat gtagactagg ctagtctcaa acttggatcc tctgccctgg    660
cctcctatgt gttggatttt aggtatgcat caccacatgt ggctagatgc ctgccctctc    720
tccctctctc cctcccttcc ttcctatctg tcttttcttg aaaaaagaac taacatatct    780
caggctggcc ttgaactcat taagtagcca aggatgacct tctgcttcca tcttctgagt    840
gctgagatga caggcatgag tactgtgccg gtttatggag tgtcaaggac tgaacccagg    900
gcttagtgca tgctaggtaa acatgcgtca caccgagtca catctccaga ccttcttcac    960
ctttaaaaat tatactgatt ggtggttagg tatgtgtgta tatgtgtacc acaacacaca   1020
tgtcaaggtc agaggacaac taatgattat cttcttacac tatatgggcc ctggtatcca   1080
acttcagatt gccaggcttg gtggcaagca cccattttac ctactgagcc atctcaaaga   1140
ccctacacca ttttaaaagg gagttatttc tttctatatg tatggggggt ttgcctctgt   1200
atgtctgtgc cccatgccca tgaaggccca cagagaccag agagagcata gagtctcctg   1260
taactggaat tacagatagt tgggatctat caagtggagg ttaggaacct aactcaggtc   1320
ttctgcaaga gtagcagtca cggagccatc tcttcagtcc cactctctcc ttcattttga   1380
agaataggcc aaactacatt ctgcttatcc attcacccac cagtggatgt aggcttgctc   1440
tgcatatgcc tattttaaga aatgctgctg tggacagatg tatgagtatt gtgtcatctc   1500
ctcttagtgt ctctgcatac aaatgattgt ttctgcatgt atgcatatgt atcattttcc   1560
tctgactaag aatgtttttt cctttcctgg tttcacataa tgcgattgcg atgtatcttc   1620
tttgttctca gattttgctg agctctctgg atctgtgagc ttatgatttt tatctagttt   1680
ggaaattttt cagctctttt cctctccagt tgtattttct gcctaatttc ttgttctcat   1740
tcaggagtgt gtttggcacc atgcttctcc tcacgtgcct gtctgtgctg acctttggat   1800
gccacccact tctatgcctt caaattcatt aacctttctt ttcacagcat ccaatttgcc   1860
actggtgcat tttccattcc agatgctggc gttcttgttc atctccagaa ctttagggct   1920
gtcttcgctc atgtaaatac ctcctgtgcc gccacttcac cttcagcctg tgaaacccag   1980
tcacagtaat atttttgctg accttgtcta tgactggtga tactggttca ccccacatag   2040
ttttcttttg gtcacagaaa tgaaaaaagg ttactgagac aggttggggt attagacact   2100
gcaaccgtaa atccttaaaa atatatataa ttttaagatt tataggatgt gtgtgtgtgt   2160
gttgtgtgtg tgtttgtgtg tgacacatgt acatatgatg cccccaagag tgcagaagaa   2220
ggcattggat cccctagagc tagagtgtta ggaatttgta agccacttta cataggtatg   2280
gggaactgac ctctggtcct cttgcaatac taataactgt tcttaactac taagctatct   2340
ctctagctcc tttttctttt taactttgat tttatttccc ttattttccc tccccctgtg   2400
tgtgtgtgtg tgtgcgcata tttgtgtttg gacatttaag ttcgtgtatc tatgtgtgta   2460
tatgtttgtg tgtgtgtata tgtatgtaga tctttatata tgtgtgtgca tgtttgtatg   2520
tatatgcaca tatgtgtgtt tgtagcatgt atatgtgtgt atttatgtat gtttgtgtgt   2580
gttcatgtgc acataaaaga agcatgtgca cacagaagca agtgcatgtt tgtgcatata   2640
tgtgtatatg tttgcatata ggtatatgtg tgtatatatt tgtatgtgca cacatgtttg   2700
```

-continued

```
tgtgtgtgtg cgtgtgcgca cgcacatgca cagagaccag aaatcaaact caggtgtatt   2760
tctctgaaag tgaggctttt gagcatagtc tctctgggga cctagggcct gcaagctcca   2820
gggatccacc tgtctctgtt tccccagcac tgagggttct ggagatcttg cctgcatggc   2880
aagcatttac tgactgagcc ctccttcaag tccttcttcc ttgtttctct ttgacttcag   2940
agtgagctac atgtcacctg gatcttcctt tctgccttta ttgcatctag cctgtgcttg   3000
ggacacttgc tttccaggat gtcttgccat cggtaaggac accctagaat atttgctgtt   3060
gtatatatgg cagcttggtc caatgtctga tgatttggta aaggtgtctt ctactagcag   3120
gccaagtggc ttcttcccag tggcactgtc cacttccagg gcatggcttg gaaccaagct   3180
gtctctccaa ggtgtcagtg agggtttcag ggtgtcataa tggtaggcca tctatgctga   3240
gccagctgat cctctgcctg tcattcacca gtaaacttgg ggagtgtccc cttttgttcc   3300
atgagaccca ggcatgttat agaatgtaga ctccattgtt gagtgcctca gagccacctg   3360
atagaggttg ttgaaagatg gctgggtctg cgccattccc aaggggatgg aatggacaag   3420
ggagccacac aggcagatgg ctctcagaac agcatgtgga aagctgagac tgaatgccaa   3480
gggctgggtc tcatctgact gggtttgtcc aggttgtccc tacttggaga tggagctcag   3540
agagtgggag gcaaactcca ttctcaggaa tccagagtag acgtggggca tcctccaagg   3600
gcagagtgga aatctagctg gagaagaggt ctggccacag atggacaact agagggaaag   3660
aagacagatg gtactgatgt catgagtatg gagacttccc tgtgaaggaa acatgggagt   3720
gacatgggct gagggaaaag gaggacaaga tcagcctgcc atgaattaag tttgggaagc   3780
tgtggagcat tgaggttcag tccacatgtc acatggataa aaactgtggc ttgtaccaga   3840
agctttgcct gcgttagttc tgtcccaaag ctaaaggggt aggggagatg gttcagtggt   3900
tctatttttt tttttttttt tttttttttt ttttggacgg gtttctctgt atagccctgg   3960
ctatcctgga actactttgt agaccaggct ggctttgaac taaaatccgc ctgccttgcc   4020
tccaagtgct gggattaaag gctgtgccac caccgcccgg caagaacact agttcttaac   4080
ggctttcaag gacccagttt cacttgtgct cttccagtat acacagttag ttcccagcac   4140
ccatgtagta gctacaacca ctcagttcca gagaacctga gtctctcttc ttgcctctgt   4200
ggatactgac atatatactg caagcaaacc acccacactc aacataaaat aaatattgga   4260
ttttaaaatt ttaaaccatt aaagcagtta aaaaaggtaa aaattaggct gagatagcta   4320
agttggcatg tgctggctgt gcatgagaac ctggctttga actcagagtc tacttctaaa   4380
agccagggat gctagcttgt aatcccatca ctgggaagac agagtcaaag gatccctggc   4440
accagctggc tagtgagccc ctgatacaag ccagtaagaa tccctgtctt aaagtttgga   4500
gctgagacga aaggatggac catgtagaga ctgccatatc cagggatcca ccccataatg   4560
agcttccaaa cgctgacacc attgcatgca ctagcaggat tttatcgaaa ggacccagat   4620
gtagctgtct cttgtgagac tatgccgggg cctagcaaac acagaagtgg atgctcacag   4680
tcagctattg gatggatcat agggctccca atggaggagc tagagaaagt acccaaggag   4740
ctaaagggat ctgcaaccct ataggtggaa caacattatg aactaaccag taccccggag   4800
ctcttgactc tagctgcata tgtatcaaaa gatggcctag tcagccatca ctggaaagag   4860
aggcccattg gacttgcaaa ctgtatatgc cccagtacag gggaacgcca gggccaaaaa   4920
aaatggaatg agtggtaggg aagtgggggg gagggtatgg ggaacttttg gaatagcatt   4980
ggaaatgtaa taggaaaata tgtaataaaa aataaaaata aattaaaaaa aatccctgtc   5040
```

```
ttaaacaaaa caaaacaaac aacaaaaaac ccaaacacaa caaaaggata aatggcacaa   5100
cacccaaggt tgtcctctgg cacatattct acacacagtg catgtatgca ccgatacacc   5160
ctcacacaca tactcttatg cacacagtat acatatgcac ccacacatcc tcacacacac   5220
tcttctacac acagcgtaca tatgcactca cacaacctca tatgcatact cttatgcaca   5280
cagtatacat atgcatccac acaccctcac acacactgtt ctacacacaa tgcacatatg   5340
cacccacaca cactcacata catactctta tgcacacagt atacatatgc atccacacac   5400
cctcacacac agtcttctac acacagttca cgtatgcacc acacacactc acacacatac   5460
tcttatgcac acagtataca tatgcaccca catccataca aacatgtata cacacacaca   5520
cacacacaca cacacatcaa cattaaaata acattttgta gtacataaac aggaccagaa   5580
gttccagaca gtgtctatac ttcttttgct gggaaacatt tatggtgttt ttgtaatgtc   5640
tgtggcagca tttgctccct agcatgtgac actgactgta tagcctgcaa agcatgacag   5700
atttgctaac aggtcctcag aaaaagctgt tttgccccat gcttgaaagc tcaaggatgg   5760
agtcacacag ccagggataa atgacccctg caaaggagag gtgccaagga gcaggcaggg   5820
cacaagccat gtcaaaatct tccagctgat ttttgagaca taatcatgca ccacacactt   5880
cattgaacca ttaaaccaca gccatgtaaa ctgtagcata gtcagcttgt gtgcatgtat   5940
gtgccatagc caattgtcca gattgtgtgg agatcagatt ctccagaata tcagtccttg   6000
cctgctacct ttctgagaca aggtctctct gttgttgttg tgtattctaa gctaactgac   6060
ccttgagctt acagtgagtg tcgtctccgt ctcccattgt gtcatagcaa tgctgaggta   6120
caggaatgtg ttcccatgcc aggctttaca tgggttctgg ggattcaact tcaggccact   6180
gtgcttgcat ggcaagcact ttatctgctg agccatttcc ccaagctcct tagaacattg   6240
tgattaaaag gaaattcata ccctgtagcc agtacctccc cctcattctt gtccccgtgt   6300
ctatttctgt ctctgtggat tggcctgttc tggacagttc ttgtaaatga catcatgtaa   6360
tatgtggtct ttcggttttt ccttctttca ctcactcatg tctaccaaca ccatgatgcc   6420
agtcagtgtt ttatttcttc tcttggctga acaatatttc cttctgagtc agttcatgct   6480
ttatccatcc atttgtctgt tatggacatc tggctgtttc aaaacattta aatgaagatc   6540
acatggctaa ggatagagcc agagcccaag ccccccaaaa gagatgtatg aaactcttat   6600
gatcagggga gaactgcttc tggagcaaga gaactgccac caggatggtt agaggatgtg   6660
ggtacgtgaa gttaagaaat gaaggggcac acctaggaga cgccaatccc tagggaactg   6720
tcacctttaa gctgaggaag gtaggttggg cttgcagaaa gtacgagggc caggatgggg   6780
gaggggccaa ggtgggaaag gtgctgagta ggatgagatg ctggctttat agaagtaggg   6840
tatgtaccag cctgagagga aggaaatatg gtgagacccc tgaaagagtc gtgagtcttt   6900
acacacacac acacacacac acacacacac acacacacac acagacacac acacagacac   6960
acggtgatgt acctaagttg ctagattgcc tagaatgcac cacattgtct agcatgtatc   7020
atatatgaag ccctgggttc catctccagc atcacataca atgagtgtga cggtgcatgc   7080
ctataatcta tctggagata taagaagaag atagacgttc tgaagttcac agtcatcctt   7140
agctatgtag tgaattaagg gctaacctaa gcttcaggca gactctccca ccaccacccc   7200
taaatggagg aaaagtacaa aaaacaactt aggaaaggca gggaggaaac agggcagcag   7260
tggtctccgt acagtgaggg tttgcagatc aaacctcctc agggcaccag gatacaaact   7320
gtttccatct cttctgtata tgtgtgcatg cttgcgtgtg caaggatgag cacagcagtg   7380
tgtatggagg ttggaggata tcttggatgt tggtccttcc cttccagcct gtttaagata   7440
```

```
gacgttgttg ttcattattg cagtcctggg gctaagctgg cttgaaagtt tgaaagaatt   7500
ctcttcttgg catcttgggt ttctatgggt tctgaggatt tgaactcagg tcctcacact   7560
tgcacagcaa gtgctttact taccattctc cccagaccaa ctggattgct ccaaacagca   7620
gagaagtgac tagacttatc caagtgctct tagcagacac ccgggaaatt tcgactcact   7680
gcccacttcc cacagcaagg ttatcaaaag gctggattag gatgatacag ccttgacgaa   7740
tcctggagag tcatggaacc tgcaggcagc cccacactgg cagtacatgc tccaaggcag   7800
tgcgaaagca gagagaagcc tggttttggt agccctcccc cagtcggata tttacaaaga   7860
aagtaactcc aggttactac ccacaggata gaccacttga accctatagg tcttgcttgg   7920
ctcccaagca cctacctagt cctttgaggg aaaaattggg cttgctacgg ccttgagagc   7980
acacttctgg gacaatgggg caaaactgag actttgacaa ggtcagtgca tttcccttcc   8040
ccttcaacct tccctccacc ggcctcaggg gaaggatggg actgagaggt ctgctggaat   8100
ccgaagaagt gttattgaac aaaaagtcca ggaaccgaac aaaaactagt ctgggtagat   8160
tcaccattag gaaaagagac ccagacttgg agagctggct gtaaggtgca gatgggtgac   8220
agtgtgagaa aggagtggac ttgattgtat tctctcaggt cagggcaacc ggtcctgggg   8280
attcttgaaa acacagaggc atggggtgtg catgaagggg ctaaatgggt acaggtgccc   8340
aaggaacatg aaatttccca ttactggtct gaaccactcc tcaagccctt ctcacactca   8400
aggggcacag gtgtgctcct gcaatgcgtg gacaccgggt cctggtggag gagcagggtg   8460
gggcggagtg ggcgtggagc cttgtgcgag acactccccc atctctggag ccacgcgcca   8520
ggcgtacgct tccttctggc cccggcatag gaccgcgcca attgtcattg gccaaacggg   8580
cgatcccaga ttggctgaga ccccggctcc cgcctcctcc gccaggggga gggacgtggg   8640
tgccggttta gaggctcgtg ctaccctagg gggtcgcgct cttctgcctc ctacctcttg   8700
gtcaccgcaa agcttggtcc ggttcttcat ccggctgcaa gcgctaggtg tgcggagacc   8760
tggcagctct tggggcttaa gggctgagca ccaggacggg tggaggtgcc tgtagagtac   8820
attcggaccc tctctcggac cctctctcag cccctgagtg tgcgggacct gcggagcgca   8880
gttcgggatc tgcactcgag gatttttcga ggacgcaata agctaagcat ctgcccggag   8940
catggaagca cgtcagtagg ccatgaactg cacccgggag gggtgggggt ggaagcgcac   9000
ggtgtcagct ttgcagaatg tgtacgccaa ggggagggtg aagcgtggcg ggagggcgag   9060
gcgaaggaag gagggcgtga gaaaggaggc ggtggcgggc ggaggagagt tatctatact   9120
ttttaaaaaa aaggagccgc ttgagccgcg taaagggaga cttggggagc gcctgacagc   9180
acgcgcggga cacgagagta ccacgcttcc ctactctttc agaccttgac tggtacgggg   9240
tcccaggact gcaggaggcc agcgacgcgt gccctaggga gtcctgcagc agtgccctgc   9300
ctgaggcccg tgaaggtgca aacgtccact tcccaccgca cccggttcct cgcgagcact   9360
tttcctgtgc cgcaccagaa ctcgtagcag gggcccaggg gctgaatgca agcttgatgg   9420
acggcggcgc gctgcccaga ctcatgccca cctcgtctgg agtcgctgga gcctgcgctg   9480
ctcggcggag acaagcgtct ccggaattgc tgcgctgcag ccggcggcgg cgatctggag   9540
caaccgaggc cagcagcagc tcggctgccg tggcacgccg caatgagcgc gagcgcaacc   9600
gcgtaaagct ggtaaacttg ggcttccagg cgctgcggca gcacgtgccg cacggcggcg   9660
ccaacaagaa gctgagtaag gtggagacgc tgcgctccgc ggtagagtac attcgtgcgc   9720
tgcagcggct gctcgcagag cacgacgcgg tgcgtgccgc gctcgctggg gggctgttaa   9780
```

-continued

```
cacccgctac tccgccgtcc gatgagtgcg cgcagccctc tgcctcccct gccagcgcgt   9840
ctctgtcctg cgcctctacg tctccgtccc cggaccgcct gggctgctct gagcctacct   9900
ccccgcgctc cgcctactcg tcggaggaaa gcagctgcga gggagagcta agcccgatgg   9960
agcaggagct gcttgacttt tccagttggt tagggggcta ctgagcatcc caccccccta  10020
aggtaagttc caggacggcg gggaggcgaa gcagtaaggg agacacgtgg tgggcgggcc  10080
tgacacttag cgccacgggg accctgtgca gccaggactc agctggggcg atcacttgga  10140
tttcgcgcac gcttcatttt tcctcaacct ttttcaagcc tgagcaagac cggcgtttgt  10200
ttgtccggga ttgcaaaact tcctctcaga gctctgctgt gggtggggga aggggaggcc  10260
aggggagggg agcggcctca gggccgggcc ggcgaggtcc cagtgctgtc agagcctggc  10320
cgagtcgggt gctggaggcg gggtgagttt gcattgcaaa tcgcgtccta ggccggggtg  10380
cggagtgagt cggctggagc gggcccctga gtcacggcgg gcaggttctg agcgtgcgcc  10440
ccgcccccgt cggcgcctct gagcggatcg aggcacccat gagttgagac tccaaaacta  10500
atcaagcaaa cgaaactgcc tactgcgcct tgggaggtgg ggcggtgtcc gtacacattg  10560
acacctttta tcttcttcac agctgcatcc ctgggtgact cctggtggac ctacctgctt  10620
ctagcccaag aaacctgggc ctatgcctta cccatgctgt ctagtgcagc ctgaccaaat  10680
gccaagtgct gactgacctc tgctcggcct ccacgccgcg gaatgacatc ttccatcttc  10740
cggaccttgc agcatcagga cttggaaatt tctcaggata aagattttta caatgacaat  10800
ctacttttta tcaattaact tgaactgttg taggactcta ctgaaaatat gaagaattat  10860
ttttatacaa aggatcctta agcttggagc acaataaaga tgacctctgt ccctcacccc  10920
cactgtctag aacttccaac ctggccaaag tgtggaccgg ttgggcctga ggcaagatgc  10980
ctggctgcac ccttcttcct cttctgaagc ctatactgac gctgatgttt ggccagtgtg  11040
ggaaccctgc tgttgcaaag tgtactattc tataaaagtt gtttttcatt ggtgtttgca  11100
gtgccttgta ccttctcaac cttgcatctg tctcaccctt gttccccagg tgcggtctaa  11160
gctggggtgg atagtactag cccagatttc tctcgagacc tgtattgcat gggtggatac  11220
aaaggtattg ggtgcctact ctagccatct ctccagagat ggaaaagcaa ttcagacacc  11280
taggaaggca aggtagctgt ctgtgagcct gtgtctgccc tccagggtgg ctctcccctg  11340
ggaaggatct gtgtaagagg ggcaagtgca gggtgctagg ctgaaggcag agctctggat  11400
tgtgggcatc tctaggccca ggtctctctt ccttaccact tgggtggccc ttggcaaatt  11460
gccttatttg caaatggtat tgagcttaaa gctccctccc aggttttgga taacctgccc  11520
atgagcttgc agccagtgtg tgctaggcac ccgtgctgac tgctagggtc agtggccatc  11580
gtgaggccct gcagatagat ctttacttta agattctcta gtgagcaagg aagacctgga  11640
agcttcctca gtactcccca cacaagttcc ctagcctagg gagccaagct gtgattgcta  11700
agatattacc tggctccacc tttgaccccc gagcctccga agctttgaag tctccgtgtg  11760
tccaaagctc ccttttattg caggggtttg ggaggggctg aggggatccc caggtggttt  11820
tagggtgctt caggcatccc ttcagaaggg agtggtcagg gcacaaccgt tggagctatg  11880
ggaatcagga agtgctgtgc aatggagcag atgccttcca ggtacctgtg gtggctatac  11940
agaaggcagt atacaagaag ctcaatctgt attatgatag ctgggctcct tccctgcagg  12000
acccagaacc ccaaaagcca gggtcaaagt tgaatctgta actttggccc cagcttgtca  12060
gcttctctga tgaaggtcag gctcagttgg ggtcaggcca agcacagctt ggagccacaa  12120
aactgagtgg acctgcctta gaggacaaaa tggggcatgg caaggccatt gagggagggc  12180
```

-continued

```
caccctcttc ccaggagccc gttgccagcc agtgtgttca ctgaactagg ggacctgaat  12240
tgtcccctga tttctttcct gtttcttaaa gtggcttatg gggaatggag gggttgctgg  12300
aagcgtgagc tcccttgtgt ccataaattc ccagtggtgt caatggtgtg cccctgttgt  12360
attatgggat atctctgaag tcttcattaa acaactttat tggctcacat ctgtaatctg  12420
aacacttagg agactgagat aggaggacag tccaagctca aaggggtagg gatgaggatg  12480
ggggctagga aggaggaaag gcagatggct cagtaggtga cagtgcttgc tgtgagagta  12540
taagggcccg cattgaactc ttcaaaaccc acagagaaat tggatattaa agcacatctg  12600
taatcccggt gctcctatgg aaagaaggga ggcagagaca gggggaatct tcaggaggta  12660
tccaagccag ctaggctggc acacacaacg gaaaaacaag agcctcctat gtcaaacaag  12720
gtggaaggtg aggaacaaca cttgatgttg tcctccgatc ttcatgcatg agtaggtgca  12780
tacacaaccc aggcacaaag gaacccttct gcttcaggaa ctgagggtgt actgctgtgt  12840
ctgaaagaaa ctccaccctt agggaactta ctttctgctg gagatgagcc tattggcaag  12900
aggcatgtac cagcttcatg ggtaatcaag tgaaaagaaa ctgcttaaag cccaatagcc  12960
gggttgtggc ttaaggaggc tttctgcaac ttccaccctg ctgtcttcct ccacgtggtt  13020
ttgaagcatc tccagactgc acaatttcct tgcctaagga aaccctttat cacccatggt  13080
gatgaaagtg cagcttgcca gccagtggca ccgtttcttt tctgatgtat agaaccaggg  13140
tccatcccat gtctaaacac caaacttgca aggtctctta agcctcttgg aagcaatttg  13200
tcccagggat cacgtgccac acgaagcata gacaccacac ctgggagacc aatctcgggt  13260
ggatgccagc ttccagacag ataatgtgtc ctttgtatac cagtctaggg gctggccagg  13320
ctacagcaga agtctggaac tgtatccatc tgtctatata gtgctgacct cgtggggtag  13380
tcacgtgtcc tgtgataccc cagggttcag ctgagcttct aggttagtct gtcaatcaag  13440
gctatgttac tcaaggtgtc tttcattccc gggcagcacc attgaagaca caatactccc  13500
cagatactgt cttcccaaag gggcccaggc agtcctggga gcccagctat caatcagcct  13560
ttagagtccc agaaccctga gctctacagg gacatagaaa caatcctcct gctgcaatat  13620
gcaggctgtc cagggcagct tgagaaatgt ctgaggcaca gagcaaagca agtggagttt  13680
cagcaggttc ctgtccgtca tctttctttg gttttgagca gccttctcct gccatgtgtc  13740
cccatcatgc tggtggcccg aaacgtcaga gctcacagac tgattatttc aagtctttat  13800
attgtagtga caggaagccg gctgaggccc acgtcttact ctaaaagggc aaaggagtag  13860
ccgtgagagg atttaaaatg caaagcttct ctttctttgg tgctttctgt cctgcactca  13920
ctaatttaat gccattgtca ggaaaggagc catttaatgg cagttggttc tctatatcca  13980
aaggctctcc atccatagtt tgaaaaatgt ttgtgtgtgc atgcatgcat gtataagtat  14040
agtacatgtg catgtgtgaa tgtgtggagg gcagaggctg acgttgggcg tcttcaatta  14100
ttctgcacct tagcttttga gacagggtct cactgggcct gaagctcatt tatagggtat  14160
attggctgcc tggaaagcct gggtttttat atgggtgcag aggtcaaact catgtgttca  14220
tgtttttgta gtacttaaat gtttgagcta tctttccagc ccattgaaaa tattttgaga  14280
tgtttgggta tggtggtgca aacctttaat ttcagcactc agaaggcagt ggcaggcgaa  14340
tctctgattt tcagatcagc ctggtttata gctctagttc caggacaacc agagctacaa  14400
agaaaacaaa atgacctcta aaaaacaaaa ccaaaacaaa atgttttaag aaacaatttt  14460
actcatcgta aacatgtggg gacctttccc ttgtcacata cagtgttctg ttgtcgtggt  14520
```

-continued

```
gcagggtcag tccctgcggg aggattaaag cacaggaggg tacatgtagg ctctgtaaca  14580
tactacagac ttcgacagaa gagttttgag aagtcctttt tggtatctca aaaaggtggt  14640
agtttcccaa atcggtcacc ctcaagtata aaagaccaac cagaataagt gggcatgcat  14700
gttgttgcca tctgtctttt ttgttgcata atgccagtta gacgtgcaaa tgccagaaca  14760
tttagctagc atacagaaac taagacagga catagttccc agtaccccag aggtacctca  14820
tggccaaagt ccagtagttt tcatagtgtg ccagtactgt ccatccttgc ttactggtgg  14880
gaaagagaag gacaagacag gcttggtggc acatgctttt aaacccagca ctgagggtgg  14940
agtggggggg gcagggctct atgaatttta aggtcatcct gatctacata gtaagttcca  15000
ggtcaaccaa ggtgtcacag taagactgtg tctcaaacaa cagccacgac aaagagagac  15060
ttgggatgac cttgctctcc tgtcaatatc ttcagcataa gaagttgtcc gtttgatgta  15120
gggaagtctc tttccgagag atagatgtag tcccttgtcc cttaactctt catgcttact  15180
tcatctcttt cctgcctttg aagccaagtt ctggtttgaa tgggaaatgt ggtccttgga  15240
cactgagctt gctcagctct gggtttaact agaagacttt atggtgtggg tggcaagact  15300
ggacacaaca gagcaacaat gtctccttat tgaacaagta tactccagag tctcctgacc  15360
ttcaccctcc cactaggggt caaaggtaag agtagcagga atttcaagat agggatactg  15420
tggggcccat ggggctgcag aggtctgatg cctaagaagc tggtcctcaa atcacccaca  15480
gaactgccgt gtgaagagac cccacatatc acttgcttcc tgcccctctt gagaccacag  15540
ccccttgtag acagtgacac ccaggcatgt ccagcagcag aagggatgtg acatggatca  15600
cttttgtcaa tggggccctg ttactcttac acaccctccc ttctcataag attggtgacc  15660
ttcagagacg tgggtaccaa agcagcacgt ctgtgtccag aagtaactgg cctgatgaca  15720
ggctgggcaa acctagtgtg gagtgaggct gaagggccct gatctagggc tgtcaagagc  15780
gaaggtaggg gctgtaggac agggagggcc ttggaggctt cacagcacag gtaggccctt  15840
gggtaggtgc atgttgccgc ctctgctctc ctgaaagagg ggtctggccc ggtgagtggc  15900
ttctcagatt cagtctgagt ggttggtttg gcttggctct gagttctgag ggcctgggaa  15960
tggctttctg ttctgaagcc tagaggagat gagagagagg aagaaaggat ccagaagctg  16020
attgtatggg gtctaggctg taagggcagg tgactagggg agggtggagg atgctgccag  16080
ggagaagaca cagcacaaag acacagaaag ttccaacctc cccggggggc acatcctcct  16140
ggactcttta agggttttac cctatctaac agccataggt acccagagaa agactccatg  16200
tgaacaggcc acacacccct tatgcctgcc tgaggcaggg actggatgtt tgctgttttc  16260
tgcttacgta gagggactgg tctgccagtt agagaggagc caggacccag ctcagacctc  16320
taggacactc taacccccttc caagcatgtg aggaaaaggc ccatgctctg agcctggaga  16380
ccagagccag gtgctcgggg ctcaggaagg actccctaaa aggccgactg gaagaggtaa  16440
ctctgccttg accaccaggc cctgcttcac ctcagatcc                        16479
```

<210> SEQ ID NO 32
<211> LENGTH: 5616
<212> TYPE: DNA
<213> ORGANISM: Homo sapiens

<400> SEQUENCE: 32

```
ccccggcgca gcgcggccgc agcagcctcc gccccccgca cggtgtgagc gcccgacgcg     60
gccgaggcgg ccggagtccc gagctagccc cggcggccgc cgccgcccag accggacgac    120
aggccacctc gtcggcgtcc gcccgagtcc ccgcctcgcc gccaacgcca caaccaccgc    180
```

-continued

```
gcacggcccc ctgactccgt ccagtattga tcgggagagc cggagcgagc tcttcgggga    240
gcagcgatgc gaccctccgg gacggccggg gcagcgctcc tggcgctgct ggctgcgctc    300
tgcccggcga gtcgggctct ggaggaaaag aaagtttgcc aaggcacgag taacaagctc    360
acgcagttgg gcacttttga agatcatttt ctcagcctcc agaggatgtt caataactgt    420
gaggtggtcc ttgggaattt ggaaattacc tatgtgcaga ggaattatga tctttccttc    480
ttaaagacca tccaggaggt ggctggttat gtcctcattg ccctcaacac agtggagcga    540
attcctttgg aaaacctgca gatcatcaga ggaaatatgt actacgaaaa ttcctatgcc    600
ttagcagtct tatctaacta tgatgcaaat aaaaccggac tgaaggagct gcccatgaga    660
aatttacagg aaatcctgca tggcgccgtg cggttcagca acaaccctgc cctgtgcaac    720
gtggagagca tccagtggcg ggacatagtc agcagtgact ttctcagcaa catgtcgatg    780
gacttccaga accacctggg cagctgccaa aagtgtgatc caagctgtcc caatgggagc    840
tgctggggtg caggagagga gaactgccag aaactgacca aaatcatctg tgcccagcag    900
tgctccgggc gctgccgtgg caagtccccc agtgactgct gccacaacca gtgtgctgca    960
ggctgcacag gcccccggga gagcgactgc ctggtctgcc gcaaattccg agacgaagcc   1020
acgtgcaagg acacctgccc cccactcatg ctctacaacc ccaccacgta ccagatggat   1080
gtgaaccccg agggcaaata cagctttggt gccacctgcg tgaagaagtg tccccgtaat   1140
tatgtggtga cagatcacgg ctcgtgcgtc cgagcctgtg gggccgacag ctatgagatg   1200
gaggaagacg gcgtccgcaa gtgtaagaag tgcgaagggc cttgccgcaa agtgtgtaac   1260
ggaataggta ttggtgaatt taaagactca ctctccataa atgctacgaa tattaaacac   1320
ttcaaaaact gcacctccat cagtggcgat ctccacatcc tgccggtggc atttaggggt   1380
gactccttca cacatactcc tcctctggat ccacaggaac tggatattct gaaaaccgta   1440
aaggaaatca cagggttttt gctgattcag gcttggcctg aaaacaggac ggacctccat   1500
gcctttgaga acctagaaat catacgcggc aggaccaagc aacatggtca gttttctctt   1560
gcagtcgtca gcctgaacat aacatccttg ggattacgct ccctcaagga gataagtgat   1620
ggagatgtga taatttcagg aaacaaaaat ttgtgctatg caaatacaat aaactggaaa   1680
aaactgtttg ggacctccgg tcagaaaacc aaaattataa gcaacagagg tgaaaacagc   1740
tgcaaggcca caggccaggt ctgccatgcc ttgtgctccc ccgagggctg ctggggcccg   1800
gagcccaggg actgcgtctc ttgccggaat gtcagccgag gcagggaatg cgtggacaag   1860
tgcaaccttc tggagggtga gccaagggag tttgtggaga actctgagtg catacagtgc   1920
cacccagagt gcctgcctca ggccatgaac atcacctgca caggacgggg accagacaac   1980
tgtatccagt gtgcccacta cattgacggc ccccactgcg tcaagacctg cccggcagga   2040
gtcatgggag aaaacaacac cctggtctgg aagtacgcag acgccggcca tgtgtgccac   2100
ctgtgccatc caaactgcac ctacggatgc actgggccag gtcttgaagg ctgtccaacg   2160
aatgggccta agatcccgtc catcgccact gggatggtgg gggccctcct cttgctgctg   2220
gtggtggccc tggggatcgg cctcttcatg cgaaggcgcc acatcgttcg gaagcgcacg   2280
ctgcggaggc tgctgcagga gagggagctt gtggagcctc ttacacccag tggagaagct   2340
cccaaccaag ctctcttgag gatcttgaag gaaactgaat tcaaaaagat caaagtgctg   2400
ggctccggtg cgttcggcac ggtgtataag ggactctgga tcccagaagg tgagaaagtt   2460
aaaattcccg tcgctatcaa ggaattaaga gaagcaacat ctccgaaagc caacaaggaa   2520
```

-continued

```
atcctcgatg aagcctacgt gatggccagc gtggacaacc cccacgtgtg ccgcctgctg   2580
ggcatctgcc tcacctccac cgtgcagctc atcacgcagc tcatgccctt cggctgcctc   2640
ctggactatg tccgggaaca caaagacaat attggctccc agtacctgct caactggtgt   2700
gtgcagatcg caaagggcat gaactacttg gaggaccgtc gcttggtgca ccgcgacctg   2760
gcagccagga acgtactggt gaaaacaccg cagcatgtca agatcacaga ttttgggctg   2820
gccaaactgc tgggtgcgga agagaaagaa taccatgcag aaggaggcaa agtgcctatc   2880
aagtggatgg cattggaatc aattttacac agaatctata cccaccagag tgatgtctgg   2940
agctacgggg tgaccgtttg ggagttgatg acctttggat ccaagccata tgacggaatc   3000
cctgccagcg agatctcctc catcctggag aaaggagaac gcctccctca gccacccata   3060
tgtaccatcg atgtctacat gatcatggtc aagtgctgga tgatagacgc agatagtcgc   3120
ccaaagttcc gtgagttgat catcgaattc tccaaaatgg cccgagaccc ccagcgctac   3180
cttgtcattc agggggatga aagaatgcat ttgccaagtc ctacagactc caacttctac   3240
cgtgccctga tggatgaaga agacatggac gacgtggtgg atgccgacga gtacctcatc   3300
ccacagcagg gcttcttcag cagcccctcc acgtcacgga ctcccctcct gagctctctg   3360
agtgcaacca gcaacaattc caccgtggct tgcattgata gaaatgggct gcaaagctgt   3420
cccatcaagg aagacagctt cttgcagcga tacagctcag accccacagg cgccttgact   3480
gaggacagca tagacgacac cttcctccca gtgcctgaat acataaacca gtccgttccc   3540
aaaaggcccg ctggctctgt gcagaatcct gtctatcaca atcagcctct gaaccccgcg   3600
cccagcagag acccacacta ccaggacccc cacagcactg cagtgggcaa ccccgagtat   3660
ctcaacactg tccagcccac ctgtgtcaac agcacattcg acagccctgc ccactgggcc   3720
cagaaaggca gccaccaaat tagcctggac aaccctgact accagcagga cttctttccc   3780
aaggaagcca agccaaatgg catctttaag ggctccacag ctgaaaatgc agaataccta   3840
agggtcgcgc cacaaagcag tgaatttatt ggagcatgac cacggaggat agtatgagcc   3900
ctaaaaatcc agactctttc gatacccagg accaagccac agcaggtcct ccatcccaac   3960
agccatgccc gcattagctc ttagacccac agactggttt tgcaacgttt acaccgacta   4020
gccaggaagt acttccacct cgggcacatt ttgggaagtt gcattccttt gtcttcaaac   4080
tgtgaagcat ttacagaaac gcatccagca agaatattgt ccctttgagc agaaatttat   4140
ctttcaaaga ggtatatttg aaaaaaaaaa aaagtatatg tgaggatttt tattgattgg   4200
ggatcttgga gtttttcatt gtcgctattg atttttactt caatgggctc ttccaacaag   4260
gaagaagctt gctggtagca cttgctaccc tgagttcatc caggcccaac tgtgagcaag   4320
gagcacaagc cacaagtctt ccagaggatg cttgattcca gtggttctgc ttcaaggctt   4380
ccactgcaaa acactaaaga tccaagaagg ccttcatggc cccagcaggc cggatcggta   4440
ctgtatcaag tcatggcagg tacagtagga taagccactc tgtcccttcc tgggcaaaga   4500
agaaacggag gggatggaat tcttccttag acttactttt gtaaaaatgt ccccacggta   4560
cttactcccc actgatggac cagtggtttc cagtcatgag cgttagactg acttgtttgt   4620
cttccattcc attgttttga aactcagtat gctgcccctg tcttgctgtc atgaaatcag   4680
caagagagga tgacacatca aataataact cggattccag cccacattgg attcatcagc   4740
atttggacca atagcccaca gctgagaatg tggaatacct aaggatagca ccgcttttgt   4800
tctcgcaaaa acgtatctcc taatttgagg ctcagatgaa atgcatcagg tcctttgggg   4860
catagatcag aagactacaa aaatgaagct gctctgaaat ctcctttagc catcacccca   4920
```

acccccccaaa attagtttgt gttacttatg gaagatagtt ttctcctttt acttcacttc 4980
aaaagctttt tactcaaaga gtatatgttc cctccaggtc agctgccccc aaaccccctc 5040
cttacgcttt gtcacacaaa aagtgtctct gccttgagtc atctattcaa gcacttacag 5100
ctctggccac aacagggcat tttacaggtg cgaatgacag tagcattatg agtagtgtgg 5160
aattcaggta gtaaatatga aactagggtt tgaaattgat aatgctttca caacatttgc 5220
agatgtttta gaaggaaaaa agttccttcc taaaataatt tctctacaat tggaagattg 5280
gaagattcag ctagttagga gcccaccttt tttcctaatc tgtgtgtgcc ctgtaacctg 5340
actggttaac agcagtcctt tgtaaacagt gttttaaact ctcctagtca atatccaccc 5400
catccaattt atcaaggaag aaatggttca gaaaatattt tcagcctaca gttatgttca 5460
gtcacacaca catacaaaat gttccttttg cttttaaagt aatttttgac tcccagatca 5520
gtcagagccc ctacagcatt gttaagaaag tatttgattt ttgtctcaat gaaaataaaa 5580
ctatattcat ttccactcta aaaaaaaaaa aaaaaa 5616

<210> SEQ ID NO 33
<211> LENGTH: 2156
<212> TYPE: DNA
<213> ORGANISM: Homo sapiens

<400> SEQUENCE: 33
cgggcccgtt gcaagatggc ggcggccatg ctgggccccg gggctgtgtg tgcgcagcgg 60
gcggcggcgc ggcccggaag gctggcgcgg cgacggcgtt agcccggccc tcggcccctc 120
tttgcggccg ctccctccgc ctattccctc cttgctcgag atggatctgc ccgtgggccc 180
cggcgcggcg gggcccagca acgtcccggc cttcctgacc aagctgtgga ccctcgtgag 240
cgacccggac accgacgcgc tcatctgctg gagcccgagc gggaacagct tccacgtgtt 300
cgaccagggc cagtttgcca aggaggtgct gcccaagtac ttcaagcaca acaacatggc 360
cagcttcgtg cggcagctca acatgtatgg cttccggaaa gtggtccaca tcgagcaggg 420
cggcctggtc aagccagaga gagacgacac ggagttccag cacccatgct tcctgcgtgg 480
ccaggagcag ctccttgaga acatcaagag gaaagtgacc agtgtgtcca ccctgaagag 540
tgaagacata aagatccgcc aggacagcgt caccaagctg ctgacggacg tgcagctgat 600
gaaggggaag caggagtgca tggactccaa gctcctggcc atgaagcatg agaatgaggc 660
tctgtggcgg gaggtggcca gccttcggca gaagcatgcc cagcaacaga aagtcgtcaa 720
caagctcatt cagttcctga tctcactggt gcagtcaaac cggatcctgg gggtgaagag 780
aaagatcccc ctgatgctga acgacagtgg ctcagcacat tccatgccca agtatagccg 840
gcagttctcc ctggagcacg tccacggctc gggcccctac tcggccccct ccccagccta 900
cagcagctcc agcctctacg cccctgatgc tgtggccagc tctggaccca tcatctccga 960
catcaccgag ctggctcctg ccagccccat ggcctccccc ggcgggagca tagacgagag 1020
gcccctatcc agcagccccc tggtgcgtgt caaggaggag ccccccagcc cgcctcagag 1080
cccccgggta gaggaggcga gtcccgggcg cccatcttcc gtggacaccc tcttgtcccc 1140
gaccgccctc attgactcca tcctgcggga gagtgaacct gcccccgcct ccgtcacagc 1200
cctcacggac gccagggggcc acacggacac cgagggccgg cctccctccc ccccgcccac 1260
ctccacccct gaaaagtgcc tcagcgtagc ctgcctggac aagaatgagc tcagtgacca 1320
cttggatgct atggactcca acctggataa cctgcagacc atgctgagca gccacggctt 1380
cagcgtggac accagtgccc tgctggacct gttcagcccc tcggtgaccg tgcccgacat 1440
gagcctgcct gaccttgaca gcagcctggc cagtatccaa gagctcctgt ctccccagga 1500
gccccccagg cctcccgagg cagagaacag cagcccggat tcagggaagc agctggtgca 1560
ctacacagcg cagccgctgt tcctgctgga ccccggctcc gtggacaccg ggagcaacga 1620
cctgccggtg ctgtttgagc tgggagaggg ctcctacttc tccgaagggg acggcttcgc 1680
cgaggacccc accatctccc tgctgacagg ctcggagcct cccaaagcca aggaccccac 1740
tgtctcctag aggccccgga ggagctgggc cagccgccca cccccacccc cagtgcaggg 1800
ctggtcttgg ggaggcaggg cagcctcgcg gtcttgggca ctggtgggtc ggccgccata 1860
gccccagtag gacaaacggg ctcgggtctg ggcagcacct ctggtcagga gggtcaccct 1920
ggcctgccag tctgccttcc cccaaccccg tgtcctgtgg tttggttggg gcttcacagc 1980
cacacctgga ctgaccctgc aggttgttca tagtcagaat tgtattttgg atttttacac 2040
aactgtcccg ttccccgctc cacagagata cacagatata tacacacagt ggatggacgg 2100
acaagacagg cagagatcta taaacagaca ggctctaaaa aaaaaaaaaa aaaaaa 2156

<210> SEQ ID NO 34
<211> LENGTH: 2207
<212> TYPE: DNA
<213> ORGANISM: Homo sapiens

<400> SEQUENCE: 34
ctcttgaaga gggctggtat atttgtgcct gctggaggtg gaattaacag taagaaggag 60
aaagggattg aatggactta caggaaggat ttcaagtaaa ttcagggaaa cacatttact 120
tgaatagtac aacctagagt attattttac actaagacga cacaaaagat gttaaagtta 180
tcaccaagct gccggacaga tatatattcc aacaccaagg tgcagatcag catagatctg 240
tgattcagaa atcaggattt gttttggaaa gagctcaagg gttgagaaga actcaaaagc 300
aagtgaagat tactttggga actacagttt atcagaagat caacttttgc taattcaaat 360
accaaaggcc tgattatcat aaattcatat aggaatgcat aggtcatctg atcaaataat 420
attagccgtc ttctgctaca tcaatgcagc aaaaactctt aacaactgtg gataattgga 480
aatctgagtt tcagctttct tagaaataac tactcttgac atattccaaa atatttaaaa 540
taggacagga aaatcggtga ggatgttgtg ctcagaaatg tcactgtcat gaaaaatagg 600
taaatttgtt ttttcagcta ctgggaaact gtacctccta gaaccttagg tttttttttt 660
ttttaagagg acaagaagga ctaaaaatat caacttttgc ttttggacaa aaatgcatct 720
gactgtattt ttacttaagg gtattgtggg tttcctctgg agctgctggg ttctagtggg 780
ttatgcaaaa ggaggtttgg gagacaatca tgttcactcc agttttattt atagaagact 840
acggaaccac gaaagacggg aaatacaaag ggaaattctc tctatcttgg gtttgcctca 900
cagacccaga ccattttcac ctggaaaaca agcgtcctct gcacctctct ttatgctgga 960
tctctacaat gccatgacca atgaagaaaa tcctgaagag tcggagtact cagtaagggc 1020
atccttggca gaagagacca gaggggcaag aaagggatac ccagcctctc ccaatgggta 1080
tcctcgtcgc atacagttat ctcggacgac tcctctgacc acccagagtc ctcctctagc 1140
cagcctccat gataccaact ttctgaatga tgctgacatg gtcatgagct ttgtcaactt 1200
agttgaaaga gacaaggatt tttctcacca gcgaaggcat tacaaagaat ttcgatttga 1260
tcttacccaa attcctcatg gagaggcagt gacagcagct gaattccgga tatacaagga 1320
ccggagcaac aaccgatttg aaaatgaaac aattaagatt agcatatatc aaatcatcaa 1380
ggaatacaca aatagggatg cagatctgtt cttgttagac acaagaaagg cccaagcttt 1440
agatgtgggt tggcttgtct ttgatatcac tgtgaccagc aatcattggg tgattaatcc 1500
ccagaataat ttgggcttac agctctgtgc agaaacaggg gatggacgca gtatcaacgt 1560
aaaatctgct ggtcttgtgg gaagacaggg acctcagtca aaacaaccat tcatggtggc 1620
cttcttcaag gcgagtgagg tacttcttcg atccgtgaga gcagccaaca aacgaaaaaa 1680
tcaaaaccgc aataaatcca gctctcatca ggactcctcc agaatgtcca gtgttggaga 1740
ttataacaca agtgagcaaa aacaagcctg taagaagcac gaactctatg tgagcttccg 1800
ggatctggga tggcaggact ggattatagc accagaagga tacgctgcat tttattgtga 1860
tggagaatgt tcttttccac ttaacgccca tatgaatgcc accaaccacg ctatagttca 1920
gactctggtt catctgatgt ttcctgacca cgtaccaaag ccttgttgtg ctccaaccaa 1980
attaaatgcc atctctgttc tgtactttga tgacagctcc aatgtcattt tgaaaaaata 2040
tagaaatatg gtagtacgct catgtggctg ccactaatat taaataatat tgataataac 2100
aaaaagatct gtattaaggt ttatggctgc aataaaaagc atactttcag acaaacgggg 2160
aatttcctaa aaaaaaaaaa aaaaaaaaaa aaaaaaaaaa aaaaaaa 2207

<210> SEQ ID NO 35
<211> LENGTH: 1878
<212> TYPE: DNA
<213> ORGANISM: Homo sapiens

<400> SEQUENCE: 35
gggcgcagcg gggcccgtct gcagcaagtg accgacggcc gggacggccg cctgcccccct 60 ctgccacctg gggcggtgcg ggcccggagc ccggagcccg ggtagcgcgt agagccggcg 120
cgatgcacgt gcgctcactg cgagctgcgg cgccgcacag cttcgtggcg ctctgggcac 180
ccctgttcct gctgcgctcc gccctggccg acttcagcct ggacaacgag gtgcactcga 240
gcttcatcca ccggcgcctc cgcagccagg agcggcggga gatgcagcgc gagatcctct 300
ccattttggg cttgccccac cgcccgcgcc cgcacctcca gggcaagcac aactcggcac 360
ccatgttcat gctggacctg tacaacgcca tggcggtgga ggagggcggc gggcccggcg 420
gccagggctt ctcctacccc tacaaggccg tcttcagtac ccagggcccc cctctggcca 480
gcctgcaaga tagccatttc ctcaccgacg ccgacatggt catgagcttc gtcaacctcg 540
tggaacatga caaggaattc ttccacccac gctaccacca tcgagagttc cggtttgatc 600
tttccaagat cccagaaggg gaagctgtca cggcagccga attccggatc tacaaggact 660
acatccggga acgcttcgac aatgagacgt tccggatcag cgtttatcag gtgctccagg 720
agcacttggg cagggaatcg gatctcttcc tgctcgacag ccgtaccctc tgggcctcgg 780
aggagggctg gctggtgttt gacatcacag ccaccagcaa ccactgggtg gtcaatccgc 840
ggcacaacct gggcctgcag ctctcggtgg agacgctgga tgggcagagc atcaacccca 900
agttggcggg cctgattggg cggcacgggc cccagaacaa gcagcccttc atggtggctt 960
tcttcaaggc cacggaggtc cacttccgca gcatccggtc cacggggagc aaacagcgca 1020
gccagaaccg ctccaagacg cccaagaacc aggaagccct gcggatggcc aacgtggcag 1080
agaacagcag cagcgaccag aggcaggcct gtaagaagca cgagctgtat gtcagcttcc 1140
gagacctggg ctggcaggac tggatcatcg cgcctgaagg ctacgccgcc tactactgtg 1200
agggggagtg tgccttccct ctgaactcct acatgaacgc caccaaccac gccatcgtgc 1260
agacgctggt ccacttcatc aacccggaaa cggtgcccaa gccctgctgt gcgcccacgc 1320
agctcaatgc catctccgtc ctctacttcg atgacagctc caacgtcatc ctgaagaaat 1380
acagaaacat ggtggtccgg gcctgtggct gccactagct cctccgagaa ttcagaccct 1440
ttggggccaa gtttttctgg atcctccatt gctcgccttg gccaggaacc agcagaccaa 1500
ctgccttttg tgagaccttc ccctccctat ccccaacttt aaaggtgtga gagtattagg 1560
aaacatgagc agcatatggc ttttgatcag tttttcagtg gcagcatcca atgaacaaga 1620
tcctacaagc tgtgcaggca aaacctagca ggaaaaaaaa acaacgcata aagaaaaatg 1680
gccgggccag gtcattggct gggaagtctc agccatgcac ggactcgttt ccagaggtaa 1740
ttatgagcgc ctaccagcca ggccacccag ccgtgggagg aagggggcgt ggcaaggggt 1800
gggcacattg gtgtctgtgc gaaaggaaaa ttgacccgga agttcctgta ataaatgtca 1860
caataaaacg aatgaatg 1878

<210> SEQ ID NO 36
<211> LENGTH: 5434
<212> TYPE: DNA
<213> ORGANISM: Homo sapiens

<400> SEQUENCE: 36
cgtccgcgtg gggggggtgt gtgcccgcct tgcgcatgcg tgttccctgg gcatggccgg 60
ctccgttcca tccttctgca cagggtatcg cctctctccg tttggtacat cccctcctcc 120
cccacgcccg gactggggtg gtagacgcgc ctccgctcat cgcccctccc catcggtttc 180
cgcgcgaaaa gccggggcgc ctgcgctgcc gccgccgcgt ctgctgaagc ctccgagatg 240
ccggcgcgta ccgccccagc ccgggtgccc acactggccg tcccggccat ctcgctgccc 300
gacgatgtcc gcaggcggct caaagatttg gaaagagaca gcttaacaga aaaggaatgt 360
gtgaaggaga aattgaatct cttgcacgaa tttctgcaaa cagaaataaa gaatcagtta 420
tgtgacttgg aaaccaaatt acgtaaagaa gaattatccg aggagggcta cctggctaaa 480
gtcaaatccc ttttaaataa agatttgtcc ttggagaacg gtgctcatgc ttacaaccgg 540
gaagtgaatg gacgtctaga aaacgggaac caagcaagaa gtgaagcccg tagagtggga 600
atggcagatg ccaacagccc ccccaaaccc ctttccaaac ctcgcacgcc caggaggagc 660
aagtccgatg gagaggctaa gcctgaacct tcacctagcc ccaggattac aaggaaaagc 720
accaggcaaa ccaccatcac atctcatttt gcaaagggcc ctgccaaacg gaaacctcag 780
gaagagtctg aaagagccaa atcggatgag tccatcaagg aagaagacaa agaccaggat 840
gagaagagac gtagagttac atccagagaa cgagttgcta gaccgcttcc tgcagaagaa 900
cctgaaagag caaaatcagg aacgcgcact gaaaaggaag aagaaagaga tgaaaaagaa 960
gaaaagagac tccgaagtca aaccaaagaa ccaacaccca aacagaaact gaaggaggag 1020
ccggacagag aagccagggc aggcgtgcag gctgacgagg acgaagatgg agacgagaaa 1080
gatgagaaga agcacagaag tcaacccaaa gatctagctg ccaaacggag gcccgaagaa 1140
aaagaacctg aaaaagtaaa tccacagatt tctgatgaaa aagacgagga tgaaaaggag 1200
gagaagagac gcaaaacgac cccccaaagaa ccaacggaga aaaaaatggc tcgcgccaaa 1260
acagtcatga actccaagac ccaccctccc aagtgcattc agtgcgggca gtacctggac 1320
gaccctgacc tcaaatatgg gcagcaccca ccagacgcgg tggatgagcc acagatgctg 1380
acaaatgaga agctgtccat ctttgatgcc aacgagtctg gctttgagag ttatgaggcg 1440
cttccccagc acaaactgac ctgcttcagt gtgtactgta agcacggtca cctgtgtccc 1500

-continued

```
atcgacaccg gcctcatcga gaagaatatc gaactcttct tttctggttc agcaaaacca   1560
atctatgatg atgacccgtc tcttgaaggt ggtgttaatg gcaaaaatct tggccccata   1620
aatgaatggt ggatcactgg ctttgatgga ggtgaaaagg ccctcatcgg cttcagcacc   1680
tcatttgccg aatacattct gatggatccc agtcccgagt atgcgcccat atttgggctg   1740
atgcaggaga agatctacat cagcaagatt gtggtggagt tcctgcagag caattccgac   1800
tcgacctatg aggacctgat caacaagatc gagaccacgg ttcctccttc tggcctcaac   1860
ttgaaccgct tcacagagga ctccctcctg cgacacgcgc agtttgtggt ggagcaggtg   1920
gagagttatg acgaggccgg ggacagtgat gagcagccca tcttcctgac gccctgcatg   1980
cgggacctga tcaagctggc tggggtcacg ctgggacaga ggcgagccca ggcgaggcgg   2040
cagaccatca ggcattctac cagggagaag gacaggggac ccacgaaagc caccaccacc   2100
aagctggtct accagatctt cgatactttc ttcgcagagc aaattgaaaa ggatgacaga   2160
gaagacaagg agaacgcctt taagcgccgg cgatgtggcg tctgtgaggt gtgtcagcag   2220
cctgagtgtg ggaaatgtaa agcctgcaag gacatggtta aatttggtgg cagtggacgg   2280
agcaagcagg cttgccaaga gcggaggtgt cccaatatgg ccatgaagga ggcagatgac   2340
gatgaggaag tcgatgataa catcccagag atgccgtcac ccaaaaaaat gcaccagggg   2400
aagaagaaga aacagaacaa gaatcgcatc tcttgggtcg gagaagccgt caagactgat   2460
gggaagaaga gttactataa gaaggtgtgc attgatgcgg aaaccctgga agtgggggac   2520
tgtgtctctg ttattccaga tgattcctca aaaccgctgt atctagcaag ggtcacggcg   2580
ctgtgggagg acagcagcaa cggcagatg tttcacgccc actggttctg cgctgggaca   2640
gacacagtcc tcggggccac gtcggaccct ctggagctgt tcttggtgga tgaatgtgag   2700
gacatgcagc tttcatatat ccacagcaaa gtgaaagtca tctacaaagc cccctccgaa   2760
aactgggcca tggagggagg catggatccc gagtccctgc tggaggggga cgacgggaag   2820
acctacttct accagctgtg gtatgatcaa gactacgcga gattcgagtc ccctccaaaa   2880
acccagccaa cagaggacaa caagttcaaa ttctgtgtga gctgtgcccg tctggctgag   2940
atgaggcaaa aagaaatccc cagggtcctg gagcagctcg aggacctgga tagccgggtc   3000
ctctactact cagccaccaa gaacggcatc ctgtaccgag ttggtgatgg tgtgtacctg   3060
ccccctgagg ccttcacgtt caacatcaag ctgtccagtc ccgtgaaacg cccacggaag   3120
gagcccgtgg atgaggacct gtacccagag cactaccgga aatactccga ctacatcaaa   3180
ggcagcaacc tggatgcccc tgagccctac cgaattggcc ggatcaaaga gatcttctgt   3240
cccaagaaga gcaacggcag gcccaatgag actgacatca aaatccgggt caacaagttc   3300
tacaggcctg agaacaccca caagtccact ccagcgagct accacgcaga catcaacctg   3360
ctctactgga gcgacgagga ggccgtggtg gacttcaagg ctgtgcaggg ccgctgcacc   3420
gtggagtatg gggaggacct gcccgagtgc gtccaggtgt actccatggg cggccccaac   3480
cgcttctact tcctcgaggc ctataatgca aagagcaaaa gctttgaaga tcctcccaac   3540
catgcccgta gccctggaaa caaagggaag ggcaagggaa aagggaaggg caagcccaag   3600
tcccaagcct gtgagccgag cgagccagag atagagatca agctgcccaa gctgcggacc   3660
ctggatgtgt tttctggctg cgggggggttg tcggagggat tccaccaagc aggcatctct   3720
gacacgctgt gggccatcga gatgtgggac cctgcggccc aggcgttccg gctgaacaac   3780
cccggctcca cagtgttcac agaggactgc aacatcctgc tgaagctggt catggctggg   3840
```

gagaccacca actcccgcgg ccagcggctg ccccagaagg gagacgtgga gatgctgtgc 3900
ggcgggccgc cctgccaggg cttcagcggc atgaaccgct tcaattcgcg cacctactcc 3960
aagttcaaaa actctctggt ggtttccttc ctcagctact gcgactacta ccggccccgg 4020
ttcttcctcc tggagaatgt caggaacttt gtctccttca agcgctccat ggtcctgaag 4080
ctcaccctcc gctgcctggt ccgcatgggc tatcagtgca ccttcggcgt gctgcaggcc 4140
ggtcagtacg gcgtggccca gactaggagg cgggccatca tcctggccgc ggcccctgga 4200
gagaagctcc ctctgttccc ggagccactg cacgtgtttg ctccccgggc ctgccagctg 4260
agcgtggtgg tggatgacaa gaagtttgtg agcaacataa ccaggttgag ctcgggtcct 4320
ttccggacca tcacggtgcg agacacgatg tccgacctgc cggaggtgcg gaatggagcc 4380
tcggcactgg agatctccta caacggggag cctcagtcct ggttccagag gcagctccgg 4440
ggcgcacagt accagcccat cctcagggac cacatctgta aggacatgag tgcattggtg 4500
gctgcccgca tgcggcacat cccccttggcc ccagggtcag actggcgcga tctgcccaac 4560
atcgaggtgc ggctctcaga cggcaccatg gccaggaagc tgcggtatac ccaccatgac 4620
aggaagaacg gccgcagcag ctctggggcc ctccgtgggg tctgctcctg cgtggaagcc 4680
ggcaaagcct gcgaccccgc agccaggcag ttcaacaccc tcatcccctg gtgcctgccc 4740
cacaccggga accggcacaa ccactgggct ggcctctatg gaaggctcga gtgggacggc 4800
ttcttcagca caaccgtcac caaccccgag cccatgggca agcagggccg cgtgctccac 4860
ccagagcagc accgtgtggt gagcgtgcgg gagtgtgccc gctcccaggg cttccctgac 4920
acctaccggc tcttcggcaa catcctggac aagcaccggc aggtgggcaa tgccgtgcca 4980
ccgcccctgg ccaaagccat tggcttggag atcaagcttt gtatgttggc caaagcccga 5040
gagagtgcct cagctaaaat aaaggaggag gaagctgcta aggactagtt ctgccctccc 5100 gtcaccccctg tttctggcac caggaatccc caacatgcac tgatgttgtg tttttaacat 5160
gtcaatctgt ccgttcacat gtgtggtaca tggtgtttgt ggccttggct gacatgaagc 5220
tgttgtgtga ggttcgctta tcaactaatg atttagtgat caaattgtgc agtactttgt 5280
gcattctgga ttttaaaagt tttttattat gcattatatc aaatctacca ctgtatgagt 5340
ggaaattaag actttatgta gtttttatat gttgtaatat ttcttcaaat aaatctctcc 5400
tataaaccaa aaaaaaaaaa aaaaaaaaaa aaaa 5434

<210> SEQ ID NO 37
<211> LENGTH: 6082
<212> TYPE: DNA
<213> ORGANISM: Homo sapiens

<400> SEQUENCE: 37
ataacgtctt tgtcactaaa atgttcccca ggggccttcg gcgagtcttt ttgtttggtt 60
ttttgttttt aatctgtggc tcttgataat ttatctagtg gttgcctaca cctgaaaaac 120
aagacacagt gtttaactat caacgaaaga actggacggc tccccgccgc agtcccactc 180
cccgagtttg tggctggcat ttgggccacg ccgggctggg cggtcacagc gaggggcgcg 240
cagtttgggg tcacacagct ccgcttctag gccccaacca ccgttaaaag gggaagcccg 300
tgccccatca ggtccgctct tgctgagccc agagccatcc cgcgctctgc gggctgggag 360
gcccgggcca ggacgcgagt cctgcgcagc cgaggttccc cagcgccccc tgcagccgcg 420
cgtaggcaga gacggagccc ggccctgcgc ctccgcacca cgcccgggac cccacccagc 480
ggcccgtacc cggagaagca gcgcgagcac ccgaagctcc cggctggcgg cagaaaccgg 540

-continued

```
gagtggggcc gggcgagtgc gcggcatccc aggccggccc gaacgctccg cccgcggtgg    600
gccgacttcc cctcctcttc cctctctcct tcctttagcc cgctggcgcc ggacacgctg    660
cgcctcatct cttggggcgt tcttccccgt tggccaaccg tcgcatcccg tgcaactttg    720
gggtagtggc cgtttagtgt tgaatgttcc ccaccgagag cgcatggctt gggaagcgag    780
gcgcgaaccc ggcccccgaa gggccgccgt ccgggagacg gtgatgctgt tgctgtgcct    840
gggggtcccg accggccgcc cctacaacgt ggacactgag agcgcgctgc tttaccaggg    900
cccccacaac acgctgttcg gctactcggt cgtgctgcac agccacgggg cgaaccgatg    960
gctcctagtg ggtgcgccca ctgccaactg gctcgccaac gcttcagtga tcaatcccgg   1020
ggcgatttac agatgcagga tcggaaagaa tcccggccag acgtgcgaac agctccagct   1080
gggtagccct aatggagaac cttgtggaaa gacttgtttg gaagagagag acaatcagtg   1140
gttgggggtc acactttcca gacagccagg agaaaatgga tccatcgtga cttgtgggca   1200
tagatggaaa aatatatttt acataaagaa tgaaaataag ctccccactg gtggttgcta   1260
tggagtgccc cctgatttac gaacagaact gagtaaaaga atagctccgt gttatcaaga   1320
ttatgtgaaa aaatttggag aaaattttgc atcatgtcaa gctggaatat ccagttttta   1380
cacaaaggat ttaattgtga tgggggcccc aggatcatct tactggactg gctctctttt   1440
tgtctacaat ataactacaa ataaatacaa ggcttttta gacaaacaaa atcaagtaaa    1500
atttggaagt tatttaggat attcagtcgg agctggtcat tttcggagcc agcatactac   1560
cgaagtagtc ggaggagctc ctcaacatga gcagattggt aaggcatata tattcagcat   1620
tgatgaaaaa gaactaaata tcttacatga aatgaaaggt aaaaagcttg gatcgtactt   1680
tggagcttct gtctgtgctg tggacctcaa tgcagatggc ttctcagatc tgctcgtggg   1740
agcacccatg cagagcacca tcagagagga aggaagagtg tttgtgtaca tcaactctgg   1800
ctcgggagca gtaatgaatg caatggaaac aaacctcgtt ggaagtgaca aatatgctgc   1860
aagatttggg gaatctatag ttaatcttgg cgacattgac aatgatggct ttgaagatgt   1920
tgctatcgga gctccacaag aagatgactt gcaaggtgct atttatattt acaatggccg   1980
tgcagatggg atctcgtcaa ccttctcaca gagaattgaa ggacttcaga tcagcaaatc   2040
gttaagtatg tttggacagt ctatatcagg acaaattgat gcagataata atggctatgt   2100
agatgtagca gttggtgctt ttcggtctga ttctgctgtc ttgctaagga caagacctgt   2160
agtaattgtt gacgcttctt taagccaccc tgagtcagta aatagaacga aatttgactg   2220
tgttgaaaat ggatggcctt ctgtgtgcat agatctaaca ctttgtttct catataaggg   2280
caaggaagtt ccaggttaca ttgttttgtt ttataacatg agtttggatg tgaacagaaa   2340
ggcagagtct ccaccaagat tctatttctc ttctaatgga acttctgacg tgattacagg   2400
aagcatacag gtgtccagca gagaagctaa ctgtagaaca catcaagcat ttatgcggaa   2460
agatgtgcgg gacatcctca ccccaattca gattgaagct gcttaccacc ttggtcctca   2520
tgtcatcagt aaacgaagta cagaggaatt cccaccactt cagccaattc ttcagcagaa   2580
gaaagaaaaa gacataatga aaaaaacaat aaactttgca aggttttgtg cccatgaaaa   2640
ttgttctgct gatttacagg tttctgcaaa gattgggttt ttgaagcccc atgaaaataa   2700
aacatatctt gctgttggga gtatgaagac attgatgttg aatgtgtcct tgtttaatgc   2760
tggagatgat gcatatgaaa cgactctaca tgtcaaacta cccgtgggtc tttatttcat   2820
taagatttta gagctggaag agaagcaaat aaactgtgaa gtcacagata actctggcgt   2880
```

-continued

```
ggtacaactt gactgcagta ttggctatat atatgtagat catctctcaa ggatagatat   2940
tagctttctc ctggatgtga gctcactcag cagagcggaa gaggacctca gtatcacagt   3000
gcatgctacc tgtgaaaatg aagaggaaat ggacaatcta aagcacagca gagtgactgt   3060
agcaatacct ttaaaatatg aggttaagct gactgttcat gggtttgtaa acccaacttc   3120
atttgtgtat ggatcaaatg atgaaaatga gcctgaaacg tgcatggtgg agaaaatgaa   3180
cttaactttc catgttatca acactggcaa tagtatggct cccaatgtta gtgtggaaat   3240
aatggtacca aattctttta gcccccaaac tgataagctg ttcaacattt tggatgtcca   3300
gactactact ggagaatgcc actttgaaaa ttatcaaaga gtgtgtgcat tagagcagca   3360
aaagagtgca atgcagacct tgaaaggcat agtccggttc ttgtccaaga ctgataagag   3420
gctattgtac tgcataaaag ctgatccaca ttgtttaaat ttcttgtgta attttgggaa   3480
aatggaaagt ggaaaagaag ccagtgttca tatccaactg gaaggccggc catccatttt   3540
agaaatggat gagacttcag cactcaagtt tgaaataaga gcaacaggtt ttccagagcc   3600
aaatccaaga gtaattgaac taaacaagga tgagaatgtt gcgcatgttc tactggaagg   3660
actacatcat caaagaccca aacgttattt caccatagtg attatttcaa gtagcttgct   3720
acttggactt attgtacttc tgttgatctc atatgttatg tggaaggctg gcttctttaa   3780
aagacaatac aaatctatcc tacaagaaga aaacagaaga gacagttgga gttatatcaa   3840
cagtaaaagc aatgatgatt aaggacttct ttcaaattga gagaatggaa aacagactca   3900
ggttgtagta aagaaattta aaagacactg tttacaagaa aaaatgaatt ttgtttggac   3960
ttcttttact catgatcttg tgacatatta tgtcttcatg caaggggaaa atctcagcaa   4020
tgattactct ttgagataga agaactgcaa aggtaataat acagccaaag ataatctctc   4080
agcttttaaa tgggtagaga aacactaaag cattcaattt attcaagaaa agtaagccct   4140
tgaagatatc ttgaaatgaa agtataactg agttaaatta tactggagaa gtcttagact   4200
tgaaatacta cttaccatat gtgcttgcct cagtaaaatg aaccccactg ggtgggcaga   4260
ggttcatttc aaatacatct ttgatacttg ttcaaaatat gttctttaaa aatataattt   4320
tttagagagc tgttcccaaa ttttctaacg agtggaccat tatcacttta aagcccttta   4380
tttataatac atttcctacg ggctgtgttc caacaaccat ttttttcag cagactatga   4440
atattatagt attataggcc aaactggcaa acttcagact gaacatgtac actggtttga   4500
gcttagtgaa attacttctg gataattatt tttttataat tatggatttc accatctttc   4560
tttctgtata tatacatgtg tttttatgta ggtatatatt taccattctt cctatctatt   4620
cttcctataa cacaccttta tcaagcatac ccaggagtaa tcttcaaatc ttttgttata   4680
ttctgaaaca aaagattgtg agtgttgcac tttacctgat acacgctgat ttagaaaata   4740
cagaaaccat acctcactaa taactttaaa atcaaagctg tgcaaagact agggggccta   4800
tacttcatat gtattatgta ctatgtaaaa tattgactat cacacaacta tttccttgga   4860
tgtaattctt tgttaccctt tacaagtata agtgttacct tacatggaaa cgaagaaaca   4920
aaattcataa atttaaattc ataaatttag ctgaaagata ctgattcaat ttgtatacag   4980
tgaatataaa tgagacgaca gcaaaatttt catgaaatgt aaaatatttt tatagtttgt   5040
tcatactata tgaggttcta ttttaaatga ctttctggat tttaaaaaat ttctttaaat   5100
acaatcattt ttgtaatatt tattttatgc ttatgatcta gataattgca gaatatcatt   5160
ttatctgact ctgccttcat aagagagctg tggccgaatt ttgaacatct gttataggga   5220
gtgatcaaat tagaaggcaa tgtggaaaaa caattctggg aaagatttct ttatatgaag   5280
```

-continued tccctgccac tagccagcca tcctaattga tgaaagttat ctgttcacag gcctgcagtg 5340
atggtgagga atgttctgag atttgcgaag gcatttgagt agtgaaatgt aagcacaaaa 5400
cctcctgaac ccagagtgtg tatacacagg aataaacttt atgacattta tgtattttta 5460
aaaaactttg tatcgttata aaaaggctag tcattctttc aggagaacat ctaggatcat 5520
agatgaaaaa tcaagccccg atttagaact gtcttctcca ggatggtctc taaggaaatt 5580
tacatttggt tctttcctac tcagaactac tcagaaacaa ctatatattt caggttatct 5640
gagcacagtg aaagcagagt actatggttg tccaacacag gcctctcaga tacaagggga 5700
acacaattac atattgggct agattttgcc cagttcaaaa tagtatttgt tatcaactta 5760
ctttgttact tgtatcatga attttaaaac cctaccactt taagaagaca gggatgggtt 5820
attctttttt ggcaggtagg ctatataact atgtgatttt gaaatttaac tgctctggat 5880
tagggagcag tgaatcaagg cagacttatg aaatctgtat tatatttgta acagaatata 5940
ggaaatttaa cataattgat gagctcaaat cctgaaaaat gaaagaatcc aaattatttc 6000
agaattatct aggttaaata ttgatgtatt atgatggttg caaagttttt ttgtgtgtcc 6060
aataaacaca ttgtaaaaaa aa 6082

<210> SEQ ID NO 38
<211> LENGTH: 2283
<212> TYPE: DNA
<213> ORGANISM: Homo sapiens

<400> SEQUENCE: 38
cggccgcgag ttgtgactgg agccacgatg cacggccagg cgcggtgaga agccagcccg 60
tagtgcctcc cgaaggagcc cgggcgcagg gagggtcgcc ctgaggacac ggaggccgcc 120
aggcaggcca agggccgagg tgactgggct ggggcggtag ggaaggagcg agtgcgcctg 180
gctgcctccg cacggagttg tccctctctg ttttcgattg acacaaacac ttctccaaaa 240
gcggggaaac ctaagcaaca acagcaatca acaccaagat cttcctccta ccctcccctc 300
tttcccttct cccgcggtcg gccctcgccc cctcccccag gcccagcgcg ggcgctcggc 360
gcgtccagac ccgcggcgcg atgccggcag tttaggatcc aaagcttctc tgctcctttt 420
gttctttcct tcccttttttt aaaaaaagag gggggaaatc ccagtggtgg gcagcctggc 480
acgcacacag tcgccctcat accccgacaa aagcagatgc actttgactt ctgacagctc 540
tacctcaagc cccggagaac tcagcggcgc tttcctcgca acccgagctc ggcgagtcgt 600
cgtcttcttc ttctccgttt ttatttattt atttccgttc ccgccgccgt tctcgctgac 660
cttcactcct ccgcgggctc tgagcagaag ggtcgcattc tctcccgcct gagacttctt 720
ttcctcgccc cgggagctca ggcggcgccg ctccagcccg gggccccggg actccccggc 780
tgcacacttc actgagacgc ccccccaggc cccgatcagc ctcgtttcct ccaccctact 840
ttgatttcct ggtgcgagtt ttggcttgca cggccgagtg tgtgtcctct ttttggagag 900
actggggagc tcgtgccgat tgtcttcagg agtcatcccc tgggctctac tttgcccctc 960
tctctctctg ggcctcatca gaccaaacca aagaccatgg ttcactgtgc cggctgcaaa 1020
aggcccatcc tggaccgctt tctcttgaac gtgctggaca gggcctggca cgtcaagtgc 1080
gtccagtgct gtgaatgtaa atgcaacctg accgagaagt gcttctccag ggaaggcaaa 1140
ctctactgca agaacgactt cttccggtgt ttcggtacca aatgcgcagg ctgcgctcag 1200
ggcatctccc ctagcgacct ggtgcggaga gcgcggagca aagtgtttca cctgaactgc 1260
ttcacctgca tgatgtgtaa caagcagctc tccactggcg aggaactcta catcatcgac 1320
gagaataagt tcgtctgcaa agaggattac ctaagtaaca gcagtgttgc caaagagaac 1380
agccttcact cggccaccac gggcagtgac cccagtttgt ctccggattc ccaagacccg 1440
tcgcaggacg acgccaagga ctcggagagc gccaacgtgt cggacaagga agcgggtagc 1500
aacgagaatg acgaccagaa cctgggcgcc aagcggcggg gaccgcgcac caccatcaaa 1560
gccaagcagc tggagacgct gaaggccgcc ttcgctgcta cacccaagcc cacccgccac 1620
atccgcgagc agctggcgca ggagaccggc ctcaacatgc gcgtcattca ggtctggttc 1680
cagaaccggc gctccaagga gcggaggatg aagcagctga gcgccctggg cgcccggcgc 1740
cacgccttct tccgcagtcc gcgccggatg cggccgctgg tggaccgcct ggagccgggc 1800
gagctcatcc ccaatggtcc cttctccttc tacggagatt accagagcga gtactacggg 1860
cccgggggca actacgactt cttcccgcaa ggcccccgt cctcgcaggc ccagacacca 1920
gtggacctac ccttcgtgcc gtcatctggg ccgtccggga cgcccctggg tggcctggag 1980
cacccgctgc cgggccacca cccgtcgagc gaggcgcagc ggtttaccga catcctggcg 2040
cacccacccg gggactcgcc cagccccgag cccagcctgc ccgggcctct gcactccatg 2100
tcggccgagg tcttcggacc cagcccgccc ttctcgtcgc tgtcggtcaa cggtggggcg 2160
agctacggaa accacctgtc ccaccccccc gaaatgaacg aggcggccgt gtggtagcgg 2220
ggtctcgcac ggtctgcgga gttcgtggtt gtacagaaat gaacctttat ttaagaaaaa 2280
tag 2283

<210> SEQ ID NO 39
<211> LENGTH: 1485
<212> TYPE: DNA
<213> ORGANISM: Homo sapiens

<400> SEQUENCE: 39
tcctggagct gtgaggagat tcgggccgtc accctgcctc ccctgcgtcc cgccaccggc 60
cgcttctgtc ctcggaccca ttccaacaat ctcgtaaaac atggtggatt actatgaagt 120
tctaggcgtg cagagacatg cctcacccga ggatattaaa aaggcatatc ggaaactggc 180
actgaagtgg catccagata aaaatcctga gaataaagaa gaagcagaga gaaaattcaa 240
gcaagtagcg gaggcatatg aagtgctgtc ggatgctaag aaacgggaca tctatgacaa 300
atatggcaaa gaaggattaa atggtggagg aggaggtgga agtcattttg acagtccatt 360
tgaatttggc ttcacattcc gtaacccaga tgatgtcttc agggaatttt ttggtggaag 420
ggacccattt tcatttgact tctttgaaga cccttttgag gacttctttg ggaatcgaag 480
gggtccccga ggaagcagaa gccgagggac ggggtcgttt ttctctgcgt tcagtggatt 540
tccgtctttt ggaagtggat tttcttcttt tgatacagga tttacttcat ttgggtcact 600
aggtcacggg ggcctcactt cattctcttc cacgtcattt ggtggtagtg gcatgggcaa 660
cttcaaatcg atatcaactt caactaaaat ggttaatggc agaaaaatca ctacaaagag 720
aattgtcgag aacggtcaag aaagagtaga agttgaagaa gatggccagt taaagtcctt 780
aacaataaat ggtaaggagc agctgctgcg cttggataac aagtaattca acgcacgcac 840
ttaacagaaa tgttaaacta taacaagcac catttgagga ttaacaggaa catttttttg 900
aagatttcaa acgaactcga ctttcagtat aattgtacct aaagtattta taaacagctc 960
atcggagcct ctatttgtca tagacttttg agttgattgt tgggaccaca taataggacc 1020 atttttttt tgtctttaaa attgttgtaa atctctgtat gcactttgct tttttattaa 1080

```
acgtactcca aggtgagtct tgactcttta gtgtaggaca agattgtaca ctaacaccag   1140

catggacctg cttttcattg tgtctgaaat gtgagccacg tagtgtcggc ctgctgtgaa   1200

gttaacattg ccaggacgat tcttctacag aaataatttc aatttttttc agtatttagt   1260

agtgaaagat attaatacat taatggtaat acatttctgg tttaatataa attaaggatg   1320

ttttctagtt gtgcatgaat gctggcaact tagtaagttt tgacaattgt ttaaatatgt   1380

aatgttaagc ttaggtttaa aaaagtaaag ctggtaaact gggtctttgt catttgcttt   1440

aaaaaaaaaa aaaaagaaaa taaatgcgaa tgtgttggtg cattc                   1485


<210> SEQ ID NO 40
<211> LENGTH: 3538
<212> TYPE: DNA
<213> ORGANISM: Rattus norvegicus

<400> SEQUENCE: 40

ggtgcccaca gggcttgact agtgggattt gggggagcag tgggtgcagc gagcctggtc     60

cgttgactgc cagcagtaga caccggccgt gtgtggggga ggcggctagc tcagtggcct    120

tgggccgcgt ggcctggcgg tagaggagcc atggtttcta agttgagcca gctgcagacg    180

gagctcctgg ctgctctgct cgagtcgggc ctgagcaaag aggctctgat ccaggctctg    240

ggggagcccg ggccctacct gatggttgga gatggtcccc tggacaaggg ggagtcctgc    300

ggtgggactc gaggggacct gaccgagctg cccaatggcc tgggggagac gcgtggctcg    360

gaagatgaca cggatgacga tggggaagac ttcgcgccac ccattctgaa agagctggag    420

aacctcagcc cagaggaggc agcccaccag aaagccgtgg tggagtcact tcttcaggag    480

gacccatggc gcgtggcaaa gatggtcaag tcgtacctgc agcaacacaa catcccccag    540

cgggaggtgg tggacactac gggtctcaac cagtcccacc tgtcccagca cctcaacaag    600

ggcaccccca tgaagacgca gaagcgggcc gcgctgtaca cctggtacgt ccgcaagcag    660

cgagaggtgg ctcagcaatt cacccacgcg gggcagggcg gactgattga agagcccaca    720

ggtgatgagc tgccaaccaa aaaggggcgg aggaaccggt tcaagtgggg ccccgcatcc    780

cagcagatcc tgttccaggc ttacgagagg cagaagaacc ccagcaagga agagcgagag    840

accttggtgg aggagtgcaa tagggcggag tgcatccaga gaggggtgtc accatcgcag    900

gcccaggggc taggctccaa ccttgtcacc gaggtgcgtg tctacaactg gtttgccaac    960

cggcgcaagg aagaagcctt tcggcataag ctggccatgg acacgtataa cgggcctcca   1020

cccgggccag gccccggccc tgcgctacct gcccacagtt ccccgggcct gcccacaacc   1080

accctctctc ccagtaaggt ccacggtgtg cggtatggac agtctgcaac cagcgaggca   1140

gctgaggtgc cctccagcag cggaggtccc ttagtcacag tgtctgcggc cttacaccaa   1200

gtgtccccca caggcttgga gcccagcagc ctgctgagca ccgaggccaa gctggtctca   1260

gccacggggg gtcccctgcc tcccgtcagc accctgacag cactgcacag cttggagcag   1320

acgtctccag gtctcaacca gcagccgcag aaccttatca tggcctcgct gcctggggtc   1380

atgaccatcg gcccagggga gcccgcctcc ctgggtccca cgttcactaa cacgggtgcc   1440

tctaccctgg tcattggtct ggcctccaca caggcacaga gcgtgccagt catcaacagc   1500

atggggagca gcctgaccac cctgcagccg gtccagtttt cccagccact gcacccttcc   1560

tatcagcagc ctctcatgcc ccctgtacag agccacgtgg cccagagtcc cttcatggca   1620

accatggccc agctgcagag cccccacgcc ctgtacagcc acaagcctga ggtggcccag   1680
```

tacacgcata caagcctgct tccgcagacc atgctgatca cagacaccaa cctcagcacc 1740
cttgccagcc tcacgcccac caagcaggtc ttcacctcag acacagaggc ctccagtgag 1800
cctgggcttc atgagccgtc gtctccagcc acaaccattc acatccccag ccaggacccg 1860
tcaaacatcc agcacctgca gcctgctcac cggctcagca ccagtcccac agtgtcctcc 1920
agcagcctgg tgttgtacca gagttctgac tccaacgggc acagccacct gctgccatcc 1980
aaccacggtg tcatcgagac ttttatctcc acccagatgg cctcctcctc ccagtaacca 2040
tggtgactgc ctcccaggag ctgggctccc agagcctgca caggggggaga ggagggccac 2100 agccatgctg cctggagggt gttggagcct gccacctgcc acaggctgct ggccttccca 2160
gaactctatg ccttcatgct gcagctgctc ctccatcatc agaaagggat ggctctgagg 2220
tgtctcctca gcctgagggg caagcctcaa ggagccggag gacagcccaa tctggaccgc 2280
catccctgct ggttagaata gaaaacttaa tgcttggaac agaaggggga agcctgtatt 2340
gctggcaccc tccagtcaga gcttgcaggc cctgaaggat ctctgctgag ctcggaggcc 2400
ctacatcaac atggctgcca tctgtctcct gtgcctccca ggccactcca ccctgcgcca 2460
gagacccatg tgcctcttgg tgggttaccc tccctccaca ggatcttcca ggcagttctc 2520
tggctaggct tgggagccta gggagcaggg ctctcctagg ctttccccta ctaagtcgct 2580
cttcctcccg gccccaggac ctcatttgtt tccgtgaccg tatcttctga tgccagcttg 2640
gcatcttgcc tgcactagaa aggctgcttc agggctaaga ttgtcaccct tgttccttag 2700
ggcacgtaac tcatgccaag gtcacatcct aggcaatcac ctcctctggc tgcagggccc 2760
tacaacttcc ttcctggtgt gagagacgtg tagaactcgg aagacaaggc ctgagcaatg 2820
tctagtggag agagtgctga gaccagcaga gagaagccac ccaaggggct aggggctggc 2880
agctattctg atctctggcc tgctgcagag agcctggccc tcagtgggct ccccccctcag 2940 cctggaaaga gccagcgccc cctgcagcct acggccggtc atgggcaagc ctagatgttt 3000
atttaacttt tagtaaagcc agtaagaagt gtgtagtagc ttcctgatta cctaggcatc 3060
tgtggccagg agggacggtg gagggaaggc agagggaagc agggtgaagg caggggcctg 3120
agctgtcggc aggctcatgg gatatgtgtt tacacatctt tttgttcaac tggaaatgag 3180
gtgaggtgac tgcctggatt tctgtgtcct cctcggtact gcaagaaacc cacccagtcc 3240
aggtgtggtg ccattcccag agtcttaagc tggggtgaca aagcgtatcc ggggtgtggg 3300
tggaaggatc ccactgtggt tttatgagac gtccccctaa cattgagcac agaggatgtg 3360
cctcggtggc acaatgcctg cctggtaagt gtaaagccac gggtttgatc cccggcactc 3420
aaacaacaac gcactgacag ctccttgtaa ctacgcagga ggcaaaccag gagactggcc 3480
aggttgagct acagagacac agacaaacaa taaacaaaaa gggttggtac tgaccagg 3538

<210> SEQ ID NO 41
<211> LENGTH: 3084
<212> TYPE: DNA
<213> ORGANISM: Homo sapiens

<400> SEQUENCE: 41
aagatctaaa aacggacatc tccaccgtgg gtggctcctt tttctttttc tttttttccc 60
acccttcagg aagtggacgt ttcgttatct tctgatcctt gcaccttctt ttggggaaac 120
ggggcccttc tgcccagatc ccctctcttt tctcggaaaa caaactacta agtcggcatc 180
cggggtaact acagtggaga gggtttccgc ggagacgcgc cgccggaccc tcctctgcac 240
tttggggagg cgtgctccct ccagaaccgg cgttctccgc gcgcaaatcc cggcgacgcg 300

-continued

```
gggtcgcggg gtggccgccg gggcagcctc gtctagcgcg cgccgcgcag acgcccccgg    360
agtcgccagc taccgcagcc ctcgccgccc agtgcccttc ggcctcgggg cgggcgcctg    420
cgtcggtctc cgcgaagcgg gaaagcgcgg cggccgccgg gattcgggcg ccgcggcagc    480
tgctccggct gccggccggc ggccccgcgc tcgcccgccc cgcttccgcc cgctgtcctg    540
ctgcacgaac ccttccaact ctcctttcct cccccacct tgagttaccc ctctgtcttt    600
cctgctgttg cgcgggtgct cccacagcgg agcggagatt acagagccgc cgggatgccc    660
caactctccg gaggaggtgg cggcggcggg ggggacccgg aactctgcgc cacggacgag    720
atgatcccct tcaaggacga gggcgatcct cagaaggaaa agatcttcgc cgagatcagt    780
catcccgaag aggaaggcga tttagctgac atcaagtctt ccttggtgaa cgagtctgaa    840
atcatcccgg ccagcaacgg acacgaggtg gccagacaag cacaaacctc tcaggagccc    900
taccacgaca aggccagaga acaccccgat gacggaaagc atccagatgg aggcctctac    960
aacaagggac cctcctactc gagttattcc gggtacataa tgatgccaaa tatgaataac   1020
gacccataca tgtcaaatgg atctctttct ccacccatcc cgagaacatc aaataaagtg   1080
cccgtggtgc agccatccca tgcggtccat cctctcaccc ccctcatcac ttacagtgac   1140
gagcactttt ctccaggatc acacccgtca cacatcccat cagatgtcaa ctccaaacaa   1200
ggcatgtcca gacatcctcc agctcctgat atccctactt tttatccctt gtctccgggt   1260
ggtgttggac agatcacccc acctcttggc tggcaaggtc agcctgtata tcccatcacg   1320
ggtggattca ggcaacccta cccatcctca ctgtcagtcg acacttccat gtccaggttt   1380
tcccatcata tgattcccgg tcctcctggt ccccacacaa ctggcatccc tcatccagct   1440
attgtaacac ctcaggtcaa acaggaacat ccccacactg acagtgacct aatgcacgtg   1500
aagcctcagc atgaacagag aaaggagcag gagccaaaaa gacctcacat taagaagcct   1560
ctgaatgctt ttatgttata catgaaagaa atgagagcga atgtcgttgc tgagtgtact   1620
ctaaaagaaa gtgcagctat caaccagatt cttggcagaa ggtggcatgc cctctcccgt   1680
gaagagcagg ctaaatatta tgaattagca cggaaagaaa gacagctaca tatgcagctt   1740
tatccaggct ggtctgcaag agacaattat ggtaagaaaa agaagaggaa gagagagaaa   1800
ctacaggaat ctgcatcagg tacaggtcca agaatgacag ctgcctacat ctgaaacatg   1860
gtggaaaacg aagctcattc ccaacgtgca aagccaaggc agcgacccca ggacctcttc   1920
tggagatgga agcttgttga aaacccagac tgtctccacg gcctgcccag tcgacgccaa   1980
aggaacactg acatcaattt taccctgagg tcactgctag agacgctgat ccataaagac   2040
aatcactgcc aacccctctt tcgtctactg caagagccaa gttccaaaat aaagcataaa   2100
aaggtttttt aaaaggaaat gtaaaagcac atgagaatgc tagcaggctg tggggcagct   2160
gagcagcttt tctcccccca tatctgcgtg cacttcccag agcatcttgc atccaaacct   2220
gtaacctttc ggcaaggacg gtaacttggc tgcatttgcc tgtcatgcgc aactggagcc   2280
agcaaccagc tatccatcag caccccagtg gaggagttca tggaagagtt ccctctttgt   2340
ttctgcttca tttttctttc ttttcttttc tcctaaagct tttatttaac agtgcaaaag   2400
gatcgttttt ttttgctttt ttaaacttga attttttttaa tttacacttt ttagttttaa   2460
ttttcttgta tattttgcta gctatgagct tttaaataaa attgaaagtt ctggaaaagt   2520
ttgaaataat gacataaaaa gaagccttct ttttctgaga cagcttgtct ggtaagtggc   2580
ttctctgtga attgcctgta acacatagtg gcttctccgc ccttgtaagg tgttcagtag   2640
```

-continued

```
agctaaataa atgtaatagc caaaccccac tctgttggta gcaattggca gccctatttc   2700

agtttatttt ttcttctgtt ttcttctttt ctttttttaa acagtaaacc ttaacagatg   2760

cgttcagcag actggtttgc agtgaatttt catttctttc cttatcaccc ccttgttgta   2820

aaaagcccag cacttgaatt gttattactt taaatgttct gtatttgtat ctgtttttat   2880

tagccaatta gtgggatttt atgccagttg ttaaaatgag cattgatgta cccatttttt   2940

aaaaaagcaa gcacagcctt tgcccaaaac tgtcatccta acgtttgtca ttccagtttg   3000

agttaatgtg ctgagcattt ttttaaaaga agctttgtaa taaaacattt ttaaaaattg   3060

tcatttaaaa aaaaaaaaaa aaaa                                          3084
```

<210> SEQ ID NO 42
<211> LENGTH: 2108
<212> TYPE: DNA
<213> ORGANISM: Strongylocentrotus purpuratus

<400> SEQUENCE: 42

```
gggaccgcct cggaggcaga agagccgcga ggagccagcg gagcaccgcg ggctggggcg     60

cagccacccg ccgctcctcg agtcccctcg cccctttccc ttcgtgcccc ccggcagcct    120

ccagcgtcgg tccccaggca gcatggtgag gtctgctccc ggaccctcgc caccatgtac    180

gtgagctacc tcctggacaa ggacgtgagc atgtacccta gctccgtgcg ccactctggc    240

ggcctcaacc tggcgccgca gaacttcgtc agccccccgc agtacccgga ctacggcggt    300

taccacgtgg cggccgcagc tgcagcggca gcgaacttgg acagcgcgca gtccccgggg    360

ccatcctggc cggcagcgta tggcgcccca ctccgggagg actggaatgg ctacgcgccc    420

ggaggcgccg cggccgccgc caacgccgtg gctcacggcc tcaacggtgg ctccccggcc    480

gcagccatgg gctacagcag ccccgcagac taccatccgc accaccaccc gcatcaccac    540

ccgcaccacc cggccgccgc gccttcctgc gcttctgggc tgctgcaaac gctcaacccc    600

ggccctcctg ggcccgccgc caccgctgcc gccgagcagc tgtctcccgg cggccagcgg    660

cggaacctgt gcgagtggat gcggaagccg gcgcagcagt ccctcggcag ccaagtgaaa    720

accaggacga aagacaaata tcgagtggtg tacacggacc accagcggct ggagctggag    780

aaggagtttc actacagtcg ctacatcacc atccggagga aagccgagct agccgccacg    840

ctggggctct ctgagaggca ggttaaaatc tggtttcaga accgcagagc aaaggagagg    900

aaaatcaaca agaagaagtt gcagcagcaa cagcagcagc agccaccaca gccgcctccg    960

ccgccaccac agcctcccca gcctcagcca ggtcctctga gaagtgtccc agagcccttg   1020

agtccggtgt cttccctgca agcctcagtg tctggctctg tccctggggt tctggggcca   1080

actggggggg tgctaaaccc caccgtcacc cagtgaccca ccggggtctg cagcggcaga   1140

gcaattccag gctgagccat gaggagcgtg gactctgcta gactcctcag gagagacccc   1200

tcccctccca cccacagcca tagacctaca gacctggctc tcagaggaaa aatgggagcc   1260

aggagtaaga caagtgggat ttggggcctc aagaaatata ctctcccaga tttttacttt   1320

ttcccatctg gctttttctg ccactgagga gacagaaagc ctccgctggg cttcattccg   1380

gactggcaga agcattgcct ggactgacca caccaaccag gccttcatcc tcctccccag   1440

ctcttctctt cctagatctg caggctacac ctctggctag agccgagggg agagagggac   1500

tcaagggaaa ggcaagcttg aggccaagat ggctgctgcc tgctcatggc cctcggaggt   1560

ccagctgggc ctcctgcctc cgggcaggca aggtttacac tgcggaagcc aaaggcagct   1620

aagatagaaa gctggactga ccaaagactg cagaaccccc aggtggcctg cgtctttttt   1680
```

ctcttccctt cccagaccag gaaaggcttg gctggtgtat gcacagggtg tggtatgagg 1740
gggtggttat tggactccag gcctgaccag ggggcccgaa cagggacttg tttagagagc 1800
ctgtcaccag agcttctctg ggctgaatgt atgtcagtgc tataaatgcc agagccaacc 1860
tggacttcct gtcattttca caatcttggg gctgatgaag aagggggtgg ggggagtttg 1920
tgttgttgtt gctgctgttt gggttgttgg tctgtgtaac atccaagcca gagtttttaa 1980
agccttctgg atccatgggg ggagaagtga tatggtgaag ggaagtgggg agtatttgaa 2040
cacagttgaa ttttttctaa aaagaaaaag agataaatga gctttccaga aaaaaaaaaa 2100
aaaaaaaa 2108

<210> SEQ ID NO 43
<211> LENGTH: 2756
<212> TYPE: DNA
<213> ORGANISM: Homo sapiens

<400> SEQUENCE: 43
atgcagttag gggagcagct cttggtgagc tcagtgaacc tgcctggcgc gcacttctac 60
ccgctggaga gtgcgcgagg cggcagcggc gggagcgctg gccacctccc cagcgcggcc 120
ccctctcctc agaagttgga cttagacaaa gcgtccaaga agttttccgg cagtctctcc 180
tgcgaggcgg tgagcgggga gcccgcagcc gccagcgcag gggcccccgc ggccatgctt 240
agtgacaccg acgccgggga cgcatttgcc agcgctgcgg cagtggccaa gccggggccc 300
ccggacggcc gcaagggctc cccctgcggg gaggaggagc tgccctccgc cgctgcagcc 360
gccgccgccg ccgccgccgc ggctgcggcc actgcgcgct actccatgga cagcctgagc 420
tccgagcggt actacctcca gtcccccggt cctcaggggt cggagctggc tgcgccctgc 480
tcactcttcc cgtaccaggc ggcggctggg gcgccccacg gacctgtgta cccggctcct 540
aacggggcgc gctaccccta cggctccatg ctgccccccg gcggcttccc cgcggctgtg 600
tgcccacccg ggagggcgca gttcggccca ggagccggtg cgggcagtgg cgcgggcggt 660
agcagcggcg gggggcggcgg cccgggcacc tatcagtaca gccagggggc tccgctctac 720
gggccgtacc ctggagccgc agcggcggga tcttgcggag gactgggggg cctgggggtt 780
ccaggttctg gcttccgtgc ccacgtctac ctgtgcaacc ggcctctgtg gctcaaattc 840
caccgccacc aaactgagat gatcattacg aaacagggca ggcgcatgtt tcctttcttg 900
agcttcaaca taaacggact caatcccact gcccactaca atgtgttcgt agaggtggtg 960
ctggcggacc ccaaccactg gcgcttccag gggggcaaat gggtgacctg tggcaaagcc 1020
gacaataaca tgcagggcaa caaaatgtat gttcacccag agtctcctaa tactggttcc 1080
cactggatga gacaggagat ttcattcggg aaattaaaac tcaccaataa caaaggcgca 1140
aataacaaca acacccagat gatagtctta caatccttac acaaatacca accccgactg 1200
catattgttg aagttacaga ggatggcgtg gaggacttga atgagccctc aaagacccag 1260
acttttacct tctcagaaac gcaattcatt gcagtgactg cctaccaaaa caccgatatt 1320
actcaactaa agattgatca taacccettt gcaaaaggct tcagagacaa ctatgattca 1380
tcccatcaga ttgtccctgg aggtcggtac ggcgttcaat ccttcttccc ggagcccttt 1440
gtcaacactt tacctcaagc ccgctattat aatggcgaga gaaccgtgcc acagaccaac 1500
ggcctccttt caccccaaca gagcgaagag gtggccaacc ctccccagcg gtggcttgtc 1560
acgcctgtcc agcaacctgg gaccaacaaa ctagacatca gttcctatga atctgaatat 1620
acttctagca cattgctccc atatggcatt aaatccttgc cccttcagac atcccatgcc 1680
ctggggtatt acccagaccc aacctttcct gcaatggcag ggtggggagg tcgaggttct 1740
taccagagga agatggcagc tggactacca tggacctcca gaacaagccc cactgtgttc 1800
tctgaagatc agctctccaa ggagaaagtg aaagaggaaa ttggctcttc ttggatagag 1860
acaccccctt ccatcaaatc tctagattcc aatgattcag gagtatacac cagtgcttgt 1920
aagcgaaggc ggctgtctcc tagcaactcc agtaatgaaa attcaccctc cataaagtgt 1980
gaggacatta atgctgaaga gtatagtaaa gacacctcaa aaggcatggg agggtattat 2040
gctttttaca caactcccta aagagttatt ttaacctcaa aaattagcta actttttgca 2100
gatggacttg gtggtgtttt ttgttgtctt ctttgcctag gttgccaaaa agatgtttgc 2160
cttccacctt gatgcatcct gttttgtgca attctctaaa agaaggtgcc aaagcttttt 2220
gattgctgca ggtaactgaa acaaacctag catttttaaa aaataagatt aatggaagac 2280
tttaaggtat tttaaaattc gaagggtatc caaggttctg tatttattta ttggggagac 2340
actaaccctt caaagaagca ggctgtgaac attgggtgcc cagtgctatc agatgagtta 2400
aaacctttga ttctcatttc tatttgtaaa ttcttaagca aatagaagcc gagtgttaag 2460
gtgttttgct tctgaaagag ggctgtgcct tccgtttcag aaggagacat tttgctgtta 2520
cattctgcca ggggcaaaag atactaggcc caggagtcaa gaaaagcttt tgtgaaagtg 2580
atagtttcac ctgactttga ttccttaacc cccggctttt ggaacaagcc atgtttgccc 2640
tagtccagga ttgcctcact tgagacttgc taggcctctg ctgtgtgctg ggtggccag 2700 tgggactcag gagagagcaa gctaaggagt caccaaaaaa aaaaaaaaaa aaaaaa 2756

<210> SEQ ID NO 44
<211> LENGTH: 1219
<212> TYPE: DNA
<213> ORGANISM: Homo sapiens

<400> SEQUENCE: 44
gggagcgggc gagtaggagg gggcgccggg ctatatatat agcggcctcg gcctcgggcg 60
ggcctggcgc tcagggaggc gcgcactgct cctcagagtc ccagctccag ccgcgcgctt 120
tccgcccggc tcgccgctcc atgcagccgg ggtagagccc ggcgcccggg ggccccgtcg 180
cttgcctccc gcacctcctc ggttgcgcac tcccgcccga ggtcggccgt gcgctcccgc 240
gggacgccac aggcgcagct ctgcccccca gcttcccggg cgcactgacc gcctgaccga 300
cgcacgccct cgggccggga tgtcggggcc cgggacggcc gcggtagcgc tgctcccggc 360
ggtcctgctg gccttgctgg cgccctgggc gggccgaggg ggcgccgccg cacccactgc 420
acccaacggc acgctggagg ccgagctgga gcgccgctgg gagagcctgg tggcgctctc 480
gttggcgcgc ctgccggtgg cagcgcagcc caaggaggcg gccgtccaga gcggcgccgg 540
cgactacctg ctgggcatca agcggctgcg gcggctctac tgcaacgtgg gcatcggctt 600
ccacctccag gcgctccccg acggccgcat cggcggcgcg cacgcggaca cccgcgacag 660
cctgctggag ctctcgcccg tggagcgggg cgtggtgagc atcttcggcg tggccagccg 720
gttcttcgtg gccatgagca gcaagggcaa gctctatggc tcgcccttct tcaccgatga 780
gtgcacgttc aaggagattc tccttcccaa caactacaac gcctacgagt cctacaagta 840
ccccggcatg ttcatcgccc tgagcaagaa tgggaagacc aagaagggga accgagtgtc 900
gcccaccatg aaggtcaccc acttcctccc caggctgtga ccctccagag gacccttgcc 960
tcagcctcgg gaagcccctg ggagggcagt gcgagggtca ccttggtgca ctttcttcgg 1020

-continued atgaagagtt taatgcaaga gtaggtgtaa gatatttaaa ttaattattt aaatgtgtat 1080
atattgccac caaattattt atagttctgc gggtgtgttt tttaattttc tggggggaaa 1140
aaaagacaaa acaaaaaacc aactctgact tttctggtgc aacagtggag aatcttacca 1200
ttggatttct ttaacttgt 1219

<210> SEQ ID NO 45
<211> LENGTH: 2193
<212> TYPE: DNA
<213> ORGANISM: Homo sapiens

<400> SEQUENCE: 45
cgggagccca tggagcactg tcctcagaga tgcgcaggtt aggctcactg tctaggccag 60
gcccacctta gtcactgtgg actggcaatg gaagctcttc ctggacacac ctgccctagc 120
cctcaccctg ggtggaagga gaaatgagct tggcttgcaa ctcagaccat tccacggagg 180
catcctccct tccctgggct ggtgaataaa agtttcctga ggtcaaggac ttccttttcc 240
ctgccaaaat ggtgtccaga actttgaggc cagaggtgat ccagtgattt gggagctgca 300
ggtcacacag gctgctcaga gggctgctga acaggatgtc ctcggacgac aggcacctgg 360
gctccagctg cggctccttc atcaagactg agccgtccag cccgtcctcg ggcattgatg 420
ccctcagcca ccacagcccc agtggctcgt ccgacgccag cggcggcttt ggcctggccc 480
tgggcaccca cgccaacggt ctggactcgc cacccatgtt tgcaggcgcc gggctgggag 540
gcaccccatg ccgcaagagc tacgaggact gtgccagcgg catcatggag gactcggcca 600
tcaagtgcga gtacatgctc aacgccatcc ccaagcgcct gtgcctcgtg tgcggggaca 660
ttgcctctgg ctaccactac ggcgtggcct cctgcgaggc ttgcaaggcc ttcttcaaga 720
ggactatcca agggaacatt gagtacagct gcccggccac caacgagtgc gagatcacca 780
aacggaggcg caagtcctgc caggcctgcc gcttcatgaa atgcctcaaa gtggggatgc 840
tgaaggaagg tgtgcgcctt gatcgagtgc gtggaggccg tcagaaatac aagcgacggc 900
tggactcaga gagcagccca tacctgagct tacaaatttc tccacctgct aaaaagccat 960
tgaccaagat tgtctcatac ctactggtgg ctgagccgga caagctctat gccatgcctc 1020
cccctggtat gcctgagggg gacatcaagg ccctgaccac tctctgtgac ctggcagacc 1080
gagagcttgt ggtcatcatt ggctgggcca agcacatccc aggcttctca agcctctccc 1140
tgggggacca gatgagcctg ctgcagagtg cctggatgga aatcctcatc ctgggcatcg 1200
tgtaccgctc gctgccctat gacgacaagc tggtgtacgc tgaggactac atcatggatg 1260
aggagcactc ccgcctcgcg gggctgctgg agctctaccg ggccatcctg cagctggtac 1320
gcaggtacaa gaagctcaag gtggagaagg aggagtttgt gacgctcaag gccctggccc 1380
tcgccaactc cgattccatg tacatcgagg atctagaggc tgtccagaag ctgcaggacc 1440
tgctgcacga ggcactgcag gactacgagc tgagccagcg ccatgaggag ccctggagga 1500
cgggcaagct gctgctgaca ctgccgctgc tgcggcagac ggccgccaag gccgtgcagc 1560
acttctatag cgtcaaactg cagggcaaag tgcccatgca caaactcttc ctggagatgc 1620
tggaggccaa ggcctgggcc agggctgact ccccttcagga gtggaggcca ctggagcaag 1680
tgccctctcc cctccaccga gccaccaaga ggcagcatgt gcatttccta actcccttgc 1740
cccctccccc atctgtggcc tgggtgggca ctgctcaggc tggataccac ctggaggttt 1800
tccttccgca gagggcaggt tggccaagag cagcttagag gatctcccaa ggatgaaaga 1860

-continued

```
atgtcaagcc atgatggaaa atgccccttc caatcagctg ccttcacaag cagggatcag   1920

agcaactccc cggggatccc caatccacgc ccttctagtc caacccccct caatgagaga   1980

ggcaggcaga tctcacccag cactaggaca ccaggaggcc agggaaagca tctctggctc   2040

accatgtaac atctggcttg gagcaagtgg gtgttctgca caccaggcag ctgcacctca   2100

ctggatctag tgttgctgcg agtgacctca cttcagagcc cctctagcag agtggggcgg   2160

aagtcctgat ggttggtgtc catgaggtgg aag                                2193
```

<210> SEQ ID NO 46
<211> LENGTH: 1750
<212> TYPE: DNA
<213> ORGANISM: Homo sapiens

<400> SEQUENCE: 46

```
gcggtcttat ataagccaga tccgcagggg agtccgcaga agggttaaac aggtctttgg     60

gcttcggcga cctcgcccgc ggcagaaacc ggtaagaaga cagtgggctg cgcgtctcat    120

tttcagcctt gcccggactc tcccaaagcc ggcgcccagt agtggctcca gagcccacag    180

gtggcccccg gcagtctctg ggcgcatgg agcggcgtta atagggctgg cggcgcaggc    240

cagtagccgc tccaacatga acctcgtggg cagctacgca caccatcacc accatcacca    300

cccgcaccct gcgcacccca tgctccacga acccttcctc ttcggtccgg cctcgcgctg    360

tcatcaggaa aggccctact tccagagctg gctgctgagc ccggctgacg ctgccccgga    420

cttccctgcg ggcgggccgc cgcccgcggc cgctgcagcc gccaccgcct atggtcctga    480

cgccaggcct gggcagagcc ccgggcggct ggaggcgctt ggcggccgtc ttggccggcg    540

gaaaggctca ggacccaaga aggagcggag acgcactgag agcattaaca gcgcattcgc    600

ggagttgcgc gagtgcatcc ccaacgtgcc ggccgacacc aagctctcca agatcaagac    660

tctgcgccta gccaccagct acatcgccta cctgatggac gtgctggcca aggatgcaca    720

gtctggcgat cccgaggcct tcaaggctga actcaagaag gcggatggcg gccgtgagag    780

caagcggaaa agggagctgc agcagcacga aggttttcct cctgccctgg gcccagtcga    840

gaagaggatt aaaggacgca ccggctggcc gcagcaagtc tgggcgctgg agttaaacca    900

gtgagccgag gcccgcgccg aggacctggc caggccagcc actcctgaag ccccgggagg    960

agaggaaggc agcggcgaac gccaggctct gggctccggc gactggtgct acgcatcccg   1020

cggagcttct gctgagcgcc ggcaggtcgt cggctgcaac cacacacttg gatcgcacgt   1080

gcaatgtcct ttgatttttt ttaatacatt aagagaaaga gaaatatata tatatccacc   1140

cccagcccaa ccgagggcgg cccttggcgg caacatgcaa gaaggaggga ctgtcgaacc   1200

caagggctca aagacgcact cttccaccct tttggagcga atttagaacc tcagccctat   1260

ctccatttcc ctatctggct ctttctctct tgtccctcca tatgatccgc cccgacgccg   1320

tcttctctaa ttaaaatgca ataaggaatc aattcttttc ttgcctgaga aagagaacca   1380

gacgcaggaa gatgaaaggc tgccctttgt tcttcgaatc gtggtggttt tattttattt   1440

ttctttttgt cgctgcactt cctgtttagt tccaagggaa acactttctc tctttctctg   1500

tctctctctt ttcttccttc ttttccttcc tttttgtttc tatctaaata aaagctttcc   1560

ctgtgttgga aagtttttat gtatttaaac tacctaccat gcctgttgtg ctcaggtgtt   1620

tgttcatcct gccatcccca acccttttct acctcaagtc tgtgtgacca ctcacagccc   1680

ccctcccttc gccaaagcag tgtctatgct cttgattaat aaaacatttt ctgaaatcaa   1740

aaaaaaaaaa                                                          1750
```

<210> SEQ ID NO 47
<211> LENGTH: 1558
<212> TYPE: DNA
<213> ORGANISM: Homo sapiens

<400> SEQUENCE: 47
cagcgagtga gaggggaagg ggcgccaggc gagcacccgg gagccagcgg gacctgggca 60
ggggcgcccg gagcaggcgc gcatggcggg ccccgcgcgg ggatccggct ggaagagagc 120
gtagcacggc tcgcacgagt ccggggccga tgtaccaggt gagcggccag cgcccctctg 180
gctgcgacgc gccctatgga gcccccagcg cagccccggg cccagcccag accctatccc 240
tccttcctgg gctggaggta gtaacaggat ccactcaccc tgcggaggca gcaccagagg 300
agggctccct ggaggaggcg gcaacccca tgccccaagg caatggccct ggcatccccc 360
agggcctgga cagcactgac ctcgacgtcc ccacagaagc tgttacatgc cagcctcagg 420
ggaacccctt gggctgcacc ccacttctgc cgaatgactc tggccacccc tcagagctgg 480
gcggcaccag acgggcgggg aatggtgccc tgggtggccc caaggcccac cggaagttgc 540
agacacaccc atctctcgcc agccagggca gcaagaagag taagagcagc agcaaatcca 600
ccacctccca gatcccctc caggcacagg aagactgctg tgtccactgc atcctgtcct 660
gcctgttctg cgagttcctg acgctgtgca acatcgtcct ggactgcgcc acctgtggct 720
cctgcagctc ggaggactcg tgcctctgct gctgctgctg tggctctggc gagtgtgccg 780
actgcgacct gccctgcgac ctggactgcg gcatcctgga tgcctgctgc gagtccgcgg 840
actgcctgga gatctgcatg gagtgctgtg ggctctgctt ctcctcctga gcctctgtcg 900
ggggctaagc cagcctggcg cccctgcaga ttccagcagg gtccctctga gtggggccag 960
gcccaggact gtcacacaag gcttgagaag ccccctctcc ctggtcctct cctacccacc 1020
catgtcctct cagaacccca gccttgaaaa tagtgggggg cactcagagg ggccacctcc 1080
tcagccgtgg gtggtgggcc catggcagag aagcctgaac tctttactgg gttaccaggt 1140
tcatacattg ctgaggacct gacaggacaa cctaggggca gggctggggt gggggccgca 1200
gagggcagcc agggctgggg aacactgtga aagttacttg gggagggtgg gccggtgggg 1260
ccgtagctct ctacctctcc ctgctcctgg tgcctgcctc tctcctccac cccaggctta 1320
gaggacagaa aaatgtgaag agacgcccca cccaccctca gccagccctc tccagtctcc 1380
tttcctaggc ttttttgggg gcctaaccca cgcagtcacc ccagagggca gggctaggcg 1440
agagcctggg gtggggcggg agggggaaca gtatggaaaa gactggaagg ggaaaggaag 1500
ggaagggagg gaggtctgtt ctatctgttg ctgtaaataa agatatttgt ccatctct 1558

<210> SEQ ID NO 48
<211> LENGTH: 1720
<212> TYPE: DNA
<213> ORGANISM: Mus musculus

<400> SEQUENCE: 48
tgaccaccct ataaaagggg cgtgactcct caacgagcgc cactcgggta cgggagaagc 60
agctggtacc actctggcca ggacctcgga accaagaatc cgcagaagct ggtgacttaa 120
caacccaccg cgctccggtc atggaatctc acaaaaagtg cccctgctgc tactgcactg 180
acttgaagac ctttgttgga gcagtgaagg aggaaacact tcagggtcag tcggtgccgc 240
ctcgacgcgt ttagattcga gaagaactcg ggaggacaac ttttttttt ctgtgcgcgc 300

-continued

```
gcacgtatgc gcgcgcacag aaggtgacga agtgcggtca gcttctcgga ccttcgcagt    360
caccgccgct cctttagagt ggcgcctcgc tcttcccact cttcccagcc ctacctaggc    420
tccaaaccgc ttttcttttt tttttctttt tttcttttcc cccttctcca gatccacagc    480
ctagcttgag ctcaacgctt ttggagggag cagactacca ggaaaacgcg gaatctgaaa    540
caactttcta ctccgacttt ggagccagcc cgaaggagga agaagtggag atggagaact    600
ctctgttcaa ctccatgttt ctggaagaag caaactacca ggaacccgag ggattcgaac    660
cctcaagagg agaagcagca gcgccggttg cagaagcacc gcaagcctgg aatgggaatg    720
aaaaccttgg aggcggcttc ctggaggcca acgctcagct gggggaggcg gatgccgccc    780
ctgtgcggca gtccctgatg cgtcctctga tgcagcctgt tgctcagtct tcgccgcaac    840
ccctgcccgc aaacccgctg caggccccgc agcagcccga ggagcaggag gaggaggagg    900
aggagcagcc gggggaggag caaccccaac aggagccgaa gcctcgccgc taccgcatct    960
gcttcacccc gatccaactg caggagctgg aggccttttt ccagcgcgtc cagtacccgg   1020
acctgtttgc tagagtggag cttgcccgac gcctgggctt acctgaacct agagtgcagg   1080
tttggtttca gaacagaagg gccaagtgga gacgacttcg gcgggcacag gcattcagaa   1140
acatggttcc agtcgccatg agtccccctg tgggtgtcta tcttgatgat cattatggcc   1200
ccatccctat tgtggaggtt atttggaagt gctacccaat ggtgcctcgt cccatgcatc   1260
ctcaaatgat gcctcttcca cccaggcccc ctccaggatt cagaatgcct ccaccattta   1320
ggccacctcc tctgccacct tttccctggc cacctgtacc acctgatgcg cacataccca   1380
atgcagcaag ggaatataac cccttcccct tccccttccc ctttcccttt cccttcccca   1440
acccattccc caaccccaac cctaacccca accccaaccc caaccccaac cccaacccca   1500
accaaaattt tgcaggtccc agatacagat actgaagtct acatcagttt tccaaaagtg   1560
tttttcaatc agatttatat cgtttgtaaa cactatcacg cattacctgt caagaagctg   1620
ttaaacgaaa tgtacaaagt taatgccttc tttgttttga ttttcaataa aagtttggat   1680
tagcagcaaa aaaaaaaaaa aaaaaaaaaa aaaaaaaaaa                         1720
```

<210> SEQ ID NO 49
<211> LENGTH: 68774
<212> TYPE: DNA
<213> ORGANISM: Homo sapiens

<400> SEQUENCE: 49

```
ttaacagatg taaacaataa tatgtaaatt atgttaaaat acctttgcag taaactaaat     60
aagtggatca atgtaatctg cgcagtacat atacaacttc taagaatgca aagctgttca    120
atagcataat gggatttttg ttaaaatttt aattaaattt gtattaaaca ttttgtgagc    180
gatacatgaa aatggaagta ctttgtagtg ctaaaattgt agtgctaaaa taggggggatg   240
ggtggaacag gtttccagtg tcagactcct ttagtttgcc tcccacatta cttacctgct    300
ggatgtccct tgcttaccct ctttgtttct gtttccttaa ttgcaaaatg gaaatagcag    360
tagaacctac ctcatcgttg ttgtgaggat taaatgagta aatacatata aagcattttg    420
gacagtgcct acctcgaata gctcaatgct tcctattacc aggaaacaaa aattagccgg    480
gcgtggtggt gcgcgcctgt aatcccagct actcaggagg ctgaggcagg ataactgctt    540
gaacccggga gggagaggtt gcagtgagcc aagatcgcac cactgcactc cagcctgggc    600
gatggagcaa gactccgtct cagaaaaaaa taaagaaaaa agaaaataaa tctgcacagc    660
catcatctta ttgattccct attaaaaact cctcactggc caggtgtggt ggctcacgcc    720
```

-continued

```
tgtaatccca acagtttgtg agaccgaggc gggcagattg cctgatgtca ggagttcgag    780
accagcctgg ccaacgtcgt gaaactccat ctctactaaa aatacaaaaa acattagcca    840
ggcgtgtggc gtgcgcctgt aatcccagct actcaggaga ctgaggcagg ggaattgctt    900
gaaccgggga ggtggaggtt gcagtgagcc gagattgcgc cactgcactc cagcctgggc    960
gacagagaga gactctgtct caaaaacaga caaacaaaac tcctcactct gtccctgtca   1020
ctgaccaaag aagttaccca ttctcaaatt actttcttca tccattgcct ccaattttgg   1080
ctggcaatat ctcccatacc aaaccgttaa cacctggatc cttttagact accggttcca   1140
tagcaggcat tcaaaagtta gtcatttaac tttttcacca gggacaaaag tccttaaaag   1200
aggaaaaaaa ctggaaagga ttacaaatca ccatgtgaag tttaggtgct ctttagcacc   1260
taaagaggat ttacaagata cattgtctgc acggcaacca ctcagacgaa tccaccacca   1320
agcgaaggtt tttagtaaaa tatccttttt tttttttttg agacggagtt tcgctcttgt   1380
tgcccagact ggcgtgcagt ggcgctatct cggctcactg caacctctgc ctcccaggtt   1440
caagcgattc tcctgcctca gcctcccaag aagctgggat tacaggcatg cgccaccacg   1500
cccggctaat tttgtatttt tagtagagac ggggtttcgc catgttggcc aggctggttt   1560
cgaacccctg gccacaggtg atccggccgc ctcggcctcc caaagtgctg ggattacaga   1620
cgcgagccac cgcgcccagc ctaaaatacc cattttaatt gcatttcaat gacgttactc   1680
ggtcattgac ctcttacgca aggagggcga gattagggag acagctggac ttcttcctcg   1740
ccctcccttc actggactgg ctggcgcagt gagtagccct gcccttggac gatttggcat   1800
tttcattggt caatttttct taggaggctg gccgtgtgtt gactccgcct actatatagg   1860
cggggtctcc ccgccgcagg ggctgggatg ctgggggctg ctgaagccgc catcttggat   1920
tccgcggtag cggaggcggc ggtcaggcgc cgcttctggg gagtggcctt tcttttcccc   1980
tccctcccgg ttcggtggcg gcggctcctc ccactggggg ggggggtggc gcggcggcgg   2040
tggcatctgc ggccatggcg gcgactactg ccaaccccgg tgaggagacg gaggactggg   2100
gcgcctctaa aggggagggg ccgaagggc tgacaactaa ggagacccag ggctgagggg   2160
acgcagctgg agctgaaggc gccggggcgg ggcgggggcc gcgagagacg gtgggggagc   2220
ggtgacctgg ggaggggccc gatcccgggg acttgggtag actcgagtat acccaaggga   2280
gcgagggggc aggtgggagt tgagggggc tccctgtcct gacctccgtt ggagcggcag   2340
ccagtgcggg gctggcccgc cctcactcct cggtcggcgt ctggtctgtg atgtggtcct   2400
cttttaaccc tctgcccgct ggagccgctt gatgccgaaa actgtaggca gagtgtctcg   2460
gtttacttta agagtagttt ggattcataa accctggacc acactgctct ttagttgagg   2520
cgttgcttcc aaacatttaa aggtttagat tttaatttaa aaaataaaaa atggacattc   2580
tttgatatat acgacgtttc tttaggctgt tacctcccac ccgcaacccc cgtccccgtc   2640
tccgtccccg gactatactt tgaaacttag atcttgtgtt aagagggcct gtaggtcttt   2700
gcctgctgag ggcaggggtt tgtgtaatgg ttatggttcc ggacaggtct ttagttccac   2760
agccccaggt ttaaatcttg ttaggcctac gtcgaggcaa tttccaaact ctttcagaaa   2820
agtttgattc cacaccattt ctcaatttca aaaaataatc aaatatcaaa aaggtttggt   2880
ctgttttgtc taagagatgg agtagggtgt agtgcagttc tagagagatc agatcttcaa   2940
attactagtc ccagccctct ttcctctatg ttacagttat tcctctttag aaggcatttc   3000
attttagggg tctagtttat cttggagacc ttggttattc ttgccaaata aagtctatcc   3060
```

-continued

```
ttttccaaaa accaatatat ttgatagcct taaaaagggc cttgagatat gtgtgtgtgt   3120
gttgcgtggg gcggagaatt tcttgaaaat aaaacagtag gagtgattac ccccatcccc   3180
acgttgaaat ttaaattaga tttttttca tgttactgaa aggcagtatg attttgcaat   3240
atccagattt tgataggaca gttgaatcac tgaaatttct tttctaccgt gtttctggga   3300
atagctattt taagaaatgg ttaatttgtc acgtcatttt tttttaatct tttaaatttt   3360
ttttgaagga aagggaggta aaattaatcg caaaaattac attgcaggaa gtgctgagtg   3420
atagaataaa actataaaac aggaaaaatg ccgttatgtc aaacctgacc ttgtagtaat   3480
ataacctatc tgtgaactat ggaataaata aacaagattt ttaactgatc acacattgca   3540
aaatacttat ataaccctag ttaaattgca aagcatttct cttattaaga agtggcctgg   3600
gtaaacaagt tttagttcat atgtcagaag ctttttttcca gctgtgtggg tggggttgct   3660
ttattttgtt ttgtttttg aacaacagca accagaatga cagcctcttg accatatttt   3720
cataagctga tcaatatcag cttaaatctt agcagaaaat agcatatgtt agtgtgtatg   3780
tgtgtgtgca gaatccttgt taatgaaaca gctttgttta ctatgctttg gctgcttgct   3840
tctgcaattt ttagatttcc tttttctttt tctttgtttt cctttctcct ctcccctctc   3900
tcctgtcccc tctcccctct ttttcttttg ctacagggtc ttgctccttg ctctgtcgcc   3960
cagtctggag tgcagtggca agatcactgc tcacggcagc ctccacctca ggggctcaag   4020
tgatcctctc acgatcagcc tcccgaatag ctgggactac aggtgccttg ccaccatgcg   4080
cggttaattt ttaaattttt ttgtagagac agatgccttg ctatgttgcc catgctgatc   4140
ttgatctcct ggtctcaagc aagccttgcc tcagtctctc caagttggga atacagatgt   4200
gagacacttt gaccagattt ctttttgat gttgaaaaat tattccatct cttctgactt   4260
attgatccca tgttcagttc aatcaaatca gaagatatat tttctttttt cttttctccc   4320
tttgctcttg tatatcatga ggaagagatc agagatacat tgtggatttt ttcagtagcc   4380
tgttgctttt tgggaaatga gattaatgaa tggagggaca taggtggaaa tgtactgtgc   4440
ttagtgaaag taaatgtttt caggtcagaa ttctttgcta cactgtcata ccttctttcc   4500
ttagagccat tttaaggact agggacacca tgcctatttc tttgagtttt ttctactttg   4560
tatttttgct ggagtactaa tttttttttt tttttttttt tttttacaat tcttgttagt   4620
tttgtcaaga ttttaaaaaa tatttcactc tttaaccttc acttcagtta atcctttttta   4680
aaaataatac ttatttttat ttttcagaca ggttcttgct ctgtctccca gactgtagtg   4740
caatggtgta atcacagctc actgtagcct tgaactcctg agctcaagtg atcttcccac   4800
ctcagcctcc tgagtatctg ggtctacaga cacacaccac cacacctgga tacattttttt   4860
aacttttttgt agaaatggga tcttgctatg ttgcccaggc tgatcttgaa ctcctgtcct   4920
caagcaatcc tcccacctta gcctcctaaa ctgctgggat tataggtgtg agccactgac   4980
ccggccaagt taatccttag ggttagtaat agtgcttgaa catgttaatt gtgctggtgg   5040
ccctgcagtg tttttcaagg ggaccacgtt cttctgcatt tttcactgtg gtgctgcatt   5100
agaagaagag taaaatatgg ttggtactct ctaagagttg tgttgaagta atagttctgt   5160
gatgattttt tttctcgaat tgataattct tcatattcta tcatttttca ctagttctac   5220
ttatcactgg caagtagaac tcggtgggta ggtggtccat gaaactttag gctgtttctt   5280
atctatggac tagacaagtt ttgttttgtt ttttttttgt ttgtttgttt gttttgagac   5340
agagtctcac tctgtcgccc aggctggagt gcagtggtgc tatcttggct cactgcaagc   5400
tccgcctccc aggttcacgc cattctcctg cctcagcctc ccgagtagct gggactacag   5460
```

```
gtacccgcca ccacgcccgg ctaatttttt tttttgtatt tttagtagag acagggtttc   5520
accctgttag ccagggtggt ctcgatctcc tgaccttgtg atccgcctgc ctcggcctcc   5580
caaagtgctg ggattacagg cttgagtcac cgtgcccggc ccggactaga caagttttga   5640
ggaacacatt ttttttcccc ataggagagg gtcttgctct gtcactgagg ctggagtgca   5700
gtgacacaat catggctcac tgcagccttg accttctggg agcatgtgat cctcccactt   5760
cagcctcctg agtaggtggg accacaggtg tgcaccaccg tggctggcta attttaaatt   5820
tttttagag acagggtctt gctatgttgc ccaggctggt ctttaactcc tggcctcaag   5880
tgatcttcct gcgttgggca ctccccaaga gctgggatta taggcatgac caccatgccc   5940
agccaaggtg gaacactttt taaattgaat gtgtcatttg taatgcattg gctgagggaa   6000
cagttgggag gagattaggt atttgattta caattccaaa ttcaaactag agatgttgaa   6060
tgagtttgta gtaagtgtag gtttttatct ctcttgattc tggtattctc attagcagag   6120
aattcttttt gtgctattat gtacaagtta ctgtggatga agaatgtaga aggaaaaggg   6180
taataccgtt tgggtttgta aggctgtcat ttaggaagaa aatttttttt agctaatttt   6240
cacctatata acttagtttt aactgcgtca attaacacaa ttcttacctg ttacctttat   6300
ttaccttttt cagatatggg aaaataggaa ttcatgcaat gtaaagttaa gatgtcaaga   6360
tattctttta tggccaggtg tggtggctcg tgcctctaat ccctttggga ggccgaggca   6420
ggccgattgc ttgagcccag gaatttgaga ccagcccgga caacgtgacg aaaccccttt   6480
actacaaaaa atacaaaaaa ttttccgggc actgtggtgc acttctatag tcccagctac   6540
ttgggaggct gagatgggag tatcacctga gcctggaaag ttgaagctgc agtgagctgt   6600
gatcatgcca ctgtactcca gcctgggtgt tggagtgaga ccctgtcccc caacaaaaaa   6660
agagatagta ttttattata ttgcaaaggc cttttttttt tttttttttt tttttgaga   6720
cagggtctta ctgtgtcgcc caggctggag tgcaatggcg tgatcttggc tcactgcaac   6780
ctccgcctcc tgggttcaag ctattctccc gcctcagcct cccgagtagc tgggattaca   6840
ggcacctgcc atcacgccgg ctaatttttt atttttaata gagacagggt ttctccatgt   6900
tggccaggct ggtcttgaac tcctcacctc aggtgatccg cccaccttgg cctcccaaag   6960
tgctgggatt acaggcgtga gccgccatgc tccgccgcca tctgttttta agaatgctgc   7020
cttggccggg catggtggct catgcctgta atcctagcat tttgggaggc cgaagtgggc   7080
agatcacctg aggtcaggag ttcaagacca gcctggccaa catggagaaa ccctgtctct   7140
actaaaaata caaaaattag ccaggcatgg tggcaggtgc ctgtaatccc agctactcgg   7200
gaggctgagg cgggagaatc gcttgaacct ggaaggtggt ggttgcagtg agctgagatc   7260
gtaccactgc actctagcct gggcgacaga gtgagactcc gtctaaaaaa aaaaaaaaaa   7320
aaaaaaaaac cacgactgcc taatatgcca taatgacttt agtaagtaga catcagtgaa   7380
tcttcaggtt ggaaatatga caacacctat cattttacac ttaaggagac aaacccaggg   7440
aaaggagtgg ataattaagt tccttctata tgccaggctg cactttccta ttttgttgct   7500
aatctttatg tctagtctgt agcaactgtc tccaactttt cacataaact cttcaaattt   7560
atgtcacttt tcataatttc gtcaatgtat tttcttgttt taaagttttt attattttag   7620
atagtgaccg ggtctcacta tattgccccg gctggtctca aactcctggg ctcaagcaat   7680
cctcctgcct cggcctccca gagtgccggg gttacaggtg tgagccaccc tctgaggccc   7740
attttatatt ttccctccac gttttcattg tagttgaatg gacaagtaag tttatggatt   7800
```

-continued

```
caacagtata cttagggctg gacatggtgg ctcatacctg taatcctagc actttgggag   7860
gctgatgtag gtggattgct tgagcccaaa agtttgagac cagcctgggc aacgtggtga   7920
aaccccatct gtacaaaaaa atacaaaaaa ttagcagggt gtggtagcat tccctgtagt   7980
cccagctacg tgggagactg agatgcgagg atgacctgag cctgggaggt tgaggctgca   8040
gtgagccatg attgtgccac tgcattcctg tctgggtgac taggagacag agtgagaccc   8100
tgtctcaaaa aacacaacaa aaccagcata cttaggatat aagttccatg agagcagaac   8160
ttttgctttc cttgtttacc agagcattgc agtgcttaca gtgggtgcct agtatgttgg   8220
attagagttc aatgtatgtt tgtggaataa aaatgaatgt aaaacccact gttaatatga   8280
aataccttg aagggataaa actaattaag ccattgacat catgaatttg tactaactat   8340
aataatatct aatatttatt agtaatactt accagctgtt ctcatttaat ttttataaca   8400
atcgtattag gtaagtatta ttattcttgt tttacagatg aggaaactaa ggcacagaga   8460
gtgaataagt aacttgtctg aagtcacata gctactagaa gttagagaca gaattttatt   8520
gttggcagtc catctacaca gtcatcattc ttaatctcca agttatgatt ttttccattg   8580
tgacttagag tcaccttcct actgaaatat agtacaatgg atatcttttg agaaggaggt   8640
aggtggagta ttgtcttttt tgtagatgaa aagggtgaaa taccacatta ggcagcctgg   8700
gggcaaggca ttgcttggtt ggagaaccaa gtgcaaggtg ctaaaaaaag gagctagaac   8760
agtagtttcc aggctgagtg tggtggctca tacctgtaat ctcagcactt tgagaggcca   8820
gggtgagagg attgtttaag cccaggagtt ggagaccagc ctgagcaata tagggagacc   8880
ttgtctccac aaaaatatat ataaaaaaat tagctagatg tggtggtgga tgcctatagt   8940
cccaactact tgggaggctg aggtggtggg aggatctctg agcttgctag gtcagggctg   9000
cagtgagcca tgatcatgcc actggactct aatctggttg acagagtgag cccctgtctc   9060
taggaaaaaa aaaaaaaaag gagtagtttc ctaaaatctt ttctgtaaca ttctataatt   9120
cttcattttg ttttgttttg tttttttgag actgagtgtc cttctgtcac ccaggctggg   9180
gtgcagtggc acgatctcag ctcactgcaa gctccgcctc ccaggttcac gccattctcc   9240
tgcctcatcc tcgcgagtag ctgggactac aggcatccac caccatgccc tgctaatttt   9300
ttgtgttttt agtggagatg gggtttcact gtgttagcca ggatggcctc gatctcctga   9360
ccttgtgatc cgcccacctc agcctcccaa agtgctggga ttataggctt gagctagcgc   9420
gcccagccta acattctata tttctttctc ctagttctat gtttcaattc tttaaatact   9480
tttaagggtt tttttgagac aaggtcctgt tgtgtcagcc aggctggagt gcagtagcgt   9540
gaccatagct tcctgcaaca cctccaattc ctaggctcaa gcgattctca ctcctcagtt   9600
tcctgaatag ttgggaccat aggtatgcac catcatgccc agctaatttt ttaattttgt   9660
agagacagga tctcgctatg ttgcccaggc tggtcctttt ttttttaaat tttattatta   9720
tttttgaga cggagtcttg ctttgtcacc caggctggag tgcagtggcg tgatctcggc   9780
tcactgcaac ctctgcctcc cgggtttaag cgattctcct gcctcagcct cctgtagctg   9840
ggactacagg cacgtgccac cgcgcctggc taatttttgt gtttttagta gagacggggt   9900
ttcaccatgt tggccaggat ggtctcgatc tcctgacctc gtgatctgcc cacctcggcc   9960
tcccaaagtg ctgggattac aggcgtgagc caccgcgccc ggcctgccca ggctggtctt  10020
gaactactgt cctcgagtga tcctcctgct gttggcctcc cagattgctg agattacagg  10080
catgaatcat gcactgcagc ttttaggatt gttattagaa tcctctacaa gttcttgata  10140
ctccataatt gagcctctcc tagaaacttg gtttcagaga cactgttgct aggtctttat  10200
```

```
cactgattgt tccttctttg tcctttttgc ttatctttct gcttgtttct ttctcttgtt  10260
cagtatgctt ctacttttct cttctcaccc ttgaggctag gactcttctt tgagacaggg  10320
tcttgactct tttttgagac agggtcttgc tatgttgccc acgttggtct tggattcctg  10380
agctcaaatg atcctcccac ctctgcttcc tgagtagctg ggattacaag tgtacaccac  10440
agtgcccggc ttggggctag aactaaatag taaaccaagc agtttccttc atttcttccc  10500
atttgcccac ctacctgcct ttctagctgc ttgccttcct acttcaattt gacattcact  10560
tggtacctac catagtcctc ttccctttgt attagtccat tctcacactg ctataaataa  10620
ctacctgaga ctgggtaatt tatgaagaaa agaggtttaa ttgactcata gttccgcagg  10680
ctgtatggga ggcagggctg gggaggcctc aggaaacttg gaatcatggc ggaaggcgaa  10740
ggggaagcaa gcatgtcttc acatggctgg caggatagag ggagagaagg ggaaggtgct  10800
acacactttc aaacaaccag atctcttgag aactctatca tgagagagca ttaggggaat  10860
ggtgctaaac ctttggaaac caccccctatg atccaataac ctcccaccag actgcacctt  10920
caacactggg gattacaatt tgacatgata tttgggtgga gacacacaga gccaaaccat  10980
atcacccttt atttatcttt tatgtataaa agactccaaa aatttcattc ctggcttctc  11040
acataaacta ctttcctata tttttatcta tttaaaagat atctctctct ttttctttta  11100
aagttgagac agggttttac tatgttgccc aggctggtct tgaaatcctg ggctcaagca  11160
ttcctcccac ttcagcaacc tgagtagctg gactacaggt gtgtgccatt gtgcctggct  11220
gcatctctgt ttgaatagtt tttttttttt ttaatttata gaaatgaggt ctcactgtat  11280
tgcccagact ggtcttgaac tgctgagctc aagtagtccc cccatcttgg tctccctagt  11340
agctgggatt ataggtgtat gacacgatgc ccagctctat ttgagtaatc tgtttttttt  11400
tgttgttgtt gttttttttta aagacagagt ctttctgtgt tgcccaggct ggagtgcagt  11460
ggtgcgatct tggctcaccg cagcctccgc ctcctaggtt caaatgattt ttgtgcctca  11520
gcctctcgag tagctgggac tacagtgtgc caccacgcct ggctaatttt ttgtatcttt  11580
agtagagatg gggtttcacc atgttggcca ggctggtctt gaactcccgt cctcaagtga  11640
tccacctgcc ttggcctccc acagtgctgg gattacaagt gtgagccatt gcgcccagcc  11700
tctatttgaa taatctttaa catcctatat atgtatgtac tcaccagtat ttcctttaaa  11760
tctgctgttc ttcctacctt tctgtatctt tcatcactat cacaattcag tttttcattt  11820
ccccaggcta aggaactata agtgtttgga ttttattttt tatgtgttta tctgggttat  11880
taactcttct caggtctttt gccaaatata cgtgtgtgtg tgtgtatatg tatgtgtgta  11940
tacatacata tataaaagtt atttaaatca aaactataca tccatatatt aatatttaaa  12000
gacttagata gttttataaa atgtttgtta caaaaaaatt ataagggagt cctctgctcc  12060
ctttctctca tttccttctc tccagtggca tcatttttat ttcttttaac agaattcttt  12120
gtttctgttt aaataaagtg tcccagtgaa agacattagt ttccagatca aaggggctgt  12180
gcacacatca aggcccatta tgctgaaatt tcagcatcag atagagaata tcctataagc  12240
ttcagagaga ataagattat tcacattcaa aagattcagg tatcagattg gtcttttttc  12300
tcagtagtca tgctggaaag tagaagacct tggaacaggc tgactgacct tggtggctca  12360
cgcctgtaat cccagcattt tgggaggctg aggcaggtgg atcacctgag gtcaggagtt  12420
tgggaccagc ctggccaaca tggtgaaacc ccgtctctac taaaaataca aagattagtt  12480
ggacgtggtg gtgtgtgcct gtagtaccag ctacttggga ggctgaggca ggagaattgc  12540
```

-continued

```
ttgaacctgg gaagcagagg ttgcagtgag ccgagatcac gccactgcac accagcctgg  12600
gcaaaagagc gaagactctg tctcaaaaaa aaaaaaaaaa actttggagt aatgccttca  12660
aaattctgag ggaaaataaa ttctaattta gaattccata gctaggcaaa ctatcaatta  12720
gtgaaataga agaaatattt tcatacatcc aaggcatttc ttacaccctt tcaggaatcc  12780
actagaagat aggctctacc agtaggagat agtaaaccaa gaaagtggag atacgaaata  12840
taggaaatag gcagtataac acagaagaaa aatgaagcat gtagtatgca tacattggtg  12900
ttagttttcc tgttttcagt acgggtccct cactttcacc tttacgtcgt gttcactaga  12960
ctgtaagacc tttgatttat actctccaga gagtaaatct gtcttttgac agaatggaga  13020
ggggtagttg ccttggttag aaggaataga gaaaaggatc taggaatcca tctctgtagt  13080
aaacagatgc tgaactaatt ctccttattt tcacttcatt caccctaccc tgcataccca  13140
gagttacctg gactcaccag cttctgagac tttggggaat tccatagcgt aaattgagtt  13200
ggttttctgc tttttccctt gtcagtttag gatttagttc ttgtcgatct cccaaggcaa  13260
tagtccattt tatctctagt ttcaaaaaaa ttattgctct tcttctctta ttctttccat  13320
ccttgtggtt ttatgtcttg tgtaaaaatt tttgctttta aaaatttttt tcctgtgtgt  13380
gagtgaagag agaagagagt agaaatagat agatacattt aattcactat ccttactcag  13440
aagttgcata gtttaaaatt ttagaagtaa ctaccttttc gttgtgccat cctcatttag  13500
gcctttatca ccttgttttt tttattaatc ttgtcttcct acttctatta cttcaaactt  13560
taaatctgtc agattaattt taatttatat tttcatcttg ttactcagac ttaaagttat  13620
atgtttgtct ttgttgaatc tgatccaggt gtttcatcgt ggcattcaaa gctttctctt  13680
ggttagcact tgacatctta ccttttatag gtctttttct ttcttttttt tttttttttt  13740
gatttaaaga aaaccatttt gttttcttca ggggcaattt tttttttaca ttccaccaca  13800
tattatttat atgtttatca tatttctttt atttatttat ttatttattt atttattttt  13860
tattatactt taagttttag ggtacatgtg cacattgtgc aggttagtta catatgtata  13920
catgtgccat gctggtgcgc tgcacccact aactggtcat ctagcattag gtatatctcc  13980
caatgctatc cctccccccct cccccccaccc caccacagtc cccagagtgt gatattcccc  14040
ttcctgtgtc catgtgatct cattgttcag ttcccaccta tgagtgagaa tatgcggtgt  14100
ttggtttttt gatcttgcga tagtttactg agaatgatga tttccaattt cgtccatgtc  14160
cctacaaagg acatgaactc atcatttttt atggctgcat agtattccat ggtgtatatg  14220
tgccacattt tcttaatcca gtctatcatt gttggacatt tgggttggtt ccaataggtc  14280
tttttcttta cagctcttca cagttgctgt tatgtgtcac ctaatgacac tttggtcatc  14340
aaaggactgc atgtatgatg gtggtcccat aagattataa tggagatgaa aaattcctat  14400
tgcccagtga catcatagtt gtcataaggt cttagcacaa cacattactt tttctatgtt  14460
tagatacata aatagttacc actgagttat agttgcctac agtattcagt atagtaacat  14520
gttgtacagg ttgggagtaa taggctgtta ctgggagtaa taggctacat ataggtatgt  14580
aggctataca cctacatacc taggtgtgta gtggctgtac catctagatt tgtgtaagta  14640
tactcaatga tattcacaca atgttgaaat ctcctaatga cacatttctc agaacatatc  14700
cctgttgtta agtgatacat aactgtattt tcatatctcc ctttagactt gctcatgtac  14760
ttttatctat gtggaatgcc tttttcttct tctttacttt tttttttgga gacggagttt  14820
tgctcttgtt gcccaggctg gagttcagtg gctcgattgg ctcactgcaa cctctgcctc  14880
ctgggttcaa gcaattctcc tatctcagcc tcctgagtag ctgggattac aggcgcctgg  14940
```

-continued taatttttta tatttttagt agagacgggg tttcaccatg ttggtcaggc tggtctcgaa 15000
ctcctgacct taggtgatcc acccacctcg gcctcccaaa gtgttgggat tacaggcgtg 15060
agccactgtg cctggtctcc tttacttttt ttaaggccca gtttgattta cctttttgaa 15120
acttccccat gggctggttg cctgccttct ttatttcctt tagtttcctc ttcatattga 15180
gcatcttctc tgcaagtact atgccaggcc ttaatttaaa ccaggattat cttctctgaa 15240
tttacctggc actctttttt ttttttttga gacagagtct cattctgttg cccaggctgg 15300
agtgcagtgg catgatctcg gctcactgca gcctttgcct cccaggcgat tctcatgcct 15360
cagtctccca agtagctggg attatagacg tgtaccacca cacctgacta atttttgtat 15420
ttttagtaga gacgggattt tgccgtgttg gtcaggctgg tctcaaactt gaccttaagt 15480
gatctaccca cctcagcctc ctaaagtgct ggggttacag gcatcagcca ccgtgcctgg 15540
cctccatggt aatctttttt tttttttttt tttgagacgg aatcttgctc tgtcacccag 15600
gctagagtgc agtggcacga tcttggctca ttgcaacctc cgccttttgt gttcaagcga 15660
ttcttctgcc tcagcctccc gagtagctgg gactacaggt gtgcgccacc atgcctggct 15720
aatttttgta tttttagtag acacggagtt tcaccatatt ggccaggctg gtctcgaact 15780
cctgatgtcg tgatctgcct gcctcggcct ctcaaagtgc taggattaca ggtttgactc 15840
catggtactc ttatatccta tataaacgta ttactaaaag tatgaacttt tttttttttt 15900
tttttttttt tacagaggca ggatctcact atgttgctca ggctagtttt gaactcctga 15960
gctcaagcaa tcctcatgcc ttgacctccc aaagtgctgg gattataggc atgagccact 16020
gcacttggcc ctgaactttt ttttttaatg gaaaaagtgt tttttcttag gaaagtaaca 16080
tatgcttact atttcaaatt tataggctga aatagaaaaa ttagcagtaa cataaaaata 16140
tactcagcct taatgtatgt taaactaaca gtggtaattg tttttttacca agaaaatgac 16200 cacaaatttg aaggattccc aaaacacagt gctgttggag gtatggctaa attgatgcag 16260
tggatgaggc tttaaattgg tataacctcc ttggcaggta atgggcaatc agagttttaa 16320
atgtgtctac ccttaggccc agggagtcat tttcagaaat aatatggaag tactggcacc 16380
tgtgcatgaa gatacacaat gatgttcctt gaaacattat ttataatagt gaaggtttga 16440
atgtcataac tatacattta tagtacagag tactatgtaa ctgttaaaaa gaatgatcta 16500
cgtgtgtatt tattgccata gcaatatatt gttacgtgga agggaaaaag ttcagaataa 16560
gtacatctgt acttatggtg gggttatggc ttgataaacc cattgtaaat tgaaaacatc 16620
ctaagtcaaa aatacattta atacacttaa cctattctta gcctagacta ccttaaatgt 16680
gtgtggaata cttacattag cctgcagtgg gcaaaataat ctaacttaaa ttctacttta 16740
taataaagta ctggatatta tgtaatttac agaacactgt acattacact gaaattgtaa 16800
tggtttccca ctatcataaa ggtgaaaagc cctacatgga accattataa gtcaggactg 16860
tttgtatagt atgacccttt tttttgggta aaaattaccg aaaccctggc tgggcgtggt 16920
gactcatgcc tgtaatcagg cacataccac atgtatggcc aattttgttc attttttttta 16980 gagatagggt ctcactgtgt tgcccagggt ggtcttgaac ttctggactc aaatgatcct 17040
cctccctcgg ccttttaaag tgctagcctt acaggtgtaa gccaccatgt tcagccccac 17100
agtttcttta tccgttaacc tgtagataga cacttgggtt gccctcaccc ttgactactg 17160
ttgaatagta cttctgtgaa cgtgggtata caaatgtttc tttgagaccc tgctttcaat 17220
tctttcaggt atatacccag aggtggaatt gctggatcat gtggtaattc tatttttaat 17280

-continued

```
ttaatttttt ttttgcgatg ttgtcttgct gtgtttccca gcctgatctt ggactcaaga  17340
ttctcctgcc tcagaccccg agtagctggg actacaggtg cgcaccactg cacccagttt  17400
tatttttaat ttttggaggc atctccatac tgttttctat tgctgttacg ccattttaca  17460
tttccactag cagtgcataa gggttttaat ttctccacat ccttgccaac cctttattta  17520
tttatatatt tttggataat agtcatctta atgagtagca aatgctttct cattgtggtt  17580
ttgatttgca tttccctagc gattggttat gttgagcact ttacatgtat ttattggcca  17640
ttagtatatc ttctttgtag aaatgcttgt tcaagttctt tgcccatttt aaaattgggt  17700
ttgctttttg ttgagttgta ggagctcttt atatattttg ttttattttt tatttgttta  17760
ttttttgag gcagagtctt tctctgtcgc tcaggctgga gtgcagtggt gcgatcttgg  17820
ttcactgcag tctccgcctc ctgggttcaa ttaattctcc ctgcctcagc ttcccgagta  17880
gctgggatta caggtgccca ccaccattcc tggctaattg ttgtattttt agtagagatg  17940
ggatttcacc atgttgatca ggctggtctc gaactgctga cctcaggtga tatgcccgcc  18000
ttggcctccc aaagtgctgg gattacaggt gtgagccacc gtgcctggcc actctttata  18060
tattttggat attctgtgtt gcatatatga ttcgaaaatt ttttttctg ctgggcacgg  18120
tggctcatgc ctgtaatcct agcattttgg gaggctgagg tgggcggatc acttgaggtc  18180
aggagttaaa gaccagcctg gccaacatgg tgaaacccca tctctaataa aaatacaaaa  18240
attagccagg cgtggtggtg cgtgcctgta atcccagcta tttgggaggc tgaggctcga  18300
gaatcacttg aacccgagag ttggaggttg cagggagcca agattgcgcc actgcactcc  18360
agcctgggcg acagagtgag actctaactc aaaaaaaaaa aaaaagaatt ttttttttc  18420
tattccatgg gttgcctttt cactctgttg gtagtgttat ttgatgcaca aaatattgta  18480
cactatacag tatgaactaa caaaaaaacaa tgagatgtgt gtagatagat attcatgatg  18540
tatattgaaa tgacgagcaa gttgaagatc aggcctccat tttttactaa gagaaaaatg  18600
cacccttttt tttttttag acaggatctt gctctgttgc ccagggtgga gtgcagtggt  18660
gcaatcacga ctcactgcag cctcgacttc ccaggctcaa gtgatcctcc cacatcaacc  18720
tcttgagtag ctgggactac aggcatgggc caccatgctg gctaacttgt attttttgta  18780
cagatgaggt ttcactgtgt tgcaaaggct agtctcgaac tcctgggctc aagtgatctg  18840
cccaccttgg tctcccaaag ctctaggatt ccaggcatcc gccactgtgc ccagcctgca  18900
cctctttttg attacagagt taggtatata taaactgaga ttgaaaaata agagaaaata  18960
tactcagggc tgggctcagt ggctcaaacc tgtaattcca gtgctttggg aagctgaggt  19020
gggagtattg cttgagctca ggagtttgag accagcctgg ggaacacagt gagaccctat  19080
ctctacaaag aaaaaaaaag aaaaaaaaaa tcaccgaggt gtggtggtac ccatctgtag  19140
tcccagctac ttaggaagct gagacaggag gatcactgga gcccgggagg ttgaggctgc  19200
agtaagccat gatcatgcca ctgtactcca gcctgggctg gacaaagtga gaccctgtct  19260
taaaaaaaaa aaaaaaaaag tactcagctg ttactaatgg ttactgctgg gggatgagat  19320
tgaattggaa ggagagagga gaggtacggg gggcaggaaa gggagacaat aatgagggac  19380
tttcagtttt actttacata attttctttt aagtattgga atttaggtga tttttccttt  19440
ggggttttct gtattttcca atcacaataa ataaaataag ttataaatat ttgttgcatg  19500
aatgaaatgt ataaacccat ttatgtatgt atttttttaa aattagtata ttattaagtc  19560
tatacaatat tagtatattg ttatgtatgt ataagctttt taacatgaag tttgcagaat  19620
atagtacttc ttccaaactc tatgacatgg ggggaactga agtatgggga tatcttgtac  19680
```

cagtgtaaga attcaagaag agaccgtgtg tggtggctca tgcctataat cccagcactt 19740
tgggatgcca aagcaggatg atctcttgga gctaggcgtt caagaccagc ctgggcaaca 19800
tatcaagacc ccatctctaa aaaaaaaaaa aaaaattaac tgggtgtggt agtgcgggcc 19860
tatagtccta gctattccag aagctgaggt gggaggattg cttgagccca ggagtttgag 19920
gctgtagtga cctataccag tgattatacc agtgcactct agcccaggca acagagtgag 19980
acctggtctc aaaaaaaaaa aaaaaaatca agaagagcaa tctggatatg agcatttggg 20040
atttttagca aactgctgag attttgtcta tagcttgaac ctttctttta gctaacttga 20100
tgatactgat gataagcaag gactgtcttt ttaaaaatgt ttacttcatt attttcctga 20160
cagaaatgac atcagatgta ccatcactgg gtccagccat tgcctctgga aactctggac 20220
ctggaattca aggtggagga gccattgtcc agagggctat taagcggcga ccagggtgag 20280
tttgagtgta gtgtgttatg aatatctctc ctataaacca actttagttg ctgaatttat 20340
ttagttgctg aactcacttc gctattcctg accatctcac ttcaacttga ttacttacta 20400
cactactgtc atataagtct ccttagtccc tgtatttttg tttatgaaga atttgttttt 20460
atccaagttt cccgtaagca gttctttttt taaaccaaaa tttccgtaag ataaaggact 20520
gtagctaagc ccagagattt tactatgcct gagaaaactg tttgctgctt tcattaagct 20580
ttgtttctgt tttcccaaaa tcattttggt aggctgcttt tctgaattta gagaatgctg 20640
agctctagaa tagctgtctt ctaagttatt gatatgttgc ttggtttgga atgcagagtc 20700
cattcagctc caaaagtatt tattaaattc ctaattagtg ttatggcatt gtgctgattc 20760
caagtaggat acaaagatga ataagacaca gtccttgttt ctaagttggt tgtgttctga 20820
tagaaataat tattatacac atgaatatat gatagaatat gcctagtttt gttaggaaca 20880
aatttgatac tatgtttttc tgtgtatgga aatatgcatt tgttggtaaa gactgagaaa 20940
agcttcagaa aggaggttgc cttagagggg cctggaagaa tgggcactat tttatttact 21000
ttttggtatt aaattttcct ttttccttct ttttcttttt aaaaattgtg cagctaatta 21060
taaccagtct ttaagttttg tcccaccaat agtaatggaa gagtgatgct tgggttcagt 21120
ggtaacatga gtaacatatt aagacttgtt atatgttcag tagctttaca gattttaacc 21180
atttgctgaa gcataagctg aataagtaac tttctaagat tgtaaagcta gtaagtgtca 21240
gatataggat atgaacctta ggggtttagc tttgtagctt actctttaaa cactgtgtta 21300
tgtttatgta cagtaacaaa caaaagtatt ataaatatca aaattagggc atcacttgag 21360
aaagtcatag tatatttaaa atggaatgct atgtagttat aagcgacaaa tatgtttcag 21420
tgtagaaaga tgttcacaat ctattaagaa aggttacagt attatagtat ttcactgtca 21480
aaagatatgt ataacatgta cataggaaaa aactgaaaga atatatacca catttctggg 21540
taatagtatt atgggtgact tacggtttct tttgtttttg atttttcaga tttttgaaat 21600
gaacatgtat gattggtaat cagaaaaata tattaaagga agtctttaaa aattttcttt 21660
ttggtttttt tagagacagg gtcttgtacc ctggctggag tgcagaggca caatcatggc 21720
ccactgcagc ctcaaactcc tgctcaagca gtcctcctgc cttggcctcc caaagtactg 21780
ggattacagg cgtgagccac ttcacctgtc ctaaaagaag tcttttaata tttcttttat 21840
ttttatttac ttatttattt tcgaggcaga gtcttgctct tttgccaggc tggagtgcag 21900
tggtgtgatc ttggctcact gcaatctcca cctctctggt tcaagggatt ctcctgcctc 21960
agcctcccaa gcagctggga ctacaggcgt gcgccaccac gcccagctaa tttttgtatt 22020

-continued

```
tttagtagag atgggatttc accacgttgg ccaggctggt ctcgaactcc tgacctcagg  22080
tgatatgccc accttggcct cccaaagtgc tgggattaca ggcatgagcc accatgcccg  22140
gcctaatatt tcttttattt atttatttta tttttttattt ttttgagatg gagtctcgct  22200
ctgtcgccca ggctggagtg cagtagtgtg atctcagctc actgtaacct ccacctccca  22260
ggttcacgcc attctcctgt ctcagcctcc cgagtagctg ggactacagg cgcccgccat  22320
gatgcccgac taattttttt gtattttcag tagagacggg gtttcaccgt gttagccagg  22380
atggtctcga tctcctgacc tcgtgatcca cccgccttgg cctcccgaag tgcgggatta  22440
caggcacgag ccactgcacc cggcccatat ttcttttaaa gaaagattgg aaaatacaga  22500
aagttagaaa gaacaataaa aaggccaaaa tctactacca tgttttttag tgcatgtcct  22560
tcagtcttta tatgtaaatt gtttttaata gttatgtaat tatatagttt tacatggcct  22620
agtcttttca ccttatataa ataataagca atacacacgc acacacacat tttggcacct  22680
tatataaata ataagcaata cacacacaca cacatttcgg agacagagtc ttgctctgtt  22740
gcccaggctg gagtgcagtg gcatgatcat ggctcattgt agcctcaact tcttgggccc  22800
aggaagcaat cctcctactt cagttctccg agtagctggg accacaggca catggcacca  22860
tacctggcta tttttttttt ttttttaaa gacatggtct cactacgttg accaggctgg  22920
tctaaaactc ctaggctcaa gcagccctcc catctcgacg tcctaaagtg ttgggattac  22980
agacatgacc tactgtacct ggccctttaa aaaaatattg ttacatattc tatataaaca  23040
taatttttat ttattttttt ttgagacgga gtctcgcttt gttgtccagg ctggagtgcg  23100
gtgatgcgat cttggctcac tgcaagctcc gcctcctggg ttcatgctat tctcctgcct  23160
cagcctcccg agtagctggg actacaggcg tccaccacca cgtctggcta attttttttt  23220
tttttgtatt tttagtagag acggggtttt accatattag ccaggatggt ctccatctcc  23280
tgacttcgtg atccgcctgc cttggcttct caaagtgctg ggattacagg catgagccac  23340
tgcgcacagc cataaacata atttttaatg gttgcgtgaa aggatgtact taacttccta  23400
ttttgggaca tctaaattgt tttgaagatt ttgctgttac atatgatgct aaaaagaact  23460
tctttgtacc taaacttttt tttcctattt catattattt ctttagattc ttagaaatag  23520
agttattggg ctgagcacgg aggctcatac ctgtagtgcc agcactttgg gaggctgagg  23580
taggaggatt acttgagccc aggaattcaa gaccagcctg ggaaaaatgg cgagactttt  23640
ttttctttga cttagcaatt atctttcttt tccttccttc cttcattttt ttcctttgac  23700
ttagcaatta cctttccctc cctccttccc tctctttccc cttccctttt tttttttttt  23760
tttttgaga tgtagtttcg ctcttgttgc ctaggctgga gtgcagtggc gcaattttgg  23820
ctcactgcaa cctctgcctc ccgggttcag gcaattctca tgcctcagcc tcccgagtag  23880
ctgggattac aggtgcccgc caccacaccc agctaatttt tgtattttta gtagagacga  23940
ggtttcacca tgttgactgg gctggtcttg aactcctgac ctcaagtgat ccgcctgcct  24000
cagcttccca aagtgctggg attgcagatg tgagccacag tggctggccc cttttctttt  24060
ttgagacagg gtcttgccat gtcactgagg ttggagtgca gtggcccaat ctcagctcac  24120
tgcagccttg acctcccagg ctcaaggcct gcagcccctc ccgccccccc aacccaagta  24180
gctaggacta cacatgcgcc accatgcctg gttagttttt gtatgttttg tagagacggg  24240
atttcaccgt gttgcccagg ctggtcttaa actcctgagt tcaagtagtc tgctcgcctt  24300
ggcctcccaa agtgcgtgga ctacaggtgt gagcaaccat gcctggctga gattttttaa  24360
aataaaaaaa tttagttgag tgcagtggtg ggctcctata gttccagcta attgggaggc  24420
```

caagatggga ggatcccttg agcccaggag ctcaaggtgg cagtgagcta tgatcatgcc 24480
actgtactcc agcctgagta acagagtgag agcttgtctc ttaaaaagaa agaaaggaag 24540
agatagagag aaagaaagaa tttgagttac tgggtagata gataggattt tacaggtgac 24600
cagattaggg gattcaggaa ggaggaagag gagcaaacac tttcaggatt gatgctgtat 24660
gtgtacttca aatgcgaccc atctagaggc ccataatatc aaggtatccc aatagtagaa 24720
gtaaaaagag tgatcactag gttaaggtgg taacatgagc aatattttag ttcaatagtg 24780
tacagagatt ataaggggat tggtctattt tattgtttat aatctttcct aatctccttt 24840
aaagaaattc acttcttctt tccctgaatg tctgtagcat gttgattgta ccccttatgt 24900
gacactttcc tattctcact tgttttatat ttgtatttct ctaggtgaag agccccttga 24960
gggcaaggtt cttgttttta cctcacctag cacagtgtct tgaatgaagt atatattaca 25020
tgtttattag atcaatgaag gaaagaaaca ttatctaaca atcttcgtag gtattaagtc 25080
actcctttat gtaagatcac tgctttgaaa gatgtttcag aaatttggta acacggctta 25140
gagcagactc tagaaatgaa acatggacct gaattattta cgttaatttt ttcttatttt 25200
ttctgagtgg attcctgctc cctttacaga ggttgtagtc tgattgaaaa ctctggcaaa 25260
gattgactgc tactctagga aagtgttaag gtagcagaag gtacttttgt ttctattgcc 25320
cagttttgta cttttttttt ttgagatgga gtcttgcagt tgtcgcccag gcttgagtgc 25380
aatggtgcga tcttggctca ctgaaacctc cacctcccgg gttccagcaa ttctcctgcc 25440
tcagcctcct gagtagctga gattacaggc acccgccacc atgcccagct aatttttgta 25500
tttttagtag agatggggtt tcagcatgtt ggccaggctg atctcgaact cctgacctca 25560
ggtgatccac ccacctcagc cttccaaagt gctgggatta caggcgtgag ccaccactcc 25620
tggccccagt tttgtacttc tttgcctagt ttgggactat gaacaagagg aaatgtagct 25680
ttgtttgact tctgccactt cctctttcca ttcttccatt tgggtgggtg ttccggtagc 25740
ttgtgttgag aaattttaac ttcttaatgt tttgtattat cagcaggctt aaagtattta 25800
ttgttggctt tcctcaggct ggattttgat gatgatggag aagggaacag taaatttttg 25860
aggtaagaga ctgaaaaact ttccttagat gtctgatatt aaaaattagt ttatgatctt 25920
tatacttctg acttgtaaat ttttgtcctt aggtctaagg agagtacttc atcctaaaac 25980
tataaatatt catatatctc agaaaatttt taagcattcc gttaatatct ctagagaaag 26040
gacctcagtg aggagaggac ggcatttaca aaccctctgt atcagttctc tgctacttca 26100
tagcctaaaa agaacaacag ttcgttattt ctcaattctg tggattgact gcatgtttat 26160
tctgcttatc tcacctagac tcactcataa gactgcattc tcagctggtc agctgagaac 26220
tggactcagc tgggatggct gggtatttct gtctatgtgt ttttttatcc tcaaggaggc 26280
cagactgaat tttttcatgt ggtgatggct acaatctaca gcacaaatcc cagtgtgcaa 26340
gtgcttatca agcctctgct tatatgacat ttgcttatgt cccattggcc aaagcaagtc 26400
atatgttcca ggtgtgagtg tgtgaggggg ttacacaagg aagtacatac tgagaggtgt 26460
aattcattgg ttgaggtgtc attaatctgt gactctgtca taccctctga cacctgttga 26520
cacctcttat aggtagcagg aattggaatt tgtatttttt gtttttgttt tttttttttt 26580
tgagacggag tcttgctctg tcgccaggag tgcagtggtg caatctcggc tcactgcaac 26640
ctccgcctcc tgggttctag cgattctcct gcctcagcct cccaagtagc cgggactaca 26700
ggtgcgtgcc accatgccca gctaattttt gtatttttat tttttatttt tttattaatt 26760

-continued

```
ttcttttta ttgatcattc ttgggtgttt ctcgcagagg gggatttggc agggtcatag  26820
gacaatagtg gagggaaggt cagcagataa acaagtgaac aaaggtctct ggttttccta  26880
ggcagaggac cctgcggcct tccacagtgt ttgtgtccct gggtacttga gattagggag  26940
tggtgatgac tcttaatgcg catgctgcct tcaagcatct gtttaacaaa gcacatcttg  27000
caccgccctt aatccattta accctgagtg gacacagcac atgtttcaga gagcactggg  27060
ttgggggtaa ggtcatagat caacagcatc ccaaggcaga agaatttttc ttagtacaga  27120
acaaaataga gtctcctatg tctacttctt tctacacaga cacagcaaca atctgatttc  27180
tctatctttt ccccacattt ccccctttc tattcgacaa aaccgccatc gtcatcatgg  27240
cccgttctca atgagctgtt gggtacacct cccagacggg gtggcggccg ggcagagggg  27300
ctcctcactt cccagaaggg gtggccgggc agaggcgccc cccacctccc ggacggggcg  27360
gcggctgggc ggaggcgccc ccaccaccct cccggatggg gcggctggcc gggcgggggc  27420
tggcccccgc ctctctcctg gacggggtgg ctggccaggc gggggctgcc ccccacctcc  27480
cggacggggc ggctgccggg cggagatgct cctcacttcc cggacggggc ggctgcgggg  27540
cggaggggct cctcacttct cagacggggc ggctgccggg cggaggggct cctcacttct  27600
cagacggggt ggctgccggg cagaggggct cctcaattct cagacggggc ggctgccggg  27660
cggaggggct cctcacctcc cagacggggt cgtggccggg cagaggcgct cctcacctcc  27720
cagacggggt ggcggggcag aggcgctccc cacatctcag aggatgggct gcggggcaga  27780
gaccctcctc acttcctaga cgggatggcg gccgggaaga ggcgctcctc agttcccaga  27840
ctgggcagcc gggcagaggg gctcctcaca tcccagacga tgggcggcca ggcagagatg  27900
ctcctcactt cccagacggg gtggcggcca ggcagaggct gcaatcctgg cactttggga  27960
agccaaggca ggcggctggg aggtggaggt tgtagcgagc cgagatcacg ccactgcact  28020
ccagcctggg caacattgag cactgagtga acgagactca gtctgcaatc ccggcacctc  28080
gggaggccga ggctggcgga tcactcacgg ttaggagctg gagaccagcc cggccaaccc  28140
agcgaaaccc cgtctccacc aaaaaaatac gaaaaccagt caggcgtggc ggcgcgcgac  28200
tgcaatcgca ggcactcggc aggctgaggc aggagaatca ggcagggagg ttgcagtgag  28260
cggagatggc agcagtacag tccagcttcg gctcggcatc agagggagac cgtggaaaga  28320
gagggagagg gagaccgtgg ggagagggag accgtgggga gagggagatg gagagggaga  28380
gggctaattt ttgtattttt agtagaaaca gggtttcacc atgttgggca ggatggtctc  28440
gatctcttga cctcgtgatc cgccctcctc ggcctcccaa agtgctggga ttacaggtgt  28500
gaggaatttg tatttttgag ttgttaatat tctggagctt ttaaaatgga ctatttattt  28560
gtttgttttt ttgagacaga gtcttcctct gttgcccagg ctggagtgca gtgctgcagt  28620
cttggctcac tacaacttct gccttccagg ttcaagcgat tctagtgcct cagcctcctg  28680
agtagctggg actaccacac ctggctaatt tttgtatttt tagtagagac ggggtttcac  28740
catgttagcc agactggtct tgaactcttg gccttaagtg gtccacctgc ctcagcttcc  28800
caaagggctg gggttatagg cataagccac catgtccagc ctattttctt cttatttttt  28860
tgagacaggg tcttactctg tcacccagac tggagtgcag tggcacagtc tcggctcact  28920
acagcctcga actccaggc tcaagcgatc ctcccacctc agtctcccaa gtagctgggt  28980
ctacaggtgt gagccataat acctggctaa ttttaaaatg atgttgccca ggctggtctt  29040
aaactcctgt gctcaagcaa tcctcccacc ttggccttcc aaagtgttgg gattacaggc  29100
atgagccact gtacccggcc tgaaaatgga ccttttaata tattgatgaa ggagttcttt  29160
```

```
cagaaaaggg ggatattctt gctgaagacc aattgcttgt cttcttttca agtaagaaaa  29220
acagtaagac tcaaaaggaa gagaactttg accgcaatct gctttttttc tttccagagt  29280
tgaaaatatt acccaggtag tctgtacgtt gctgagtaac agacaatttg ataaaggagc  29340
ccaatgaaaa aaaaatgatt tgattgtgtg ggtgcccaga tttaatatca tttatttatt  29400
ttctttcttt cttttttttt gagactgatt ttcactcttg ttgcccaggc tggagtgcaa  29460
tggtatgatc tcggctcacc gcaacctctg cctcccaggt tcaagcgatt ctcctgcctc  29520
agcctcccga gtagctggga ttacaggcat gcactaccat gcccggctaa ttttgtattt  29580
ttagtagaga tggggtttct ccatgttggt caggctggtc ttgaactgcc gacctcaggt  29640
gatccgccca cctcggcctc ccaaagtgct gggattatag gcatgagcca ccacacccgg  29700
cccatttctt tttcttattt gtttgttttg ttaactaagt tttttcttta attgggaaag  29760
taatataagt gtattttatt acagaaattt caggctgggc ctggtggctt acacctgtaa  29820
tcccagcact ttaggaggct gaggtgggtg gatcgcttaa gctctggaat tcaggaccag  29880
tctgggcaac atggcaaaac tccatctgta caaaaaatgt tacaaaaatt agctggaagt  29940
gctggtgtgt gcctgtagtc tcagctactc gggaagctga ggtgggaggg tggtttgagt  30000
cctggaagca gagattgcag tgagccgagg ttgcgccact gctctccaac ctgggcgacc  30060
ttgcctcaaa aaagaaaaac aacaaaattt caaacagtgc agagttatat atagtgaaag  30120
cacatcttcg ttttactttg gaccttcaga actccttttt ttttttttga gaggagtctc  30180
gctcttgttg cccacgttgg agtgcagtgg ttcgatctct gctcattgcg tcctccgcct  30240
cctgagttca agctattctc ctgcctcagc ctcctgagta gctgggatta caggcgcctg  30300
ccaccatgcc cggctaattt ttgtactttt agtagcgaca aggtttcgcc atgttggcca  30360
ggctggtctc aaactcctga tccactcggc tcggcctccc aaagtgctgg gattacaagt  30420
gtgggccact gcccccagcc tggaccttca aaactcttta gacaactaca gtttccagtt  30480
tgttgagtat ccttccaaaa atagtatata tagaattgta tataaatgtg tatgtgtgag  30540
catacacaca cttatctcct cagttttttt tacacaaagg atgtccatat tgataaattg  30600
cttgccattt tttagtttta tattgcttca tacagttaat agcatctatc ttcttttttt  30660
atagtaacat ttaaagttaa ggctcatatt tctggctact cactagatga actttgccaa  30720
atactcttga aaacaacaac cgtgacttgg ccatcataaa gaaatagttg caagtggaag  30780
tataattctc taagaggtct cttgagactt aatgagtctc agtaaatgtg aagaagggaa  30840
gagatttcaa tttctggaga agatagactt tttcaaacag ctttattgag aattcctcct  30900
attgagaatc ctgaattata atgatacatg ctattagtgg aacttcactg tgtgtatgaa  30960
agatatgagg gtaaccacta gtcttttttt atacccgtga attagctcta accctgagtc  31020
attgcttcca taaaatccag tagtcacaac tacatgcaga tccaaagaga ggttcgtttg  31080
tccttttcct aaccataaaa aaagactatc atagtttatc ttaccaagtc gggttgttgt  31140
gcctgagaaa agcactgccg aattcccttt ccccccttctt tttttttttt tttttttttg  31200
agacggagtc tcgctctgtt gccacaaatg cagtggtgtg atctcagctc actgcaacct  31260
ccgcctccca ggttcaagtg gttctgctgc ctcagcctcc gaagtagctg ggactataag  31320
cacgtgccac cacacccagc taatttttgt atttttagta gagacggggt ttcaccatgt  31380
tggccagagt ggtctggatc tcttgacttc gtgatccgcc cagtgttggc ctcccaaagt  31440
gctgggatta caggcgtgag ccactgcgcc cagcctcccc cttctttttc tgggtatata  31500
```

-continued

```
tatacaaaat aatcgaaggc agaatcttga agagatattt gcacactcat gtttattggc  31560
ccattttgcg caatagataa gaggtcgaag taaccgaaat gtccactgac agatgaatgg  31620
ttacagaaaa tgtagtatgt acatacaagg gaatattatt cagccttaaa aagaaagaac  31680
ctgtcatatg ctgcaagatg gatgaatctt aaggacatta tactgaaaga ataagccaat  31740
aacaaaaaga caattactgt atgattccac ttacatgagg tatctacaag tagtcaaatt  31800
catagacaca gaaagtaaaa tggtggttgc taggggttgg ggtgaaggag aaatgagaaa  31860
atggtgtttg atgagtatag agtttcagtt ttgcaagatg aaaaagttct agatatctgt  31920
tgcacaacaa tgtgaatatg gttagcacta ctcaactgta cacttaaaaa tggtatacag  31980
taaattttat gtgtttttta ccagaattaa aaaaaaaccc aaaactaacc ccttacttta  32040
gaattgtgct gacaggccag tcagctgtgt tgtcattaga tcatcatctt tttttggtgt  32100
gtctggtaag ggtaatggaa ataccagaaa cctgacaaat aatagttgtg ggtcttttaa  32160
gttctatggg gtgctgctgt tatttctatc actttgtgat gcttttccat tggctttttt  32220
tctattgaat attttcaccc ctttctagtt tacttttcag agtgaaatag atataacaag  32280
tgtaatgctt tgaaacaatc ctttttctct ccttcaggtg tgatgatgat cagatgtcta  32340
acgataagga gcggtttgcc aggtaatatt gtagtaggta atatattgta atatataata  32400
tgatccatgt tgtagaacca gacagtccta gcatattgac ttaatttttt ctggatgaga  32460
cggaatttct ctgtttaata tctttcctat ttggaagtat gtgaaactta gtattataac  32520
tatcatttat gttcaggtga catggcttca aactggcggt atattttata cagtgttttt  32580
ctgtgtatgt gataactaaa gcaatgtgct tgcaaggttt ccataggagc acaaattatg  32640
gattttgtgc ttgcatttat tattaaatgg atctacaaaa ataggaatac agataatggt  32700
tctgtaatta atttatttat tttgagacag agtcttgctc tgttgcccag gctggagtgc  32760
aatggcgcca tctcggctca ctgcaacctt cacctcctgg gttcaagcga ttctcctgcc  32820
tcagcctcct gagtagctgg gattataggc ccctgccacc acgcccagct aatttttgta  32880
tttttagtag agatggggtt tcaccatgtt ggtcagggtg atcttgaact cctgaccttg  32940
tgatccgccc gcctcggcct cccaaagtgc tgggattata ggtgtgagcc accgcacccg  33000
gcctatttta tttttttgag acagagtctc actccatcac ccatgctgta gtacagtggt  33060
gtaatctcgg ctcactgtaa cctctgcctc ctgggttcaa gctgttcttc cacctcagcc  33120
tccctagtag ctgggaatat gggcatttgc caccatgcct agctaatttt tgtaataatt  33180
ttttttagca gagatggggt ttcaccatgt tggccaggct tgtctcgaac tcctcacctc  33240
aagcgattca cccacctcag cctcccaaag tgctgggatt acaggtgtga gccattgtgc  33300
ctggcctatt attttatttt aagatatgta tattttttag agacattgtt ttcattgtgt  33360
ttcccaggct ggagtacagt ggcatgatca tagctcactg cagcctcaaa ctctggggtt  33420
tcagtgatcc tcctacctca gcttcccaaa tattgggatt atatgcatag ccaccatgcc  33480
tggttggtcc tgttttttta aaaatgacag taagaggcgg ggagtggtgg catatgcctg  33540
taattccagc actttgggag gcagatgcag gtggatcact tgaggtcagg agttcaaaac  33600
cagcctggcc aacatggtga aaccccatct ctactaaaaa tataaaaatt agccgggcat  33660
catggtgggc actcataatc ccagctactc tagaggctga ggcatgagaa ttgcatgagc  33720
ccgggaggtg gaggttgcag tgagcagaga tggcaccatt gcactccagc ctgggtgaca  33780
gcaagatttt gtgtcagaaa aaaaaaaaaa agacagtaag gaaacagttt ttgtgacaag  33840
tagagttttg attgaaaaaa acttaaattt gtttaaatta cctatcaaga tgatgaaata  33900
```

```
tactttttt tattaaattc ttaaatgtca gttttctttt tagaaagttt ttattaaata  33960
ttaggcaata aattatttct tttttgaaaa ttaagtttgt agctacctca gaaagatgaa  34020
taattcgtta tttcaaaatc cagtgattaa ctgagcactt agcacttagt atttgttcgt  34080
tgctgatgct cctggtctcg ggaacatact ttaagaaccg ttgatgtaga gagattagaa  34140
atatcagggg aagtagttaa aaactattct ggagtggtga gatgcaatct caggctttga  34200
attagagggt attacataaa atgcattgta gggatatttc tctggtagca gttatagaat  34260
tgattaaagg gatggactgt tagactgtag ggaggtagat aggaagctgt tgaaataata  34320
agacagctat aaaatcatga gggcctgggt tacagtggca gtggtaacag gaaaggagtg  34380
aagttaagag gtttttgaag aataatttgt ttatcgaaac taattgaaat aaatatttgt  34440
aaagtcttta ggatgtgaac catctctaaa atgagaagtt aatcatagat atttggagga  34500
tagtttttca agcttcattg aaaagtcagg ccatcagtta ttattggcag tatcttgatg  34560
aaatttcaaa aagccatgaa aacatcgcat gaatgatttt ggttttcatt tgtcctgctt  34620
aatgtgcata tatttcattc agaaatactg aggtggatta gggattgtgg atctgtagta  34680
gtagtagtag tagaaatagg aattttagat gcttaacttt tttttaaata acagaattca  34740
ttcatatgat gtgttaaggt agtgcccctc acatatcctc cttgggatat agagggtctt  34800
aaaagctgaa aacttcttga aaaacttttg ggattatatg catagccacc atgcctggtt  34860
agtcctgttc ttttaaaaat gacagtaaga ggccgggagt ggtggcttat gcctgtaatt  34920
ccagcacttt gggaggcaga ggcaaaagtt gctcaacttt ttgaaaaaaa agaagtttgt  34980
agtttgttaa ggaactatct agaagaaata acccaaggaa tgtaaaactc taaactgctg  35040
aatatcactc agttctcctt ctcttgtcat cagaatatat gcgtaaattt ttacattctt  35100
cttcattgtt actgtgttat tttctgccta ttgaccattt tataaaaaca ttcccatata  35160
ttgataaggt tattgtattt gtcattttta atagctaaat aatcttttag cttgttaacc  35220
tgtcatactt agacatttta ttcagggcct ctttatctat ataaatatat ttaaaatgga  35280
attgacacat tcctgacaca atggcctgcc aacaccttgc tatttcctca gttgccaccc  35340
atcattacag tatctcagtt ttctagaaaa atttagtgat ggttctttgt atccttctcc  35400
agtggagagg gaattgttac ttttgatcca ttcctgtgtg gctatactgc agagaaatgg  35460
caaaaggacc gaatcaaagt taataattat tttaggaaca aatcaataat agaagatatg  35520
ccagaaacct acctcttaga gttatttata taatttctcc agtgaaatct ggttggttat  35580
tttgtcattg tgtggcacgt gcatgtgttg tttgtgtgag agggagagag attatatttg  35640
tcatcacttg tttgatagta tcatctttaa tgtactctgt ctttaatttc ttcattatag  35700
aatagcacat gtggatatca ttttctttcc agattgggag cagtgcatga aaatggtatt  35760
cctgaattcc cttggttggt tcttgttcag actctgtata tctttggtcc ctacagagat  35820
cgattggcaa aatgctttct gtgtttagat catgttaatt tactatatat tggctttgct  35880
tttatgttga cctttatctt gtaagttact ttttctttat cctaacagat ggctttgtag  35940
agttacaggc aaggttcctg cctataattc catttccctc ctctcttctc tgcatctgtt  36000
tagttctata tccttttctc tcttctttct cctttttcttt tttttctcc ctccatttcc  36060
tctccctccc tccttccttt tttcccttcc tccctccccc cttccttcct tcttttttat  36120
tttaatttta gcttagttca ttaattctat ttttaggtcg gatgatgagc agagctctgc  36180
ggataaagag agacttgcca ggtaggagaa cagtgtcttt tagcatgatg aagcagatga  36240
```

-continued tgctgctttt tctatccttt ttcttactct ttcttttctt cccctttctc tttgtatttt 36300
tccttatctg tggcaagaga ggacaagatt ttttagaagt ttgagtgtaa caggaacttt 36360
ggcttccccc atcagaaagt gggtgagttg agggaacttt gcttagggat ttaagaaatt 36420
gctattagtt ttaagttttt ttttcttttt ctctttatgt cagtactaag tttcacagaa 36480
caaaaagctc ttagaaggaa tgcaaccgtg ccagttggtg ctttaacagg gaaatactct 36540
ttttatcaga aaaccaataa atatatctgt atttgtgatt agttcccagt atttaggcct 36600
cagcatttac tccacacctc taggaaactc acacctattt tcctatgaag actcacagcc 36660
tagattattc tcacaacaga actagtgttg ctttggtgac cgaatccttt cttgcggtag 36720
ttttctagaa aagttttagt ttccttgatg tggctattta aaagaccagg tttctgtact 36780
tacgtgtcag aaatctgtca gatactagga agatgagtgc tttatgtttg agaatagaat 36840
tttatgtctt aggcaaagtg taactaaata tgggcctatg tggtgagacc ctttttgcca 36900
tttagaaagg agactctaga attctcttgg gagactgttg tttgtaatgt agaaatgctg 36960
cagaagaaat atgcatagac ttttctgttt tctagtatct gtgatttggg ggtgacttag 37020
gaaatagatc attgatgcca atacccattt ttactatatt ccccctttttt tctactattt 37080
cctctttaat ctgggtcaca aactcatttt gctgccagtt taactcgagc ttcttactaa 37140
ccctttcact gttcagaaaa tggatttggc atgatgtggt ggagaaaaca ttgtattggg 37200
aagagagcag cctggggaaa gtcacttacc tacttgacct ccctttgctc ttctcagaaa 37260
aaagagattt atgttagatt tttaattttc ttactttctt tttttttgg acaaagaact 37320
tttgttcaag tagaattctt aagtggtaac agaaataaat aaaagagata aagcaggccg 37380
ggcgcagtgg ctcatgcttg taaccctagc actttgggag gccgaggcag gcagatcacg 37440
aggtcaagag atggagaata tcctggccaa cttggtgaaa ccgcgtctct actaaaaata 37500
aaaaaaaaaa aaactgggcg tggtggtgtg cgcctgtagt cccagctacc tgggaggctg 37560
agatagcaga attgcttgaa cccagaaggc ggaggttgca gtgagccgag atcccgccac 37620
tgtactccag cctgggtgac agagcaagac tccatctcaa aaaaaaaaaa aaaaaaaaag 37680
aagaagagag ataaggcaaa tatttgagta gaagcagaaa tgcagcatgt tgcatgatta 37740
tctccttgag gcatccccat ggaggacact gagaaactta atgggctttt aaaaattcct 37800
gttggaaaac tgctggatta ttcctgttaa cagtgatatc tttctgtctt aattttgagg 37860
aagtcagtgt tggagctgtg gtctatttac ctgggtgaga ttcaaattgt cttgtcagac 37920
ctttaatcat cctcctctcc attccactcc tccagttaac ttcgtcccag actggggacc 37980
catatgggac ttttagtaga tggtgtatct taagtcttgt aagaagttta gtgcactggc 38040
agcacaccca gataaagaag gtaggacttt gtgcattaat gggccaaata aaacttcaaa 38100
atcttcaaat tctgcctttt aatgttgcaa ataagagaga ggcttaccat attttataga 38160
ccaaggaaat ctgtactatc aattcttgta tcagctatgg agccacatac ttgagttggc 38220
aaaaattggt ccttttattt tctggccttt aaatagttga attagtaagc atgggagtta 38280
accaagctga ggttatatgt tccataggaa cttaagtgag taaaatcagc atttaaaaat 38340
actatctttt tttttctctt gttttttgtt ttttgttttt ttttgaaatg gagtcttgct 38400
ctgccaccca ggctgaagtg cagtggtgtg atctcagctc actgcaacct ccacctccca 38460
gattcaagtg attctcctgt ctcagcctcc caagtagctg ggattacaga tgcatgccac 38520
tgtgccctgc taatttttgt atttttagta gagacaggat ttcaccatgt tggccaggcc 38580
ggtctcaaac tcctggcctc aagtaatcca cctgcctcca tctcccaaag tgctgggatt 38640

-continued acaggcatga gccaccatgc ctgacctgtc gtttcttaaa acagcttttg ttctgaggga 38700
gtggtaattt acaaaggatg tgaagtttcc aggaaatagg gggaagggaa ttacattatc 38760
ttcttgttct ctgtctgcct tattagttct gtttcatgct tgctttgcat gagaaggttg 38820
gcaaacctta ttttaactgc tgagacttaa gcatcactaa atctgaatac cacattcttc 38880
agcagcacac ttggtatcca tatcactctc cctgctacca aatgaccaga tgtgaccacc 38940
tggatggggc ttctctttct ttccatgcag ggaaaatcac agtgaaattg aacggcggcg 39000
acggaacaag atgacagcct acatcacaga actgtcagat atggtaccca cctgtagtgc 39060
cctggctcga aaaccagaca agctaaccat cttacgcatg gcagtttctc acatgaagtc 39120
cttgcgggga actggcaaca catccactga tggctcctat aagccgtctt tcctcactga 39180
tcaggtctct gggacttata gttctgagag agtctggaat ctgggtgaat ctcttgaaag 39240
ttttcgtttt ttggacaaga attcagcttt tcaggaagaa gtcagacaat gggaaaacga 39300
atttcaatcc ttggctataa cattaattag cattgggaca atgagaagta gagaagagtt 39360
gtgaaaacta tttaataagc taataagtat taatatttga gaacttgact catgaatata 39420
gcatatagga tggaagaaga acagtggaat cacagaggaa atgactatgt ccatggaacc 39480
aattttcttt cttgccttta gggttataga agatggaaga aatctatttc ttatccctga 39540
agcagcttct agttttagta atagaatgaa tctgtcccac ctttggtgat agaagaactg 39600
agagtctaat tgttgcttag ggatgtgctc tgttacatgt gatcactatg aaaaaaagaa 39660
ggcgtaaaca ttttctgcct ttcaggaact tcatctgaat ataagtatgt gagtggcagg 39720
atatcacaga aaataacagg aaaatgcata aagagaggaa ttgtattttt taattagtaa 39780
ttttatgtgg gactagatag acatactgaa gggatggcta aagtgaatag aatggctaga 39840
cttgagtgag gatggttagg gaagacttct gagggtaagg aagccatgtt ctgttttggt 39900
tattaaaata acatgatcat tgcagaaaaa tttggaaaat gtaggaggta taaggaagaa 39960
aaaaatttac ttcagtatca atcaagtatt ccccttaatgc caccaattta atcaaatgat 40020
tagaaagaag gagagaatat agtttgagaa aatggaataa gaattttcca aataggatgg 40080
tctacttaaa actacatact ttgtagctat atacattgaa atagttaata tgttctaaca 40140
gtacatgtgc aagtattcaa cagactccag ttatgcacct tttgtgggca aaccaggtgt 40200
gttgtgctgt gagaaataga aagaatggtg agacaaatgg ttttctggtg gaaacagaca 40260
tgtaaataaa taaattaaac atagaactag ttctataata gaagtgctgt aatgaatcct 40320
gtaaaatgca gatatggaaa atgagttggg gagtagtgtt gtggattttg ggaagcactt 40380
gagcaaaaac ctagaagtgt ggaataattg ggttatgcaa agaaagtcaa gtggtttagc 40440
atgtttttgg tagataatag gaaggtaggc tgggatctaa tgatggaatg tttaggtgtt 40500
aaagaattta gattttaatt tttatgcagt ggggagacat aaaaaatgta ttagatctgg 40560
tagcatttta aggattgatt gaaagcaggg cgactactta attagttttg gtaaaagatg 40620
actaggacag tgacaaagca ttggaaagta gaatcgataa aactgaatta tcactggaat 40680
gtgagagaat agttagattt tgaggcttct agcttaggag gatgctgtta agaatattgg 40740
aagagcacgg caggtttttt tttttaagag ggaaataatg attcaggttt tgggatgttg 40800
atgttgagtt gctggtagaa tatttataaa tattttacag atacttgaaa ttcaagtctg 40860
ctgaaagctc aggaaaaaac gttagtcatg tctagggcta tagacttggt tattatttcg 40920
tagtggggaa gagtgaatat ggtttcccag gaagaaagta tggtattaat aaagagggct 40980

-continued

```
taagatgaac tttggaaatg tctacattta agacttgaac aaaggaaagg aagtctgaaa  41040
cagaagagga agcaaaaatt ggagtacagt ctcatagaag aaggtaggga aaaataaaat  41100
ttaaaggata agatggacga cattgtcaca ttctgcagag aggttgaata aagtgatgaa  41160
gacccaggaa aagggacttg aattggtaat taggaggaca ttagtaacct cattaaaaat  41220
atatgtatgc tgttcctggc agaacaaaaa ccaaaccaaa caggaaaaca gtagtttaga  41280
gtgagagtga agtgggattg agaaataatt gaaaggtaag aggataaagc cagtgaatat  41340
aacattattc ttagtataag cttgctgctg aaaaagagag atgaggtggg tcaaactgag  41400
ggaagattta tctagaattg agaaaacttg atcattttta taggcctgaa gggaaagaga  41460
gaaagtggga atatttgtca agcaagatcc taaaaagaga ccagagagga tggaattaag  41520
aagtcaatta ttgttcatgg taagcctttt tttttttgag acagggtctc ttgctctgtc  41580
gctcaggctg gagtgtggtg gtatgatctc ggctcactgc aacctctgct tcccaggctc  41640
aggtgatcct cccacctcag cctccggagt agctgggact acaggcgtgt gccaccacac  41700
ctggctagtt ttgtttttgt ttttgttttg ttttgttttg tttgtttgta aagatggagt  41760
ttcgccccat tgcctaggct ggtcttgaac tcctggactc agtgaccctc ccactttgac  41820
ctcccaaagt gctgggatta ccggcgggag ccgctgtgcc tagcccaagc ctttttattc  41880
ttcttgaatc ctgagataga gaggaagagg tggatagtga catagagaaa gtgaggaaac  41940
atgtattaga aaaaactttc ttatcgatga actacattta gggtggaaac ctgtggctgt  42000
ggatcaggtg tgaaccagca gttgcttacg gagagatgca tgtggcctga agtgtcttac  42060
ttcttcctgt gaatagaaat acttgttttt tcagagtaaa atattaactt ctatttcttt  42120
ttcttgcgca ggaactgaaa catttgatct tggaggcagc agatggcttt ctgtttattg  42180
tctcatgtga gacaggcagg gtggtgtatg tgtctgactc cgtgactcct gttttgaacc  42240
agccacagtc tgaatggttt ggcagcacac tctatgatca ggtgcaccca gatgatgtgg  42300
ataaacttcg tgagcagctt tccacttcag aaaatgccct gacaggtgag agttatgtgt  42360
atgggaaatg aatgagaagt cctttcttgt ttttttcctg agacttaaga gatgttttag  42420
ctgttaaatt ggtttgttga ctctggcaag gcttcaagaa ttttctactt taatgaatat  42480
agtcagttct ttttatccat atgagattat ctactttgtg gctcagcctt agaaaatatt  42540
tcattggtga taatatttta catttatctt aatattggta taaatagaac agtaaaagcc  42600
aaacctacaa tacttttttt tttccgttct aaaagaatta tccatgtttt tatctcattt  42660
gtatggataa ttatctggta ttttttctac ctcctggtgc ttggctttgt gctaggttca  42720
atgataacag ctttttattc tatagatatg gttattggtc aatgtataag gtgttttctg  42780
ttgttgttgt tgttgttgtt tgtatctgta ctgttgttct ttttttctcc cctattttat  42840
tatgttcagt cttttggcca gagtttggct agaggaaaca agtcatatct attcttgagc  42900
aactctagaa aaaaatttaa agtggaagca gataaaaaaa ctggtagtta aaatgcaaga  42960
aatttcaata tactcatatt agtgttgttg atctttagtt ttcctccttt tttcccaccc  43020
aaaaaagaga cagggtctct ctcttgccta ggctggagta cggtggcaca tcatagctta  43080
ctgtaatctt gaactcttct gggctcagta atctgcctgc ttacagcttc ttgagtagct  43140
aggagtagtt catgtcacca cacttgacca atttttaaat tttttgtaga gacaggttct  43200
gtctgttgcc cagactggtc tcaaactcct ggccttcagc attcctcctc ccatcttggc  43260
ttctcaaagg gctgggatta tcggcatgag ccaccacact tgaccagttt tcccctcctt  43320
tatgttttta tgatttcatt tttctagttc ttccttttcc ccaaaagttg ttcttcgttt  43380
```

-continued

```
ctgtataata aagaagacaa acagatctat atgtttctat aacatataaa attacttggt  43440
tttttctttt ttaaaatttt ttctttttat tctttttttt ttttttgaga caaggtcttg  43500
ctttattgct gaggctagag tacagtgact cttcacaggc acagtcatag cacactacag  43560
cctcaaactc ctgccctcaa gcagtcctcc tgcctcagcc tcctgattag ctgggactac  43620
agaaaagtac ttgtttttca accaatgaca tttactctgt atgtatgtct gtatgtgtat  43680
acagataatc agctatgaga atatagcctt gcctcttgtt ttctactact actttccact  43740
cctacttttc cttgcacaat gttattttca atgctgcctt tgaacttaag agtgagattc  43800
attgatgata attgaagtat tttaggcttg aaaaaaaatt catctcctgc ttggtcagtt  43860
ctgttataag caaggagatt aagggcatga ataggatgct tacttatctt tgccttcagt  43920
atctctcccc ctcttcccca cacacaaaaa tgcactccag actgctcttc acatcttcct  43980
tcagggcgta tcctggatct aaagactgga acagtgaaaa aggaaggtca gcagtcttcc  44040
atgagaatgt gtatgggctc aaggagatcg tttatttgcc gaatgaggtg agtgtcaagc  44100
tgaggattgt gatttggtat aggaaggatc aagagctgag agttttattt ctgtcagagt  44160
taagttggat tagctccagt ggattaaatt taactctcca tacccagatg gattgtaaca  44220
cagaataaag tatttggaaa gggaactaac gtttctgaac ttgccagaca ctatgatagg  44280
tgctttatat ctgtcatctt attttatcct cacaattgcc ttgtagtgta agattgatgg  44340
ttaccatttt gcagatggaa aaacagatat aaagaaatga acttggccag gtgcagtggc  44400
tcaaggctgt aatcccagca ctttaggagg ctgaggcgag tggatcacct gaggtcagga  44460
gtttgagacc agcctggcca acatggtgaa accccatctc tactaaaaaa aaacaacaac  44520
aaaattagac gggcgtggtg gcgtgcgccc ataatcccag ccacttggag gctgaggcag  44580
gacaattgct tgaacccagg aggtggaggt tgcagtgagc cgagattgtg ccattacact  44640
ccagcctagg caaaaagagt gaaactctgt ctcaaaaaaa aaaaaaagaa aaagaaaaag  44700
aaatgaattt cccactgtta catactgttt gatacaggat tttgttttaa ttcatagtag  44760
tctgactaca aaacctctac tttttccctg ttacaacaca aggcaatatc catttactca  44820
gaccatttct tctttttttt tttggttaga aatttgagac ttcctatgtc tttcagtagg  44880
tgtttagtgt ttataaatta tatactgtac gttttaggat tctgtagaaa atatggtggt  44940
cctttctata caggtacaaa aggcatctca gggtcacaaa gttcaggcta tataatggaa  45000
attgactaca ttgtactgag aggatagttg ctagaaatta tgggtaggat attaaaggtt  45060
tgcttggaga ggcacaaaat tgaacattat gtggtttagt gatttatttt tatttttatt  45120
tatttatttt tttgagacag agtcttgctc tgttgcccag gctggagtgc agtggcatga  45180
tcttgggtca ttacaacctc tacctcctgg gttcaagcga ttctcatgcc tcagtttcct  45240
gagtagctgg attgccacca cagctggcta atttttgtat ttttagtaaa acagtgtttc  45300
accatgttgg ccaggctggc ctcaaactct tgacctcaag tgattcgcct gcgtcagcct  45360
cccaaagtgc tgagattaca ggcctgaacc actgcaccca gcgtgtaatt tagagtagct  45420
tctagaccca gactgctgga ttttgtttta atccatattc tatggatttg aattctagct  45480
ttgatgctat cttctgaaac cttggatgat tacatgacta cattgtgctt tgatttcatc  45540
atctcacatt ggcgataatg ttaatactga ctttataaag ttgttatgaa gattagatga  45600
attaatatat gtaaagatat ttagaacaga gcatgacaca tattaaccct atgtaagttt  45660
tatttttgtt ttaaaggata gggagaggga aagtagcatt ggcaggagta tcccaatatg  45720
```

-continued

```
tggacatggc taatgcaaag acataggcaa gagcaagata ataatgaact gtagcaatta  45780
cattaagttg tggttaatgt agagcaggag taagcaaacc acagcccttt atttgtaaat  45840
aaagttttat tggaacatag ccatgcccat atttttacat attatctatg gctattttca  45900
tgctataatg ctagagttga ctagttgcaa cagactttct ggcccgcaaa gctgaaaata  45960
tgtactatct ggtcctttac agaaaaagct tgccaactct tgatgttgag aatgtttgca  46020
tatgaagaac atatggaaca ttttgacttc aaattctaaa agttttagaa atactaaact  46080
tgacctatct ttatccttca ttattagtag cattaccaat tttctatgtc tggttgtatc  46140
cagagcatgt tattctgcta ttactgtgga aagttcttg atagggcagt ctgattgctt  46200
ttaatctctt tattccttga aacaggtgtg gcagtagctc tgtggaccca gtttctgtga  46260
ataggctgag ctttgtgagg aacagatgca ggtgagatcc taagtggtga aaaccaaagg  46320
gatggccaaa tacctgcaga gatcatcaca tttttacctg tcttactgta gtcgttcctt  46380
cagcagctct cacttgcatc ccttacctcc cacttaacat cccttacctc ccacttactt  46440
tttttctggc aatatttcc taaacttcta aaacttctct tgaaaatcct gtttaaggaa  46500
gtcgctatgc tattttacct actttcctcc tactgcatac cttttggtta ctttactttg  46560
gcaagggtaa aaatgtggcg gtcatttttg ggtgggaaag atgattatcc tgttttctaa  46620
actcctaaga gcataaactt aaaagtacta aggcagcatt gccctttgag ttttacgggt  46680
agattttttt tttttttttc aaactcctgt aactcttcta ggaatggact tggctctgta  46740
aaggatgggg aacctcactt cgtggtggtc cactgcacag gctacatcaa ggcctggccc  46800
ccagcaggta agaaagtgaa atagtaaata tttcccttg gtacagttgg ttcctcacag  46860
agtccatgaa agctaatatt tattatatac ctggtatatg aaatgtactt ttgtgtaaga  46920
tgaaagaaaa taggaaaaga aaatgtacaa tccttccctt ccattattga gcttttattc  46980
cagttgagga gatagataac tcaggctgga aaatgattca gtattggctg tgtcacagaa  47040
tgtggttttt atgtgaacaa atttatactg aacatatgta ttctaagcat ttgttgcaaa  47100
gaaacttaga cattgaatgc agttaatttg agaaagattt ctaaagtagg aacaagactt  47160
tgagagaaaa ggggaaaatg cctttattgt aataacttat caagaggata ttctctgcaa  47220
agactttaaa tcaagctttg agcagattag ctttaccaga acttgaggtc aaacaaggaa  47280
tgtgagaaag gtgattgggt tgcaggatca aagttttaag ttggcttgtc agagtttcca  47340
aatcttagca actttattac ttccctgctg cctgggtatt attggaaagt aggggttttg  47400
gggagacaga aactaagaga aaagagaagc aaggtgatgt gttttggaaa aaggttaaac  47460
tttggatgtg gagaaacctg gatgtgattc ctgtcattgt tacttattag tggcatcacc  47520
tagggtaagt tgcttgacct ttataaagct cagttttctc atctgtaatt cagagttagt  47580
acatcctgta tagggttttt gtgaggatta gatttaatgt aaggaaagca tccagcccag  47640
tgcctggcat atggcaggta acccaataaa agtaattaat gtaatttaaa aaaatttaac  47700
tgaagtagta atgacatttg aactacttag tctatatact atataagcca cacagttaaa  47760
gtatgtgatc tttcatacct ctatgtagca tcaaggaata ctatttttct ggataaaaag  47820
agtataacta tgcaaaaaac aggggagaaa tgcagtcttc ttccctttct gtgtaaaaca  47880
ttggttttc tcttttccaa gggacatgaa taactattga tggttggtat aacttcattt  47940
tgggttgctt gctaacttta aaagttacag attaggcaaa gcataaattt tctgcctata  48000
acatggtcat agaatggatg tcttcatatg tgccatattt ggccagcata gtttttttaga  48060
gtactctggg taggacttgt attttccagt ttactataat taacatgggt aaaatgtagg  48120
```

aattaatata tatgtaaata cttaaaacaa tgactggcat atatggtaag ttttatatac 48180
ttgtttattc ttatttatca ttctctattg ctttatgctt agcctcttca taactagatg 48240
tattttgttt tgttttgctt tttggttttt tttttgagag ggagtctcac tctgtctgtc 48300
gcccaggctg gagtgcagta gtgcgatctc ggctcactgc atcctccgcc tcctgggttc 48360
aagtgattct ctcacctcag cctcccaagt agctgggatt acaggtgcat gccaccatgc 48420
ctggctaatt tttgtatttt tagtagagat ggggtttcac tgtgtcggcc aggctggtcc 48480
tcaagtgatc cgcccacctt ggcttcccaa agtgttggga ttacaggcgt cagccacggt 48540
gcctggccca taaataggtc tattttgaat ctttacttgt ctgagttttg aaggcatttg 48600
agttggaggt ccccgttaaa ccttttaacg tcacgtttct gaaggtgttt ccctcccaga 48660
tgatgaccca gaggctggcc agggaagcaa gttttgccta gtggccattg gcagattgca 48720
ggcaagtatg aattttccac atctatattc ccgttcaatt agagcagatc ttcaggactc 48780
attcctgtta attttctttt actttctgaa tacaaatgaa gaattccata aaactctcaa 48840
aatttgaagg aatatggcat ttatagtgac cattgctatt cttggattta agtaaagttg 48900
aaaagtatga gaggagggag atctttttcc ccttgtctta attttagctt tactatgctt 48960
aattttctat ttccagttaa tttcctttgc ccctatacaa aagaagaaag atccttttca 49020
ttgtatcatt acctgactaa caatagaaaa gtggaattat tttgattttt tcataagtat 49080
agataagttt cttggttact tgtaccatat caacctgagt aatgagttca gcatagccag 49140
tatgtggatt ttagattgaa taaactttat tcttacttta ctaacttggt aaagtgtaaa 49200
tgtatgggag cagagctaga ccttatgcct tgtctgattg tgattgtcat tttttttttcc 49260
tttttggata aaatgtgaaa gtttagaaag tcctaaaact gggaatctta tgtctatgca 49320
aaagaccatg aggagatagg aaatacatct gtaaataatg gtatcatttt acctcatttt 49380
tatctcttca ctctcaggta actagttctc ccaactgtac agacatgagt aatgtttgtc 49440
aaccaacaga gttcatctcc cgacacaaca ttgagggtat cttcactttt gtggatcacc 49500
gctgtgtggc tactgttggc taccagccac aggtgaggag ctggagctcc attaggcctc 49560
cattttcctt tggctatgtt gacattatgt aatcatgtag ttcctaagac agccaaaaca 49620
tatcaacctc agttgagaaa aagagatcat catattctgt tagtacctaa cattattttc 49680
agcttcctat taggactgtc atctcatgta gagaaatatg gcttgtcaaa ccaggtggga 49740
gcagcaggta caaatatgta tttattttt gttgttgata ttaatacaga tgattcaaag 49800
gtactcatat taattagtta taccagtata gctacattta gataattcat gtaattacct 49860
aaatgaataa tggcccataa aacatgcaga tttagcacca gttattataa tttactcatg 49920
caacagacca gttagccatc tctgaattga cgcatcatat aaacttttaa aactgttgtg 49980
ggtcggaagg acttctggct gtggctatgt gaaagaggtt ggtgaaaaag aggtcttgaa 50040
aacaaagaac aaagagaatt tacactacct gattcaacac taactataaa gctattacca 50100
agacactgtg gtgttggtgt aaggatagat atatagatca atagaccaga ataaggtcta 50160
ttcttatact tgtcaactaa ttttcagcaa aggtgacaag acaattcaat ggataaaata 50220
aatatttcta acaaatggaa caattggata tctgtatgca aaaaaaaaaa aaaacaaaaa 50280
aaaaaccaca cccaaaaatg aaaacacata gatcttacct catacaattt acaaaaatca 50340
gcttagaggc ctaaatgtgt aagagctaaa gttacaaata aactcctagg agaaaatctt 50400
tgtgattttg agttaggcaa aagatttctt acactaaaag catgattcac agaagaaaaa 50460
aaattataaa ttggatttaa ttgtaattaa aatttgccct ctttaaagga tattattaag 50520
aaaatgaaaa gaccagacat aaatggagag aaaatagtta caagtcatat acctgaaaga 50580
ggatttgtac caggaatata taaacaactc attaagacaa acagctggta aaaaagagca 50640
taagacttga catttgactg aagaataaat atgcatttat gcacatgaaa agatgctcaa 50700
catcttttta ccattaggaa agtgcaaatt aaaatcacaa tgagatacca ctatataccc 50760
actagaatgg ctgtaatcaa aaagtattgg tgaaaatgtg tagaagctgg aaggaaccct 50820
catacattgc tgatagacat gtaaaatggt atagctacta gctttgcaaa agcattttgg 50880
cagtttccta caaagttaaa catactctta gcctataacc tagcaatttt attcctgagt 50940
atctacctaa gagaaatgaa aacatgttca cccatagatt tgtacacagt tcatatctgt 51000
attattcata atagccaaaa aaatgaaaac tatttaaacg tccattaaca ttttgtaaat 51060
gaatacacaa ctgtgttgta tccatgtgag aatactactg agcataaaaa ggaataaact 51120
actgataatg cagccatgta gatgaacttc aaaaatacca tgctcaatga aagaagccag 51180
acccaaaaga ccacatatta tgttgtttta tttatatgaa atttgtagaa atagcagaac 51240
tagagaggca gaaagcagat ttgtggttgg ctggggagtt ggagtgggag cagagattga 51300
ctgcagatgg cacaagggaa catcttgggg cagtgaatgt gttctgaaac tggattgtgg 51360
taatcattgc acaactataa atttagtaga catcatcaaa tcatacactt agaatggctg 51420
aattatgaat gtaaatttta tctaaaattt ataatctcat taaaataaat gtataatatt 51480
ctgagaaaga aaaatgtttt agaagccagc tccttaacag attctgcctt tttttagtag 51540
atttcatctt ttgtttattg tctttttttt ttctcctcct cacttaacta taatcttagg 51600
attaaaacag aagaaataaa atccaggtcc ccagctgatg gaccaggcca gttagatgac 51660
cataaaatta tatatgttgg ctgggcacgg tggctcacac ctgtaatccc agcgctttgg 51720
gaggccgagg cgggtggatc acttgaggtc aggagttcga gaccagcctg accaacatgg 51780
tgaaaccctg tctctattta aaaaaataca aaattagcca ggtgtggtag cacacccctg 51840
taatcccagc tacttgggag gttgagacag gaaaattgct tgaactcagg aggtggaggt 51900
tgcagtgagc caagatcgcg ccatcgtact ccagcctggg caacaagagc gaaactccat 51960
cttaaaaaaa aaaaagtata tatcttactc ttctttctgt attctaggaa ctcttaggaa 52020
agaatattgt agaattctgt catcctgaag accagcagct tctaagagac agcttccaac 52080
aggtaacttt tttcctggtt tggttctgaa taaatatttg tcatattcac tccataaata 52140
ttgactactg attaactgaa cactgtggca ggcactacag ttttatgttc tttagtagtt 52200
aatctgcatt tttaaggaat agaaaaggac taatactttg aaattatgga taatgcccaa 52260
ggtatttctg tttggctttg gctatttact gtcttgtatt caattaactg tatccaagga 52320
gctgtcttta aggtatttaa actattgcgc caggcatggt ggctcatgcg cccaacctct 52380
gtagatgctg tgaaaataga tgttttcctc gtctgggcat ggtggctcac gcctataatc 52440
ccagcactct gggaggctga ggcaggtgga tcacttgagg ccaggagttc aagcccagcc 52500
tggccaacac agtgaaaccc catgtctact aaaaatacaa aaaattagcc tggtatggtg 52560
gtgcatgcct gtaatcccag gtactcggga ggctgaggca cgagaatcac ttgaacctgg 52620
gaggcagagg ttgctgtgaa ctgagatcat gccactgtac tctagcctgg atgacagagc 52680
tagactctgt ctcaaaaaaa aaaagataaa aaagaaaatt gtatacttca ctaagcttgt 52740
agtagaaaaa ttcattttat atagtttttt ttttttttta gaaggagtct agctctgtcg 52800
ccagggtgga gtgtagtgtg caatctcagc tcattgtaac ctctgcctct taggttcaag 52860
cgattctcct gtttcagccc cccgagtagc tgggattata ggcacatgct gccacgccca 52920
gctaattttt gtatttttag tagaggcggg gtttcaccac gttggccagg atggtctcga 52980
tctcctgacc tcgtgatcca cccacctcag cctcccaagg tgctaggatt acaggcatga 53040
gccattgcgc ccagcctaga ctgttctttt atggatgagt gagagtcgta atgaattata 53100
taagctgact gttaattgtc attctcaggc tccagctcct gaaaatatct ggtgaatttt 53160
atagacatgg cttttgataa cggtttttac tttgtattag acaagttaat taacctcttt 53220
aagtctcagt agtgtcgtta ttgatacaat gaatatatta atagtaccta aattcagacg 53280
gttgttggga agattaaata aggtaatgaa tataaaacac atcacccagt atttgatacg 53340
tagtattaca aaataagtgg ttagcttcta atactgttta tttttatttt tttaattttt 53400
aggaatatag agttaaaaga ttattttcta ttccatgaga ctagtatcta aaataaccta 53460
aaattggctg ggcatggtcg ctcatgcctg taatcccagc actttgggag gctgaggcag 53520
gtgatcactt gaagccagga gtttgaacca gcctggccaa catcttgaaa ccctgtctct 53580
actaaaaata caaaaattag ccgggtatgg tggctcatgc ctgtagtccc agctacttgg 53640
gaggctgagg catgagaatt gcttgaaccc aggaggcaga ggttgcagtg acccaagatt 53700
gccccactgc actccagcct gggcgataga gcaagactgt ctaaaaataa aataaaataa 53760
aaaataaaat aactaaaatt acttttaaaa aataaaagca aaacaagact aaagccaact 53820
taattttatt tatggaaacc tctgtagatg ctgtgaaaac agatgctctc atctgggtgc 53880
agtggctcac acctataatc ccagcacttt gggaggccaa ggcaggcgga tcatttgagg 53940
tcaggagttt gagaccagcc tagccaacat ggtgaaaacc cgtctctact aaaaatacaa 54000
aaattagctg ggcgtgatgg tgcacgcctc tagtccccag ctactcagga ggctgaggca 54060
ggagaatcac ttgaaccctg gaggcgaggt tgcagtgagc caagattgca ccactgcact 54120
ccagcctggc gacagagcga gactccatct caaaaaaaaa aaaaaagaaa aagaaaagaa 54180
aacagatgtt ctcaggtttc ggggaaaaaa taggattgaa gagcaatata taagctatat 54240
tctgtgtcct taaacttacc aaatttctgg tatagacttg taaagctagg tcagagtatc 54300
tttaatggat ttcccaaggg aagtagggaa acagtctttt ccttcctgga aataagttat 54360
tattcctatt tgactagaat agtattaggt tggtgcaaaa gaaattgtga tttttttgcca 54420 ttttttttaaa tggcaaaaaa tgcaattact tttgcaccaa cctaataaga aagcttgagt 54480
ctctggccgg gctcagtggc tcacgcctgt aatcctagca ctttgggagg ccgaggcagg 54540
cggatcccga ggtcgggaaa tcgagaccat cctggccaac atggtgaaac cccgtctata 54600
ctaaaaatac aaaaattagc tgggcgtggt ggcacgtgcc tataatctca gctacttggg 54660
aggctgaggc aggagaatcg cttgaaccag ggagtcggag gttgtagtga gccgagattg 54720
cgccactgca ctctagcctg gtgacagagc gagactccgt ctcaaaaaaa aaaaagtctg 54780
ggcacggtgg ctcacacttg taatcccagc actttgggag gccgaggcgg gcggatcaca 54840
aggtcaggag atcaagacca tcctggctaa catggtgaaa ccccgtctct actaaaaata 54900
caaaaaatta gctgggcgtg gtggcacgcg cctgtagtcc cagccactcg ggaggctgag 54960
gcaagaaaat cgcttgaacc cgaggggtgg tggttgcagt gagcagagat cgtgccactg 55020
cactccagcc tgggcgacag agggagactc cgtctcaaaa aaaaaaaaaa aagcttaagt 55080
ctctgaaagg aagcatgaga aatatgcttc catgtttaat cacttagttt ttactctcat 55140
tttgttttaa tattgaaaaa tattggtgcc tcaaggacaa tgacaagagt tttagggtta 55200

-continued

```
tagaaattgg aaaattttta tttatttttg taatgaaaat tttctatgag ttccactgat  55260
ggcatgaaaa ctttttcagg tagtgaaatt aaaaggccaa gtgctgtctg tcatgttccg  55320
gttccggtct aagaaccaag aatggctctg gatgagaacc agctccttta ctttccagaa  55380
cccttactca gatgaaattg agtacatcat ctgtaccaac accaatgtga agtatgtatt  55440
atacaggagt gtgaaaaaac tgtttttcct ctgttctcac aacagaaaac acttctgatg  55500
ccctatgtgg ggggtaaaca atcaagcaac aacacaaaaa tttagccggg cgtggtggca  55560
tgtgcctgta gtcccagcta ctctggaggc tgagacagga gaatcacttg aacctgagag  55620
gtggaggttg cagtgagctg ggatcatgcc actgcactcc agcctgggct acagagcgag  55680
actccatttc aaaaaaagaa aaagaaaaaa gaaatcaagc aatcagtagt ggacaccagc  55740
tgggtgtcct tccattcaat tcagttcact atctacttgg agatagcatc agatccccca  55800
atttgtgtat gcagtaccac aagactgctc ccacttctga tgccagttgc aagccccagg  55860
ttgttttacc tgtgcatctg actgaccagc tgtctcccat gaccccctac ttgggttcag  55920
tcaatttgct tgaatggctc agggaacatt tacctatgtt taccagttta ttataaagga  55980
tattacaaag gatactttgt acatcagatg aagagataga tagggcaagg taaggaggaa  56040
ggagcgcaga gctttcagac cctttctggg tgggctaccc tccggggatc tccatgtgtt  56100
tacctatcaa gaagctcctc aaacccagtc cttttgggtt ttaatggaaa tttcattatg  56160
tagccatgag tgattaaatc attggccatt ggtaatcaac ttaaccttag gtaccggctc  56220
ccctccatga ggttgagggt tagggctaaa agtcccagcc ctctaatttt accttgatct  56280
ttccagagat gagcccccat cttgaagcta cctaggggtt gccagccctc agtcaactca  56340
ttagcagaca aaaagacact tatcacactg aagattccaa agattttaat tggtaaaaat  56400
ccaggtccac ttatacatgg atttttttca gtaaatatat tagaaaattc ttttgatatt  56460
tgtgacaatt tgaaaaaccc aaaaataagc tacatagcct ggatatattg aaaaaattag  56520
aaaaagttag ccatgtcata catgaatgta ttaaatatat ataaattcta gtctatttta  56580
tcatttacta ccatacaaca tatacaaatc tattataaaa agtaaaaatg ctggacaggt  56640
gcagtggctc acacctgtaa tcccatcact ttatcacttt gggataccaa gttgggatac  56700
caagttgagc agatcacttg aggtcaggag ttcgagacca gcctggccaa catggtgaaa  56760
ccctgtctct actgaaaaaa aaaaaaaaaa aaaaaaagaaa atacaaaaat tagctgggca  56820
tggtggcaca cgcctatagt cccagctact tgggaggtta aggtatgaga atcacttgaa  56880
cctgggaggt ggaggttgca gtgagctgag atcgcaccac tgcactccag cctgggtgac  56940
agagggagac tccatctcaa aaaaaataaa aataaaaatg tatcacaacg tatacataca  57000
caccgtttgt acaatggcac catttgtagt tgagagaaat gtaaacaaat gtaaagatgc  57060
agttttaaat cataaccgcg taaagttaac tatagtatat actgtactgt tgtaataatt  57120
tggtagccac ctattgctca attgttgcca gtttgcttaa aatgctgtgt gatgctaatc  57180
atctcttcat gagcaattca ctccagtaaa ttgcatattg cagtaaacag tgaaatctca  57240
tggttcttgc atatttttca tcgtgttgag tgcaatactg aaaccttgaa taacatttgg  57300
gaacagtatg aagtgccact agtgatgctg gaagtcttcc caagaagcag ggaaaagtca  57360
tgacattata agaaaaaggt gaattgcttg atatgtacta tagaatgaag tctgcagctg  57420
tggttgcttg ccacttcata tagatgactc atcttgtaag tcatcttgta agatgatata  57480
agcttatgat aacgataaat acagtacagt gctgtaaatg cattttctct tccttatgat  57540
tttcttaata acattttctc tttagcttta ttgtaagaat acagtacata atacgtacaa  57600
```

catacaaaac gtgttcaact gcttatgtta ttggtaaggc ttctggccaa cagtaggcta 57660
ttagtagtaa cgttttggga gagtcagaag tttacagtcg aattttcgat ggcacagggg 57720
tcagtgcccc tagcctccat gttgagcaat cagttgtatt tcataaatatc acataggcat 57780 tttccaatgt tgggatttct aatgtaccaa ctcttcttag tcttatcaag ctatcccttt 57840
ctcctctact tttctagtat taaacaccat tagtttgaag ttcttcattt tccagcttat 57900
aggatttggg atagttgatc agagtagagt aaggtttttt tgttttgttt tgttttgttt 57960
tgttttttca gacagggtct cgctctggca cccaggctgg aatgcagtgg tgtgatcatg 58020
gctcactgca gcttgaacct cccaggctca agtgatcctc ccacctcagt cccctgagta 58080
gctgggacta cagacatcta ccaagacgcc tggctaattt ttgtattttt tgtagagatg 58140
ggatttttcc atgttgcaga gtctggtctt aaactcctgg gcacaagcag tccatcgtcc 58200
tcccaaagtg ctaggatcac aggcgtaagc cactgcacct ggccagagta agattttaca 58260
aacaataatt cagagactag gtcctgagat ggaagggttt agtttcaatt ctatgtatca 58320
actctttctg gaaaggacta tgttttgtac accagtttat tgctctagtc tggcaggatt 58380
ttcctctgga gcaggggtag gcaagctctt tctataagtg gggctagata gtaaatattt 58440
taggctttgt gggccatgtg gtctttattc cacctactca actctgctgt agcatgaaaa 58500
cagtcataga caaatgaaag aatggggctg tgttccagta aatctttatt tagaaaaaca 58560
ggcagtgggc ctgatttggt cagttttctt tagagcatag ctacatcctc ctctttcatt 58620
agttactgtt cctctctttt gcacttttct atttgagttt tctttctcag tttctttttt 58680
aaaaagtttt atgagatata tttcacatac catatacctc actcatttaa agtatacagt 58740
gttttttagt atatcacata gttatgtaac tcttactgca gtctaatttc agaatatttt 58800
cattccccca aaagaaattc tagatcagtt aacagtcatt ccctgttctt tcccccggct 58860
ctgaaattct gtataactat gaatctgttg tctttataaa tttgtctatt ctagactttt 58920
cgtataaatg gaatcataga ctttgtaatt cctttgtaac tggcctattt tacttagtat 58980
aatgtttaca gaggttatct gtactgatac atgttgtagc atgtatcagt acttcatttc 59040
tttttattgc caaataagat ttcattgtat ggatatacca catactgtct gtatgttcgt 59100
taatggacat ttggttgttt ctacttcttg gttatcaaaa atgcttccat atgtaaaata 59160
gggataagga actgaaaaaa tgctttcatg aatatttgtt tactagtttt tatgtggata 59220
tatgttttta ttctcttgaa ttccacccag gagtggaatt gctggccaca tagtaactct 59280
gttttacctt ttgaggaact gccaaactgt tttccaaagc tgccccatca ttttgcattc 59340
ccaggagctc tgattcctcc acatccttgt taacacttgt tattgccttt ttttttttat 59400
tgtagccatc tagtaggtat caattgtcag gttaccacct tgccatttaa tcttttcttt 59460
ctgtagaatt ggccttgaat ccacctcttg aagatcagat tatgactact tagcaaatat 59520
gaataatacc tagtgacaag ttttgtccaa ttcagtcttt agaacttgta aagtttaatt 59580
ctttgctaac taacttagta taacagagtg gattgagtta gaaattttta ttaacttagg 59640
actcaagtgg atggtcatgg tcattgtagt tctttatttt tgtctctttg catctttata 59700
ttacacaaca gccttcattt ttgtgtttcc attttgttta aatttttaaa aatttaagtt 59760
gtttgaagga ctcgagtttc tggaaataat tgctttctcc atgtttatgt atcattttcc 59820
ctaccatgat taattttaat tagcttttag ggatttgttt gtttgtttgt ttgtttcatt 59880
gagacagtgt ctcactctgt cacccaggct ggagtgcggt ggcgctatct cagctcactg 59940

-continued

```
caacctccgc ctcccaggct caagcaatcc tcccatctgt ctcctgagta tctgggacta  60000
caggagcccg ccaccacgcc tgctaatttt tgtatttttt gtagagacgg agcttcacca  60060
tgttgcccag gctggtctca aactcctgag ctcaagcaat ccaccctgcc tcagcctccc  60120
aaagtgccag gattacaggt gtaagccacc gtgcctggcc agtattttat ttttaaataa  60180
atattcttta tagaaaatgt ggaaagtatt gaaaaataca aagagaagga ataaaattct  60240
cacactccag atagtctttg ttgatgtaca gtgtacgtac tttcattttt ttacctatgc  60300
ttttaaaaaa taccttatat gaatatatac acacattcac aacaaccagg ttttgaatac  60360
ctagaaggag ttagaaccca acaagatgac ccctgtgtca tagaacatgg tttctgtttg  60420
ctgaaactga caccctagat taactatagg ataggacttt aatgaaggat ttattgattg  60480
ttccacctac agatgaatct atagagcttt acatacagaa tcttattctt ctctttctct  60540
ctctctcccc ccttcctccc tctccacccc ctctttactg tctactctgg tttcctagga  60600
actctagcca agaaccacgg cctacactct ccaacacaat ccagaggcca caactaggtc  60660
ccacagctaa tttacccctg gagatgggct caggacagct ggcacccagg taaaaaaggg  60720
tgaaataatc atctgttgag cagtcaccca gggggtggtc atttgcaatc ccatatattt  60780
tttgttcggt tggttaattt tttttttttt tttttgagaa ggagttttgc tctcattgct  60840
caggctggat ggaatacaat ggcacgatct aggctcactg tgacctctgt ctcctgggtt  60900
caagtgattc acctgcctca gcctcccaaa tagctgggat tacaggtgcc tgccaccacc  60960
cccggctaat tttttgtatt tttagtagag acggggtttt gccatgttgg ccaggctggt  61020
gtcgaactcc tgacctcagg tgatccacct gcttcggcct cccaaagtgt tgggattaca  61080
ggcatgagcc accatgcccg gcctgtttaa tttgttttaa ggttctttct ccagattctt  61140
tttaaaaaaa aatttttttt tctatttgtc ttgtcaactg gcctttgaca tataggcagc  61200
agcaacagca aacagaattg gacatggtac caggaagaga tggactggcc agctacaatc  61260
attcccaggt gagttgtgtc ctcttcgttg aagagggtag ggagtattta cttaggaagt  61320
gttctccggt actagttaga atgtacatat gttgtatatg aattttaggg ttattgaatt  61380
gtcatgttaa atctttaatg gttattttta tcattgtatt ccacaggtgg ttcagcctgt  61440
gacaaccaca ggaccagaac acagcaagcc ccttgagaag tcagatggtt tatttgccca  61500
ggatagagat ccaagatttt cagaaatcta tcacaacatc aatgcgggta tgtttctttc  61560
tcattatcct tttaaattct catttagatc acttactgat gggcatgcca ctgcccagtc  61620
agtaatcttc cagtgttttt ccacttaatc ataataccac ctgagtaaat aggaacttgc  61680
tgaactaata tactacagcc ccttgactgg ccccttcccca actccttttg gtccacagat  61740
cagagtaaag gcatctcctc cagcactgtc cctgccaccc aacagctatt ctcccagggc  61800
aacacattcc ctcctacccc ccggccggca gagaatttca ggtgagcccc gtatatatgt  61860
gctgctttac agggccctga gggattcagc tgctgaatcc aaattttatt cttcccttgc  61920
tttctctggt tacttcagaa aaagcagtga agcttgtagg gcctagcgtg aggcaaacaa  61980
gctgcttttc ttcctcctat ttctttgcac ctgtcctatt gccatgttct aggctccatc  62040
tctgtgtgtc ctggtcagtg tgtgactgtc agtctttctt gtcttttcca aattgttatc  62100
aaattttcct taacctgcag gaagtcaagg ggatctaggg atagcactag attgtccttt  62160
gattcctagc ttctgtgata aatctatcct tttaatcttt tacctcattt attcactcct  62220
aggaatagtg gcctagcccc tcctgtaacc attgtccagc catcagcttc tgcaggacag  62280
atgttggccc agatttcccg ccactccaac cccacccaag gagcaacccc aacttggacc  62340
```

```
cctactaccc gctcaggctt ttctgcccag gtaaaactta tcatctgtgt gttccctgtg  62400
tattattttt tgtttgtttg ggcttttttc cgtatgtaaa atcagtgttt tctattttaa  62460
ataccttctc cccaacccct gttctccggt ttccaatttc catctttgtt gagagtagct  62520
aattaaaaat cacagataat aaaaaaaaat ctcagtagag tctgtggttt tcaccttaaa  62580
tcagaattgc tcacttggaa cgttttgagc acgtctgatt ttcagatttg ttttggagta  62640
aattctaaga tgtttcctct ttgtttagga ctccataagg caggagcaaa ggagaaaatt  62700
aatgactaac ttacagtgat gtctgtttac aaaaaagttg aaaaattctt tttttttttt  62760
tttttgagac agagtcttgc tctgtcgccc aggctagagt gcagtggtgc gatcttggct  62820
cactgcaagc tctgcctccc gggttcacgc cattctcctg cctcagcctt ccaagtagct  62880
gggacttgta caggcgcccg ccactgcgcc taattttttt tttttgtatt tttagtagag  62940
atggggtttc accatgttag ccaggatggt ctcaacctcc tgaccttgtg atccgcccac  63000
ctcagcctcc caaagtgctg ggattacagg cgtgagccac cgcgcctggc tgaaaaattc  63060
tttttttttt tttttcttga gacagactgt cactttgttg cccaggctct ggagtgcagt  63120
ggcgcgatct cggctcactg caagctccgc ttcctgggtt catgccattc tcctgcctca  63180
gcctcccgag tagctgggac tacagggtgc tcgccaccac gcctggctaa tttttttgtat  63240
ttttagtaga gacggcattt caccgtgtta gccaagatgg tcttgatctc ttgacctcgt  63300
gatccgccct cctcggcctc ccaaagtgct gggattacag gcatgagcca ccgcatccag  63360
ccgaaaaatt cttttataat attcatatat ataatataac gcacaataaa tacactgtct  63420
aaagaaagat tctttaatat tactatatat ttatgttata caagtaatag ttttaaaaag  63480
tcaaaaccaa aagcaggttc cagaatgtta tatgcaatac gatctcaatt gtgtacaaaa  63540
tgcatgagaa aatagaaact ggaagaaatt atccaaacat gttaaccatg gaattatgaa  63600
tgattcttat tttctttata ttttccttca ctttctgaat attctataat gcatatacag  63660
aactctcatg agaaaatagt ttttataaaa aatacatcat taggaacaaa tgaatgcaga  63720
acagacagaa taatggtgca gagtagtttt tctctgcata tggtactttt tttgttgttt  63780
gtttttttga gacagagtct cgctgttgcc caggctagag tgcagtggcg cgatcttggc  63840
tcactgcaac ctctgtctcc cgggttcaag tgattctcct gcctcagcct cctgggttgc  63900
tgggattaca ggcacgtgcc accatgccca gctaattttt gtatttttag tagagacggg  63960
gatttcacca tgttggcccg gctggtctgg aactcctcac ctcaggtggt ctgcctgcct  64020
tggcctccca aagtgctggg attataggca tgagccatga gccaccccgc ctggcctgca  64080
tataatactt tactgttatg aatgcctcta gttttatata acttcacagt ttataagatg  64140
ctttcattta attcttacaa tttttattaa tcccatagtt cattgctttt ttgtaatttt  64200
atctcagctg cctaaaaaat agtgtcaaga gagattgaga gttaattgga agaaatatac  64260
aataggaaat aagtgatgag cttggttcag aaggatgcag tgattgacag tgttgactct  64320
cataggcatg gtatgtgcaa tgatgttaat gctgtatttg ttctatatcc cctctccatc  64380
tctctttagc aggtggctac ccaggctact gctaagactc gtacttccca gtttggtgtg  64440
ggcagctttc agactccatc ctccttcagc tccatgtccc tccctggtgc cccaactgca  64500
tcgcctggtg ctgctgccta ccctagtctc accaatcgtg gatctaactt tggtgagtcc  64560
agaccataag gagagtaaca ggaaaatcgc accactaaag agaaaggatt tggtagttaa  64620
agttgtttgc ctgtgttgtg ggtacactga cctgattgta gggaaatgca aggtgacaat  64680
```

ctatttagaa tttaaaacct accagctggg tgcggtggct cacgcctgta ataccagcac 64740
tttgggaggc tgaggcaggc ggatcacttg aggttgggag ttcaacccca gcctgaccaa 64800
catggagaaa ccctgtctct accgggtgtg gtaccgcatg cctgtaattc cagctactcg 64860
ggcggctgag gcaggagaat cgcttgaacc caggaggcag aggttgcggt gagctgagat 64920
cgcgcctttg cactccagcc tgggcaacaa gagtgaaact ccgtctcaaa aaaataaaaa 64980
ataaaaaaaa aaaactaccc acatgaaaaa tactttagca catataacaa aaatcatgtg 65040
aatttttata catttaatag tatgcacatt taacctaaat gagtaaagaa ctctatggaa 65100
aggctgcctg gagaagaaga attaatttag ggctgagttt tgagatagaa aaggcattga 65160
ttggcagaga gaaggacaga gttatcctag gtaaaattaa tggcttacct atagttgttt 65220
acttgtggca ttagtacaca atggaattgt gtagattgga gttgtttatt cttccttgct 65280
gtatttctag ctcctgagac tggacagact gcaggacaat tccagacacg gacagcagag 65340
ggtgtgggtg tctggccaca gtggcagggc cagcagcctc atcatcgttc aagttctagt 65400
gagcaacatg ttcaacaacc gccagcacag caacctggcc agcctgaggt cttccaggta 65460
agagagtgaa aagactttca aaaattagaa gctgggagag aaagggtcca ggaggaggag 65520
agacagtgaa ggaagcatgc ctggattgag gtgtttggtt gggggtatat gtgagaagac 65580
agagagggat aaatgtaggg atcactgtca gttattgaaa agattgcaga agctagatgc 65640
agtggtgctt gtgtatatga tgtcagcccc ttagaaggct gaagcagggg atcacttgag 65700
gccatgagtt caaagccagg ctgagcaact agcctgatcc tgtccctgtc aaacaaacaa 65760
aaaaggagta tgaattgagt gtgatacata ccatttaacc agaacagaca aatttagcac 65820
cataggaaga tgccaaagaa agttacttta gctcattcaa atagctccat atacccaagt 65880
cacagtagct ttgggtttaa aagagacaga atgattaaaa ataaaaagta gtgctcgctt 65940
cagcagcata tatactaaaa ttggaatgaa tatagagaag attagcatgg cccctgcgta 66000
aggatgacac acaaattcat gaagtgttcc atttaaaaaa ttataaaaag taaatgaaat 66060
agaacataat gattatagcc ataatggtct atttacacaa gtcctgaggg actgcaagag 66120
tgaatggagt aatcttaggc aggacaaagg aagagctggt ttaaagcaaa gattgaaaga 66180
aagcaaaaca ggtcttggtg gaaaacaaat aggataagag actccatata tgtctatagg 66240
gggttatatg aaatacagca agcagatttt tctccctttg aaaatattga gaactaggaa 66300
aaggaaaaag gtggaactgt aggaggaaga cagaagggat taggaaaaaa ggctgcgatc 66360
taaaggagtc aaagttgttg gaagtaagga aggctaagag ctcagcacag caaagactcg 66420
gggtcaggga tggtagtgca ggggaatggt ggagtagaac ttggtaagtg taagagatca 66480
aggtgtgtga cccaaactta atctttttct tttatcagga gatgctgtcc atgctgggag 66540
atcagagcaa cagctacaac aatgaagaat tccctgatct aactatgttt ccccccttt 66600
cagaatagaa ctattggggt gaggataagg ggtgggggag aaaaaatcac tgtttgtttt 66660
taaaaagcaa atctttctgt aaacagaata aaagttcctc tcccttccct tccctcaccc 66720
ctgacatgta ccccctttcc cttctggctg ttcccctgct ctgttgcctc tctaaggtaa 66780
catttataga agaaatggaa tgaatctcca aggcttttag gactgtctga aaatttgagg 66840
ctgggtgaag ttaaaacacc tttccttatg tctcctgacc tgaaattgta tagtgttgat 66900
ttgtgctgag atcaagaggc aggttagaag aacctgacat ccactgtttg ccttggatag 66960
tatggcttgt ttttggaaag aaattctgaa gagagtggag gagaggagaa atgtcctcat 67020
atttgaggac catgaaacat tgtaggtata tatggggctt tagcaagttt gagcataggc 67080

-continued tctttttgct gcctgtgagc agtccctctg gaaagaaaca tgtgagtaag tgagagagag 67140
tgtgtgtgta tgtgtgtgtg tgtgtgtgtg cgcacacatg cttctgtatt tcactctttc 67200
tccctattag ggagttatgc aaaatttgtc cccgatttta cctttgtctt tctgtgtact 67260
tttcaaagag tcctaaggag ttaaatcttc caggtatttt ccacttagta ttgcagccaa 67320
agaatattta aataaacgtc tttgctgcgc ttgcatccat gcccagccaa tatacaactg 67380
taaagcaaat atagaaagtc ggctgttgat acgattgtct gttatcgaac acattcagtg 67440
ataaagctgg gttactgctg cttttggtgc tctcacctta tctggaagat ctgcaaacat 67500
tacctaaata ggctggcaag ataaacactt tctggaaccc gagacttggc cataaagata 67560
atgctgcatt tttctgtcag aatcacatat gatgtgtgtt ctgtagaggt tatttctgca 67620
tggaaactca acttcttgga ttagccgtcc cagtgaaaat cctcattgtt ggagtgtaaa 67680
ccaaatacga agccctcttg caaagtagcc tctttcatcc catactcaaa atacccagtt 67740
tagcaagcaa ctgagattta agtctctctg gccctaagag gtttttcctc tttgctccct 67800
ccaatcttga gattgggttt tgctttagag tgcaagtatc ataattccgt atgatagatg 67860
gggccctgga cacccatctc aacagggtca cttggtaatt aacaataata gccatataaa 67920
tgcggataca ggttactacc ctcacccttt accttcctca ggtaacagtc gtagatacca 67980 gcttttttttt ttttttttt aaattggctt tggccagtag ctaaagtgca agactgaatt 68040
aatgagaaga tatattaaat gtagtcatag gggactgagg agcaagggtg gccttgaaga 68100
ggccaaagga atgtccattt gctgagtttc ccttccttat gtctccagtc tggtgccagg 68160
tagtggagta aaaaaggaga cagtttattt ttttattcta tgtgcacact tacagtatac 68220
atatatattt atatcacaat ttacgaaacc aaaaagttga gtttccaatg gaacccttgt 68280
tttttaataa tcgacttttt aaatgtgatc aggactataa tattgtacag ttattatagg 68340
gcttttgggg aaggggagga tagcgagaag atgctctggg ggttttgttt ttgcttttcc 68400
ttcagggttt tatttttgac tgttttgttt tcttgttggc catttctgta ttgctggcat 68460
ctgtgctaag ctttacagtg gcaaaaaataa tgacatgtag caaagatttt caaacaaaat 68520
attttttcct tttgtaaaat ttcttgtgtt gtgtgatctt gattgcggct ttatcattcc 68580
tttccagttc ataaacaaca ggcacccaca accagaggaa tctatagttt aagctccaga 68640
catacaaaca taaggcacat tgtgtcttta atttcaggaa tcagaaatca tagggttctg 68700
atcacattgc acgcctcccc cctcacttgt cctcctgatc ctgacacatt ctgagtaaca 68760
tcagcaggaa tgct 68774

<210> SEQ ID NO 50
<211> LENGTH: 2446
<212> TYPE: DNA
<213> ORGANISM: Homo sapiens

<400> SEQUENCE: 50
ggccgggcgg gcatgggcct tcccggcccg gagctgggag tcgaaggggc gggaggcgtg 60
atggtgaact cgcaagaagt ttgagggacg cgcgggcccc gcgcccactc cccctccacc 120
ggacacggct ggggccggcg atgcctgaga gggggtcgga ggacgcagtg aacatatatg 180
catgtacagt gtggatcctc atctgagagg agggagatga aaacacaccc acctcacagg 240
ctgttgtgag gactaagggt gcggcagtgc ctggtacatg ggagccagcg ccggcagcca 300
ccatggcgtc acgcataggg ttgcgcatgc agctcatgcg ggagcaggcg cagcaggagg 360

-continued

```
agcagcggga gcgcatgcag caacaggctg tcatgcatta catgcagcag cagcagcagc    420
agcaacagca gcagctcgga gggccgccca ccccggccat caataccccc gtccacttcc    480
agtcgccacc acctgtgcct ggggaggtgt tgaaggtgca gtcctacctg gagaatccca    540
catcctacca tctgcagcag tcgcagcatc agaaggtgcg ggagtacctg tccgagacct    600
atgggaacaa gtttgctgcc cacatcagcc cagcccaggg ctctccgaaa cccccaccag    660
ccgcctcccc aggggtgcga gctggacacg tgctgtcctc ctccgctggc aacagtgctc    720
ccaatagccc catggccatg ctgcacattg gctccaaccc tgagagggag ttggatgatg    780
tcattgacaa cattatgcgt ctggacgatg tccttggcta catcaatcct gaaatgcaga    840
tgcccaacac gctacccctg tccagcagcc acctgaatgt gtacagcagc gacccccagg    900
tcacagcctc cctggtgggc gtcaccagca gctcctgccc tgcggacctg acccagaagc    960
gagagctcac agatgctgag agcagggccc tggccaagga gcggcagaag aaagacaatc   1020
acaacttaat tgaaaggaga cgaaggttca acatcaatga ccgcatcaag gagttgggaa   1080
tgctgatccc caaggccaat gacctggacg tgcgctggaa caagggcacc atcctcaagg   1140
cctctgtgga ttacatccgg aggatgcaga aggacctgca aaagtccagg gagctggaga   1200
accactctcg ccgcctggag atgaccaaca agcagctctg gctccgtatc caggagctgg   1260
agatgcaggc tcgagtgcac ggcctcccta ccacctcccc gtccggcatg aacatggctg   1320
agctggccca gcaggtggtg aagcaggagc tgcctagcga agagggccca ggggaggccc   1380
tgatgctggg ggctgaggtc cctgaccctg agccactgcc agctctgccc ccgcaagccc   1440
cgctgcccct gcccacccag ccaccatccc cattccatca cctggacttc agccacagcc   1500
tgagctttgg gggcagggag gacgagggtc ccccgggcta ccccgaaccc ctggcgccgg   1560
ggcatggctc cccattcccc agcctgtcca agaaggatct ggacctcatg ctcctggacg   1620
actcactgct accgctggcc tctgatccac ttctgtccac catgtccccc gaggcctcca   1680
aggccagcag ccgccggagc agcttcagca tggaggaggg cgatgtgctg tgaccctggc   1740
tgcccctgtg ccagggaaca ggggccggcc tgggggctgg gagggccagg ggcacctccc   1800
tcccaccctt caggctgcac tgtgtgtgaa gtagccacct gccctgcctc cctcctcccc   1860
gttggcccct gtttggactt agtgcctgtc tggcagcctg tggggtcagg agaagcaccc   1920
ccagggcagc cctcttgact ggcgcagtgg gaagaggcct tcagcccctc tcccggagat   1980
ggaatcgcgg ggcagggagg ggcagggtgt tctagaggtg agaagagggc ctggtggaga   2040
ttccctgtct tctgagcccg agcccctcat taccagtgaa ggacatgctt gaggggttcg   2100
ggaagctcct catctgaggc aactggtcct gggggtgctc aggcctgcct ttttgggact   2160
cagatggcag gaggtccacc ccgcagcctg gtcctcggct ctcccacagg tgggcacccc   2220
ccactttggt gctaatagct ctccaccagg tggtgtgagc gcgggggctg ccagaagcgg   2280
gaggggtcac tgccggaaga gcagctgccc tccgacccct cactttgtgc ctttagtaaa   2340
cactgtgctt tgtaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaa                  2446
```

<210> SEQ ID NO 51
<211> LENGTH: 681
<212> TYPE: DNA
<213> ORGANISM: Homo sapiens

<400> SEQUENCE: 51

```
atggattggg gcacgctgca gacgatcctg gggggtgtga acaaacactc caccagcatt     60
```

ggaaagatct ggctcaccgt cctcttcatt tttcgcatta tgatcctcgt tgtggctgca 120
aaggaggtgt ggggagatga gcaggccgac tttgtctgca acaccctgca gccaggctgc 180
aagaacgtgt gctacgatca ctacttcccc atctcccaca tccggctatg ggccctgcag 240
ctgatcttcg tgtccacgcc agcgctccta gtggccatgc acgtggccta ccggagacat 300
gagaagaaga ggaagttcat caaggggggag ataaatagtg aatttaagga catcgaggag 360
atcaaaaccc agaaggtccg catcgaaggc tccctgtggt ggacctacac aagcagcatc 420
ttcttccggg tcatcttcga agccgccttc atgtacgtct tctatgtcat gtacgacggc 480
ttctccatgc agcggctggt gaagtgcaac gcctggcctt gtcccaacac tgtggactgc 540
tttgtgtccc ggcccacgga gaagactgtc ttcacagtgt tcatgattgc agtgtctgga 600
atttgcatcc tgctgaatgt cactgaattg tgttatttgc taattagata ttgttctggg 660
aagtcaaaaa agccagttta a 681

<210> SEQ ID NO 52
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 52
gagctagcca ccatggtgag caagggcgag 30

<210> SEQ ID NO 53
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 53
tcaccttgat gccgttcttc t 21

<210> SEQ ID NO 54
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 54
taactgggtc gagcacagtg atgc 24

<210> SEQ ID NO 55
<211> LENGTH: 29
<212> TYPE: DNA
<213> ORGANISM: Artificial
<220> FEATURE:
<223> OTHER INFORMATION: an artificially synthesized primer sequence

<400> SEQUENCE: 55
tcagaattga tctggtcttc aagaccttg 29

<210> SEQ ID NO 56
<211> LENGTH: 27
<212> TYPE: DNA
<213> ORGANISM: Artificial
<220> FEATURE:
<223> OTHER INFORMATION: an artificially synthesized primer sequence -continued

```
<400> SEQUENCE: 56

atgtatgcta tacgaagtta ttagggc                                   27


<210> SEQ ID NO 57
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 57

ccctcgtgga tggttgccag cagc                                      24


<210> SEQ ID NO 58
<211> LENGTH: 27
<212> TYPE: DNA
<213> ORGANISM: Artificial
<220> FEATURE:
<223> OTHER INFORMATION: an artificially synthesized primer sequence

<400> SEQUENCE: 58

cttactttgc actgaacaca cacatcc                                   27
```